US012758329B2

(12) United States Patent
Stulen et al.

(10) Patent No.: US 12,758,329 B2
(45) Date of Patent: Oct. 13, 2026

(54) CLOSED FEEDBACK CONTROL FOR ELECTROSURGICAL DEVICE

(71) Applicant: Cilag GmbH International, Zug (CH)

(72) Inventors: Foster B. Stulen, Johns Island, SC (US); Randolph C. Stewart, Cincinnati, OH (US); Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 970 days.

(21) Appl. No.: 17/405,503

(22) Filed: Aug. 18, 2021

(65) Prior Publication Data

US 2022/0039891 A1 Feb. 10, 2022

Related U.S. Application Data

(63) Continuation of application No. 16/732,853, filed on Jan. 2, 2020, now Pat. No. 11,096,752, which is a (Continued)

(51) Int. Cl.
*A61B 18/14* (2006.01)
*A61B 18/12* (2006.01)
(Continued)

(52) U.S. Cl.
CPC .............. *A61B 34/30* (2016.02); *A61B 18/12* (2013.01); *A61B 18/14* (2013.01); (Continued)

(58) Field of Classification Search
CPC .................... A61B 2017/320093; A61B 34/30
See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |

(Continued)

FOREIGN PATENT DOCUMENTS

| | | | |
|---|---|---|---|
| CA | 2535467 | A1 | 4/1993 |
| CN | 2460047 | Y | 11/2001 |

(Continued)

OTHER PUBLICATIONS

"ATM-MPLS Network Interworking Version 2.0, af-aic-0178.001" ATM Standard, The ATM Forum Technical Committee, published Aug. 2003.

(Continued)

*Primary Examiner* — Joseph A Stocklosa
*Assistant Examiner* — Ryan T Clark
(74) *Attorney, Agent, or Firm* — Vorys, Sater, Seymour and Pease LLP

(57) ABSTRACT

A robotic surgical system comprising a surgical instrument comprising an end effector comprising (i) a blade, (ii) a first jaw member including a first electrode, and (iii) a second jaw member including a second electrode. The robotic surgical system may also comprise a motor and a control circuit configured to: (i) produce control signals comprising a first control signal and a second control signal, (ii) deliver an electrosurgical energy signal to the first electrode and the second electrode via the first control signal, (iii) deliver a drive signal to the motor via the second control signal (iv) receive at least one feedback signal, (v) determine a rate of change based on a first feedback signal of the at least one feedback signal, and (vi) maintain the rate of change at a predetermined rate or within a predetermined range.

15 Claims, 52 Drawing Sheets

Related U.S. Application Data continuation of application No. 15/613,838, filed on Jun. 5, 2017, now Pat. No. 10,524,872, which is a continuation of application No. 14/987,161, filed on Jan. 4, 2016, now Pat. No. 9,713,507, which is a continuation of application No. 13/539,117, filed on Jun. 29, 2012, now Pat. No. 9,226,767.

(51) Int. Cl.

| | |
|---|---|
| ***A61B 34/30*** | (2016.01) |
| *A61B 17/00* | (2006.01) |
| *A61B 17/29* | (2006.01) |
| *A61B 17/32* | (2006.01) |
| *A61B 18/00* | (2006.01) |
| *A61B 34/37* | (2016.01) |
| *A61B 90/00* | (2016.01) |

(52) U.S. Cl.

CPC ..................... *A61B 18/1445* (2013.01); *A61B 2017/00026* (2013.01); *A61B 2017/00477* (2013.01); *A61B 2017/2929* (2013.01); *A61B 2017/320093* (2017.08); *A61B 2017/320094* (2017.08); *A61B 2017/320095* (2017.08); *A61B 2018/00601* (2013.01); *A61B 2018/00607* (2013.01); *A61B 2018/0063* (2013.01); *A61B 2018/00642* (2013.01); *A61B 2018/00702* (2013.01); *A61B 2018/00755* (2013.01); *A61B 2018/00875* (2013.01); *A61B 2018/00994* (2013.01); *A61B 2018/1455* (2013.01); *A61B 2034/301* (2016.02); *A61B 34/37* (2016.02); *A61B 2090/0807* (2016.02)

(56) References Cited

U.S. PATENT DOCUMENTS 1,813,902 A 7/1931 Bovie
2,188,497 A 1/1940 Calva
2,366,274 A 1/1945 Luth et al.
2,425,245 A 8/1947 Johnson
2,442,966 A 6/1948 Wallace
2,458,152 A 1/1949 Eakins
2,510,693 A 6/1950 Green
2,597,564 A 5/1952 Bugg
2,704,333 A 3/1955 Calosi et al.
2,736,960 A 3/1956 Armstrong
2,748,967 A 6/1956 Roach
2,845,072 A 7/1958 Shafer
2,849,788 A 9/1958 Creek
2,867,039 A 1/1959 Zach
2,874,470 A 2/1959 Richards
2,990,616 A 7/1961 Balamuth et al.
RE25,033 E 8/1961 Balamuth et al.
3,015,961 A 1/1962 Roney
3,033,407 A 5/1962 Alfons
3,053,124 A 9/1962 Balamuth et al.
3,082,805 A 3/1963 Royce
3,166,971 A 1/1965 Stoecker
3,322,403 A 5/1967 Murphy
3,432,691 A 3/1969 Shoh
3,433,226 A 3/1969 Boyd
3,489,930 A 1/1970 Shoh
3,513,848 A 5/1970 Winston et al.
3,514,856 A 6/1970 Camp et al.
3,525,912 A 8/1970 Wallin
3,526,219 A 9/1970 Balamuth
3,554,198 A 1/1971 Tatoian et al.
3,580,841 A 5/1971 Cadotte et al.
3,606,682 A 9/1971 Camp et al.
3,614,484 A 10/1971 Shoh
3,616,375 A 10/1971 Inoue
3,629,726 A 12/1971 Popescu
3,636,943 A 1/1972 Balamuth
3,668,486 A 6/1972 Silver
3,702,948 A 11/1972 Balamuth
3,703,651 A 11/1972 Blowers
3,776,238 A 12/1973 Peyman et al.
3,777,760 A 12/1973 Essner
3,805,787 A 4/1974 Banko
3,809,977 A 5/1974 Balamuth et al.
3,830,098 A 8/1974 Antonevich
3,854,737 A 12/1974 Gilliam, Sr.
3,862,630 A 1/1975 Balamuth
3,875,945 A 4/1975 Friedman
3,885,438 A 5/1975 Harris, Sr. et al.
3,900,823 A 8/1975 Sokal et al.
3,918,442 A 11/1975 Nikolaev et al.
3,924,335 A 12/1975 Balamuth et al.
3,946,738 A 3/1976 Newton et al.
3,955,859 A 5/1976 Stella et al.
3,956,826 A 5/1976 Perdreaux, Jr.
3,989,952 A 11/1976 Hohmann
4,005,714 A 2/1977 Hiltebrandt
4,012,647 A 3/1977 Balamuth et al.
4,034,762 A 7/1977 Cosens et al.
4,058,126 A 11/1977 Leveen
4,074,719 A 2/1978 Semm
4,156,187 A 5/1979 Murry et al.
4,167,944 A 9/1979 Banko
4,188,927 A 2/1980 Harris
4,200,106 A 4/1980 Douvas et al.
4,203,430 A 5/1980 Takahashi
4,203,444 A 5/1980 Bonnell et al.
4,220,154 A 9/1980 Semm
4,237,441 A 12/1980 van Konynenburg et al.
4,244,371 A 1/1981 Farin
4,281,785 A 8/1981 Brooks
4,300,083 A 11/1981 Heiges
4,302,728 A 11/1981 Nakamura
4,304,987 A 12/1981 van Konynenburg
4,306,570 A 12/1981 Matthews
4,314,559 A 2/1982 Allen
4,353,371 A 10/1982 Cosman
4,409,981 A 10/1983 Lundberg
4,445,063 A 4/1984 Smith
4,461,304 A 7/1984 Kuperstein
4,463,759 A 8/1984 Garito et al.
4,491,132 A 1/1985 Aikins
4,492,231 A 1/1985 Auth
4,494,759 A 1/1985 Kieffer
4,504,264 A 3/1985 Kelman
4,512,344 A 4/1985 Barber
4,526,571 A 7/1985 Wuchinich
4,535,773 A 8/1985 Yoon
4,541,638 A 9/1985 Ogawa et al.
4,545,374 A 10/1985 Jacobson
4,545,926 A 10/1985 Fouts, Jr. et al.
4,549,147 A 10/1985 Kondo
4,550,870 A 11/1985 Krumme et al.
4,553,544 A 11/1985 Nomoto et al.
4,562,838 A 1/1986 Walker
4,574,615 A 3/1986 Bower et al.
4,582,236 A 4/1986 Hirose
4,593,691 A 6/1986 Lindstrom et al.
4,608,981 A 9/1986 Rothfuss et al.
4,617,927 A 10/1986 Manes
4,633,119 A 12/1986 Thompson
4,633,874 A 1/1987 Chow et al.
4,634,420 A 1/1987 Spinosa et al.
4,640,279 A 2/1987 Beard
4,641,053 A 2/1987 Takeda
4,646,738 A 3/1987 Trott
4,646,756 A 3/1987 Watmough et al.
4,649,919 A 3/1987 Thimsen et al.
4,662,068 A 5/1987 Polonsky
4,674,502 A 6/1987 Imonti
4,694,835 A 9/1987 Strand
4,708,127 A 11/1987 Abdelghani
4,712,722 A 12/1987 Hood et al.
4,735,603 A 4/1988 Goodson et al.
4,739,759 A 4/1988 Rexroth et al.
4,761,871 A 8/1988 O'Connor et al.

(56) References Cited

U.S. PATENT DOCUMENTS

| | | | |
|---|---|---|---|
| 4,808,154 | A | 2/1989 | Freeman |
| 4,819,635 | A | 4/1989 | Shapiro |
| 4,827,911 | A | 5/1989 | Broadwin et al. |
| 4,830,462 | A | 5/1989 | Karny et al. |
| 4,832,683 | A | 5/1989 | Idemoto et al. |
| 4,836,186 | A | 6/1989 | Scholz |
| 4,838,853 | A | 6/1989 | Parisi |
| 4,844,064 | A | 7/1989 | Thimsen et al. |
| 4,849,133 | A | 7/1989 | Yoshida et al. |
| 4,850,354 | A | 7/1989 | Mcgurk-Burleson et al. |
| 4,852,578 | A | 8/1989 | Companion et al. |
| 4,860,745 | A | 8/1989 | Farin et al. |
| 4,862,890 | A | 9/1989 | Stasz et al. |
| 4,865,159 | A | 9/1989 | Jamison |
| 4,867,157 | A | 9/1989 | McGurk-Burleson et al. |
| 4,878,493 | A | 11/1989 | Pasternak et al. |
| 4,880,015 | A | 11/1989 | Nierman |
| 4,881,550 | A | 11/1989 | Kothe |
| 4,896,009 | A | 1/1990 | Pawlowski |
| 4,903,696 | A | 2/1990 | Stasz et al. |
| 4,910,389 | A | 3/1990 | Sherman et al. |
| 4,915,643 | A | 4/1990 | Samejima et al. |
| 4,920,978 | A | 5/1990 | Colvin |
| 4,922,902 | A | 5/1990 | Wuchinich et al. |
| 4,926,860 | A | 5/1990 | Stice et al. |
| 4,936,842 | A | 6/1990 | D'Amelio et al. |
| 4,954,960 | A | 9/1990 | Lo et al. |
| 4,965,532 | A | 10/1990 | Sakurai |
| 4,979,952 | A | 12/1990 | Kubota et al. |
| 4,981,756 | A | 1/1991 | Rhandhawa |
| 5,001,649 | A | 3/1991 | Lo et al. |
| 5,003,693 | A | 4/1991 | Atkinson et al. |
| 5,009,661 | A | 4/1991 | Michelson |
| 5,013,956 | A | 5/1991 | Kurozumi et al. |
| 5,015,227 | A | 5/1991 | Broadwin et al. |
| 5,020,514 | A | 6/1991 | Heckele |
| 5,026,370 | A | 6/1991 | Lottick |
| 5,026,387 | A | 6/1991 | Thomas |
| 5,035,695 | A | 7/1991 | Weber, Jr. et al. |
| 5,042,461 | A | 8/1991 | Inoue et al. |
| 5,042,707 | A | 8/1991 | Taheri |
| 5,052,145 | A | 10/1991 | Wang |
| 5,061,269 | A | 10/1991 | Muller |
| 5,075,839 | A | 12/1991 | Fisher et al. |
| 5,084,052 | A | 1/1992 | Jacobs |
| 5,099,840 | A | 3/1992 | Goble et al. |
| 5,104,025 | A | 4/1992 | Main et al. |
| 5,105,117 | A | 4/1992 | Yamaguchi |
| 5,106,538 | A | 4/1992 | Barma et al. |
| 5,108,383 | A | 4/1992 | White |
| 5,109,819 | A | 5/1992 | Custer et al. |
| 5,112,300 | A | 5/1992 | Ureche |
| 5,113,139 | A | 5/1992 | Furukawa |
| 5,123,903 | A | 6/1992 | Quaid et al. |
| 5,126,618 | A | 6/1992 | Takahashi et al. |
| D327,872 | S | 7/1992 | McMills et al. |
| 5,152,762 | A | 10/1992 | McElhenney |
| 5,156,633 | A | 10/1992 | Smith |
| 5,160,334 | A | 11/1992 | Billings et al. |
| 5,162,044 | A | 11/1992 | Gahn et al. |
| 5,163,421 | A | 11/1992 | Bernstein et al. |
| 5,163,537 | A | 11/1992 | Radev |
| 5,163,945 | A | 11/1992 | Ortiz et al. |
| 5,167,619 | A | 12/1992 | Wuchinich |
| 5,167,725 | A | 12/1992 | Clark et al. |
| 5,172,344 | A | 12/1992 | Ehrlich |
| 5,174,276 | A | 12/1992 | Crockard |
| D332,660 | S | 1/1993 | Rawson et al. |
| 5,176,677 | A | 1/1993 | Wuchinich |
| 5,176,695 | A | 1/1993 | Dulebohn |
| 5,184,605 | A | 2/1993 | Grzeszykowski |
| 5,188,102 | A | 2/1993 | Idemoto et al. |
| D334,173 | S | 3/1993 | Liu et al. |
| 5,190,517 | A | 3/1993 | Zieve et al. |
| 5,190,518 | A | 3/1993 | Takasu |
| 5,190,541 | A | 3/1993 | Abele et al. |
| 5,196,007 | A | 3/1993 | Ellman et al. |
| 5,203,380 | A | 4/1993 | Chikama |
| 5,205,459 | A | 4/1993 | Brinkerhoff et al. |
| 5,205,817 | A | 4/1993 | Idemoto et al. |
| 5,209,719 | A | 5/1993 | Baruch et al. |
| 5,213,569 | A | 5/1993 | Davis |
| 5,214,339 | A | 5/1993 | Naito |
| 5,217,460 | A | 6/1993 | Knoepfler |
| 5,218,529 | A | 6/1993 | Meyer et al. |
| 5,221,282 | A | 6/1993 | Wuchinich |
| 5,222,937 | A | 6/1993 | Kagawa |
| 5,226,909 | A | 7/1993 | Evans et al. |
| 5,226,910 | A | 7/1993 | Kajiyama et al. |
| 5,231,989 | A | 8/1993 | Middleman et al. |
| 5,234,428 | A | 8/1993 | Kaufman |
| 5,241,236 | A | 8/1993 | Sasaki et al. |
| 5,241,968 | A | 9/1993 | Slater |
| 5,242,339 | A | 9/1993 | Thornton |
| 5,242,460 | A | 9/1993 | Klein et al. |
| 5,246,003 | A | 9/1993 | DeLonzor |
| 5,254,129 | A | 10/1993 | Alexander |
| 5,257,988 | A | 11/1993 | L'Esperance, Jr. |
| 5,258,004 | A | 11/1993 | Bales et al. |
| 5,258,006 | A | 11/1993 | Rydell et al. |
| 5,261,922 | A | 11/1993 | Hood |
| 5,263,957 | A | 11/1993 | Davison |
| 5,264,925 | A | 11/1993 | Shipp et al. |
| 5,269,297 | A | 12/1993 | Weng et al. |
| 5,275,166 | A | 1/1994 | Vaitekunas et al. |
| 5,275,607 | A | 1/1994 | Lo et al. |
| 5,275,609 | A | 1/1994 | Pingleton et al. |
| 5,282,800 | A | 2/1994 | Foshee et al. |
| 5,282,817 | A | 2/1994 | Hoogeboom et al. |
| 5,285,795 | A | 2/1994 | Ryan et al. |
| 5,285,945 | A | 2/1994 | Brinkerhoff et al. |
| 5,290,286 | A | 3/1994 | Parins |
| 5,293,863 | A | 3/1994 | Zhu et al. |
| 5,300,068 | A | 4/1994 | Rosar et al. |
| 5,304,115 | A | 4/1994 | Pflueger et al. |
| D347,474 | S | 5/1994 | Olson |
| 5,307,976 | A | 5/1994 | Olson et al. |
| 5,309,927 | A | 5/1994 | Welch |
| 5,312,023 | A | 5/1994 | Green et al. |
| 5,312,425 | A | 5/1994 | Evans et al. |
| 5,318,525 | A | 6/1994 | West et al. |
| 5,318,563 | A | 6/1994 | Malis et al. |
| 5,318,564 | A | 6/1994 | Eggers |
| 5,318,570 | A | 6/1994 | Hood et al. |
| 5,318,589 | A | 6/1994 | Lichtman |
| 5,322,055 | A | 6/1994 | Davison et al. |
| 5,324,299 | A | 6/1994 | Davison et al. |
| 5,326,013 | A | 7/1994 | Green et al. |
| 5,326,342 | A | 7/1994 | Pflueger et al. |
| 5,330,471 | A | 7/1994 | Eggers |
| 5,330,502 | A | 7/1994 | Hassler et al. |
| 5,334,183 | A | 8/1994 | Wuchinich |
| 5,339,723 | A | 8/1994 | Huitema |
| 5,342,356 | A | 8/1994 | Ellman et al. |
| 5,342,359 | A | 8/1994 | Rydell |
| 5,344,420 | A | 9/1994 | Hilal et al. |
| 5,345,937 | A | 9/1994 | Middleman et al. |
| 5,346,502 | A | 9/1994 | Estabrook et al. |
| 5,353,474 | A | 10/1994 | Good et al. |
| 5,357,164 | A | 10/1994 | Imabayashi et al. |
| 5,357,423 | A | 10/1994 | Weaver et al. |
| 5,359,994 | A | 11/1994 | Krauter et al. |
| 5,361,583 | A | 11/1994 | Huitema |
| 5,366,466 | A | 11/1994 | Christian et al. |
| 5,368,557 | A | 11/1994 | Nita et al. |
| 5,370,645 | A | 12/1994 | Klicek et al. |
| 5,371,429 | A | 12/1994 | Manna |
| 5,374,813 | A | 12/1994 | Shipp |
| D354,564 | S | 1/1995 | Medema |
| 5,381,067 | A | 1/1995 | Greenstein et al. |
| 5,383,874 | A | 1/1995 | Jackson et al. |
| 5,383,917 | A | 1/1995 | Desai et al. |
| 5,387,207 | A | 2/1995 | Dyer et al. |
| 5,387,215 | A | 2/1995 | Fisher |

(56) References Cited

U.S. PATENT DOCUMENTS 5,389,098 A 2/1995 Tsuruta et al.
5,394,187 A 2/1995 Shipp
5,395,033 A 3/1995 Byrne et al.
5,395,312 A 3/1995 Desai
5,395,363 A 3/1995 Billings et al.
5,395,364 A 3/1995 Anderhub et al.
5,396,266 A 3/1995 Brimhall
5,396,900 A 3/1995 Slater et al.
5,400,267 A 3/1995 Denen et al.
5,403,312 A 4/1995 Yates et al.
5,403,334 A 4/1995 Evans et al.
5,406,503 A 4/1995 Williams, Jr. et al.
5,408,268 A 4/1995 Shipp
D358,887 S 5/1995 Feinberg
5,411,481 A 5/1995 Allen et al.
5,417,709 A 5/1995 Slater
5,419,761 A 5/1995 Narayanan et al.
5,421,829 A 6/1995 Olichney et al.
5,423,844 A 6/1995 Miller
5,428,504 A 6/1995 Bhatla
5,429,131 A 7/1995 Scheinman et al.
5,438,997 A 8/1995 Sieben et al.
5,441,499 A 8/1995 Fritzsch
5,443,463 A 8/1995 Stern et al.
5,445,638 A 8/1995 Rydell et al.
5,445,639 A 8/1995 Kuslich et al.
5,447,509 A 9/1995 Mills et al.
5,449,370 A 9/1995 Vaitekunas
5,451,053 A 9/1995 Garrido
5,451,161 A 9/1995 Sharp
5,451,220 A 9/1995 Ciervo
5,451,227 A 9/1995 Michaelson
5,456,684 A 10/1995 Schmidt et al.
5,458,598 A 10/1995 Feinberg et al.
5,462,604 A 10/1995 Shibano et al.
5,465,895 A 11/1995 Knodel et al.
5,471,988 A 12/1995 Fujio et al.
5,472,443 A 12/1995 Cordis et al.
5,476,479 A 12/1995 Green et al.
5,478,003 A 12/1995 Green et al.
5,480,409 A 1/1996 Riza
5,483,501 A 1/1996 Park et al.
5,484,436 A 1/1996 Eggers et al.
5,486,162 A 1/1996 Brumbach
5,486,189 A 1/1996 Mudry et al.
5,490,860 A 2/1996 Middle et al.
5,496,317 A 3/1996 Goble et al.
5,499,992 A 3/1996 Meade et al.
5,500,216 A 3/1996 Julian et al.
5,501,654 A 3/1996 Failla et al.
5,504,650 A 4/1996 Katsui et al.
5,505,693 A 4/1996 Mackool
5,507,297 A 4/1996 Slater et al.
5,507,738 A 4/1996 Ciervo
5,509,922 A 4/1996 Aranyi et al.
5,511,556 A 4/1996 DeSantis
5,520,704 A 5/1996 Castro et al.
5,522,832 A 6/1996 Kugo et al.
5,522,839 A 6/1996 Pilling
5,527,331 A 6/1996 Kresch et al.
5,531,744 A 7/1996 Nardella et al.
5,536,267 A 7/1996 Edwards et al.
5,540,681 A 7/1996 Strul et al.
5,540,684 A 7/1996 Hassler, Jr.
5,540,693 A 7/1996 Fisher
5,542,916 A 8/1996 Hirsch et al.
5,548,286 A 8/1996 Craven
5,549,637 A 8/1996 Crainich
5,553,675 A 9/1996 Pitzen et al.
5,558,671 A 9/1996 Yates
5,562,609 A 10/1996 Brumbach
5,562,610 A 10/1996 Brumbach
5,562,659 A 10/1996 Morris
5,562,703 A 10/1996 Desai
5,563,179 A 10/1996 Stone et al.
5,569,164 A 10/1996 Lurz
5,571,121 A 11/1996 Heifetz
5,573,424 A 11/1996 Poppe
5,573,533 A 11/1996 Strul
5,573,534 A 11/1996 Stone
5,577,654 A 11/1996 Bishop
5,584,830 A 12/1996 Ladd et al.
5,591,187 A 1/1997 Dekel
5,593,414 A 1/1997 Shipp et al.
5,599,350 A 2/1997 Schulze et al.
5,600,526 A 2/1997 Russell et al.
5,601,601 A 2/1997 Tal et al.
5,603,773 A 2/1997 Campbell
5,607,436 A 3/1997 Pratt et al.
5,607,450 A 3/1997 Zvenyatsky et al.
5,609,573 A 3/1997 Sandock
5,611,813 A 3/1997 Lichtman
5,618,304 A 4/1997 Hart et al.
5,618,307 A 4/1997 Donlon et al.
5,618,492 A 4/1997 Auten et al.
5,620,447 A 4/1997 Smith et al.
5,624,452 A 4/1997 Yates
5,626,587 A 5/1997 Bishop et al.
5,626,595 A 5/1997 Sklar et al.
5,626,608 A 5/1997 Cuny et al.
5,628,760 A 5/1997 Knoepfler
5,630,420 A 5/1997 Vaitekunas
5,632,432 A 5/1997 Schulze et al.
5,632,717 A 5/1997 Yoon
5,638,827 A 6/1997 Palmer et al.
5,640,741 A 6/1997 Yano
D381,077 S 7/1997 Hunt
5,647,871 A 7/1997 Levine et al.
5,649,937 A 7/1997 Bito et al.
5,649,955 A 7/1997 Hashimoto et al.
5,651,780 A 7/1997 Jackson et al.
5,653,713 A 8/1997 Michelson
5,655,100 A 8/1997 Ebrahim et al.
5,658,281 A 8/1997 Heard
5,662,662 A 9/1997 Bishop et al.
5,662,667 A 9/1997 Knodel
5,665,085 A 9/1997 Nardella
5,665,100 A 9/1997 Yoon
5,669,922 A 9/1997 Hood
5,674,219 A 10/1997 Monson et al.
5,674,220 A 10/1997 Fox et al.
5,674,235 A 10/1997 Parisi
5,678,568 A 10/1997 Uchikubo et al.
5,688,270 A 11/1997 Yates et al.
5,690,269 A 11/1997 Bolanos et al.
5,693,042 A 12/1997 Boiarski et al.
5,693,051 A 12/1997 Schulze et al.
5,694,936 A 12/1997 Fujimoto et al.
5,695,510 A 12/1997 Hood
5,700,261 A 12/1997 Brinkerhoff
5,704,534 A 1/1998 Huitema et al.
5,704,791 A 1/1998 Gillio
5,707,369 A 1/1998 Vaitekunas et al.
5,709,680 A 1/1998 Yates et al.
5,711,472 A 1/1998 Bryan
5,713,896 A 2/1998 Nardella
5,715,817 A 2/1998 Stevens-Wright et al.
5,716,366 A 2/1998 Yates
5,717,306 A 2/1998 Shipp
5,720,742 A 2/1998 Zacharias
5,720,744 A 2/1998 Eggleston et al.
5,722,980 A 3/1998 Schulz et al.
5,723,970 A 3/1998 Bell
5,728,130 A 3/1998 Ishikawa et al.
5,730,752 A 3/1998 Alden et al.
5,733,074 A 3/1998 Stock et al.
5,735,848 A 4/1998 Yates et al.
5,741,226 A 4/1998 Strukel et al.
5,743,906 A 4/1998 Parins et al.
5,752,973 A 5/1998 Kieturakis
5,755,717 A 5/1998 Yates et al.
5,759,183 A 6/1998 VanDusseldorp
5,762,255 A 6/1998 Chrisman et al.
5,766,164 A 6/1998 Mueller et al.

(56) References Cited

U.S. PATENT DOCUMENTS

| | | | |
|---|---|---|---|
| 5,772,659 | A | 6/1998 | Becker et al. |
| 5,776,130 | A | 7/1998 | Buysse et al. |
| 5,776,155 | A | 7/1998 | Beaupre et al. |
| 5,779,130 | A | 7/1998 | Alesi et al. |
| 5,779,701 | A | 7/1998 | McBrayer et al. |
| 5,782,834 | A | 7/1998 | Lucey et al. |
| 5,792,135 | A | 8/1998 | Madhani et al. |
| 5,792,138 | A | 8/1998 | Shipp |
| 5,792,165 | A | 8/1998 | Klieman et al. |
| 5,796,188 | A | 8/1998 | Bays |
| 5,797,941 | A | 8/1998 | Schulze et al. |
| 5,797,958 | A | 8/1998 | Yoon |
| 5,797,959 | A | 8/1998 | Castro et al. |
| 5,800,432 | A | 9/1998 | Swanson |
| 5,800,448 | A | 9/1998 | Banko |
| 5,800,449 | A | 9/1998 | Wales |
| 5,805,140 | A | 9/1998 | Rosenberg et al. |
| 5,807,393 | A | 9/1998 | Williamson, IV et al. |
| 5,808,396 | A | 9/1998 | Boukhny |
| 5,810,811 | A | 9/1998 | Yates et al. |
| 5,810,828 | A | 9/1998 | Lightman et al. |
| 5,810,859 | A | 9/1998 | DiMatteo et al. |
| 5,817,033 | A | 10/1998 | DeSantis et al. |
| 5,817,084 | A | 10/1998 | Jensen |
| 5,817,093 | A | 10/1998 | Williamson, IV et al. |
| 5,817,119 | A | 10/1998 | Klieman et al. |
| 5,823,197 | A | 10/1998 | Edwards |
| 5,827,271 | A | 10/1998 | Buysse et al. |
| 5,827,323 | A | 10/1998 | Klieman et al. |
| 5,828,160 | A | 10/1998 | Sugishita |
| 5,833,696 | A | 11/1998 | Whitfield et al. |
| 5,836,897 | A | 11/1998 | Sakurai et al. |
| 5,836,909 | A | 11/1998 | Cosmescu |
| 5,836,943 | A | 11/1998 | Miller, III |
| 5,836,957 | A | 11/1998 | Schulz et al. |
| 5,836,990 | A | 11/1998 | Li |
| 5,843,109 | A | 12/1998 | Mehta et al. |
| 5,851,212 | A | 12/1998 | Zirps et al. |
| 5,853,412 | A | 12/1998 | Mayenberger |
| 5,854,590 | A | 12/1998 | Dalstein |
| 5,858,018 | A | 1/1999 | Shipp et al. |
| 5,865,361 | A | 2/1999 | Milliman et al. |
| 5,873,873 | A | 2/1999 | Smith et al. |
| 5,873,882 | A | 2/1999 | Straub et al. |
| 5,876,401 | A | 3/1999 | Schulze et al. |
| 5,878,193 | A | 3/1999 | Wang et al. |
| 5,879,364 | A | 3/1999 | Bromfield et al. |
| 5,880,668 | A | 3/1999 | Hall |
| 5,883,615 | A | 3/1999 | Fago et al. |
| 5,891,142 | A | 4/1999 | Eggers et al. |
| 5,893,835 | A | 4/1999 | Witt et al. |
| 5,897,523 | A | 4/1999 | Wright et al. |
| 5,897,569 | A | 4/1999 | Kellogg et al. |
| 5,903,607 | A | 5/1999 | Tailliet |
| 5,904,681 | A | 5/1999 | West, Jr. |
| 5,906,625 | A | 5/1999 | Bito et al. |
| 5,906,627 | A | 5/1999 | Spaulding |
| 5,906,628 | A | 5/1999 | Miyawaki et al. |
| 5,910,129 | A | 6/1999 | Koblish et al. |
| 5,911,699 | A | 6/1999 | Anis et al. |
| 5,913,823 | A | 6/1999 | Hedberg et al. |
| 5,916,229 | A | 6/1999 | Evans |
| 5,921,956 | A | 7/1999 | Grinberg et al. |
| 5,929,846 | A | 7/1999 | Rosenberg et al. |
| 5,935,143 | A | 8/1999 | Hood |
| 5,935,144 | A | 8/1999 | Estabrook |
| 5,938,633 | A | 8/1999 | Beaupre |
| 5,944,718 | A | 8/1999 | Austin et al. |
| 5,944,737 | A | 8/1999 | Tsonton et al. |
| 5,947,984 | A | 9/1999 | Whipple |
| 5,954,717 | A | 9/1999 | Behl et al. |
| 5,954,736 | A | 9/1999 | Bishop et al. |
| 5,954,746 | A | 9/1999 | Holthaus et al. |
| 5,957,882 | A | 9/1999 | Nita et al. |
| 5,957,943 | A | 9/1999 | Vaitekunas |
| 5,968,007 | A | 10/1999 | Simon et al. |
| 5,968,060 | A | 10/1999 | Kellogg |
| 5,974,342 | A | 10/1999 | Petrofsky |
| D416,089 | S | 11/1999 | Barton et al. |
| 5,980,510 | A | 11/1999 | Tsonton et al. |
| 5,980,546 | A | 11/1999 | Hood |
| 5,984,938 | A | 11/1999 | Yoon |
| 5,987,344 | A | 11/1999 | West |
| 5,989,274 | A | 11/1999 | Davison et al. |
| 5,989,275 | A | 11/1999 | Estabrook et al. |
| 5,993,465 | A | 11/1999 | Shipp et al. |
| 5,993,972 | A | 11/1999 | Reich et al. |
| 5,994,855 | A | 11/1999 | Lundell et al. |
| 6,003,517 | A | 12/1999 | Sheffield et al. |
| 6,004,335 | A | 12/1999 | Vaitekunas et al. |
| 6,013,052 | A | 1/2000 | Durman et al. |
| 6,024,741 | A | 2/2000 | Williamson, IV et al. |
| 6,024,744 | A | 2/2000 | Kese et al. |
| 6,024,750 | A | 2/2000 | Mastri et al. |
| 6,027,515 | A | 2/2000 | Cimino |
| 6,031,526 | A | 2/2000 | Shipp |
| 6,033,375 | A | 3/2000 | Brumbach |
| 6,033,399 | A | 3/2000 | Gines |
| 6,036,667 | A | 3/2000 | Manna et al. |
| 6,036,707 | A | 3/2000 | Spaulding |
| 6,039,734 | A | 3/2000 | Goble |
| 6,048,224 | A | 4/2000 | Kay |
| 6,050,943 | A | 4/2000 | Slayton et al. |
| 6,050,996 | A | 4/2000 | Schmaltz et al. |
| 6,051,010 | A | 4/2000 | DiMatteo et al. |
| 6,056,735 | A | 5/2000 | Okada et al. |
| 6,063,098 | A | 5/2000 | Houser et al. |
| 6,066,132 | A | 5/2000 | Chen et al. |
| 6,066,151 | A | 5/2000 | Miyawaki et al. |
| 6,068,627 | A | 5/2000 | Orszulak et al. |
| 6,068,629 | A | 5/2000 | Haissaguerre et al. |
| 6,068,647 | A | 5/2000 | Witt et al. |
| 6,074,389 | A | 6/2000 | Levine et al. |
| 6,077,285 | A | 6/2000 | Boukhny |
| 6,080,149 | A | 6/2000 | Huang et al. |
| 6,083,191 | A | 7/2000 | Rose |
| 6,086,584 | A | 7/2000 | Miller |
| 6,090,120 | A | 7/2000 | Wright et al. |
| 6,091,995 | A | 7/2000 | Ingle et al. |
| 6,096,033 | A | 8/2000 | Tu et al. |
| 6,099,483 | A | 8/2000 | Palmer et al. |
| 6,099,542 | A | 8/2000 | Cohn et al. |
| 6,099,550 | A | 8/2000 | Yoon |
| 6,102,909 | A | 8/2000 | Chen et al. |
| 6,109,500 | A | 8/2000 | Alli et al. |
| 6,110,127 | A | 8/2000 | Suzuki |
| 6,113,594 | A | 9/2000 | Savage |
| 6,113,598 | A | 9/2000 | Baker |
| 6,117,152 | A | 9/2000 | Huitema |
| H1904 | H | 10/2000 | Yates et al. |
| 6,126,629 | A | 10/2000 | Perkins |
| 6,126,658 | A | 10/2000 | Baker |
| 6,129,735 | A | 10/2000 | Okada et al. |
| 6,129,740 | A | 10/2000 | Michelson |
| 6,132,368 | A | 10/2000 | Cooper |
| 6,132,427 | A | 10/2000 | Jones et al. |
| 6,132,429 | A | 10/2000 | Baker |
| 6,132,448 | A | 10/2000 | Perez et al. |
| 6,139,320 | A | 10/2000 | Hahn |
| 6,139,561 | A | 10/2000 | Shibata et al. |
| 6,142,615 | A | 11/2000 | Qiu et al. |
| 6,142,994 | A | 11/2000 | Swanson et al. |
| 6,144,402 | A | 11/2000 | Norsworthy et al. |
| 6,147,560 | A | 11/2000 | Erhage et al. |
| 6,152,902 | A | 11/2000 | Christian et al. |
| 6,152,923 | A | 11/2000 | Ryan |
| 6,154,198 | A | 11/2000 | Rosenberg |
| 6,156,029 | A | 12/2000 | Mueller |
| 6,159,160 | A | 12/2000 | Hsei et al. |
| 6,159,175 | A | 12/2000 | Strukel et al. |
| 6,162,194 | A | 12/2000 | Shipp |
| 6,162,208 | A | 12/2000 | Hipps |
| 6,165,150 | A | 12/2000 | Banko |
| 6,174,309 | B1 | 1/2001 | Wrublewski et al. |

(56) References Cited

U.S. PATENT DOCUMENTS

| | | | |
|---|---|---|---|
| 6,174,310 | B1 | 1/2001 | Kirwan, Jr. |
| 6,176,857 | B1 | 1/2001 | Ashley |
| 6,179,853 | B1 | 1/2001 | Sachse et al. |
| 6,183,426 | B1 | 2/2001 | Akisada et al. |
| 6,187,003 | B1 | 2/2001 | Buysse et al. |
| 6,190,386 | B1 | 2/2001 | Rydell |
| 6,193,709 | B1 | 2/2001 | Miyawaki et al. |
| 6,204,592 | B1 | 3/2001 | Hur |
| 6,205,383 | B1 | 3/2001 | Hermann |
| 6,205,855 | B1 | 3/2001 | Pfeiffer |
| 6,206,844 | B1 | 3/2001 | Reichel et al. |
| 6,206,876 | B1 | 3/2001 | Levine et al. |
| 6,210,337 | B1 | 4/2001 | Dunham et al. |
| 6,210,402 | B1 | 4/2001 | Olsen et al. |
| 6,210,403 | B1 | 4/2001 | Klicek |
| 6,214,023 | B1 | 4/2001 | Whipple et al. |
| 6,228,080 | B1 | 5/2001 | Gines |
| 6,231,565 | B1 | 5/2001 | Tovey et al. |
| 6,232,899 | B1 | 5/2001 | Craven |
| 6,233,476 | B1 | 5/2001 | Strommer et al. |
| 6,238,366 | B1 | 5/2001 | Savage et al. |
| 6,238,384 | B1 | 5/2001 | Peer |
| 6,241,724 | B1 | 6/2001 | Fleischman et al. |
| 6,245,065 | B1 | 6/2001 | Panescu et al. |
| 6,251,110 | B1 | 6/2001 | Wampler |
| 6,252,110 | B1 | 6/2001 | Uemura et al. |
| D444,365 | S | 7/2001 | Bass et al. |
| D445,092 | S | 7/2001 | Lee |
| D445,764 | S | 7/2001 | Lee |
| 6,254,623 | B1 | 7/2001 | Haibel, Jr. et al. |
| 6,257,241 | B1 | 7/2001 | Wampler |
| 6,258,034 | B1 | 7/2001 | Hanafy |
| 6,259,230 | B1 | 7/2001 | Chou |
| 6,261,286 | B1 | 7/2001 | Goble et al. |
| 6,267,761 | B1 | 7/2001 | Ryan |
| 6,270,831 | B2 | 8/2001 | Kumar et al. |
| 6,273,852 | B1 | 8/2001 | Lehe et al. |
| 6,274,963 | B1 | 8/2001 | Estabrook et al. |
| 6,277,115 | B1 | 8/2001 | Saadat |
| 6,277,117 | B1 | 8/2001 | Tetzlaff et al. |
| 6,278,218 | B1 | 8/2001 | Madan et al. |
| 6,280,407 | B1 | 8/2001 | Manna et al. |
| 6,283,981 | B1 | 9/2001 | Beaupre |
| 6,287,344 | B1 | 9/2001 | Wampler et al. |
| 6,290,575 | B1 | 9/2001 | Shipp |
| 6,292,700 | B1 | 9/2001 | Morrison et al. |
| 6,299,591 | B1 | 10/2001 | Banko |
| 6,306,131 | B1 | 10/2001 | Hareyama et al. |
| 6,306,157 | B1 | 10/2001 | Shchervinsky |
| 6,309,400 | B2 | 10/2001 | Beaupre |
| 6,311,783 | B1 | 11/2001 | Harpell |
| 6,319,221 | B1 | 11/2001 | Savage et al. |
| 6,325,795 | B1 | 12/2001 | Lindemann et al. |
| 6,325,799 | B1 | 12/2001 | Goble |
| 6,325,811 | B1 | 12/2001 | Messerly |
| 6,328,751 | B1 | 12/2001 | Beaupre |
| 6,332,891 | B1 | 12/2001 | Himes |
| 6,338,657 | B1 | 1/2002 | Harper et al. |
| 6,340,352 | B1 | 1/2002 | Okada et al. |
| 6,340,878 | B1 | 1/2002 | Oglesbee |
| 6,350,269 | B1 | 2/2002 | Shipp et al. |
| 6,352,532 | B1 | 3/2002 | Kramer et al. |
| 6,356,224 | B1 | 3/2002 | Wohlfarth |
| 6,358,246 | B1 | 3/2002 | Behl et al. |
| 6,358,264 | B2 | 3/2002 | Banko |
| 6,364,888 | B1 | 4/2002 | Niemeyer et al. |
| 6,379,320 | B1 | 4/2002 | Lafon et al. |
| D457,958 | S | 5/2002 | Dycus et al. |
| 6,383,194 | B1 | 5/2002 | Pothula |
| 6,384,690 | B1 | 5/2002 | Wilhelmsson et al. |
| 6,387,094 | B1 | 5/2002 | Eitenmuller |
| 6,387,109 | B1 | 5/2002 | Davison et al. |
| 6,388,657 | B1 | 5/2002 | Natoli |
| 6,390,973 | B1 | 5/2002 | Ouchi |
| 6,391,026 | B1 | 5/2002 | Hung et al. |
| 6,391,042 | B1 | 5/2002 | Cimino |
| 6,398,779 | B1 | 6/2002 | Buysse et al. |
| 6,402,743 | B1 | 6/2002 | Orszulak et al. |
| 6,402,748 | B1 | 6/2002 | Schoenman et al. |
| 6,405,184 | B1 | 6/2002 | Bohme et al. |
| 6,405,733 | B1 | 6/2002 | Fogarty et al. |
| 6,409,722 | B1 | 6/2002 | Hoey et al. |
| H2037 | H | 7/2002 | Yates et al. |
| 6,416,469 | B1 | 7/2002 | Phung et al. |
| 6,416,486 | B1 | 7/2002 | Wampler |
| 6,417,969 | B1 | 7/2002 | DeLuca et al. |
| 6,419,675 | B1 | 7/2002 | Gallo, Sr. |
| 6,423,073 | B2 | 7/2002 | Bowman |
| 6,423,082 | B1 | 7/2002 | Houser et al. |
| 6,425,906 | B1 | 7/2002 | Young et al. |
| 6,428,538 | B1 | 8/2002 | Blewett et al. |
| 6,428,539 | B1 | 8/2002 | Baxter et al. |
| 6,430,446 | B1 | 8/2002 | Knowlton |
| 6,432,118 | B1 | 8/2002 | Messerly |
| 6,436,114 | B1 | 8/2002 | Novak et al. |
| 6,436,115 | B1 | 8/2002 | Beaupre |
| 6,436,129 | B1 | 8/2002 | Sharkey et al. |
| 6,440,062 | B1 | 8/2002 | Ouchi |
| 6,443,968 | B1 | 9/2002 | Holthaus et al. |
| 6,443,969 | B1 | 9/2002 | Novak et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,128 | B1 | 10/2002 | Schulze |
| 6,458,130 | B1 | 10/2002 | Frazier et al. |
| 6,458,142 | B1 | 10/2002 | Faller et al. |
| 6,459,363 | B1 | 10/2002 | Walker et al. |
| 6,461,363 | B1 | 10/2002 | Gadberry et al. |
| 6,464,689 | B1 | 10/2002 | Qin et al. |
| 6,464,702 | B2 | 10/2002 | Schulze et al. |
| 6,468,270 | B1 | 10/2002 | Hovda et al. |
| 6,475,211 | B2 | 11/2002 | Chess et al. |
| 6,475,215 | B1 | 11/2002 | Tanrisever |
| 6,480,796 | B2 | 11/2002 | Wiener |
| 6,485,490 | B2 | 11/2002 | Wampler et al. |
| 6,491,690 | B1 | 12/2002 | Goble et al. |
| 6,491,701 | B2 | 12/2002 | Tierney et al. |
| 6,491,708 | B2 | 12/2002 | Madan et al. |
| 6,497,715 | B2 | 12/2002 | Satou |
| 6,500,112 | B1 | 12/2002 | Khouri |
| 6,500,176 | B1 | 12/2002 | Truckai et al. |
| 6,500,188 | B2 | 12/2002 | Harper et al. |
| 6,500,312 | B2 | 12/2002 | Wedekamp |
| 6,503,248 | B1 | 1/2003 | Levine |
| 6,506,208 | B2 | 1/2003 | Hunt et al. |
| 6,511,478 | B1 | 1/2003 | Burnside et al. |
| 6,511,480 | B1 | 1/2003 | Tetzlaff et al. |
| 6,511,493 | B1 | 1/2003 | Moutafis et al. |
| 6,514,252 | B2 | 2/2003 | Nezhat et al. |
| 6,514,267 | B2 | 2/2003 | Jewett |
| 6,517,565 | B1 | 2/2003 | Whitman et al. |
| 6,524,251 | B2 | 2/2003 | Rabiner et al. |
| 6,524,316 | B1 | 2/2003 | Nicholson et al. |
| 6,527,736 | B1 | 3/2003 | Attinger et al. |
| 6,531,846 | B1 | 3/2003 | Smith |
| 6,533,784 | B2 | 3/2003 | Truckai et al. |
| 6,537,272 | B2 | 3/2003 | Christopherson et al. |
| 6,537,291 | B2 | 3/2003 | Friedman et al. |
| 6,543,452 | B1 | 4/2003 | Lavigne |
| 6,543,456 | B1 | 4/2003 | Freeman |
| 6,544,260 | B1 | 4/2003 | Markel et al. |
| 6,551,309 | B1 | 4/2003 | LePivert |
| 6,554,829 | B2 | 4/2003 | Schulze et al. |
| 6,558,376 | B2 | 5/2003 | Bishop |
| 6,558,380 | B2 | 5/2003 | Lingenfelder et al. |
| 6,561,983 | B2 | 5/2003 | Cronin et al. |
| 6,562,035 | B1 | 5/2003 | Levin |
| 6,562,037 | B2 | 5/2003 | Paton et al. |
| 6,565,558 | B1 | 5/2003 | Lindenmeier et al. |
| 6,572,563 | B2 | 6/2003 | Ouchi |
| 6,572,632 | B2 | 6/2003 | Zisterer et al. |
| 6,572,639 | B1 | 6/2003 | Ingle et al. |
| 6,575,969 | B1 | 6/2003 | Rittman, III et al. |
| 6,582,427 | B1 | 6/2003 | Goble et al. |

(56) References Cited

U.S. PATENT DOCUMENTS 6,582,451 B1 6/2003 Marucci et al.
6,584,360 B2 6/2003 Francischelli et al.
D477,408 S 7/2003 Bromley
6,585,735 B1 7/2003 Frazier et al.
6,588,277 B2 7/2003 Giordano et al.
6,589,200 B1 7/2003 Schwemberger et al.
6,589,239 B2 7/2003 Khandkar et al.
6,590,733 B1 7/2003 Wilson et al.
6,599,288 B2 7/2003 Maguire et al.
6,602,252 B2 8/2003 Mollenauer
6,602,262 B2 8/2003 Griego et al.
6,607,540 B1 8/2003 Shipp
6,610,059 B1 8/2003 West, Jr.
6,610,060 B2 8/2003 Mulier et al.
6,611,793 B1 8/2003 Burnside et al.
6,616,450 B2 9/2003 Mossle et al.
6,619,529 B2 9/2003 Green et al.
6,620,161 B2 9/2003 Schulze et al.
6,622,731 B2 9/2003 Daniel et al.
6,623,482 B2 9/2003 Pendekanti et al.
6,623,500 B1 9/2003 Cook et al.
6,623,501 B2 9/2003 Heller et al.
6,626,848 B2 9/2003 Neuenfeldt
6,626,926 B2 9/2003 Friedman et al.
6,629,974 B2 10/2003 Penny et al.
6,632,221 B1 10/2003 Edwards et al.
6,633,234 B2 10/2003 Wiener et al.
6,635,057 B2 10/2003 Harano et al.
6,644,532 B2 11/2003 Green et al.
6,651,669 B1 11/2003 Burnside
6,652,513 B2 11/2003 Panescu et al.
6,652,539 B2 11/2003 Shipp et al.
6,652,545 B2 11/2003 Shipp et al.
6,656,132 B1 12/2003 Ouchi
6,656,177 B2 12/2003 Truckai et al.
6,656,198 B2 12/2003 Tsonton et al.
6,660,017 B2 12/2003 Beaupre
6,662,127 B2 12/2003 Wiener et al.
6,663,941 B2 12/2003 Brown et al.
6,666,860 B1 12/2003 Takahashi
6,666,875 B1 12/2003 Sakurai et al.
6,669,690 B1 12/2003 Okada et al.
6,669,710 B2 12/2003 Moutafis et al.
6,673,248 B2 1/2004 Chowdhury
6,676,660 B2 1/2004 Wampler et al.
6,678,621 B2 1/2004 Wiener et al.
6,678,899 B2 1/2004 Fiorini et al.
6,679,875 B2 1/2004 Honda et al.
6,679,882 B1 1/2004 Kornerup
6,679,899 B2 1/2004 Wiener et al.
6,682,501 B1 1/2004 Nelson et al.
6,682,544 B2 1/2004 Mastri et al.
6,685,700 B2 2/2004 Behl et al.
6,685,701 B2 2/2004 Orszulak et al.
6,685,703 B2 2/2004 Pearson et al.
6,689,145 B2 2/2004 Lee et al.
6,689,146 B1 2/2004 Himes
6,690,960 B2 2/2004 Chen et al.
6,695,840 B2 2/2004 Schulze
6,702,821 B2 3/2004 Bonutti
6,716,215 B1 4/2004 David et al.
6,719,692 B2 4/2004 Kleffner et al.
6,719,765 B2 4/2004 Bonutti
6,719,776 B2 4/2004 Baxter et al.
6,722,552 B2 4/2004 Fenton, Jr.
6,723,091 B2 4/2004 Goble et al.
D490,059 S 5/2004 Conway et al.
6,730,080 B2 5/2004 Harano et al.
6,731,047 B2 5/2004 Kauf et al.
6,733,498 B2 5/2004 Paton et al.
6,733,506 B1 5/2004 McDevitt et al.
6,736,813 B2 5/2004 Yamauchi et al.
6,739,872 B1 5/2004 Turri
6,740,079 B1 5/2004 Eggers et al.
D491,666 S 6/2004 Kimmell et al.
6,743,245 B2 6/2004 Lobdell
6,746,284 B1 6/2004 Spink, Jr.
6,746,443 B1 6/2004 Morley et al.
6,752,815 B2 6/2004 Beaupre
6,755,825 B2 6/2004 Shoenman et al.
6,761,698 B2 7/2004 Shibata et al.
6,762,535 B2 7/2004 Take et al.
6,766,202 B2 7/2004 Underwood et al.
6,770,072 B1 8/2004 Truckai et al.
6,773,409 B2 8/2004 Truckai et al.
6,773,434 B2 8/2004 Ciarrocca
6,773,435 B2 8/2004 Schulze et al.
6,773,443 B2 8/2004 Truwit et al.
6,773,444 B2 8/2004 Messerly
6,775,575 B2 8/2004 Bommannan et al.
6,778,023 B2 8/2004 Christensen
6,783,524 B2 8/2004 Anderson et al.
6,786,382 B1 9/2004 Hoffman
6,786,383 B2 9/2004 Stegelmann
6,789,939 B2 9/2004 Schrodinger et al.
6,790,173 B2 9/2004 Saadat et al.
6,790,216 B1 9/2004 Ishikawa
6,794,027 B1 9/2004 Araki et al.
6,796,981 B2 9/2004 Wham et al.
D496,997 S 10/2004 Dycus et al.
6,800,085 B2 10/2004 Selmon et al.
6,802,843 B2 10/2004 Truckai et al.
6,808,525 B2 10/2004 Latterell et al.
6,809,508 B2 10/2004 Donofrio
6,810,281 B2 10/2004 Brock et al.
6,811,842 B1 11/2004 Ehrnsperger et al.
6,814,731 B2 11/2004 Swanson
6,819,027 B2 11/2004 Saraf
6,821,273 B2 11/2004 Mollenauer
6,827,712 B2 12/2004 Tovey et al.
6,828,712 B2 12/2004 Battaglin et al.
6,835,082 B2 12/2004 Gonnering
6,835,199 B2 12/2004 McGuckin, Jr. et al.
6,840,938 B1 1/2005 Morley et al.
6,843,789 B2 1/2005 Goble
6,849,073 B2 2/2005 Hoey et al.
6,860,878 B2 3/2005 Brock
6,860,880 B2 3/2005 Treat et al.
6,863,676 B2 3/2005 Lee et al.
6,866,671 B2 3/2005 Tierney et al.
6,869,439 B2 3/2005 White et al.
6,875,220 B2 4/2005 Du et al.
6,877,647 B2 4/2005 Green et al.
6,882,439 B2 4/2005 Ishijima
6,887,209 B2 5/2005 Kadziauskas et al.
6,887,252 B1 5/2005 Okada et al.
6,893,435 B2 5/2005 Goble
6,898,536 B2 5/2005 Wiener et al.
6,899,685 B2 5/2005 Kermode et al.
6,905,497 B2 6/2005 Truckai et al.
6,908,463 B2 6/2005 Treat et al.
6,908,472 B2 6/2005 Wiener et al.
6,913,579 B2 7/2005 Truckai et al.
6,915,623 B2 7/2005 Dey et al.
6,923,804 B2 8/2005 Eggers et al.
6,923,806 B2 8/2005 Hooven et al.
6,926,712 B2 8/2005 Phan
6,926,716 B2 8/2005 Baker et al.
6,926,717 B1 8/2005 Garito et al.
6,929,602 B2 8/2005 Hirakui et al.
6,929,622 B2 8/2005 Chian
6,929,632 B2 8/2005 Nita et al.
6,929,644 B2 8/2005 Truckai et al.
6,933,656 B2 8/2005 Matsushita et al.
D509,589 S 9/2005 Wells
6,942,660 B2 9/2005 Pantera et al.
6,942,677 B2 9/2005 Nita et al.
6,945,981 B2 9/2005 Donofrio et al.
6,946,779 B2 9/2005 Birgel
6,948,503 B2 9/2005 Refior et al.
6,953,461 B2 10/2005 McClurken et al.
6,958,070 B2 10/2005 Witt et al.
D511,145 S 11/2005 Donofrio et al.
6,974,450 B2 12/2005 Weber et al.

(56) References Cited

U.S. PATENT DOCUMENTS 6,976,844 B2 12/2005 Hickok et al.
6,976,969 B2 12/2005 Messerly
6,977,495 B2 12/2005 Donofrio
6,979,332 B2 12/2005 Adams
6,981,628 B2 1/2006 Wales
6,984,220 B2 1/2006 Wuchinich
6,984,231 B2 1/2006 Goble et al.
6,988,295 B2 1/2006 Tillim
6,988,649 B2 1/2006 Shelton, IV et al.
6,994,708 B2 2/2006 Manzo
6,994,709 B2 2/2006 Iida
7,000,818 B2 2/2006 Shelton, IV et al.
7,001,335 B2 2/2006 Adachi et al.
7,001,379 B2 2/2006 Behl et al.
7,001,382 B2 2/2006 Gallo, Sr.
7,004,951 B2 2/2006 Gibbens, III
7,011,657 B2 3/2006 Truckai et al.
7,014,638 B2 3/2006 Michelson
7,018,389 B2 3/2006 Camerlengo
7,025,732 B2 4/2006 Thompson et al.
7,033,356 B2 4/2006 Latterell et al.
7,033,357 B2 4/2006 Baxter et al.
7,037,306 B2 5/2006 Podany et al.
7,041,083 B2 5/2006 Chu et al.
7,041,088 B2 5/2006 Nawrocki et al.
7,041,102 B2 5/2006 Truckai et al.
7,044,949 B2 5/2006 Orszulak et al.
7,052,494 B2 5/2006 Goble et al.
7,052,496 B2 5/2006 Yamauchi
7,055,731 B2 6/2006 Shelton, IV et al.
7,063,699 B2 6/2006 Hess et al.
7,066,893 B2 6/2006 Hibner et al.
7,066,895 B2 6/2006 Podany
7,066,936 B2 6/2006 Ryan
7,070,597 B2 7/2006 Truckai et al.
7,074,218 B2 7/2006 Washington et al.
7,074,219 B2 7/2006 Levine et al.
7,077,039 B2 7/2006 Gass et al.
7,077,845 B2 7/2006 Hacker et al.
7,077,853 B2 7/2006 Kramer et al.
7,083,075 B2 8/2006 Swayze et al.
7,083,613 B2 8/2006 Treat
7,083,618 B2 8/2006 Couture et al.
7,083,619 B2 8/2006 Truckai et al.
7,087,054 B2 8/2006 Truckai et al.
7,090,637 B2 8/2006 Danitz et al.
7,090,672 B2 8/2006 Underwood et al.
7,094,235 B2 8/2006 Francischelli
7,101,371 B2 9/2006 Dycus et al.
7,101,372 B2 9/2006 Dycus et al.
7,101,373 B2 9/2006 Dycus et al.
7,101,378 B2 9/2006 Salameh et al.
7,104,834 B2 9/2006 Robinson et al.
7,108,695 B2 9/2006 Witt et al.
7,111,769 B2 9/2006 Wales et al.
7,112,201 B2 9/2006 Truckai et al.
7,113,831 B2 9/2006 Hooven
D531,311 S 10/2006 Guerra et al.
7,117,034 B2 10/2006 Kronberg
7,118,564 B2 10/2006 Ritchie et al.
7,118,570 B2 10/2006 Tetzlaff et al.
7,118,587 B2 10/2006 Dycus et al.
7,119,516 B2 10/2006 Denning
7,124,932 B2 10/2006 Isaacson et al.
7,125,409 B2 10/2006 Truckai et al.
7,128,720 B2 10/2006 Podany
7,131,860 B2 11/2006 Sartor et al.
7,131,970 B2 11/2006 Moses et al.
7,135,018 B2 11/2006 Ryan et al.
7,135,030 B2 11/2006 Schwemberger et al.
7,137,980 B2 11/2006 Buysse et al.
7,143,925 B2 12/2006 Shelton, IV et al.
7,144,403 B2 12/2006 Booth
7,147,138 B2 12/2006 Shelton, IV
7,153,315 B2 12/2006 Miller
D536,093 S 1/2007 Nakajima et al.
7,156,189 B1 1/2007 Bar-Cohen et al.
7,156,846 B2 1/2007 Dycus et al.
7,156,853 B2 1/2007 Muratsu
7,157,058 B2 1/2007 Marhasin et al.
7,159,750 B2 1/2007 Racenet et al.
7,160,259 B2 1/2007 Tardy et al.
7,160,296 B2 1/2007 Pearson et al.
7,160,298 B2 1/2007 Lawes et al.
7,160,299 B2 1/2007 Baily
7,163,548 B2 1/2007 Stulen et al.
7,166,103 B2 1/2007 Carmel et al.
7,169,144 B2 1/2007 Hoey et al.
7,169,146 B2 1/2007 Truckai et al.
7,169,156 B2 1/2007 Hart
7,179,254 B2 2/2007 Pendekanti et al.
7,179,271 B2 2/2007 Friedman et al.
7,186,253 B2 3/2007 Truckai et al.
7,189,233 B2 3/2007 Truckai et al.
7,195,631 B2 3/2007 Dumbauld
D541,418 S 4/2007 Schechter et al.
7,198,635 B2 4/2007 Danek et al.
7,204,820 B2 4/2007 Akahoshi
7,207,471 B2 4/2007 Heinrich et al.
7,207,997 B2 4/2007 Shipp et al.
7,208,005 B2 4/2007 Frecker et al.
7,210,881 B2 5/2007 Greenberg
7,211,079 B2 5/2007 Treat
7,217,128 B2 5/2007 Atkin et al.
7,217,269 B2 5/2007 El-Galley et al.
7,220,951 B2 5/2007 Truckai et al.
7,223,229 B2 5/2007 Inman et al.
7,225,964 B2 6/2007 Mastri et al.
7,226,447 B2 6/2007 Uchida et al.
7,226,448 B2 6/2007 Bertolero et al.
7,229,455 B2 6/2007 Sakurai et al.
7,232,440 B2 6/2007 Dumbauld et al.
7,235,071 B2 6/2007 Gonnering
7,235,073 B2 6/2007 Levine et al.
7,241,294 B2 7/2007 Reschke
7,244,262 B2 7/2007 Wiener et al.
7,251,531 B2 7/2007 Mosher et al.
7,252,641 B2 8/2007 Thompson et al.
7,252,667 B2 8/2007 Moses et al.
7,258,688 B1 8/2007 Shah et al.
7,264,618 B2 9/2007 Murakami et al.
7,267,677 B2 9/2007 Johnson et al.
7,267,685 B2 9/2007 Butaric et al.
7,269,873 B2 9/2007 Brewer et al.
7,273,483 B2 9/2007 Wiener et al.
D552,241 S 10/2007 Bromley et al.
7,282,048 B2 10/2007 Goble et al.
7,285,895 B2 10/2007 Beaupre
7,287,682 B1 10/2007 Ezzat et al.
7,297,149 B2 11/2007 Vitali et al.
7,300,431 B2 11/2007 Dubrovsky
7,300,435 B2 11/2007 Wham et al.
7,300,446 B2 11/2007 Beaupre
7,300,450 B2 11/2007 Vleugels et al.
7,303,531 B2 12/2007 Lee et al.
7,303,557 B2 12/2007 Wham et al.
7,306,597 B2 12/2007 Manzo
7,307,313 B2 12/2007 Ohyanagi et al.
7,309,849 B2 12/2007 Truckai et al.
7,311,706 B2 12/2007 Schoenman et al.
7,311,709 B2 12/2007 Truckai et al.
7,317,955 B2 1/2008 McGreevy
7,318,831 B2 1/2008 Alvarez et al.
7,318,832 B2 1/2008 Young et al.
7,326,236 B2 2/2008 Andreas et al.
7,329,257 B2 2/2008 Kanehira et al.
7,331,410 B2 2/2008 Yong et al.
7,335,165 B2 2/2008 Truwit et al.
7,335,997 B2 2/2008 Wiener
7,337,010 B2 2/2008 Howard et al.
7,353,068 B2 4/2008 Tanaka et al.
7,354,440 B2 4/2008 Truckal et al.
7,357,287 B2 4/2008 Shelton, IV et al.
7,357,802 B2 4/2008 Palanker et al.

(56) References Cited

U.S. PATENT DOCUMENTS 7,361,172 B2 4/2008 Cimino
7,364,577 B2 4/2008 Wham et al.
7,367,976 B2 5/2008 Lawes et al.
7,371,227 B2 5/2008 Zeiner
RE40,388 E 6/2008 Gines
7,380,695 B2 6/2008 Doll et al.
7,380,696 B2 6/2008 Shelton, IV et al.
7,381,209 B2 6/2008 Truckai et al.
7,384,420 B2 6/2008 Dycus et al.
7,390,317 B2 6/2008 Taylor et al.
7,396,356 B2 7/2008 Mollenauer
7,403,224 B2 7/2008 Fuller et al.
7,404,508 B2 7/2008 Smith et al.
7,407,077 B2 8/2008 Ortiz et al.
7,408,288 B2 8/2008 Hara
7,412,008 B2 8/2008 Lliev
7,416,101 B2 8/2008 Shelton, IV et al.
7,416,437 B2 8/2008 Sartor et al.
D576,725 S 9/2008 Shumer et al.
7,419,490 B2 9/2008 Falkenstein et al.
7,422,139 B2 9/2008 Shelton, IV et al.
7,422,463 B2 9/2008 Kuo
7,422,582 B2 9/2008 Malackowski et al.
D578,643 S 10/2008 Shumer et al.
D578,644 S 10/2008 Shumer et al.
D578,645 S 10/2008 Shumer et al.
7,431,694 B2 10/2008 Stefanchik et al.
7,431,704 B2 10/2008 Babaev
7,431,720 B2 10/2008 Pendekanti et al.
7,435,582 B2 10/2008 Zimmermann et al.
7,441,684 B2 10/2008 Shelton, IV et al.
7,442,193 B2 10/2008 Shields et al.
7,445,621 B2 11/2008 Dumbauld et al.
7,449,004 B2 11/2008 Yamada et al.
7,451,904 B2 11/2008 Shelton, IV
7,455,208 B2 11/2008 Wales et al.
7,455,641 B2 11/2008 Yamada et al.
7,462,181 B2 12/2008 Kraft et al.
7,464,846 B2 12/2008 Shelton, IV et al.
7,464,849 B2 12/2008 Shelton, IV et al.
7,472,815 B2 1/2009 Shelton, IV et al.
7,473,145 B2 1/2009 Ehr et al.
7,473,253 B2 1/2009 Dycus et al.
7,473,263 B2 1/2009 Johnston et al.
7,479,148 B2 1/2009 Beaupre
7,479,160 B2 1/2009 Branch et al.
7,481,775 B2 1/2009 Weikel, Jr. et al.
7,488,285 B2 2/2009 Honda et al.
7,488,319 B2 2/2009 Yates
7,491,201 B2 2/2009 Shields et al.
7,491,202 B2 2/2009 Odom et al.
7,494,468 B2 2/2009 Rabiner et al.
7,494,501 B2 2/2009 Ahlberg et al.
7,498,080 B2 3/2009 Tung et al.
7,502,234 B2 3/2009 Goliszek et al.
7,503,893 B2 3/2009 Kucklick
7,503,895 B2 3/2009 Rabiner et al.
7,506,790 B2 3/2009 Shelton, IV
7,506,791 B2 3/2009 Omaits et al.
7,507,239 B2 3/2009 Shadduck
7,510,107 B2 3/2009 Timm et al.
7,510,556 B2 3/2009 Nguyen et al.
7,513,025 B2 4/2009 Fischer
7,517,349 B2 4/2009 Truckai et al.
7,520,865 B2 4/2009 Radley Young et al.
7,524,320 B2 4/2009 Tierney et al.
7,525,309 B2 4/2009 Sherman et al.
7,530,986 B2 5/2009 Beaupre et al.
7,534,243 B1 5/2009 Chin et al.
7,535,233 B2 5/2009 Kojovic et al.
D594,983 S 6/2009 Price et al.
7,540,871 B2 6/2009 Gonnering
7,540,872 B2 6/2009 Schechter et al.
7,543,730 B1 6/2009 Marczyk
7,544,200 B2 6/2009 Houser
7,549,564 B2 6/2009 Boudreaux
7,550,216 B2 6/2009 Ofer et al.
7,553,309 B2 6/2009 Buysse et al.
7,554,343 B2 6/2009 Bromfield
7,559,450 B2 7/2009 Wales et al.
7,559,452 B2 7/2009 Wales et al.
7,563,259 B2 7/2009 Takahashi
7,566,318 B2 7/2009 Haefner
7,567,012 B2 7/2009 Namikawa
7,568,603 B2 8/2009 Shelton, IV et al.
7,569,057 B2 8/2009 Liu et al.
7,572,266 B2 8/2009 Young et al.
7,572,268 B2 8/2009 Babaev
7,578,820 B2 8/2009 Moore et al.
7,582,084 B2 9/2009 Swanson et al.
7,582,086 B2 9/2009 Privitera et al.
7,582,087 B2 9/2009 Tetzlaff et al.
7,582,095 B2 9/2009 Shipp et al.
7,585,181 B2 9/2009 Olsen
7,586,289 B2 9/2009 Andruk et al.
7,587,536 B2 9/2009 McLeod
7,588,176 B2 9/2009 Timm et al.
7,588,177 B2 9/2009 Racenet
7,594,925 B2 9/2009 Danek et al.
7,597,693 B2 10/2009 Garrison
7,601,119 B2 10/2009 Shahinian
7,601,136 B2 10/2009 Akahoshi
7,604,150 B2 10/2009 Boudreaux
7,607,557 B2 10/2009 Shelton, IV et al.
7,617,961 B2 11/2009 Viola
7,621,930 B2 11/2009 Houser
7,625,370 B2 12/2009 Hart et al.
7,628,791 B2 12/2009 Garrison et al.
7,628,792 B2 12/2009 Guerra
7,632,267 B2 12/2009 Dahla
7,632,269 B2 12/2009 Truckai et al.
7,637,410 B2 12/2009 Marczyk
7,641,653 B2 1/2010 Dalla Betta et al.
7,641,671 B2 1/2010 Crainich
7,644,848 B2 1/2010 Swayze et al.
7,645,240 B2 1/2010 Thompson et al.
7,645,277 B2 1/2010 McClurken et al.
7,645,278 B2 1/2010 Ichihashi et al.
7,648,499 B2 1/2010 Orszulak et al.
7,649,410 B2 1/2010 Andersen et al.
7,654,431 B2 2/2010 Hueil et al.
7,655,003 B2 2/2010 Lorang et al.
7,658,311 B2 2/2010 Boudreaux
7,659,833 B2 2/2010 Warner et al.
7,662,151 B2 2/2010 Crompton, Jr. et al.
7,665,647 B2 2/2010 Shelton, IV et al.
7,666,206 B2 2/2010 Taniguchi et al.
7,667,592 B2 2/2010 Ohyama et al.
7,670,334 B2 3/2010 Hueil et al.
7,670,338 B2 3/2010 Albrecht et al.
7,674,263 B2 3/2010 Ryan
7,678,069 B1 3/2010 Baker et al.
7,678,105 B2 3/2010 McGreevy et al.
7,678,125 B2 3/2010 Shipp
7,682,366 B2 3/2010 Sakurai et al.
7,686,770 B2 3/2010 Cohen
7,686,826 B2 3/2010 Lee et al.
7,688,028 B2 3/2010 Phillips et al.
7,691,095 B2 4/2010 Bednarek et al.
7,691,098 B2 4/2010 Wallace et al.
7,696,441 B2 4/2010 Kataoka
7,699,846 B2 4/2010 Ryan
7,703,459 B2 4/2010 Saadat et al.
7,703,653 B2 4/2010 Shah et al.
7,708,735 B2 5/2010 Chapman et al.
7,708,751 B2 5/2010 Hughes et al.
7,708,758 B2 5/2010 Lee et al.
7,708,768 B2 5/2010 Danek et al.
7,713,202 B2 5/2010 Boukhny et al.
7,713,267 B2 5/2010 Pozzato
7,714,481 B2 5/2010 Sakai
7,717,312 B2 5/2010 Beetel
7,717,914 B2 5/2010 Kimura
7,717,915 B2 5/2010 Miyazawa

(56) References Cited

U.S. PATENT DOCUMENTS 7,721,935 B2 5/2010 Racenet et al.
7,722,527 B2 5/2010 Bouchier et al.
7,722,607 B2 5/2010 Dumbauld et al.
D618,797 S 6/2010 Price et al.
7,726,537 B2 6/2010 Olson et al.
7,727,177 B2 6/2010 Bayat
7,731,717 B2 6/2010 Odom et al.
7,738,969 B2 6/2010 Bleich
7,740,594 B2 6/2010 Hibner
7,744,615 B2 6/2010 Couture
7,749,240 B2 7/2010 Takahashi et al.
7,751,115 B2 7/2010 Song
7,753,245 B2 7/2010 Boudreaux et al.
7,753,904 B2 7/2010 Shelton, IV et al.
7,753,908 B2 7/2010 Swanson
7,762,445 B2 7/2010 Heinrich et al.
D621,503 S 8/2010 Otten et al.
7,766,210 B2 8/2010 Shelton, IV et al.
7,766,693 B2 8/2010 Sartor et al.
7,766,910 B2 8/2010 Hixson et al.
7,768,510 B2 8/2010 Tsai et al.
7,770,774 B2 8/2010 Mastri et al.
7,770,775 B2 8/2010 Shelton, IV et al.
7,771,425 B2 8/2010 Dycus et al.
7,771,444 B2 8/2010 Patel et al.
7,775,972 B2 8/2010 Brock et al.
7,776,036 B2 8/2010 Schechter et al.
7,776,037 B2 8/2010 Odom
7,778,733 B2 8/2010 Nowlin et al.
7,780,054 B2 8/2010 Wales
7,780,593 B2 8/2010 Ueno et al.
7,780,651 B2 8/2010 Madhani et al.
7,780,659 B2 8/2010 Okada et al.
7,780,663 B2 8/2010 Yates et al.
7,784,662 B2 8/2010 Wales et al.
7,784,663 B2 8/2010 Shelton, IV
7,789,883 B2 9/2010 Takashino et al.
7,793,814 B2 9/2010 Racenet et al.
7,794,475 B2 9/2010 Hess et al.
7,796,969 B2 9/2010 Kelly et al.
7,798,386 B2 9/2010 Schall et al.
7,799,020 B2 9/2010 Shores et al.
7,799,027 B2 9/2010 Hafner
7,799,045 B2 9/2010 Masuda
7,803,151 B2 9/2010 Whitman
7,803,152 B2 9/2010 Honda et al.
7,803,156 B2 9/2010 Eder et al.
7,803,168 B2 9/2010 Gifford et al.
7,806,891 B2 10/2010 Nowlin et al.
7,810,693 B2 10/2010 Broehl et al.
7,811,283 B2 10/2010 Moses et al.
7,815,238 B2 10/2010 Cao
7,815,641 B2 10/2010 Dodde et al.
7,819,298 B2 10/2010 Hall et al.
7,819,299 B2 10/2010 Shelton, IV et al.
7,819,819 B2 10/2010 Quick et al.
7,819,872 B2 10/2010 Johnson et al.
7,821,143 B2 10/2010 Wiener
D627,066 S 11/2010 Romero
7,824,401 B2 11/2010 Manzo et al.
7,832,408 B2 11/2010 Shelton, IV et al.
7,832,611 B2 11/2010 Boyden et al.
7,832,612 B2 11/2010 Baxter, III et al.
7,834,484 B2 11/2010 Sartor
7,837,699 B2 11/2010 Yamada et al.
7,845,537 B2 12/2010 Shelton, IV et al.
7,846,155 B2 12/2010 Houser et al.
7,846,159 B2 12/2010 Morrison et al.
7,846,160 B2 12/2010 Payne et al.
7,846,161 B2 12/2010 Dumbauld et al.
7,854,735 B2 12/2010 Houser et al.
D631,155 S 1/2011 Peine et al.
7,861,906 B2 1/2011 Doll et al.
7,862,560 B2 1/2011 Marion
7,862,561 B2 1/2011 Swanson et al.
7,867,228 B2 1/2011 Nobis et al.
7,871,392 B2 1/2011 Sartor
7,871,423 B2 1/2011 Livneh
7,876,030 B2 1/2011 Taki et al.
D631,965 S 2/2011 Price et al.
7,877,852 B2 2/2011 Unger et al.
7,878,991 B2 2/2011 Babaev
7,879,029 B2 2/2011 Jimenez
7,879,033 B2 2/2011 Sartor et al.
7,879,035 B2 2/2011 Garrison et al.
7,879,070 B2 2/2011 Ortiz et al.
7,883,475 B2 2/2011 Dupont et al.
7,892,606 B2 2/2011 Thies et al.
7,896,875 B2 3/2011 Heim et al.
7,897,792 B2 3/2011 Likura et al.
7,901,400 B2 3/2011 Wham et al.
7,901,423 B2 3/2011 Stulen et al.
7,905,881 B2 3/2011 Masuda et al.
7,909,220 B2 3/2011 Viola
7,909,820 B2 3/2011 Lipson et al.
7,909,824 B2 3/2011 Masuda et al.
7,918,848 B2 4/2011 Lau et al.
7,919,184 B2 4/2011 Mohapatra et al.
7,922,061 B2 4/2011 Shelton, IV et al.
7,922,651 B2 4/2011 Yamada et al.
7,931,611 B2 4/2011 Novak et al.
7,931,649 B2 4/2011 Couture et al.
D637,288 S 5/2011 Houghton
D638,540 S 5/2011 Ijiri et al.
7,935,114 B2 5/2011 Takashino et al.
7,936,203 B2 5/2011 Zimlich
7,951,095 B2 5/2011 Makin et al.
7,951,165 B2 5/2011 Golden et al.
7,954,682 B2 6/2011 Giordano et al.
7,955,331 B2 6/2011 Truckai et al.
7,956,620 B2 6/2011 Gilbert
7,959,050 B2 6/2011 Smith et al.
7,959,626 B2 6/2011 Hong et al.
7,963,963 B2 6/2011 Francischelli et al.
7,967,602 B2 6/2011 Lindquist
7,972,328 B2 7/2011 Wham et al.
7,972,329 B2 7/2011 Refior et al.
7,975,895 B2 7/2011 Milliman
7,976,544 B2 7/2011 McClurken et al.
7,980,443 B2 7/2011 Scheib et al.
7,981,050 B2 7/2011 Ritchart et al.
7,981,113 B2 7/2011 Truckai et al.
7,997,278 B2 8/2011 Utley et al.
7,998,157 B2 8/2011 Culp et al.
8,002,732 B2 8/2011 Visconti
8,002,770 B2 8/2011 Swanson et al.
8,020,743 B2 9/2011 Shelton, IV
8,025,672 B2 9/2011 Novak et al.
8,028,885 B2 10/2011 Smith et al.
8,033,173 B2 10/2011 Ehlert et al.
8,034,049 B2 10/2011 Odom et al.
8,038,693 B2 10/2011 Allen
8,048,070 B2 11/2011 O'Brien et al.
8,048,074 B2 11/2011 Masuda
8,052,672 B2 11/2011 Laufer et al.
8,055,208 B2 11/2011 Lilla et al.
8,056,720 B2 11/2011 Hawkes
8,056,787 B2 11/2011 Boudreaux et al.
8,057,468 B2 11/2011 Konesky
8,057,498 B2 11/2011 Robertson
8,058,771 B2 11/2011 Giordano et al.
8,061,014 B2 11/2011 Smith et al.
8,066,167 B2 11/2011 Measamer et al.
8,070,036 B1 12/2011 Knodel
8,070,711 B2 12/2011 Bassinger et al.
8,070,762 B2 12/2011 Escudero et al.
8,075,555 B2 12/2011 Truckai et al.
8,075,558 B2 12/2011 Truckai et al.
8,089,197 B2 1/2012 Rinner et al.
8,092,475 B2 1/2012 Cotter et al.
8,096,459 B2 1/2012 Ortiz et al.
8,097,012 B2 1/2012 Kagarise
8,100,894 B2 1/2012 Mucko et al.
8,105,230 B2 1/2012 Honda et al.

(56) References Cited

U.S. PATENT DOCUMENTS

| | | | |
|---|---|---|---|
| 8,105,323 | B2 | 1/2012 | Buysse et al. |
| 8,105,324 | B2 | 1/2012 | Palanker et al. |
| 8,114,104 | B2 | 2/2012 | Young et al. |
| 8,118,276 | B2 | 2/2012 | Sanders et al. |
| 8,128,624 | B2 | 3/2012 | Couture et al. |
| 8,133,218 | B2 | 3/2012 | Daw et al. |
| 8,136,712 | B2 | 3/2012 | Zingman |
| 8,141,762 | B2 | 3/2012 | Bedi et al. |
| 8,142,421 | B2 | 3/2012 | Cooper et al. |
| 8,142,461 | B2 | 3/2012 | Houser et al. |
| 8,147,485 | B2 | 4/2012 | Wham et al. |
| 8,147,488 | B2 | 4/2012 | Masuda |
| 8,147,508 | B2 | 4/2012 | Madan et al. |
| 8,152,801 | B2 | 4/2012 | Goldberg et al. |
| 8,152,825 | B2 | 4/2012 | Madan et al. |
| 8,157,145 | B2 | 4/2012 | Shelton, IV et al. |
| 8,161,977 | B2 | 4/2012 | Shelton, IV et al. |
| 8,162,966 | B2 | 4/2012 | Connor et al. |
| 8,170,717 | B2 | 5/2012 | Sutherland et al. |
| 8,172,846 | B2 | 5/2012 | Brunnett et al. |
| 8,172,870 | B2 | 5/2012 | Shipp |
| 8,177,800 | B2 | 5/2012 | Spitz et al. |
| 8,182,502 | B2 | 5/2012 | Stulen et al. |
| 8,186,560 | B2 | 5/2012 | Hess et al. |
| 8,186,877 | B2 | 5/2012 | Klimovitch et al. |
| 8,187,267 | B2 | 5/2012 | Pappone et al. |
| D661,801 | S | 6/2012 | Price et al. |
| D661,802 | S | 6/2012 | Price et al. |
| D661,803 | S | 6/2012 | Price et al. |
| D661,804 | S | 6/2012 | Price et al. |
| 8,197,472 | B2 | 6/2012 | Lau et al. |
| 8,197,479 | B2 | 6/2012 | Olson et al. |
| 8,197,502 | B2 | 6/2012 | Smith et al. |
| 8,207,651 | B2 | 6/2012 | Gilbert |
| 8,210,411 | B2 | 7/2012 | Yates et al. |
| 8,211,100 | B2 | 7/2012 | Podhajsky et al. |
| 8,216,223 | B2 | 7/2012 | Wham et al. |
| 8,220,688 | B2 | 7/2012 | Laurent et al. |
| 8,221,306 | B2 | 7/2012 | Okada et al. |
| 8,221,415 | B2 | 7/2012 | Francischelli |
| 8,221,418 | B2 | 7/2012 | Prakash et al. |
| 8,226,580 | B2 | 7/2012 | Govari et al. |
| 8,226,665 | B2 | 7/2012 | Cohen |
| 8,226,675 | B2 | 7/2012 | Houser et al. |
| 8,231,607 | B2 | 7/2012 | Takuma |
| 8,235,917 | B2 | 8/2012 | Joseph et al. |
| 8,236,018 | B2 | 8/2012 | Yoshimine et al. |
| 8,236,019 | B2 | 8/2012 | Houser |
| 8,236,020 | B2 | 8/2012 | Smith et al. |
| 8,241,235 | B2 | 8/2012 | Kahler et al. |
| 8,241,271 | B2 | 8/2012 | Millman et al. |
| 8,241,282 | B2 | 8/2012 | Unger et al. |
| 8,241,283 | B2 | 8/2012 | Guerra et al. |
| 8,241,284 | B2 | 8/2012 | Dycus et al. |
| 8,241,312 | B2 | 8/2012 | Messerly |
| 8,246,575 | B2 | 8/2012 | Viola |
| 8,246,615 | B2 | 8/2012 | Behnke |
| 8,246,616 | B2 | 8/2012 | Amoah et al. |
| 8,246,618 | B2 | 8/2012 | Bucciaglia et al. |
| 8,246,642 | B2 | 8/2012 | Houser et al. |
| 8,251,994 | B2 | 8/2012 | McKenna et al. |
| 8,252,012 | B2 | 8/2012 | Stulen |
| 8,253,303 | B2 | 8/2012 | Giordano et al. |
| 8,257,377 | B2 | 9/2012 | Wiener et al. |
| 8,257,387 | B2 | 9/2012 | Cunningham |
| 8,262,563 | B2 | 9/2012 | Bakos et al. |
| 8,267,300 | B2 | 9/2012 | Boudreaux |
| 8,267,935 | B2 | 9/2012 | Couture et al. |
| 8,273,087 | B2 | 9/2012 | Kimura et al. |
| D669,992 | S | 10/2012 | Schafer et al. |
| D669,993 | S | 10/2012 | Merchant et al. |
| 8,277,446 | B2 | 10/2012 | Heard |
| 8,277,447 | B2 | 10/2012 | Garrison et al. |
| 8,277,471 | B2 | 10/2012 | Wiener et al. |
| 8,282,581 | B2 | 10/2012 | Zhao et al. |
| 8,282,669 | B2 | 10/2012 | Gerber et al. |
| 8,286,846 | B2 | 10/2012 | Smith et al. |
| 8,287,485 | B2 | 10/2012 | Kimura et al. |
| 8,287,528 | B2 | 10/2012 | Wham et al. |
| 8,287,532 | B2 | 10/2012 | Carroll et al. |
| 8,292,886 | B2 | 10/2012 | Kerr et al. |
| 8,292,888 | B2 | 10/2012 | Whitman |
| 8,292,905 | B2 | 10/2012 | Taylor et al. |
| 8,295,902 | B2 | 10/2012 | Salahieh et al. |
| 8,298,223 | B2 | 10/2012 | Wham et al. |
| 8,298,225 | B2 | 10/2012 | Gilbert |
| 8,298,232 | B2 | 10/2012 | Unger |
| 8,298,233 | B2 | 10/2012 | Mueller |
| 8,303,576 | B2 | 11/2012 | Brock |
| 8,303,579 | B2 | 11/2012 | Shibata |
| 8,303,580 | B2 | 11/2012 | Wham et al. |
| 8,303,583 | B2 | 11/2012 | Hosier et al. |
| 8,303,613 | B2 | 11/2012 | Crandall et al. |
| 8,306,629 | B2 | 11/2012 | Mioduski et al. |
| 8,308,040 | B2 | 11/2012 | Huang et al. |
| 8,308,721 | B2 | 11/2012 | Shibata et al. |
| 8,319,400 | B2 | 11/2012 | Houser et al. |
| 8,323,302 | B2 | 12/2012 | Robertson et al. |
| 8,323,310 | B2 | 12/2012 | Kingsley |
| 8,328,061 | B2 | 12/2012 | Kasvikis |
| 8,328,761 | B2 | 12/2012 | Widenhouse et al. |
| 8,328,802 | B2 | 12/2012 | Deville et al. |
| 8,328,833 | B2 | 12/2012 | Cuny |
| 8,328,834 | B2 | 12/2012 | Isaacs et al. |
| 8,333,764 | B2 | 12/2012 | Francischelli et al. |
| 8,333,778 | B2 | 12/2012 | Smith et al. |
| 8,333,779 | B2 | 12/2012 | Smith et al. |
| 8,334,468 | B2 | 12/2012 | Palmer et al. |
| 8,334,635 | B2 | 12/2012 | Voegele et al. |
| 8,337,407 | B2 | 12/2012 | Quistgaard et al. |
| 8,338,726 | B2 | 12/2012 | Palmer et al. |
| 8,343,146 | B2 | 1/2013 | Godara et al. |
| 8,344,596 | B2 | 1/2013 | Nield et al. |
| 8,348,880 | B2 | 1/2013 | Messerly et al. |
| 8,348,947 | B2 | 1/2013 | Takashino et al. |
| 8,348,967 | B2 | 1/2013 | Stulen |
| 8,353,297 | B2 | 1/2013 | Dacquay et al. |
| 8,357,103 | B2 | 1/2013 | Mark et al. |
| 8,357,144 | B2 | 1/2013 | Whitman et al. |
| 8,357,149 | B2 | 1/2013 | Govari et al. |
| 8,357,158 | B2 | 1/2013 | McKenna et al. |
| 8,360,299 | B2 | 1/2013 | Zemlok et al. |
| 8,361,066 | B2 | 1/2013 | Long et al. |
| 8,361,072 | B2 | 1/2013 | Dumbauld et al. |
| 8,361,569 | B2 | 1/2013 | Saito et al. |
| 8,366,727 | B2 | 2/2013 | Witt et al. |
| 8,372,064 | B2 | 2/2013 | Douglass et al. |
| 8,372,099 | B2 | 2/2013 | Deville et al. |
| 8,372,101 | B2 | 2/2013 | Smith et al. |
| 8,372,102 | B2 | 2/2013 | Stulen et al. |
| 8,374,670 | B2 | 2/2013 | Selkee |
| 8,377,044 | B2 | 2/2013 | Coe et al. |
| 8,377,059 | B2 | 2/2013 | Deville et al. |
| 8,377,085 | B2 | 2/2013 | Smith et al. |
| 8,382,748 | B2 | 2/2013 | Geisel |
| 8,382,775 | B1 | 2/2013 | Bender et al. |
| 8,382,782 | B2 | 2/2013 | Robertson et al. |
| 8,382,792 | B2 | 2/2013 | Chojin |
| 8,388,646 | B2 | 3/2013 | Chojin |
| 8,388,647 | B2 | 3/2013 | Nau, Jr. et al. |
| 8,393,514 | B2 | 3/2013 | Shelton, IV et al. |
| 8,394,115 | B2 | 3/2013 | Houser et al. |
| 8,397,971 | B2 | 3/2013 | Yates et al. |
| 8,398,394 | B2 | 3/2013 | Sauter et al. |
| 8,398,674 | B2 | 3/2013 | Prestel |
| 8,403,926 | B2 | 3/2013 | Nobis et al. |
| 8,403,945 | B2 | 3/2013 | Whitfield et al. |
| 8,403,948 | B2 | 3/2013 | Deville et al. |
| 8,403,949 | B2 | 3/2013 | Palmer et al. |
| 8,403,950 | B2 | 3/2013 | Palmer et al. |
| 8,409,234 | B2 | 4/2013 | Stahler et al. |
| 8,414,577 | B2 | 4/2013 | Boudreaux et al. |
| 8,418,073 | B2 | 4/2013 | Mohr et al. |
| 8,418,349 | B2 | 4/2013 | Smith et al. |

(56) References Cited

U.S. PATENT DOCUMENTS 8,419,757 B2 4/2013 Smith et al.
8,419,758 B2 4/2013 Smith et al.
8,419,759 B2 4/2013 Dietz
8,423,182 B2 4/2013 Robinson et al.
8,425,410 B2 4/2013 Murray et al.
8,425,545 B2 4/2013 Smith et al.
8,430,811 B2 4/2013 Hess et al.
8,430,874 B2 4/2013 Newton et al.
8,430,876 B2 4/2013 Kappus et al.
8,430,897 B2 4/2013 Novak et al.
8,430,898 B2 4/2013 Wiener et al.
8,435,257 B2 5/2013 Smith et al.
8,437,832 B2 5/2013 Govari et al.
8,439,912 B2 5/2013 Cunningham et al.
8,439,939 B2 5/2013 Deville et al.
8,444,036 B2 5/2013 Shelton, IV
8,444,637 B2 5/2013 Podmore et al.
8,444,662 B2 5/2013 Palmer et al.
8,444,663 B2 5/2013 Houser et al.
8,444,664 B2 5/2013 Balanev et al.
8,453,906 B2 6/2013 Huang et al.
8,454,599 B2 6/2013 Inagaki et al.
8,454,639 B2 6/2013 Du et al.
8,459,525 B2 6/2013 Yates et al.
8,460,284 B2 6/2013 Aronow et al.
8,460,288 B2 6/2013 Tamai et al.
8,460,292 B2 6/2013 Truckai et al.
8,461,744 B2 6/2013 Wiener et al.
8,469,981 B2 6/2013 Robertson et al.
8,471,685 B2 6/2013 Shingai
8,479,969 B2 7/2013 Shelton, IV
8,480,703 B2 7/2013 Nicholas et al.
8,484,833 B2 7/2013 Cunningham et al.
8,485,413 B2 7/2013 Scheib et al.
8,485,970 B2 7/2013 Widenhouse et al.
8,486,057 B2 7/2013 Behnke, II
8,486,096 B2 7/2013 Robertson et al.
8,491,578 B2 7/2013 Manwaring et al.
8,491,625 B2 7/2013 Horner
8,496,682 B2 7/2013 Guerra et al.
D687,549 S 8/2013 Johnson et al.
8,506,555 B2 8/2013 Ruiz Morales
8,509,318 B2 8/2013 Tailliet
8,512,336 B2 8/2013 Couture
8,512,337 B2 8/2013 Francischelli et al.
8,512,359 B2 8/2013 Whitman et al.
8,512,364 B2 8/2013 Kowalski et al.
8,512,365 B2 8/2013 Wiener et al.
8,517,239 B2 8/2013 Scheib et al.
8,518,067 B2 8/2013 Masuda et al.
8,521,331 B2 8/2013 Itkowitz
8,523,043 B2 9/2013 Ullrich et al.
8,523,882 B2 9/2013 Huitema et al.
8,523,889 B2 9/2013 Stulen et al.
8,528,563 B2 9/2013 Gruber
8,529,437 B2 9/2013 Taylor et al.
8,529,565 B2 9/2013 Masuda et al.
8,531,064 B2 9/2013 Robertson et al.
8,535,308 B2 9/2013 Govari et al.
8,535,311 B2 9/2013 Schall
8,535,340 B2 9/2013 Allen
8,535,341 B2 9/2013 Allen
8,540,128 B2 9/2013 Shelton, IV et al.
8,546,996 B2 10/2013 Messerly et al.
8,546,999 B2 10/2013 Houser et al.
8,551,077 B2 10/2013 Main et al.
8,551,086 B2 10/2013 Kimura et al.
8,556,929 B2 10/2013 Harper et al.
8,561,870 B2 10/2013 Baxter, III et al.
8,562,592 B2 10/2013 Conlon et al.
8,562,598 B2 10/2013 Falkenstein et al.
8,562,600 B2 10/2013 Kirkpatrick et al.
8,562,604 B2 10/2013 Nishimura
8,568,390 B2 10/2013 Mueller
8,568,397 B2 10/2013 Horner et al.
8,568,400 B2 10/2013 Gilbert
8,568,412 B2 10/2013 Brandt et al.
8,569,997 B2 10/2013 Lee
8,573,461 B2 11/2013 Shelton, IV et al.
8,573,465 B2 11/2013 Shelton, IV
8,574,231 B2 11/2013 Boudreaux et al.
8,574,253 B2 11/2013 Gruber et al.
8,579,176 B2 11/2013 Smith et al.
8,579,897 B2 11/2013 Vakharia et al.
8,579,928 B2 11/2013 Robertson et al.
8,579,937 B2 11/2013 Gresham
8,585,727 B2 11/2013 Polo
8,588,371 B2 11/2013 Ogawa et al.
8,591,459 B2 11/2013 Clymer et al.
8,591,506 B2 11/2013 Wham et al.
8,591,536 B2 11/2013 Robertson
D695,407 S 12/2013 Price et al.
D696,631 S 12/2013 Price et al.
8,596,513 B2 12/2013 Olson et al.
8,597,193 B2 12/2013 Grunwald et al.
8,597,287 B2 12/2013 Benamou et al.
8,602,031 B2 12/2013 Reis et al.
8,602,288 B2 12/2013 Shelton, IV et al.
8,603,085 B2 12/2013 Jimenez
8,603,089 B2 12/2013 Viola
8,608,044 B2 12/2013 Hueil et al.
8,608,045 B2 12/2013 Smith et al.
8,608,745 B2 12/2013 Guzman et al.
8,613,383 B2 12/2013 Beckman et al.
8,616,431 B2 12/2013 Timm et al.
8,617,152 B2 12/2013 Werneth et al.
8,617,194 B2 12/2013 Beaupre
8,622,274 B2 1/2014 Yates et al.
8,623,011 B2 1/2014 Spivey
8,623,016 B2 1/2014 Fischer
8,623,027 B2 1/2014 Price et al.
8,623,040 B2 1/2014 Artsyukhovich et al.
8,623,044 B2 1/2014 Timm et al.
8,628,529 B2 1/2014 Aldridge et al.
8,628,534 B2 1/2014 Jones et al.
8,632,461 B2 1/2014 Glossop
8,636,736 B2 1/2014 Yates et al.
8,638,428 B2 1/2014 Brown
8,640,788 B2 2/2014 Dachs, II et al.
8,641,663 B2 2/2014 Kirschenman et al.
8,647,350 B2 2/2014 Mohan et al.
8,650,728 B2 2/2014 Wan et al.
8,652,120 B2 2/2014 Giordano et al.
8,652,132 B2 2/2014 Tsuchiya et al.
8,652,155 B2 2/2014 Houser et al.
8,657,489 B2 2/2014 Ladurner et al.
8,659,208 B1 2/2014 Rose et al.
8,663,214 B2 3/2014 Weinberg et al.
8,663,220 B2 3/2014 Wiener et al.
8,663,222 B2 3/2014 Anderson et al.
8,663,223 B2 3/2014 Masuda et al.
8,663,262 B2 3/2014 Smith et al.
8,668,691 B2 3/2014 Heard
8,668,710 B2 3/2014 Slipszenko et al.
8,684,253 B2 4/2014 Giordano et al.
8,685,016 B2 4/2014 Wham et al.
8,685,020 B2 4/2014 Weizman et al.
8,690,582 B2 4/2014 Rohrbach et al.
8,695,866 B2 4/2014 Leimbach et al.
8,696,366 B2 4/2014 Chen et al.
8,696,665 B2 4/2014 Hunt et al.
8,696,666 B2 4/2014 Sanai et al.
8,696,917 B2 4/2014 Petisce et al.
8,702,609 B2 4/2014 Hadjicostis
8,702,702 B1 4/2014 Edwards et al.
8,702,704 B2 4/2014 Shelton, IV et al.
8,704,425 B2 4/2014 Giordano et al.
8,708,213 B2 4/2014 Shelton, IV et al.
8,709,008 B2 4/2014 Willis et al.
8,709,031 B2 4/2014 Stulen
8,709,035 B2 4/2014 Johnson et al.
8,715,270 B2 5/2014 Weitzner et al.
8,715,277 B2 5/2014 Weizman
8,721,640 B2 5/2014 Taylor et al.

(56) References Cited

U.S. PATENT DOCUMENTS 8,721,657 B2 5/2014 Kondoh et al.
8,733,613 B2 5/2014 Huitema et al.
8,733,614 B2 5/2014 Ross et al.
8,734,443 B2 5/2014 Hixson et al.
8,738,110 B2 5/2014 Tabada et al.
8,747,238 B2 6/2014 Shelton, IV et al.
8,747,351 B2 6/2014 Schultz
8,747,404 B2 6/2014 Boudreaux et al.
8,749,116 B2 6/2014 Messerly et al.
8,752,264 B2 6/2014 Ackley et al.
8,752,749 B2 6/2014 Moore et al.
8,753,338 B2 6/2014 Widenhouse et al.
8,754,570 B2 6/2014 Voegele et al.
8,758,342 B2 6/2014 Bales et al.
8,758,352 B2 6/2014 Cooper et al.
8,758,391 B2 6/2014 Swayze et al.
8,764,735 B2 7/2014 Coe et al.
8,764,747 B2 7/2014 Cummings et al.
8,767,970 B2 7/2014 Eppolito
8,770,459 B2 7/2014 Racenet et al.
8,771,269 B2 7/2014 Sherman et al.
8,771,270 B2 7/2014 Burbank
8,771,293 B2 7/2014 Surti et al.
8,773,001 B2 7/2014 Wiener et al.
8,777,944 B2 7/2014 Frankhouser et al.
8,777,945 B2 7/2014 Floume et al.
8,779,648 B2 7/2014 Giordano et al.
8,783,541 B2 7/2014 Shelton, IV et al.
8,784,415 B2 7/2014 Malackowski et al.
8,784,418 B2 7/2014 Romero
8,790,342 B2 7/2014 Stulen et al.
8,795,274 B2 8/2014 Hanna
8,795,275 B2 8/2014 Hafner
8,795,276 B2 8/2014 Dietz et al.
8,795,327 B2 8/2014 Dietz et al.
8,800,838 B2 8/2014 Shelton, IV
8,801,710 B2 8/2014 Ullrich et al.
8,801,752 B2 8/2014 Fortier et al.
8,807,414 B2 8/2014 Ross et al.
8,808,204 B2 8/2014 Irisawa et al.
8,808,319 B2 8/2014 Houser et al.
8,814,856 B2 8/2014 Elmouelhi et al.
8,814,870 B2 8/2014 Paraschiv et al.
8,820,605 B2 9/2014 Shelton, IV
8,821,388 B2 9/2014 Naito et al.
8,827,992 B2 9/2014 Koss et al.
8,827,995 B2 9/2014 Schaller et al.
8,834,466 B2 9/2014 Cummings et al.
8,834,518 B2 9/2014 Faller et al.
8,844,789 B2 9/2014 Shelton, IV et al.
8,845,537 B2 9/2014 Tanaka et al.
8,845,630 B2 9/2014 Mehta et al.
8,848,808 B2 9/2014 Dress
8,851,354 B2 10/2014 Swensgard et al.
8,852,184 B2 10/2014 Kucklick
8,858,547 B2 10/2014 Brogna
8,862,955 B2 10/2014 Cesari
8,864,749 B2 10/2014 Okada
8,864,757 B2 10/2014 Klimovitch et al.
8,864,761 B2 10/2014 Johnson et al.
8,870,865 B2 10/2014 Frankhouser et al.
8,874,220 B2 10/2014 Draghici et al.
8,876,726 B2 11/2014 Amit et al.
8,876,858 B2 11/2014 Braun
8,882,766 B2 11/2014 Couture et al.
8,882,791 B2 11/2014 Stulen
8,888,776 B2 11/2014 Dietz et al.
8,888,783 B2 11/2014 Young
8,888,809 B2 11/2014 Davison et al.
8,899,462 B2 12/2014 Kostrzewski et al.
8,900,259 B2 12/2014 Houser et al.
8,906,016 B2 12/2014 Boudreaux et al.
8,906,017 B2 12/2014 Rioux et al.
8,911,438 B2 12/2014 Swoyer et al.
8,911,460 B2 12/2014 Neurohr et al.
8,920,412 B2 12/2014 Fritz et al.
8,920,414 B2 12/2014 Stone et al.
8,920,421 B2 12/2014 Rupp
8,926,607 B2 1/2015 Norvell et al.
8,926,608 B2 1/2015 Bacher et al.
8,926,620 B2 1/2015 Chasmawala et al.
8,931,682 B2 1/2015 Timm et al.
8,932,282 B2 1/2015 Gilbert
8,932,299 B2 1/2015 Bono et al.
8,936,614 B2 1/2015 Allen, IV
8,939,974 B2 1/2015 Boudreaux et al.
8,945,126 B2 2/2015 Garrison et al.
8,951,248 B2 2/2015 Messerly et al.
8,951,272 B2 2/2015 Robertson et al.
8,956,349 B2 2/2015 Aldridge et al.
8,960,520 B2 2/2015 McCuen
8,961,515 B2 2/2015 Twomey et al.
8,961,547 B2 2/2015 Dietz et al.
8,967,443 B2 3/2015 McCuen
8,968,283 B2 3/2015 Kharin
8,968,294 B2 3/2015 Maass et al.
8,968,296 B2 3/2015 McPherson
8,968,355 B2 3/2015 Malkowski et al.
8,974,447 B2 3/2015 Kimball et al.
8,974,477 B2 3/2015 Yamada
8,974,479 B2 3/2015 Ross et al.
8,974,932 B2 3/2015 McGahan et al.
8,979,843 B2 3/2015 Timm et al.
8,979,844 B2 3/2015 White et al.
8,979,890 B2 3/2015 Boudreaux
8,986,287 B2 3/2015 Park et al.
8,986,297 B2 3/2015 Daniel et al.
8,986,302 B2 3/2015 Aldridge et al.
8,989,855 B2 3/2015 Murphy et al.
8,989,903 B2 3/2015 Weir et al.
8,991,678 B2 3/2015 Wellman et al.
8,992,422 B2 3/2015 Spivey et al.
8,992,526 B2 3/2015 Brodbeck et al.
8,998,891 B2 4/2015 Garito et al.
9,005,199 B2 4/2015 Beckman et al.
9,011,437 B2 4/2015 Woodruff et al.
9,011,471 B2 4/2015 Timm et al.
9,017,326 B2 4/2015 DiNardo et al.
9,017,355 B2 4/2015 Smith et al.
9,017,370 B2 4/2015 Reschke et al.
9,017,372 B2 4/2015 Artale et al.
9,023,035 B2 5/2015 Allen, IV et al.
9,023,070 B2 5/2015 Levine et al.
9,023,071 B2 5/2015 Miller et al.
9,028,397 B2 5/2015 Naito
9,028,476 B2 5/2015 Bonn
9,028,478 B2 5/2015 Mueller
9,028,481 B2 5/2015 Behnke, II
9,028,494 B2 5/2015 Shelton, IV et al.
9,028,519 B2 5/2015 Yates et al.
9,031,667 B2 5/2015 Williams
9,033,973 B2 5/2015 Krapohl et al.
9,035,741 B2 5/2015 Hamel et al.
9,037,259 B2 5/2015 Mathur
9,039,690 B2 5/2015 Kersten et al.
9,039,691 B2 5/2015 Moua et al.
9,039,692 B2 5/2015 Behnke, II et al.
9,039,695 B2 5/2015 Giordano et al.
9,039,696 B2 5/2015 Assmus et al.
9,039,705 B2 5/2015 Takashino
9,039,731 B2 5/2015 Joseph
9,043,018 B2 5/2015 Mohr
9,044,227 B2 6/2015 Shelton, IV et al.
9,044,230 B2 6/2015 Morgan et al.
9,044,238 B2 6/2015 Orszulak
9,044,243 B2 6/2015 Johnson et al.
9,044,245 B2 6/2015 Condie et al.
9,044,256 B2 6/2015 Cadeddu et al.
9,044,261 B2 6/2015 Houser
9,050,083 B2 6/2015 Yates et al.
9,050,093 B2 6/2015 Aldridge et al.
9,050,098 B2 6/2015 Deville et al.
9,050,123 B2 6/2015 Krause et al.
9,050,124 B2 6/2015 Houser

(56) References Cited

U.S. PATENT DOCUMENTS 9,055,961 B2 6/2015 Manzo et al.
9,059,547 B2 6/2015 McLawhorn
9,060,770 B2 6/2015 Shelton, IV et al.
9,060,775 B2 6/2015 Wiener et al.
9,060,776 B2 6/2015 Yates et al.
9,060,778 B2 6/2015 Condie et al.
9,066,720 B2 6/2015 Ballakur et al.
9,066,723 B2 6/2015 Beller et al.
9,066,747 B2 6/2015 Robertson
9,072,523 B2 7/2015 Houser et al.
9,072,535 B2 7/2015 Shelton, IV et al.
9,072,536 B2 7/2015 Shelton, IV et al.
9,072,538 B2 7/2015 Suzuki et al.
9,072,539 B2 7/2015 Messerly et al.
9,084,624 B2 7/2015 Larkin et al.
9,089,327 B2 7/2015 Worrell et al.
9,089,360 B2 7/2015 Messerly et al.
9,095,333 B2 8/2015 Konesky et al.
9,095,362 B2 8/2015 Dachs, II et al.
9,095,367 B2 8/2015 Olson et al.
9,099,863 B2 8/2015 Smith et al.
9,101,358 B2 8/2015 Kerr et al.
9,101,385 B2 8/2015 Shelton, IV et al.
9,107,684 B2 8/2015 Ma
9,107,689 B2 8/2015 Robertson et al.
9,107,690 B2 8/2015 Bales, Jr. et al.
9,113,900 B2 8/2015 Buysse et al.
9,113,907 B2 8/2015 Allen, IV et al.
9,113,940 B2 8/2015 Twomey
9,119,657 B2 9/2015 Shelton, IV et al.
9,119,957 B2 9/2015 Gantz et al.
9,125,662 B2 9/2015 Shelton, IV
9,125,667 B2 9/2015 Stone et al.
9,144,453 B2 9/2015 Rencher et al.
9,147,965 B2 9/2015 Lee
9,149,324 B2 10/2015 Huang et al.
9,149,325 B2 10/2015 Worrell et al.
9,161,803 B2 10/2015 Yates et al.
9,165,114 B2 10/2015 Jain et al.
9,168,054 B2 10/2015 Turner et al.
9,168,085 B2 10/2015 Juzkiw et al.
9,168,089 B2 10/2015 Buysse et al.
9,173,656 B2 11/2015 Schurr et al.
9,179,912 B2 11/2015 Yates et al.
9,186,199 B2 11/2015 Strauss et al.
9,186,204 B2 11/2015 Nishimura et al.
9,186,796 B2 11/2015 Ogawa
9,192,380 B2 11/2015 Racenet et al.
9,192,421 B2 11/2015 Garrison
9,192,428 B2 11/2015 Houser et al.
9,192,431 B2 11/2015 Woodruff et al.
9,198,714 B2 12/2015 Worrell et al.
9,198,715 B2 12/2015 Livneh
9,198,718 B2 12/2015 Marczyk et al.
9,198,776 B2 12/2015 Young
9,204,879 B2 12/2015 Shelton, IV
9,204,891 B2 12/2015 Weitzman
9,204,918 B2 12/2015 Germain et al.
9,204,923 B2 12/2015 Manzo et al.
9,216,050 B2 12/2015 Condie et al.
9,216,051 B2 12/2015 Fischer et al.
9,216,062 B2 12/2015 Duque et al.
9,220,483 B2 12/2015 Frankhouser et al.
9,220,527 B2 12/2015 Houser et al.
9,220,559 B2 12/2015 Worrell et al.
9,226,750 B2 1/2016 Weir et al.
9,226,751 B2 1/2016 Shelton, IV et al.
9,226,766 B2 1/2016 Aldridge et al.
9,226,767 B2 1/2016 Stulen et al.
9,232,979 B2 1/2016 Parihar et al.
9,237,891 B2 1/2016 Shelton, IV
9,237,921 B2 1/2016 Messerly et al.
9,241,060 B1 1/2016 Fujisaki
9,241,692 B2 1/2016 Gunday et al.
9,241,728 B2 1/2016 Price et al.
9,241,730 B2 1/2016 Babaev
9,241,731 B2 1/2016 Boudreaux et al.
9,241,768 B2 1/2016 Sandhu et al.
9,247,953 B2 2/2016 Palmer et al.
9,254,165 B2 2/2016 Aronow et al.
9,259,234 B2 2/2016 Robertson et al.
9,259,265 B2 2/2016 Harris et al.
9,265,567 B2 2/2016 Orban, III et al.
9,265,926 B2 2/2016 Strobl et al.
9,265,973 B2 2/2016 Akagane
9,266,310 B2 2/2016 Krogdahl et al.
9,277,962 B2 3/2016 Koss et al.
9,282,974 B2 3/2016 Shelton, IV
9,283,027 B2 3/2016 Monson et al.
9,283,045 B2 3/2016 Rhee et al.
9,283,054 B2 3/2016 Morgan et al.
9,289,256 B2 3/2016 Shelton, IV et al.
9,295,514 B2 3/2016 Shelton, IV et al.
9,301,759 B2 4/2016 Spivey et al.
9,305,497 B2 4/2016 Seo et al.
9,307,388 B2 4/2016 Liang et al.
9,307,986 B2 4/2016 Hall et al.
9,308,009 B2 4/2016 Madan et al.
9,308,014 B2 4/2016 Fischer
9,314,261 B2 4/2016 Bales, Jr. et al.
9,314,292 B2 4/2016 Trees et al.
9,314,301 B2 4/2016 Ben-Haim et al.
9,326,754 B2 5/2016 Polster
9,326,767 B2 5/2016 Koch, Jr. et al.
9,326,787 B2 5/2016 Sanai et al.
9,326,788 B2 5/2016 Batross et al.
9,332,987 B2 5/2016 Leimbach et al.
9,333,025 B2 5/2016 Monson et al.
9,333,034 B2 5/2016 Hancock
9,339,289 B2 5/2016 Robertson
9,339,323 B2 5/2016 Eder et al.
9,339,326 B2 5/2016 McCullagh et al.
9,345,481 B2 5/2016 Hall et al.
9,345,534 B2 5/2016 Artale et al.
9,345,900 B2 5/2016 Wu et al.
9,351,642 B2 5/2016 Nadkarni et al.
9,351,726 B2 5/2016 Leimbach et al.
9,351,727 B2 5/2016 Leimbach et al.
9,351,754 B2 5/2016 Vakharia et al.
9,352,173 B2 5/2016 Yamada et al.
9,358,003 B2 6/2016 Hall et al.
9,358,065 B2 6/2016 Ladtkow et al.
9,364,171 B2 6/2016 Harris et al.
9,364,230 B2 6/2016 Shelton, IV et al.
9,364,279 B2 6/2016 Houser et al.
9,370,364 B2 6/2016 Smith et al.
9,370,400 B2 6/2016 Parihar
9,370,611 B2 6/2016 Ross et al.
9,375,206 B2 6/2016 Vidal et al.
9,375,230 B2 6/2016 Ross et al.
9,375,232 B2 6/2016 Hunt et al.
9,375,256 B2 6/2016 Cunningham et al.
9,375,264 B2 6/2016 Horner et al.
9,375,267 B2 6/2016 Kerr et al.
9,385,831 B2 7/2016 Marr et al.
9,386,983 B2 7/2016 Swensgard et al.
9,393,037 B2 7/2016 Olson et al.
9,393,070 B2 7/2016 Gelfand et al.
9,398,911 B2 7/2016 Auld
9,402,680 B2 8/2016 Ginnebaugh et al.
9,402,682 B2 8/2016 Worrell et al.
9,408,606 B2 8/2016 Shelton, IV
9,408,622 B2 8/2016 Stulen et al.
9,408,660 B2 8/2016 Strobl et al.
9,414,853 B2 8/2016 Stulen et al.
9,414,880 B2 8/2016 Monson et al.
9,421,014 B2 8/2016 Ingmanson et al.
9,421,060 B2 8/2016 Monson et al.
9,427,249 B2 8/2016 Robertson et al.
9,427,279 B2 8/2016 Muniz-Medina et al.
9,439,668 B2 9/2016 Timm et al.
9,439,669 B2 9/2016 Wiener et al.
9,439,671 B2 9/2016 Akagane
9,442,288 B2 9/2016 Tanimura

(56) References Cited

U.S. PATENT DOCUMENTS

| | | | |
|---|---|---|---|
| 9,445,784 | B2 | 9/2016 | O'Keeffe |
| 9,445,832 | B2 | 9/2016 | Wiener et al. |
| 9,451,967 | B2 | 9/2016 | Jordan et al. |
| 9,456,863 | B2 | 10/2016 | Moua |
| 9,456,864 | B2 | 10/2016 | Witt et al. |
| 9,468,438 | B2 | 10/2016 | Baber et al. |
| 9,468,498 | B2 | 10/2016 | Sigmon, Jr. |
| 9,474,542 | B2 | 10/2016 | Slipszenko et al. |
| 9,474,568 | B2 | 10/2016 | Akagane |
| 9,486,236 | B2 | 11/2016 | Price et al. |
| 9,492,146 | B2 | 11/2016 | Kostrzewski et al. |
| 9,492,224 | B2 | 11/2016 | Boudreaux et al. |
| 9,498,245 | B2 | 11/2016 | Voegele et al. |
| 9,498,275 | B2 | 11/2016 | Wham et al. |
| 9,504,483 | B2 | 11/2016 | Houser et al. |
| 9,504,520 | B2 | 11/2016 | Worrell et al. |
| 9,504,524 | B2 | 11/2016 | Behnke, II |
| 9,504,855 | B2 | 11/2016 | Messerly et al. |
| 9,510,850 | B2 | 12/2016 | Robertson et al. |
| 9,510,906 | B2 | 12/2016 | Boudreaux et al. |
| 9,522,029 | B2 | 12/2016 | Yates et al. |
| 9,522,032 | B2 | 12/2016 | Behnke |
| 9,526,564 | B2 | 12/2016 | Rusin |
| 9,526,565 | B2 | 12/2016 | Strobl |
| 9,545,253 | B2 | 1/2017 | Worrell et al. |
| 9,545,497 | B2 | 1/2017 | Wenderow et al. |
| 9,554,465 | B1 | 1/2017 | Liu et al. |
| 9,554,794 | B2 | 1/2017 | Baber et al. |
| 9,554,846 | B2 | 1/2017 | Boudreaux |
| 9,554,854 | B2 | 1/2017 | Yates et al. |
| 9,560,995 | B2 | 2/2017 | Addison et al. |
| 9,561,038 | B2 | 2/2017 | Shelton, IV et al. |
| 9,572,592 | B2 | 2/2017 | Price et al. |
| 9,574,644 | B2 | 2/2017 | Parihar |
| 9,585,714 | B2 | 3/2017 | Livneh |
| 9,592,056 | B2 | 3/2017 | Mozdzierz et al. |
| 9,592,072 | B2 | 3/2017 | Akagane |
| 9,597,143 | B2 | 3/2017 | Madan et al. |
| 9,603,669 | B2 | 3/2017 | Govari et al. |
| 9,610,091 | B2 | 4/2017 | Johnson et al. |
| 9,610,114 | B2 | 4/2017 | Baxter, III et al. |
| 9,615,877 | B2 | 4/2017 | Tyrrell et al. |
| 9,623,237 | B2 | 4/2017 | Turner et al. |
| 9,629,623 | B2 | 4/2017 | Lytle, IV et al. |
| 9,629,629 | B2 | 4/2017 | Leimbach et al. |
| 9,632,573 | B2 | 4/2017 | Ogawa et al. |
| 9,636,135 | B2 | 5/2017 | Stulen |
| 9,636,165 | B2 | 5/2017 | Larson et al. |
| 9,636,167 | B2 | 5/2017 | Gregg |
| 9,638,770 | B2 | 5/2017 | Dietz et al. |
| 9,642,644 | B2 | 5/2017 | Houser et al. |
| 9,642,669 | B2 | 5/2017 | Takashino et al. |
| 9,643,052 | B2 | 5/2017 | Tchao et al. |
| 9,649,110 | B2 | 5/2017 | Parihar et al. |
| 9,649,111 | B2 | 5/2017 | Shelton, IV et al. |
| 9,649,126 | B2 | 5/2017 | Robertson et al. |
| 9,649,173 | B2 | 5/2017 | Choi et al. |
| 9,655,670 | B2 | 5/2017 | Larson et al. |
| 9,662,131 | B2 | 5/2017 | Omori et al. |
| 9,668,806 | B2 | 6/2017 | Unger et al. |
| 9,671,860 | B2 | 6/2017 | Ogawa et al. |
| 9,674,949 | B1 | 6/2017 | Liu et al. |
| 9,675,374 | B2 | 6/2017 | Stulen et al. |
| 9,675,375 | B2 | 6/2017 | Houser et al. |
| 9,681,884 | B2 | 6/2017 | Clem et al. |
| 9,687,230 | B2 | 6/2017 | Leimbach et al. |
| 9,687,290 | B2 | 6/2017 | Keller |
| 9,690,362 | B2 | 6/2017 | Leimbach et al. |
| 9,693,817 | B2 | 7/2017 | Mehta et al. |
| 9,700,309 | B2 | 7/2017 | Jaworek et al. |
| 9,700,339 | B2 | 7/2017 | Nield |
| 9,700,343 | B2 | 7/2017 | Messerly et al. |
| 9,705,456 | B2 | 7/2017 | Gilbert |
| 9,707,004 | B2 | 7/2017 | Houser et al. |
| 9,707,027 | B2 | 7/2017 | Ruddenklau et al. |
| 9,707,030 | B2 | 7/2017 | Davison et al. |
| 9,713,507 | B2 | 7/2017 | Stulen et al. |
| 9,717,548 | B2 | 8/2017 | Couture |
| 9,717,552 | B2 | 8/2017 | Cosman et al. |
| 9,724,094 | B2 | 8/2017 | Baber et al. |
| 9,724,118 | B2 | 8/2017 | Schulte et al. |
| 9,724,120 | B2 | 8/2017 | Faller et al. |
| 9,724,152 | B2 | 8/2017 | Horlle et al. |
| 9,730,695 | B2 | 8/2017 | Leimbach et al. |
| 9,733,663 | B2 | 8/2017 | Leimbach et al. |
| 9,737,301 | B2 | 8/2017 | Baber et al. |
| 9,737,326 | B2 | 8/2017 | Worrell et al. |
| 9,737,355 | B2 | 8/2017 | Yates et al. |
| 9,737,358 | B2 | 8/2017 | Beckman et al. |
| 9,743,929 | B2 | 8/2017 | Leimbach et al. |
| 9,743,946 | B2 | 8/2017 | Faller et al. |
| 9,743,947 | B2 | 8/2017 | Price et al. |
| 9,750,499 | B2 | 9/2017 | Leimbach et al. |
| 9,757,128 | B2 | 9/2017 | Baber et al. |
| 9,757,142 | B2 | 9/2017 | Shimizu |
| 9,757,150 | B2 | 9/2017 | Alexander et al. |
| 9,757,186 | B2 | 9/2017 | Boudreaux et al. |
| 9,764,164 | B2 | 9/2017 | Wiener et al. |
| 9,770,285 | B2 | 9/2017 | Zoran et al. |
| 9,782,169 | B2 | 10/2017 | Kimsey et al. |
| 9,782,214 | B2 | 10/2017 | Houser et al. |
| 9,788,836 | B2 | 10/2017 | Overmyer et al. |
| 9,788,851 | B2 | 10/2017 | Dannaher et al. |
| 9,795,405 | B2 | 10/2017 | Price et al. |
| 9,795,436 | B2 | 10/2017 | Yates et al. |
| 9,795,808 | B2 | 10/2017 | Messerly et al. |
| 9,801,626 | B2 | 10/2017 | Parihar et al. |
| 9,801,648 | B2 | 10/2017 | Houser et al. |
| 9,802,033 | B2 | 10/2017 | Hibner et al. |
| 9,804,618 | B2 | 10/2017 | Leimbach et al. |
| 9,808,244 | B2 | 11/2017 | Leimbach et al. |
| 9,808,246 | B2 | 11/2017 | Shelton, IV et al. |
| 9,808,308 | B2 | 11/2017 | Faller et al. |
| 9,814,460 | B2 | 11/2017 | Kimsey et al. |
| 9,814,514 | B2 | 11/2017 | Shelton, IV et al. |
| 9,815,211 | B2 | 11/2017 | Cao et al. |
| 9,820,738 | B2 | 11/2017 | Lytle, IV et al. |
| 9,820,768 | B2 | 11/2017 | Gee et al. |
| 9,820,771 | B2 | 11/2017 | Norton et al. |
| 9,820,806 | B2 | 11/2017 | Lee et al. |
| 9,826,976 | B2 | 11/2017 | Parihar et al. |
| 9,826,977 | B2 | 11/2017 | Leimbach et al. |
| 9,839,443 | B2 | 12/2017 | Brockman et al. |
| 9,844,368 | B2 | 12/2017 | Boudreaux et al. |
| 9,844,374 | B2 | 12/2017 | Lytle, IV et al. |
| 9,844,375 | B2 | 12/2017 | Overmyer et al. |
| 9,848,901 | B2 | 12/2017 | Robertson et al. |
| 9,848,902 | B2 | 12/2017 | Price et al. |
| 9,848,937 | B2 | 12/2017 | Trees et al. |
| 9,861,381 | B2 | 1/2018 | Johnson |
| 9,861,428 | B2 | 1/2018 | Trees et al. |
| 9,867,612 | B2 | 1/2018 | Parihar et al. |
| 9,867,651 | B2 | 1/2018 | Wham |
| 9,867,670 | B2 | 1/2018 | Brannan et al. |
| 9,872,722 | B2 | 1/2018 | Lech |
| 9,872,725 | B2 | 1/2018 | Worrell et al. |
| 9,872,726 | B2 | 1/2018 | Morisaki |
| 9,877,720 | B2 | 1/2018 | Worrell et al. |
| 9,877,776 | B2 | 1/2018 | Boudreaux |
| 9,877,782 | B2 | 1/2018 | Voegele et al. |
| 9,878,184 | B2 | 1/2018 | Beaupre |
| 9,883,860 | B2 | 2/2018 | Leimbach et al. |
| 9,883,884 | B2 | 2/2018 | Neurohr et al. |
| 9,888,919 | B2 | 2/2018 | Leimbach et al. |
| 9,888,958 | B2 | 2/2018 | Evans et al. |
| 9,895,148 | B2 | 2/2018 | Shelton, IV et al. |
| 9,895,160 | B2 | 2/2018 | Fan et al. |
| 9,901,321 | B2 | 2/2018 | Harks et al. |
| 9,901,342 | B2 | 2/2018 | Shelton, IV et al. |
| 9,901,383 | B2 | 2/2018 | Hassler, Jr. |
| 9,901,754 | B2 | 2/2018 | Yamada |
| 9,907,563 | B2 | 3/2018 | Germain et al. |
| 9,913,642 | B2 | 3/2018 | Leimbach et al. |
| 9,913,656 | B2 | 3/2018 | Stulen |

(56) References Cited

U.S. PATENT DOCUMENTS 9,913,680 B2 3/2018 Voegele et al.
9,918,730 B2 3/2018 Trees et al.
9,924,961 B2 3/2018 Shelton, IV et al.
9,925,003 B2 3/2018 Parihar et al.
9,931,118 B2 4/2018 Shelton, IV et al.
9,937,001 B2 4/2018 Nakamura
9,943,309 B2 4/2018 Shelton, IV et al.
9,949,785 B2 4/2018 Price et al.
9,949,788 B2 4/2018 Boudreaux
9,962,182 B2 5/2018 Dietz et al.
9,968,355 B2 5/2018 Shelton, IV et al.
9,974,539 B2 5/2018 Yates et al.
9,987,000 B2 6/2018 Shelton, IV et al.
9,987,033 B2 6/2018 Neurohr et al.
9,993,248 B2 6/2018 Shelton, IV et al.
9,993,258 B2 6/2018 Shelton, IV et al.
9,993,289 B2 6/2018 Sobajima et al.
10,004,497 B2 6/2018 Overmyer et al.
10,004,501 B2 6/2018 Shelton, IV et al.
10,004,526 B2 6/2018 Dycus et al.
10,004,527 B2 6/2018 Gee et al.
D822,206 S 7/2018 Shelton, IV et al.
10,010,339 B2 7/2018 Witt et al.
10,010,341 B2 7/2018 Houser et al.
10,013,049 B2 7/2018 Leimbach et al.
10,016,199 B2 7/2018 Baber et al.
10,016,207 B2 7/2018 Suzuki et al.
10,022,142 B2 7/2018 Aranyi et al.
10,022,567 B2 7/2018 Messerly et al.
10,022,568 B2 7/2018 Messerly et al.
10,028,761 B2 7/2018 Leimbach et al.
10,028,786 B2 7/2018 Mucilli et al.
10,034,684 B2 7/2018 Weisenburgh, II et al.
10,034,704 B2 7/2018 Asher et al.
D826,405 S 8/2018 Shelton, IV et al.
10,039,588 B2 8/2018 Harper et al.
10,041,822 B2 8/2018 Zemlok
10,045,776 B2 8/2018 Shelton, IV et al.
10,045,779 B2 8/2018 Savage et al.
10,045,794 B2 8/2018 Witt et al.
10,045,810 B2 8/2018 Schall et al.
10,045,819 B2 8/2018 Jensen et al.
10,052,044 B2 8/2018 Shelton, IV et al.
10,052,102 B2 8/2018 Baxter, III et al.
10,070,916 B2 9/2018 Artale
10,080,609 B2 9/2018 Hancock et al.
10,085,748 B2 10/2018 Morgan et al.
10,085,762 B2 10/2018 Timm et al.
10,085,792 B2 10/2018 Johnson et al.
10,092,310 B2 10/2018 Boudreaux et al.
10,092,344 B2 10/2018 Mohr et al.
10,092,347 B2 10/2018 Weisshaupt et al.
10,092,348 B2 10/2018 Boudreaux
10,092,350 B2 10/2018 Rothweiler et al.
10,105,140 B2 10/2018 Malinouskas et al.
10,111,679 B2 10/2018 Baber et al.
10,111,699 B2 10/2018 Boudreaux
10,111,703 B2 10/2018 Cosman, Jr. et al.
10,117,649 B2 11/2018 Baxter, III et al.
10,117,667 B2 11/2018 Robertson et al.
10,117,702 B2 11/2018 Danziger et al.
10,123,835 B2 11/2018 Keller et al.
10,130,367 B2 11/2018 Cappola et al.
10,130,410 B2 11/2018 Strobl et al.
10,130,412 B2 11/2018 Wham
10,135,242 B2 11/2018 Baber et al.
10,136,887 B2 11/2018 Shelton, IV et al.
10,149,680 B2 12/2018 Parihar et al.
10,154,848 B2 12/2018 Chernov et al.
10,154,852 B2 12/2018 Conlon et al.
10,159,483 B2 12/2018 Beckman et al.
10,159,524 B2 12/2018 Yates et al.
10,166,060 B2 1/2019 Johnson et al.
10,172,665 B2 1/2019 Heckel et al.
10,172,669 B2 1/2019 Felder et al.
10,178,992 B2 1/2019 Wise et al.
10,179,022 B2 1/2019 Yates et al.
10,180,463 B2 1/2019 Beckman et al.
10,182,816 B2 1/2019 Shelton, IV et al.
10,182,818 B2 1/2019 Hensel et al.
10,188,385 B2 1/2019 Kerr et al.
10,188,455 B2 1/2019 Hancock et al.
10,194,907 B2 2/2019 Marczyk et al.
10,194,972 B2 2/2019 Yates et al.
10,194,973 B2 2/2019 Wiener et al.
10,194,976 B2 2/2019 Boudreaux
10,194,977 B2 2/2019 Yang
10,194,999 B2 2/2019 Bacher et al.
10,201,364 B2 2/2019 Leimbach et al.
10,201,365 B2 2/2019 Boudreaux et al.
10,201,382 B2 2/2019 Wiener et al.
10,206,676 B2 2/2019 Shelton, IV
10,226,250 B2 3/2019 Beckman et al.
10,226,273 B2 3/2019 Messerly et al.
10,231,747 B2 3/2019 Stulen et al.
10,238,385 B2 3/2019 Yates et al.
10,238,391 B2 3/2019 Leimbach et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,033 B2 4/2019 Overmyer et al.
10,245,095 B2 4/2019 Boudreaux
10,245,097 B2 4/2019 Honda et al.
10,245,104 B2 4/2019 McKenna et al.
10,251,664 B2 4/2019 Shelton, IV et al.
10,258,331 B2 4/2019 Shelton, IV et al.
10,258,505 B2 4/2019 Ovchinnikov
10,263,171 B2 4/2019 Wiener et al.
10,265,068 B2 4/2019 Harris et al.
10,265,117 B2 4/2019 Wiener et al.
10,265,118 B2 4/2019 Gerhardt
10,271,840 B2 4/2019 Sapre
10,271,851 B2 4/2019 Shelton, IV et al.
D847,989 S 5/2019 Shelton, IV et al.
10,278,721 B2 5/2019 Dietz et al.
10,285,705 B2 5/2019 Shelton, IV et al.
10,285,724 B2 5/2019 Faller et al.
10,285,750 B2 5/2019 Coulson et al.
10,292,704 B2 5/2019 Harris et al.
10,299,810 B2 5/2019 Robertson et al.
10,299,821 B2 5/2019 Shelton, IV et al.
D850,617 S 6/2019 Shelton, IV et al.
D851,762 S 6/2019 Shelton, IV et al.
10,307,159 B2 6/2019 Harris et al.
10,314,579 B2 6/2019 Chowaniec et al.
10,314,582 B2 6/2019 Shelton, IV et al.
10,314,638 B2 6/2019 Gee et al.
10,321,907 B2 6/2019 Shelton, IV et al.
10,321,950 B2 6/2019 Yates et al.
D854,151 S 7/2019 Shelton, IV et al.
10,335,149 B2 7/2019 Baxter, III et al.
10,335,182 B2 7/2019 Stulen et al.
10,335,183 B2 7/2019 Worrell et al.
10,335,614 B2 7/2019 Messerly et al.
10,342,543 B2 7/2019 Shelton, IV et al.
10,342,602 B2 7/2019 Strobl et al.
10,342,606 B2 7/2019 Cosman et al.
10,342,623 B2 7/2019 Huelman et al.
10,348,941 B2 7/2019 Elliot, Jr. et al.
10,349,999 B2 7/2019 Yates et al.
10,350,016 B2 7/2019 Burbank et al.
10,350,025 B1 7/2019 Loyd et al.
10,357,246 B2 7/2019 Shelton, IV et al.
10,357,247 B2 7/2019 Shelton, IV et al.
10,357,303 B2 7/2019 Conlon et al.
10,363,084 B2 7/2019 Friedrichs
10,368,861 B2 8/2019 Baxter, III et al.
10,368,865 B2 8/2019 Harris et al.
10,376,263 B2 8/2019 Morgan et al.
10,376,305 B2 8/2019 Yates et al.
10,390,841 B2 8/2019 Shelton, IV et al.
10,398,439 B2 9/2019 Cabrera et al.
10,398,466 B2 9/2019 Stulen et al.

(56) References Cited

U.S. PATENT DOCUMENTS

| | | | |
|---|---|---|---|
| 10,398,497 | B2 | 9/2019 | Batross et al. |
| 10,405,857 | B2 | 9/2019 | Shelton, IV et al. |
| 10,405,863 | B2 | 9/2019 | Wise et al. |
| 10,413,291 | B2 | 9/2019 | Worthington et al. |
| 10,413,293 | B2 | 9/2019 | Shelton, IV et al. |
| 10,413,297 | B2 | 9/2019 | Harris et al. |
| 10,413,352 | B2 | 9/2019 | Thomas et al. |
| 10,413,353 | B2 | 9/2019 | Kerr et al. |
| 10,420,552 | B2 | 9/2019 | Shelton, IV et al. |
| 10,420,579 | B2 | 9/2019 | Wiener et al. |
| 10,420,607 | B2 | 9/2019 | Woloszko et al. |
| D865,175 | S | 10/2019 | Widenhouse et al. |
| 10,426,471 | B2 | 10/2019 | Shelton, IV et al. |
| 10,426,507 | B2 | 10/2019 | Wiener et al. |
| 10,426,546 | B2 | 10/2019 | Graham et al. |
| 10,426,978 | B2 | 10/2019 | Akagane |
| 10,433,837 | B2 | 10/2019 | Worthington et al. |
| 10,433,849 | B2 | 10/2019 | Shelton, IV et al. |
| 10,433,865 | B2 | 10/2019 | Witt et al. |
| 10,433,866 | B2 | 10/2019 | Witt et al. |
| 10,433,900 | B2 | 10/2019 | Harris et al. |
| 10,441,279 | B2 | 10/2019 | Shelton, IV et al. |
| 10,441,308 | B2 | 10/2019 | Robertson |
| 10,441,310 | B2 | 10/2019 | Olson et al. |
| 10,441,345 | B2 | 10/2019 | Aldridge et al. |
| 10,448,948 | B2 | 10/2019 | Shelton, IV et al. |
| 10,448,950 | B2 | 10/2019 | Shelton, IV et al. |
| 10,448,986 | B2 | 10/2019 | Zikorus et al. |
| 10,456,140 | B2 | 10/2019 | Shelton, IV et al. |
| 10,456,193 | B2 | 10/2019 | Yates et al. |
| 10,463,421 | B2 | 11/2019 | Boudreaux et al. |
| 10,463,887 | B2 | 11/2019 | Witt et al. |
| 10,470,762 | B2 | 11/2019 | Leimbach et al. |
| 10,470,764 | B2 | 11/2019 | Baxter, III et al. |
| 10,478,182 | B2 | 11/2019 | Taylor |
| 10,478,190 | B2 | 11/2019 | Miller et al. |
| 10,485,542 | B2 | 11/2019 | Shelton, IV et al. |
| 10,485,543 | B2 | 11/2019 | Shelton, IV et al. |
| 10,485,607 | B2 | 11/2019 | Strobl et al. |
| D869,655 | S | 12/2019 | Shelton, IV et al. |
| 10,492,785 | B2 | 12/2019 | Overmyer et al. |
| 10,492,849 | B2 | 12/2019 | Juergens et al. |
| 10,499,914 | B2 | 12/2019 | Huang et al. |
| 10,507,033 | B2 | 12/2019 | Dickerson et al. |
| 10,512,795 | B2 | 12/2019 | Voegele et al. |
| 10,517,595 | B2 | 12/2019 | Hunter et al. |
| 10,517,596 | B2 | 12/2019 | Hunter et al. |
| 10,517,627 | B2 | 12/2019 | Timm et al. |
| 10,524,787 | B2 | 1/2020 | Shelton, IV et al. |
| 10,524,789 | B2 | 1/2020 | Swayze et al. |
| 10,524,854 | B2 | 1/2020 | Woodruff et al. |
| 10,524,872 | B2 | 1/2020 | Stewart et al. |
| 10,531,874 | B2 | 1/2020 | Morgan et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,979 | B2 | 1/2020 | Shelton, IV et al. |
| 10,542,982 | B2 | 1/2020 | Beckman et al. |
| 10,542,991 | B2 | 1/2020 | Shelton, IV et al. |
| 10,543,008 | B2 | 1/2020 | Vakharia et al. |
| 10,548,504 | B2 | 2/2020 | Shelton, IV et al. |
| 10,548,655 | B2 | 2/2020 | Scheib et al. |
| 10,555,769 | B2 | 2/2020 | Worrell et al. |
| 10,561,560 | B2 | 2/2020 | Boutoussov et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,632 | B2 | 2/2020 | Miller et al. |
| 10,575,892 | B2 | 3/2020 | Danziger et al. |
| 10,582,928 | B2 | 3/2020 | Hunter et al. |
| 10,588,625 | B2 | 3/2020 | Weaner et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,595,929 | B2 | 3/2020 | Boudreaux et al. |
| 10,595,930 | B2 | 3/2020 | Scheib et al. |
| 10,603,036 | B2 | 3/2020 | Hunter et al. |
| 10,610,224 | B2 | 4/2020 | Shelton, IV et al. |
| 10,610,286 | B2 | 4/2020 | Wiener et al. |
| 10,610,313 | B2 | 4/2020 | Bailey et al. |
| 10,617,412 | B2 | 4/2020 | Shelton, IV et al. |
| 10,617,420 | B2 | 4/2020 | Shelton, IV et al. |
| 10,617,464 | B2 | 4/2020 | Duppuis |
| 10,624,635 | B2 | 4/2020 | Harris et al. |
| 10,624,691 | B2 | 4/2020 | Wiener et al. |
| 10,631,858 | B2 | 4/2020 | Burbank |
| 10,631,859 | B2 | 4/2020 | Shelton, IV et al. |
| 10,631,928 | B2 | 4/2020 | Basu et al. |
| 10,632,630 | B2 | 4/2020 | Cao et al. |
| RE47,996 | E | 5/2020 | Turner et al. |
| 10,639,034 | B2 | 5/2020 | Harris et al. |
| 10,639,035 | B2 | 5/2020 | Shelton, IV et al. |
| 10,639,037 | B2 | 5/2020 | Shelton, IV et al. |
| 10,639,092 | B2 | 5/2020 | Corbett et al. |
| 10,639,098 | B2 | 5/2020 | Cosman et al. |
| 10,646,269 | B2 | 5/2020 | Worrell et al. |
| 10,646,292 | B2 | 5/2020 | Solomon et al. |
| 10,653,413 | B2 | 5/2020 | Worthington et al. |
| 10,660,692 | B2 | 5/2020 | Lesko et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,677,764 | B2 | 6/2020 | Ross et al. |
| 10,682,136 | B2 | 6/2020 | Harris et al. |
| 10,682,138 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,884 | B2 | 6/2020 | Wiener et al. |
| 10,688,321 | B2 | 6/2020 | Wiener et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,119 | B2 | 6/2020 | Smith |
| 10,702,270 | B2 | 7/2020 | Shelton, IV et al. |
| 10,702,329 | B2 | 7/2020 | Strobl et al. |
| 10,709,446 | B2 | 7/2020 | Harris et al. |
| 10,709,469 | B2 | 7/2020 | Shelton, IV et al. |
| 10,709,906 | B2 | 7/2020 | Nield |
| 10,716,615 | B2 | 7/2020 | Shelton, IV et al. |
| 10,722,233 | B2 | 7/2020 | Wellman |
| D893,717 | S | 8/2020 | Messerly et al. |
| 10,729,458 | B2 | 8/2020 | Stoddard et al. |
| 10,729,494 | B2 | 8/2020 | Parihar et al. |
| 10,736,629 | B2 | 8/2020 | Shelton, IV et al. |
| 10,736,685 | B2 | 8/2020 | Wiener et al. |
| 10,751,108 | B2 | 8/2020 | Yates et al. |
| 10,751,138 | B2 | 8/2020 | Giordano et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,294 | B2 | 9/2020 | Jones |
| 10,765,427 | B2 | 9/2020 | Shelton, IV et al. |
| 10,765,470 | B2 | 9/2020 | Yates et al. |
| 10,772,629 | B2 | 9/2020 | Shelton, IV et al. |
| 10,772,630 | B2 | 9/2020 | Wixey |
| 10,779,821 | B2 | 9/2020 | Harris et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,845 | B2 | 9/2020 | Timm et al. |
| 10,779,849 | B2 | 9/2020 | Shelton, IV et al. |
| 10,779,879 | B2 | 9/2020 | Yates et al. |
| 10,786,253 | B2 | 9/2020 | Shelton, IV et al. |
| 10,786,276 | B2 | 9/2020 | Hirai et al. |
| 10,806,454 | B2 | 10/2020 | Kopp |
| 10,813,638 | B2 | 10/2020 | Shelton, IV et al. |
| 10,820,938 | B2 | 11/2020 | Fischer et al. |
| 10,828,058 | B2 | 11/2020 | Shelton, IV et al. |

(56) References Cited

U.S. PATENT DOCUMENTS 10,835,245 B2 11/2020 Swayze et al.
10,835,246 B2 11/2020 Shelton, IV et al.
10,835,247 B2 11/2020 Shelton, IV et al.
10,835,307 B2 11/2020 Shelton, IV et al.
10,842,492 B2 11/2020 Shelton, IV et al.
10,842,523 B2 11/2020 Shelton, IV et al.
10,842,563 B2 11/2020 Gilbert et al.
D906,355 S 12/2020 Messerly et al.
10,856,867 B2 12/2020 Shelton, IV et al.
10,856,868 B2 12/2020 Shelton, IV et al.
10,856,869 B2 12/2020 Shelton, IV et al.
10,856,870 B2 12/2020 Harris et al.
10,856,896 B2 12/2020 Eichmann et al.
10,856,929 B2 12/2020 Yates et al.
10,856,934 B2 12/2020 Trees et al.
10,874,465 B2 12/2020 Weir et al.
D908,216 S 1/2021 Messerly et al.
10,881,399 B2 1/2021 Shelton, IV et al.
10,881,401 B2 1/2021 Baber et al.
10,881,409 B2 1/2021 Cabrera
10,881,449 B2 1/2021 Boudreaux et al.
10,888,322 B2 1/2021 Morgan et al.
10,888,347 B2 1/2021 Witt et al.
10,893,863 B2 1/2021 Shelton, IV et al.
10,893,864 B2 1/2021 Harris et al.
10,893,883 B2 1/2021 Dannaher
10,898,186 B2 1/2021 Bakos et al.
10,898,256 B2 1/2021 Yates et al.
10,912,559 B2 2/2021 Harris et al.
10,912,580 B2 2/2021 Green et al.
10,912,603 B2 2/2021 Boudreaux et al.
10,918,385 B2 2/2021 Overmyer et al.
10,925,659 B2 2/2021 Shelton, IV et al.
D914,878 S 3/2021 Shelton, IV et al.
10,932,766 B2 3/2021 Tesar et al.
10,932,847 B2 3/2021 Yates et al.
10,945,727 B2 3/2021 Shelton, IV et al.
10,952,788 B2 3/2021 Asher et al.
10,959,727 B2 3/2021 Hunter et al.
10,966,741 B2 4/2021 Illizaliturri-Sanchez et al.
10,966,747 B2 4/2021 Worrell et al.
10,973,516 B2 4/2021 Shelton, IV et al.
10,973,517 B2 4/2021 Wixey
10,973,520 B2 4/2021 Shelton, IV et al.
10,980,536 B2 4/2021 Weaner et al.
10,987,105 B2 4/2021 Cappola et al.
10,987,123 B2 4/2021 Weir et al.
10,987,156 B2 4/2021 Trees et al.
10,993,715 B2 5/2021 Shelton, IV et al.
10,993,716 B2 5/2021 Shelton, IV et al.
10,993,763 B2 5/2021 Batross et al.
11,000,278 B2 5/2021 Shelton, IV et al.
11,000,279 B2 5/2021 Shelton, IV et al.
11,020,114 B2 6/2021 Shelton, IV et al.
11,020,140 B2 6/2021 Gee et al.
11,033,322 B2 6/2021 Wiener et al.
11,039,834 B2 6/2021 Harris et al.
11,045,191 B2 6/2021 Shelton, IV et al.
11,045,192 B2 6/2021 Harris et al.
11,045,275 B2 6/2021 Boudreaux et al.
11,051,840 B2 7/2021 Shelton, IV et al.
11,051,873 B2 7/2021 Wiener et al.
11,058,424 B2 7/2021 Shelton, IV et al.
11,058,447 B2 7/2021 Houser
11,058,448 B2 7/2021 Shelton, IV et al.
11,058,475 B2 7/2021 Wiener et al.
11,064,997 B2 7/2021 Shelton, IV et al.
11,065,048 B2 7/2021 Messerly et al.
11,083,455 B2 8/2021 Shelton, IV et al.
11,083,458 B2 8/2021 Harris et al.
11,090,048 B2 8/2021 Fanelli et al.
11,090,049 B2 8/2021 Bakos et al.
11,090,104 B2 8/2021 Wiener et al.
11,096,688 B2 8/2021 Shelton, IV et al.
11,096,752 B2 8/2021 Stulen et al.
11,109,866 B2 9/2021 Shelton, IV et al.
11,129,611 B2 9/2021 Shelton, IV et al.
11,129,666 B2 9/2021 Messerly et al.
11,129,669 B2 9/2021 Stulen et al.
11,129,670 B2 9/2021 Shelton, IV et al.
11,134,942 B2 10/2021 Harris et al.
11,134,978 B2 10/2021 Shelton, IV et al.
11,141,154 B2 10/2021 Shelton, IV et al.
11,141,213 B2 10/2021 Yates et al.
11,147,551 B2 10/2021 Shelton, IV
11,147,553 B2 10/2021 Shelton, IV
11,160,551 B2 11/2021 Shelton, IV et al.
11,166,716 B2 11/2021 Shelton, IV et al.
11,172,929 B2 11/2021 Shelton, IV
11,179,155 B2 11/2021 Shelton, IV et al.
11,179,173 B2 11/2021 Price et al.
11,191,539 B2 12/2021 Overmyer et al.
11,191,540 B2 12/2021 Aronhalt et al.
11,197,668 B2 12/2021 Shelton, IV et al.
11,202,670 B2 12/2021 Worrell et al.
11,207,065 B2 12/2021 Harris et al.
11,207,067 B2 12/2021 Shelton, IV et al.
11,213,293 B2 1/2022 Worthington et al.
11,213,294 B2 1/2022 Shelton, IV et al.
11,219,453 B2 1/2022 Shelton, IV et al.
11,224,426 B2 1/2022 Shelton, IV et al.
11,224,497 B2 1/2022 Shelton, IV et al.
11,229,437 B2 1/2022 Shelton, IV et al.
11,229,450 B2 1/2022 Shelton, IV et al.
11,229,471 B2 1/2022 Shelton, IV et al.
11,229,472 B2 1/2022 Shelton, IV et al.
11,234,698 B2 2/2022 Shelton, IV et al.
11,241,235 B2 2/2022 Shelton, IV et al.
11,246,592 B2 2/2022 Shelton, IV et al.
11,246,625 B2 2/2022 Kane et al.
11,246,678 B2 2/2022 Shelton, IV et al.
11,253,256 B2 2/2022 Harris et al.
11,259,803 B2 3/2022 Shelton, IV et al.
11,259,805 B2 3/2022 Shelton, IV et al.
11,259,806 B2 3/2022 Shelton, IV et al.
11,259,807 B2 3/2022 Shelton, IV et al.
11,266,405 B2 3/2022 Shelton, IV et al.
11,266,430 B2 3/2022 Clauda et al.
11,272,931 B2 3/2022 Boudreaux et al.
11,278,280 B2 3/2022 Shelton, IV et al.
11,284,890 B2 3/2022 Nalagatla et al.
11,291,440 B2 4/2022 Harris et al.
11,291,444 B2 4/2022 Boudreaux et al.
11,291,445 B2 4/2022 Shelton, IV et al.
11,291,447 B2 4/2022 Shelton, IV et al.
11,291,451 B2 4/2022 Shelton, IV
11,298,127 B2 4/2022 Shelton, IV
11,298,129 B2 4/2022 Bakos et al.
11,298,130 B2 4/2022 Bakos et al.
11,304,695 B2 4/2022 Shelton, IV et al.
11,304,696 B2 4/2022 Shelton, IV et al.
11,304,699 B2 4/2022 Shelton, IV et al.
11,311,306 B2 4/2022 Shelton, IV et al.
11,311,326 B2 4/2022 Boudreaux
11,311,342 B2 4/2022 Parihar et al.
D950,728 S 5/2022 Bakos et al.
D952,144 S 5/2022 Boudreaux
11,317,915 B2 5/2022 Boudreaux et al.
11,324,503 B2 5/2022 Shelton, IV et al.
11,324,527 B2 5/2022 Aldridge et al.
11,324,557 B2 5/2022 Shelton, IV et al.
11,331,100 B2 5/2022 Boudreaux et al.
11,331,101 B2 5/2022 Harris et al.
11,337,747 B2 5/2022 Voegele et al.
11,344,362 B2 5/2022 Yates et al.
11,350,938 B2 6/2022 Shelton, IV et al.
11,357,503 B2 6/2022 Bakos et al.
11,361,176 B2 6/2022 Shelton, IV et al.
11,369,377 B2 6/2022 Boudreaux et al.
11,376,098 B2 7/2022 Shelton, IV et al.
11,382,642 B2 7/2022 Robertson et al.
11,389,161 B2 7/2022 Shelton, IV et al.
11,389,164 B2 7/2022 Yates et al.
11,399,837 B2 8/2022 Shelton, IV et al.

(56) References Cited

U.S. PATENT DOCUMENTS

| | | | |
|---|---|---|---|
| 11,399,855 | B2 | 8/2022 | Boudreaux et al. |
| 11,406,382 | B2 | 8/2022 | Shelton, IV et al. |
| 11,413,060 | B2 | 8/2022 | Faller et al. |
| 11,419,606 | B2 | 8/2022 | Overmyer et al. |
| 11,419,626 | B2 | 8/2022 | Timm et al. |
| 11,424,027 | B2 | 8/2022 | Shelton, IV |
| 11,426,167 | B2 | 8/2022 | Shelton, IV et al. |
| 11,426,191 | B2 | 8/2022 | Vakharia et al. |
| D964,564 | S | 9/2022 | Boudreaux |
| 11,446,029 | B2 | 9/2022 | Shelton, IV et al. |
| 11,452,525 | B2 | 9/2022 | Shelton, IV et al. |
| 11,464,511 | B2 | 10/2022 | Timm et al. |
| 11,464,512 | B2 | 10/2022 | Shelton, IV et al. |
| 11,464,601 | B2 | 10/2022 | Shelton, IV et al. |
| 11,471,155 | B2 | 10/2022 | Shelton, IV et al. |
| 11,471,156 | B2 | 10/2022 | Shelton, IV et al. |
| 11,471,206 | B2 | 10/2022 | Henderson et al. |
| 11,471,209 | B2 | 10/2022 | Yates et al. |
| 11,478,242 | B2 | 10/2022 | Shelton, IV et al. |
| 11,484,310 | B2 | 11/2022 | Shelton, IV et al. |
| 11,504,122 | B2 | 11/2022 | Shelton, IV et al. |
| 11,517,309 | B2 | 12/2022 | Bakos et al. |
| 11,529,137 | B2 | 12/2022 | Shelton, IV et al. |
| 11,529,139 | B2 | 12/2022 | Shelton, IV et al. |
| 11,553,971 | B2 | 1/2023 | Shelton, IV et al. |
| 11,559,304 | B2 | 1/2023 | Boudreaux et al. |
| 11,559,307 | B2 | 1/2023 | Shelton, IV et al. |
| 11,559,308 | B2 | 1/2023 | Yates et al. |
| 11,559,347 | B2 | 1/2023 | Wiener et al. |
| 11,571,210 | B2 | 2/2023 | Shelton, IV et al. |
| 11,576,672 | B2 | 2/2023 | Shelton, IV et al. |
| 11,576,677 | B2 | 2/2023 | Shelton, IV et al. |
| 11,583,306 | B2 | 2/2023 | Olson et al. |
| 11,589,865 | B2 | 2/2023 | Shelton, IV et al. |
| 11,589,888 | B2 | 2/2023 | Shelton, IV et al. |
| 11,589,916 | B2 | 2/2023 | Shelton, IV et al. |
| 11,607,219 | B2 | 3/2023 | Shelton, IV et al. |
| 11,638,587 | B2 | 5/2023 | Shelton, IV et al. |
| 11,653,920 | B2 | 5/2023 | Shelton, IV et al. |
| 11,659,023 | B2 | 5/2023 | Shelton, IV et al. |
| 11,660,089 | B2 | 5/2023 | Shelton, IV et al. |
| 11,660,163 | B2 | 5/2023 | Shelton, IV et al. |
| 11,666,368 | B2 | 6/2023 | Henderson et al. |
| 11,666,375 | B2 | 6/2023 | Scheib et al. |
| 11,678,880 | B2 | 6/2023 | Shelton, IV et al. |
| 11,678,925 | B2 | 6/2023 | Henderson et al. |
| 11,684,402 | B2 | 6/2023 | Shelton, IV et al. |
| 11,684,412 | B2 | 6/2023 | Shelton, IV et al. |
| 11,684,434 | B2 | 6/2023 | Shelton, IV |
| 11,696,759 | B2 | 7/2023 | Shelton, IV et al. |
| 11,696,761 | B2 | 7/2023 | Shelton, IV |
| 11,696,776 | B2 | 7/2023 | Shelton, IV et al. |
| 11,701,111 | B2 | 7/2023 | Shelton, IV et al. |
| 11,707,318 | B2 | 7/2023 | Shelton, IV et al. |
| 11,717,311 | B2 | 8/2023 | Weir et al. |
| 11,717,706 | B2 | 8/2023 | Wiener et al. |
| 11,723,716 | B2 | 8/2023 | Fiebig et al. |
| 11,744,636 | B2 | 9/2023 | Shelton, IV et al. |
| 11,751,872 | B2 | 9/2023 | Zeiner et al. |
| 11,751,929 | B2 | 9/2023 | Shelton, IV et al. |
| 11,759,251 | B2 | 9/2023 | Shelton, IV et al. |
| 11,766,287 | B2 | 9/2023 | Wiener et al. |
| 11,771,419 | B2 | 10/2023 | Shelton, IV et al. |
| 11,779,329 | B2 | 10/2023 | Shelton, IV et al. |
| 11,779,387 | B2 | 10/2023 | Salguero et al. |
| 11,786,291 | B2 | 10/2023 | Sarley et al. |
| 11,786,294 | B2 | 10/2023 | Shelton, IV et al. |
| 2001/0025173 | A1 | 9/2001 | Ritchie et al. |
| 2001/0025183 | A1 | 9/2001 | Shahidi |
| 2001/0025184 | A1 | 9/2001 | Messerly |
| 2001/0031950 | A1 | 10/2001 | Ryan |
| 2001/0039419 | A1 | 11/2001 | Francischelli et al. |
| 2002/0002377 | A1 | 1/2002 | Cimino |
| 2002/0002380 | A1 | 1/2002 | Bishop |
| 2002/0019649 | A1 | 2/2002 | Sikora et al. |
| 2002/0022836 | A1 | 2/2002 | Goble et al. |
| 2002/0029036 | A1 | 3/2002 | Goble et al. |
| 2002/0029055 | A1 | 3/2002 | Bonutti |
| 2002/0032452 | A1 | 3/2002 | Tierney et al. |
| 2002/0049551 | A1 | 4/2002 | Friedman et al. |
| 2002/0052617 | A1 | 5/2002 | Anis et al. |
| 2002/0077550 | A1 | 6/2002 | Rabiner et al. |
| 2002/0107517 | A1 | 8/2002 | Witt et al. |
| 2002/0123749 | A1 | 9/2002 | Jain |
| 2002/0133152 | A1 | 9/2002 | Strul |
| 2002/0151884 | A1 | 10/2002 | Hoey et al. |
| 2002/0156466 | A1 | 10/2002 | Sakurai et al. |
| 2002/0156493 | A1 | 10/2002 | Houser et al. |
| 2002/0165577 | A1 | 11/2002 | Witt et al. |
| 2002/0177373 | A1 | 11/2002 | Shibata et al. |
| 2002/0177862 | A1 | 11/2002 | Aranyi et al. |
| 2003/0009164 | A1 | 1/2003 | Woloszko et al. |
| 2003/0014053 | A1 | 1/2003 | Nguyen et al. |
| 2003/0014087 | A1 | 1/2003 | Fang et al. |
| 2003/0036705 | A1 | 2/2003 | Hare et al. |
| 2003/0040758 | A1 | 2/2003 | Wang et al. |
| 2003/0050572 | A1 | 3/2003 | Brautigam et al. |
| 2003/0055443 | A1 | 3/2003 | Spotnitz |
| 2003/0073981 | A1 | 4/2003 | Whitman et al. |
| 2003/0109778 | A1 | 6/2003 | Rashidi |
| 2003/0109875 | A1 | 6/2003 | Tetzlaff et al. |
| 2003/0114851 | A1 | 6/2003 | Truckai et al. |
| 2003/0130693 | A1 | 7/2003 | Levin et al. |
| 2003/0139741 | A1 | 7/2003 | Goble et al. |
| 2003/0144680 | A1 | 7/2003 | Kellogg et al. |
| 2003/0158548 | A1 | 8/2003 | Phan et al. |
| 2003/0171747 | A1 | 9/2003 | Kanehira et al. |
| 2003/0176778 | A1 | 9/2003 | Messing et al. |
| 2003/0181898 | A1 | 9/2003 | Bowers |
| 2003/0199794 | A1 | 10/2003 | Sakurai et al. |
| 2003/0204199 | A1 | 10/2003 | Novak et al. |
| 2003/0208186 | A1 | 11/2003 | Moreyra |
| 2003/0212332 | A1 | 11/2003 | Fenton et al. |
| 2003/0212363 | A1 | 11/2003 | Shipp |
| 2003/0212392 | A1 | 11/2003 | Fenton et al. |
| 2003/0212422 | A1 | 11/2003 | Fenton et al. |
| 2003/0225332 | A1 | 12/2003 | Okada et al. |
| 2003/0229344 | A1 | 12/2003 | Dycus et al. |
| 2004/0030254 | A1 | 2/2004 | Babaev |
| 2004/0030330 | A1 | 2/2004 | Brassell et al. |
| 2004/0047485 | A1 | 3/2004 | Sherrit et al. |
| 2004/0054364 | A1 | 3/2004 | Aranyi et al. |
| 2004/0064151 | A1 | 4/2004 | Mollenauer |
| 2004/0087943 | A1 | 5/2004 | Dycus et al. |
| 2004/0092921 | A1 | 5/2004 | Kadziauskas et al. |
| 2004/0092992 | A1 | 5/2004 | Adams et al. |
| 2004/0094597 | A1 | 5/2004 | Whitman et al. |
| 2004/0097911 | A1 | 5/2004 | Murakami et al. |
| 2004/0097912 | A1 | 5/2004 | Gonnering |
| 2004/0097919 | A1 | 5/2004 | Wellman et al. |
| 2004/0097996 | A1 | 5/2004 | Rabiner et al. |
| 2004/0116952 | A1 | 6/2004 | Sakurai et al. |
| 2004/0122423 | A1 | 6/2004 | Dycus et al. |
| 2004/0132383 | A1 | 7/2004 | Langford et al. |
| 2004/0138621 | A1 | 7/2004 | Jahns et al. |
| 2004/0142667 | A1 | 7/2004 | Lochhead et al. |
| 2004/0143263 | A1 | 7/2004 | Schechter et al. |
| 2004/0147934 | A1 | 7/2004 | Kiester |
| 2004/0147945 | A1 | 7/2004 | Fritzsch |
| 2004/0158237 | A1 | 8/2004 | Abboud et al. |
| 2004/0167508 | A1 | 8/2004 | Wham et al. |
| 2004/0176686 | A1 | 9/2004 | Hare et al. |
| 2004/0176751 | A1 | 9/2004 | Weitzner et al. |
| 2004/0181242 | A1 | 9/2004 | Stack et al. |
| 2004/0193150 | A1 | 9/2004 | Sharkey et al. |
| 2004/0193153 | A1 | 9/2004 | Sartor et al. |
| 2004/0193212 | A1 | 9/2004 | Taniguchi et al. |
| 2004/0199193 | A1 | 10/2004 | Hayashi et al. |
| 2004/0215132 | A1 | 10/2004 | Yoon |
| 2004/0243147 | A1 | 12/2004 | Lipow |
| 2004/0249374 | A1 | 12/2004 | Tetzlaff et al. |
| 2004/0260273 | A1 | 12/2004 | Wan |
| 2004/0260300 | A1 | 12/2004 | Gorensek et al. |
| 2004/0267311 | A1 | 12/2004 | Viola et al. |

(56) References Cited

U.S. PATENT DOCUMENTS

2005/0015125 A1 1/2005 Mioduski et al.
2005/0020967 A1 1/2005 Ono
2005/0021018 A1 1/2005 Anderson et al.
2005/0021065 A1 1/2005 Yamada et al.
2005/0021078 A1 1/2005 Vleugels et al.
2005/0033278 A1 2/2005 McClurken et al.
2005/0033337 A1 2/2005 Muir et al.
2005/0070800 A1 3/2005 Takahashi
2005/0080427 A1 4/2005 Govari et al.
2005/0088285 A1 4/2005 Jei
2005/0090817 A1 4/2005 Phan
2005/0096683 A1 5/2005 Ellins et al.
2005/0099824 A1 5/2005 Dowling et al.
2005/0107777 A1 5/2005 West et al.
2005/0131390 A1 6/2005 Heinrich et al.
2005/0143769 A1 6/2005 White et al.
2005/0149108 A1 7/2005 Cox
2005/0165429 A1 7/2005 Douglas et al.
2005/0171522 A1 8/2005 Christopherson
2005/0171533 A1 8/2005 Latterell et al.
2005/0177184 A1 8/2005 Easley
2005/0182339 A1 8/2005 Lee et al.
2005/0187576 A1 8/2005 Whitman et al.
2005/0188743 A1 9/2005 Land
2005/0192610 A1 9/2005 Houser et al.
2005/0192611 A1 9/2005 Houser
2005/0206583 A1 9/2005 Lemelson et al.
2005/0222598 A1 10/2005 Ho et al.
2005/0234484 A1 10/2005 Houser et al.
2005/0249667 A1 11/2005 Tuszynski et al.
2005/0256405 A1 11/2005 Makin et al.
2005/0261588 A1 11/2005 Makin et al.
2005/0262175 A1 11/2005 Iino et al.
2005/0267464 A1 12/2005 Truckai et al.
2005/0271807 A1 12/2005 Iljima et al.
2005/0273090 A1 12/2005 Nieman et al.
2005/0288659 A1 12/2005 Kimura et al.
2006/0025757 A1 2/2006 Heim
2006/0030797 A1 2/2006 Zhou et al.
2006/0030848 A1 2/2006 Craig et al.
2006/0058825 A1 3/2006 Ogura et al.
2006/0063130 A1 3/2006 Hayman et al.
2006/0064086 A1 3/2006 Odom
2006/0066181 A1 3/2006 Bromfield et al.
2006/0074442 A1 4/2006 Noriega et al.
2006/0079874 A1 4/2006 Faller et al.
2006/0079879 A1 4/2006 Faller et al.
2006/0095046 A1 5/2006 Trieu et al.
2006/0109061 A1 5/2006 Dobson et al.
2006/0142656 A1 6/2006 Malackowski et al.
2006/0159731 A1 7/2006 Shoshan
2006/0190034 A1 8/2006 Nishizawa et al.
2006/0206100 A1 9/2006 Eskridge et al.
2006/0206115 A1 9/2006 Schomer et al.
2006/0211943 A1 9/2006 Beaupre
2006/0217700 A1 9/2006 Garito et al.
2006/0217729 A1 9/2006 Eskridge et al.
2006/0224160 A1 10/2006 Trieu et al.
2006/0247558 A1 11/2006 Yamada
2006/0253050 A1 11/2006 Yoshimine et al.
2006/0259026 A1 11/2006 Godara et al.
2006/0259102 A1 11/2006 Slatkine
2006/0264809 A1 11/2006 Hansmann et al.
2006/0264995 A1 11/2006 Fanton et al.
2006/0265035 A1 11/2006 Yachi et al.
2006/0270916 A1 11/2006 Skwarek et al.
2006/0271030 A1 11/2006 Francis et al.
2006/0293656 A1 12/2006 Shadduck et al.
2007/0016235 A1 1/2007 Tanaka et al.
2007/0016236 A1 1/2007 Beaupre
2007/0021738 A1 1/2007 Hasser et al.
2007/0027468 A1 2/2007 Wales et al.
2007/0032704 A1 2/2007 Gandini et al.
2007/0055228 A1 3/2007 Berg et al.
2007/0056596 A1 3/2007 Fanney et al.
2007/0060935 A1 3/2007 Schwardt et al.
2007/0063618 A1 3/2007 Bromfield
2007/0066971 A1 3/2007 Podhajsky
2007/0067123 A1 3/2007 Jungerman
2007/0073185 A1 3/2007 Nakao
2007/0073341 A1 3/2007 Smith et al.
2007/0074584 A1 4/2007 Talarico et al.
2007/0106317 A1 5/2007 Shelton et al.
2007/0118115 A1 5/2007 Artale et al.
2007/0129726 A1 6/2007 Eder et al.
2007/0130771 A1 6/2007 Ehlert et al.
2007/0135803 A1 6/2007 Belson
2007/0149881 A1 6/2007 Rabin
2007/0156163 A1 7/2007 Davison et al.
2007/0166663 A1 7/2007 Telles et al.
2007/0173803 A1 7/2007 Wham et al.
2007/0173813 A1 7/2007 Odom
2007/0173872 A1 7/2007 Neuenfeldt
2007/0175955 A1 8/2007 Shelton et al.
2007/0185474 A1 8/2007 Nahen
2007/0191712 A1 8/2007 Messerly et al.
2007/0191713 A1 8/2007 Eichmann et al.
2007/0203483 A1 8/2007 Kim et al.
2007/0208336 A1 9/2007 Kim et al.
2007/0208340 A1 9/2007 Ganz et al.
2007/0219481 A1 9/2007 Babaev
2007/0232926 A1 10/2007 Stulen et al.
2007/0232928 A1 10/2007 Wiener et al.
2007/0236213 A1 10/2007 Paden et al.
2007/0239101 A1 10/2007 Kellogg
2007/0249941 A1 10/2007 Salehi et al.
2007/0260242 A1 11/2007 Dycus et al.
2007/0265560 A1 11/2007 Soltani et al.
2007/0265613 A1 11/2007 Edelstein et al.
2007/0265616 A1 11/2007 Couture et al.
2007/0265620 A1 11/2007 Kraas et al.
2007/0275348 A1 11/2007 Lemon
2007/0287933 A1 12/2007 Phan et al.
2007/0288055 A1 12/2007 Lee
2007/0299895 A1 12/2007 Johnson et al.
2008/0005213 A1 1/2008 Holtzman
2008/0013809 A1 1/2008 Zhu et al.
2008/0015473 A1 1/2008 Shimizu
2008/0015575 A1 1/2008 Odom et al.
2008/0033465 A1 2/2008 Schmitz et al.
2008/0039746 A1 2/2008 Hissong et al.
2008/0046122 A1 2/2008 Manzo et al.
2008/0051812 A1 2/2008 Schmitz et al.
2008/0058775 A1 3/2008 Darian et al.
2008/0058845 A1 3/2008 Shimizu et al.
2008/0071269 A1 3/2008 Hilario et al.
2008/0077145 A1 3/2008 Boyden et al.
2008/0082039 A1 4/2008 Babaev
2008/0082098 A1 4/2008 Tanaka et al.
2008/0097501 A1 4/2008 Blier
2008/0114355 A1 5/2008 Whayne et al.
2008/0114364 A1 5/2008 Goldin et al.
2008/0122496 A1 5/2008 Wagner
2008/0125768 A1 5/2008 Tahara et al.
2008/0147058 A1 6/2008 Horrell et al.
2008/0147062 A1 6/2008 Truckai et al.
2008/0147092 A1 6/2008 Rogge et al.
2008/0161809 A1 7/2008 Schmitz et al.
2008/0167670 A1 7/2008 Shelton et al.
2008/0171938 A1 7/2008 Masuda et al.
2008/0177268 A1 7/2008 Daum et al.
2008/0188755 A1 8/2008 Hart
2008/0200940 A1 8/2008 Eichmann et al.
2008/0208108 A1 8/2008 Kimura
2008/0208231 A1 8/2008 Ota et al.
2008/0214967 A1 9/2008 Aranyi et al.
2008/0234709 A1 9/2008 Houser
2008/0243162 A1 10/2008 Shibata et al.
2008/0255413 A1 10/2008 Zemlok et al.
2008/0275440 A1 11/2008 Kratoska et al.
2008/0281200 A1 11/2008 Voic et al.
2008/0281315 A1 11/2008 Gines
2008/0287944 A1 11/2008 Pearson et al.
2008/0287948 A1 11/2008 Newton et al.

(56) References Cited

U.S. PATENT DOCUMENTS

2008/0296346 A1 12/2008 Shelton, IV et al.
2008/0300588 A1 12/2008 Groth et al.
2009/0012516 A1 1/2009 Curtis et al.
2009/0023985 A1 1/2009 Ewers
2009/0036913 A1 2/2009 Wiener et al.
2009/0043293 A1 2/2009 Pankratov et al.
2009/0048537 A1 2/2009 Lydon et al.
2009/0048589 A1 2/2009 Takashino et al.
2009/0054886 A1 2/2009 Yachi et al.
2009/0054889 A1 2/2009 Newton et al.
2009/0054894 A1 2/2009 Yachi
2009/0065565 A1 3/2009 Cao
2009/0076506 A1 3/2009 Baker
2009/0082716 A1 3/2009 Akahoshi
2009/0082766 A1 3/2009 Unger et al.
2009/0088745 A1 4/2009 Hushka et al.
2009/0088785 A1 4/2009 Masuda
2009/0090763 A1 4/2009 Zemlok et al.
2009/0101692 A1 4/2009 Whitman et al.
2009/0105750 A1 4/2009 Price et al.
2009/0112206 A1 4/2009 Dumbauld et al.
2009/0118751 A1 5/2009 Wiener et al.
2009/0131885 A1 5/2009 Akahoshi
2009/0131934 A1 5/2009 Odom et al.
2009/0138025 A1 5/2009 Stahler et al.
2009/0143678 A1 6/2009 Keast et al.
2009/0143799 A1 6/2009 Smith et al.
2009/0143800 A1 6/2009 Deville et al.
2009/0157064 A1 6/2009 Hodel
2009/0163807 A1 6/2009 Sliwa
2009/0177119 A1 7/2009 Heidner et al.
2009/0179923 A1 7/2009 Amundson et al.
2009/0182322 A1 7/2009 D'Amelio et al.
2009/0182331 A1 7/2009 D'Amelio et al.
2009/0182332 A1 7/2009 Long et al.
2009/0182333 A1 7/2009 Eder et al.
2009/0192441 A1 7/2009 Gelbart et al.
2009/0198272 A1 8/2009 Kerver et al.
2009/0204114 A1 8/2009 Odom
2009/0216157 A1 8/2009 Yamada
2009/0223033 A1 9/2009 Houser
2009/0240244 A1 9/2009 Malis et al.
2009/0248021 A1 10/2009 McKenna
2009/0248022 A1 10/2009 Falkenstein et al.
2009/0254077 A1 10/2009 Craig
2009/0254080 A1 10/2009 Honda
2009/0259149 A1 10/2009 Tahara et al.
2009/0264909 A1 10/2009 Beaupre
2009/0270771 A1 10/2009 Takahashi
2009/0270812 A1 10/2009 Litscher et al.
2009/0270853 A1 10/2009 Yachi et al.
2009/0270891 A1 10/2009 Beaupre
2009/0270899 A1 10/2009 Carusillo et al.
2009/0287205 A1 11/2009 Ingle
2009/0292283 A1 11/2009 Odom
2009/0299141 A1 12/2009 Downey et al.
2009/0306639 A1 12/2009 Nevo et al.
2009/0327715 A1 12/2009 Smith et al.
2010/0004508 A1 1/2010 Naito et al.
2010/0022825 A1 1/2010 Yoshie
2010/0030233 A1 2/2010 Whitman et al.
2010/0030248 A1* 2/2010 Palmer ........... A61B 17/320092
606/169
2010/0034605 A1 2/2010 Huckins et al.
2010/0036370 A1 2/2010 Mirel et al.
2010/0036373 A1 2/2010 Ward
2010/0042093 A9 2/2010 Wham et al.
2010/0049180 A1 2/2010 Wells et al.
2010/0057081 A1 3/2010 Hanna
2010/0057118 A1 3/2010 Dietz et al.
2010/0063437 A1 3/2010 Nelson et al.
2010/0063525 A1 3/2010 Beaupre et al.
2010/0063528 A1 3/2010 Beaupre
2010/0081863 A1 4/2010 Hess et al.
2010/0081864 A1 4/2010 Hess et al.
2010/0081883 A1 4/2010 Murray et al.
2010/0094323 A1 4/2010 Isaacs et al.
2010/0106173 A1 4/2010 Yoshimine
2010/0109480 A1 5/2010 Forslund et al.
2010/0145335 A1 6/2010 Johnson et al.
2010/0158307 A1 6/2010 Kubota et al.
2010/0168741 A1 7/2010 Sanai et al.
2010/0181966 A1 7/2010 Sakakibara
2010/0187283 A1 7/2010 Crainich et al.
2010/0193566 A1 8/2010 Scheib et al.
2010/0204721 A1 8/2010 Young et al.
2010/0222714 A1 9/2010 Muir et al.
2010/0222752 A1 9/2010 Collins, Jr. et al.
2010/0225209 A1 9/2010 Goldberg et al.
2010/0228249 A1 9/2010 Mohr et al.
2010/0228250 A1 9/2010 Brogna
2010/0234906 A1 9/2010 Koh
2010/0256635 A1 10/2010 McKenna et al.
2010/0274160 A1 10/2010 Yachi et al.
2010/0274278 A1 10/2010 Fleenor et al.
2010/0280368 A1 11/2010 Can et al.
2010/0298743 A1 11/2010 Nield et al.
2010/0305564 A1 12/2010 Livneh
2010/0331742 A1 12/2010 Masuda
2010/0331871 A1 12/2010 Nield et al.
2011/0004233 A1 1/2011 Muir et al.
2011/0015627 A1* 1/2011 DiNardo ............ A61B 18/1445
606/34
2011/0015632 A1 1/2011 Artale
2011/0015650 A1 1/2011 Choi et al.
2011/0022032 A1 1/2011 Zemlok et al.
2011/0028964 A1 2/2011 Edwards
2011/0071523 A1 3/2011 Dickhans
2011/0082494 A1 4/2011 Kerr et al.
2011/0106141 A1 5/2011 Nakamura
2011/0112400 A1 5/2011 Emery et al.
2011/0125149 A1 5/2011 El-Galley et al.
2011/0125151 A1 5/2011 Strauss et al.
2011/0144640 A1 6/2011 Heinrich et al.
2011/0160725 A1 6/2011 Kabaya et al.
2011/0238010 A1 9/2011 Kirschenman et al.
2011/0238079 A1 9/2011 Hannaford et al.
2011/0273465 A1 11/2011 Konishi et al.
2011/0278343 A1 11/2011 Knodel et al.
2011/0279268 A1 11/2011 Konishi et al.
2011/0284014 A1 11/2011 Cadeddu et al.
2011/0290856 A1 12/2011 Shelton, IV et al.
2011/0295295 A1 12/2011 Shelton, IV et al.
2011/0306967 A1 12/2011 Payne et al.
2011/0313415 A1 12/2011 Fernandez et al.
2012/0004655 A1 1/2012 Kim et al.
2012/0016413 A1 1/2012 Timm et al.
2012/0022519 A1 1/2012 Huang et al.
2012/0022526 A1 1/2012 Aldridge et al.
2012/0022528 A1 1/2012 White et al.
2012/0022583 A1 1/2012 Sugalski et al.
2012/0041358 A1 2/2012 Mann et al.
2012/0053597 A1 3/2012 Anvari et al.
2012/0059286 A1 3/2012 Hastings et al.
2012/0059289 A1 3/2012 Nield et al.
2012/0071863 A1 3/2012 Lee et al.
2012/0078244 A1 3/2012 Worrell et al.
2012/0080344 A1 4/2012 Shelton, IV
2012/0101493 A1 4/2012 Masuda et al.
2012/0101495 A1 4/2012 Young et al.
2012/0109186 A1 5/2012 Parrott et al.
2012/0116222 A1 5/2012 Sawada et al.
2012/0116265 A1 5/2012 Houser et al.
2012/0116266 A1 5/2012 Houser et al.
2012/0116381 A1 5/2012 Houser et al.
2012/0136279 A1 5/2012 Tanaka et al.
2012/0136347 A1 5/2012 Brustad et al.
2012/0136386 A1 5/2012 Kishida et al.
2012/0143182 A1 6/2012 Ullrich et al.
2012/0143211 A1 6/2012 Kishi
2012/0150049 A1 6/2012 Zielinski et al.
2012/0150169 A1 6/2012 Zielinksi et al.
2012/0172904 A1 7/2012 Muir et al.
2012/0191091 A1 7/2012 Allen

(56) References Cited

U.S. PATENT DOCUMENTS

2012/0193396 A1 8/2012 Zemlok et al.
2012/0211542 A1 8/2012 Racenet
2012/0226266 A1 9/2012 Ghosal et al.
2012/0234893 A1 9/2012 Schuckmann et al.
2012/0253328 A1 10/2012 Cunningham et al.
2012/0253329 A1 10/2012 Zemlok et al.
2012/0265241 A1 10/2012 Hart et al.
2012/0296239 A1 11/2012 Chernov et al.
2012/0296325 A1 11/2012 Takashino
2012/0296371 A1 11/2012 Kappus et al.
2013/0023925 A1 1/2013 Mueller
2013/0071282 A1 3/2013 Fry
2013/0085510 A1 4/2013 Stefanchik et al.
2013/0103031 A1 4/2013 Garrison
2013/0123776 A1 5/2013 Monson et al.
2013/0158659 A1 6/2013 Bergs et al.
2013/0158660 A1 6/2013 Bergs et al.
2013/0165929 A1 6/2013 Muir et al.
2013/0190760 A1 7/2013 Allen, IV et al.
2013/0214025 A1 8/2013 Zemlok et al.
2013/0253256 A1 9/2013 Griffith et al.
2013/0253480 A1 9/2013 Kimball et al.
2013/0264369 A1 10/2013 Whitman
2013/0267874 A1 10/2013 Marcotte et al.
2013/0277410 A1 10/2013 Fernandez et al.
2013/0296843 A1 11/2013 Boudreaux et al.
2013/0321425 A1 12/2013 Greene et al.
2013/0334989 A1 12/2013 Kataoka
2013/0345701 A1 12/2013 Allen, IV et al.
2014/0001231 A1 1/2014 Shelton, IV et al.
2014/0001234 A1 1/2014 Shelton, IV et al.
2014/0005640 A1 1/2014 Shelton, IV et al.
2014/0005663 A1 1/2014 Heard et al.
2014/0005678 A1 1/2014 Shelton, IV et al.
2014/0005702 A1 1/2014 Timm et al.
2014/0005705 A1 1/2014 Weir et al.
2014/0005718 A1 1/2014 Shelton, IV et al.
2014/0014544 A1 1/2014 Bugnard et al.
2014/0077426 A1 3/2014 Park
2014/0107538 A1 4/2014 Wiener et al.
2014/0121569 A1 5/2014 Schafer et al.
2014/0135804 A1 5/2014 Weisenburgh, II et al.
2014/0163541 A1 6/2014 Shelton, IV et al.
2014/0163549 A1 6/2014 Yates et al.
2014/0180274 A1 6/2014 Kabaya et al.
2014/0194868 A1 7/2014 Sanai et al.
2014/0194874 A1 7/2014 Dietz et al.
2014/0194875 A1 7/2014 Reschke et al.
2014/0207124 A1 7/2014 Aldridge et al.
2014/0207135 A1 7/2014 Winter
2014/0221994 A1 8/2014 Reschke
2014/0236152 A1 8/2014 Walberg et al.
2014/0246475 A1 9/2014 Hall et al.
2014/0249557 A1 9/2014 Koch, Jr. et al.
2014/0263541 A1 9/2014 Leimbach et al.
2014/0263552 A1 9/2014 Hall et al.
2014/0276794 A1 9/2014 Batchelor et al.
2014/0276797 A1 9/2014 Batchelor et al.
2014/0276798 A1 9/2014 Batchelor et al.
2014/0303605 A1 10/2014 Boyden et al.
2014/0303612 A1 10/2014 Williams
2014/0357984 A1 12/2014 Wallace et al.
2014/0373003 A1 12/2014 Grez et al.
2015/0014392 A1 1/2015 Williams et al.
2015/0025528 A1 1/2015 Arts
2015/0032150 A1 1/2015 Ishida et al.
2015/0048140 A1 2/2015 Penna et al.
2015/0066027 A1 3/2015 Garrison et al.
2015/0080876 A1 3/2015 Worrell et al.
2015/0080887 A1 3/2015 Sobajima et al.
2015/0080889 A1 3/2015 Cunningham et al.
2015/0088122 A1 3/2015 Jensen
2015/0100056 A1 4/2015 Nakamura
2015/0112335 A1 4/2015 Boudreaux et al.
2015/0119901 A1 4/2015 Steege
2015/0157356 A1 6/2015 Gee
2015/0164533 A1 6/2015 Felder et al.
2015/0164534 A1 6/2015 Felder et al.
2015/0164535 A1 6/2015 Felder et al.
2015/0164536 A1 6/2015 Czarnecki et al.
2015/0164537 A1 6/2015 Cagle et al.
2015/0230796 A1 8/2015 Calderoni
2015/0238260 A1 8/2015 Nau, Jr.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272657 A1 10/2015 Yates et al.
2015/0272659 A1 10/2015 Boudreaux et al.
2015/0282879 A1 10/2015 Ruelas
2015/0289364 A1 10/2015 Ilkko et al.
2015/0313667 A1 11/2015 Allen, IV
2015/0317899 A1 11/2015 Dumbauld et al.
2015/0351765 A1 12/2015 Valentine et al.
2015/0351857 A1 12/2015 Vander Poorten et al.
2015/0374430 A1 12/2015 Weiler et al.
2015/0374457 A1 12/2015 Colby
2016/0000437 A1 1/2016 Giordano et al.
2016/0038228 A1 2/2016 Daniel et al.
2016/0044841 A1 2/2016 Chamberlain
2016/0045248 A1 2/2016 Unger et al.
2016/0051314 A1 2/2016 Batchelor et al.
2016/0051316 A1 2/2016 Boudreaux
2016/0066913 A1 3/2016 Swayze et al.
2016/0120601 A1 5/2016 Boudreaux et al.
2016/0175025 A1 6/2016 Strobl
2016/0175029 A1 6/2016 Witt et al.
2016/0206342 A1 7/2016 Robertson et al.
2016/0228171 A1 8/2016 Boudreaux
2016/0249910 A1 9/2016 Shelton, IV et al.
2016/0262786 A1 9/2016 Madan et al.
2016/0270842 A1 9/2016 Strobl et al.
2016/0296251 A1 10/2016 Olson et al.
2016/0296252 A1 10/2016 Olson et al.
2016/0296270 A1 10/2016 Strobl et al.
2016/0317216 A1 11/2016 Hermes et al.
2016/0331455 A1 11/2016 Hancock et al.
2016/0358849 A1 12/2016 Jur et al.
2017/0020614 A1 1/2017 Jackson et al.
2017/0065331 A1 3/2017 Mayer et al.
2017/0086909 A1 3/2017 Yates et al.
2017/0119426 A1 5/2017 Akagane
2017/0135751 A1 5/2017 Rothweiler et al.
2017/0164972 A1 6/2017 Johnson et al.
2017/0164997 A1 6/2017 Johnson et al.
2017/0189095 A1 7/2017 Danziger et al.
2017/0202595 A1 7/2017 Shelton, IV
2017/0209145 A1 7/2017 Swayze et al.
2017/0224332 A1 8/2017 Hunter et al.
2017/0224405 A1 8/2017 Takashino et al.
2017/0231628 A1 8/2017 Shelton, IV et al.
2017/0281186 A1 10/2017 Shelton, IV et al.
2017/0296169 A1 10/2017 Yates et al.
2017/0296177 A1 10/2017 Harris et al.
2017/0296180 A1 10/2017 Harris et al.
2017/0303954 A1 10/2017 Ishii
2017/0312018 A1 11/2017 Trees et al.
2017/0325874 A1 11/2017 Noack et al.
2017/0333073 A1 11/2017 Faller et al.
2017/0348043 A1 12/2017 Wang et al.
2017/0348044 A1 12/2017 Wang et al.
2017/0367772 A1 12/2017 Gunn et al.
2018/0014872 A1 1/2018 Dickerson
2018/0085157 A1 3/2018 Batchelor et al.
2018/0132850 A1 5/2018 Leimbach et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.

(56) References Cited

U.S. PATENT DOCUMENTS

2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0188125 A1 7/2018 Park et al.
2018/0206904 A1 7/2018 Felder et al.
2018/0221045 A1 8/2018 Zimmerman et al.
2018/0250066 A1 9/2018 Ding et al.
2018/0271578 A1 9/2018 Coulombe
2018/0289432 A1 10/2018 Kostrzewski et al.
2018/0303493 A1 10/2018 Chapolini
2018/0325517 A1 11/2018 Wingardner et al.
2018/0333179 A1 11/2018 Weisenburgh et al.
2018/0353245 A1 12/2018 Mccloud et al.
2018/0368844 A1 12/2018 Bakos et al.
2019/0000459 A1 1/2019 Shelton, IV et al.
2019/0000461 A1 1/2019 Shelton, IV et al.
2019/0029746 A1 1/2019 Dudhedia et al.
2019/0038283 A1 2/2019 Shelton, IV et al.
2019/0053818 A1 2/2019 Nelson et al.
2019/0104919 A1 4/2019 Shelton, IV et al.
2019/0117293 A1 4/2019 Kano et al.
2019/0125361 A1 5/2019 Shelton, IV et al.
2019/0125384 A1 5/2019 Scheib et al.
2019/0125390 A1 5/2019 Shelton, IV et al.
2019/0175258 A1 6/2019 Tsuruta
2019/0183504 A1 6/2019 Shelton, IV et al.
2019/0200844 A1 7/2019 Shelton, IV et al.
2019/0200977 A1 7/2019 Shelton, IV et al.
2019/0200981 A1 7/2019 Harris et al.
2019/0200987 A1 7/2019 Shelton, IV et al.
2019/0201029 A1 7/2019 Shelton, IV et al.
2019/0201030 A1 7/2019 Shelton, IV et al.
2019/0201045 A1 7/2019 Yates et al.
2019/0201048 A1 7/2019 Stulen et al.
2019/0201104 A1 7/2019 Shelton, IV et al.
2019/0201594 A1 7/2019 Shelton, IV et al.
2019/0206564 A1 7/2019 Shelton, IV et al.
2019/0206569 A1 7/2019 Shelton, IV et al.
2019/0209201 A1 7/2019 Boudreaux et al.
2019/0223941 A1 7/2019 Kitamura et al.
2019/0269455 A1 9/2019 Mensch et al.
2019/0290265 A1 9/2019 Shelton, IV et al.
2019/0298353 A1 10/2019 Shelton, IV et al.
2019/0366562 A1 12/2019 Zhang et al.
2019/0388091 A1 12/2019 Eschbach et al.
2020/0054321 A1 2/2020 Harris et al.
2020/0078085 A1 3/2020 Yates et al.
2020/0078609 A1 3/2020 Messerly et al.
2020/0100825 A1 4/2020 Henderson et al.
2020/0113622 A1 4/2020 Honegger
2020/0129261 A1 4/2020 Eschbach
2020/0138473 A1 5/2020 Shelton, IV et al.
2020/0188047 A1 6/2020 Itkowitz et al.
2020/0222111 A1 7/2020 Yates et al.
2020/0222112 A1 7/2020 Hancock et al.
2020/0268430 A1 8/2020 Takei et al.
2020/0315623 A1 10/2020 Eisinger et al.
2020/0315712 A1 10/2020 Jasperson et al.
2020/0405302 A1 12/2020 Shelton, IV et al.
2020/0410177 A1 12/2020 Shelton, IV
2021/0100579 A1 4/2021 Shelton, IV et al.
2021/0153927 A1 5/2021 Ross et al.
2021/0177481 A1 6/2021 Shelton, IV et al.
2021/0177494 A1 6/2021 Houser et al.
2021/0177496 A1 6/2021 Shelton, IV et al.
2021/0186492 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0186553 A1 6/2021 Green et al.
2021/0186554 A1 6/2021 Green et al.
2021/0196266 A1 7/2021 Shelton, IV et al.
2021/0196267 A1 7/2021 Shelton, IV et al.
2021/0196268 A1 7/2021 Shelton, IV et al.
2021/0196269 A1 7/2021 Shelton, IV et al.
2021/0196270 A1 7/2021 Shelton, IV et al.
2021/0196302 A1 7/2021 Shelton, IV et al.
2021/0196305 A1 7/2021 Strobl
2021/0196306 A1 7/2021 Estera et al.
2021/0196307 A1 7/2021 Shelton, IV
2021/0196334 A1 7/2021 Sarley et al.
2021/0196335 A1 7/2021 Messerly et al.
2021/0196336 A1 7/2021 Faller et al.
2021/0196344 A1 7/2021 Shelton, IV et al.
2021/0196345 A1 7/2021 Messerly et al.
2021/0196346 A1 7/2021 Leuck et al.
2021/0196349 A1 7/2021 Fiebig et al.
2021/0196352 A1 7/2021 Messerly et al.
2021/0196353 A1 7/2021 Gee et al.
2021/0196354 A1 7/2021 Shelton, IV et al.
2021/0196357 A1 7/2021 Shelton, IV et al.
2021/0196358 A1 7/2021 Shelton, IV et al.
2021/0196359 A1 7/2021 Shelton, IV et al.
2021/0196361 A1 7/2021 Shelton, IV et al.
2021/0196362 A1 7/2021 Shelton, IV et al.
2021/0196363 A1 7/2021 Shelton, IV et al.
2021/0196364 A1 7/2021 Shelton, IV et al.
2021/0212754 A1 7/2021 Olson
2021/0220036 A1 7/2021 Shelton, IV et al.
2021/0236195 A1 8/2021 Asher et al.
2021/0282804 A1 9/2021 Worrell et al.
2021/0393288 A1 12/2021 Shelton, IV et al.
2021/0393314 A1 12/2021 Wiener et al.
2021/0393319 A1 12/2021 Shelton, IV et al.
2022/0071655 A1 3/2022 Price et al.
2022/0167982 A1 6/2022 Shelton, IV et al.
2022/0168005 A1 6/2022 Aldridge et al.
2022/0168039 A1 6/2022 Worrell et al.
2022/0226014 A1 7/2022 Clauda, IV et al.
2022/0304736 A1 9/2022 Boudreaux
2022/0313297 A1 10/2022 Aldridge et al.
2022/0346863 A1 11/2022 Yates et al.
2022/0387067 A1 12/2022 Faller et al.
2022/0406452 A1 12/2022 Shelton, IV
2023/0038162 A1 2/2023 Timm et al.
2023/0048996 A1 2/2023 Vakharia et al.
2023/0270486 A1 8/2023 Wiener et al.
2023/0277205 A1 9/2023 Olson et al.

FOREIGN PATENT DOCUMENTS

CN 1634601 A 7/2005
CN 1775323 A 5/2006
CN 1922563 A 2/2007
CN 2868227 Y 2/2007
CN 201029899 Y 3/2008
CN 101474081 A 7/2009
CN 101516285 A 8/2009
CN 101522112 A 9/2009
CN 102100582 A 6/2011
CN 102149312 A 8/2011
CN 202027624 U 11/2011
CN 102792181 A 11/2012
CN 103281982 A 9/2013
CN 103379853 A 10/2013
CN 203468630 U 3/2014
CN 104001276 A 8/2014
CN 104013444 A 9/2014
CN 104434298 A 3/2015
CN 107374752 A 11/2017
DE 3904558 A1 8/1990
DE 9210327 U1 11/1992
DE 4300307 A1 7/1994
DE 29623113 U1 10/1997
DE 20004812 U1 9/2000
DE 20021619 U1 3/2001
DE 10042606 A1 8/2001
DE 10201569 A1 7/2003
DE 102012109037 A1 4/2014
EP 0171967 A2 2/1986
EP 0336742 A2 10/1989

(56) References Cited

FOREIGN PATENT DOCUMENTS

| | | | |
|---|---|---|---|
| EP | 0136855 | B1 | 11/1989 |
| EP | 0705571 | A1 | 4/1996 |
| EP | 1698289 | A2 | 9/2006 |
| EP | 1862133 | A1 | 12/2007 |
| EP | 1972264 | A1 | 9/2008 |
| EP | 2060238 | A1 | 5/2009 |
| EP | 1747761 | B1 | 10/2009 |
| EP | 2131760 | A1 | 12/2009 |
| EP | 1214913 | B1 | 7/2010 |
| EP | 1946708 | B1 | 6/2011 |
| EP | 1767164 | B1 | 1/2013 |
| EP | 2578172 | A2 | 4/2013 |
| EP | 2668922 | A1 | 12/2013 |
| EP | 2076195 | B1 | 12/2015 |
| EP | 2510891 | B1 | 6/2016 |
| EP | 3476302 | A2 | 5/2019 |
| EP | 3476331 | A1 | 5/2019 |
| EP | 3694298 | A1 | 8/2020 |
| GB | 2032221 | A | 4/1980 |
| GB | 2317566 | A | 4/1998 |
| JP | S50100891 | A | 8/1975 |
| JP | S5968513 | U | 5/1984 |
| JP | S59141938 | A | 8/1984 |
| JP | S62221343 | A | 9/1987 |
| JP | S62227343 | A | 10/1987 |
| JP | S62292153 | A | 12/1987 |
| JP | S62292154 | A | 12/1987 |
| JP | S63109386 | A | 5/1988 |
| JP | S63315049 | A | 12/1988 |
| JP | H01151452 | A | 6/1989 |
| JP | H01198540 | A | 8/1989 |
| JP | H0271510 | U | 5/1990 |
| JP | H02286149 | A | 11/1990 |
| JP | H02292193 | A | 12/1990 |
| JP | H0337061 | A | 2/1991 |
| JP | H0425707 | U | 2/1992 |
| JP | H0464351 | A | 2/1992 |
| JP | H0430508 | U | 3/1992 |
| JP | H04152942 | A | 5/1992 |
| JP | H 0541716 | A | 2/1993 |
| JP | H0576482 | A | 3/1993 |
| JP | H0595955 | A | 4/1993 |
| JP | H05115490 | A | 5/1993 |
| JP | H0670938 | A | 3/1994 |
| JP | H06104503 | A | 4/1994 |
| JP | H0824266 | A | 1/1996 |
| JP | H08229050 | A | 9/1996 |
| JP | H08275951 | A | 10/1996 |
| JP | H08299351 | A | 11/1996 |
| JP | H08336545 | A | 12/1996 |
| JP | H09130655 | A | 5/1997 |
| JP | H09135553 | A | 5/1997 |
| JP | H09140722 | A | 6/1997 |
| JP | H105237 | A | 1/1998 |
| JP | 10127654 | A | 5/1998 |
| JP | H10295700 | A | 11/1998 |
| JP | H11128238 | A | 5/1999 |
| JP | H11169381 | A | 6/1999 |
| JP | 2000210299 | A | 8/2000 |
| JP | 2000271142 | A | 10/2000 |
| JP | 2000271145 | A | 10/2000 |
| JP | 2000287987 | A | 10/2000 |
| JP | 2001029353 | A | 2/2001 |
| JP | 2002059380 | A | 2/2002 |
| JP | 2002186901 | A | 7/2002 |
| JP | 2002263579 | A | 9/2002 |
| JP | 2002330977 | A | 11/2002 |
| JP | 2003000612 | A | 1/2003 |
| JP | 2003010201 | A | 1/2003 |
| JP | 2003116870 | A | 4/2003 |
| JP | 2003126104 | A | 5/2003 |
| JP | 2003126110 | A | 5/2003 |
| JP | 2003153919 | A | 5/2003 |
| JP | 2003339730 | A | 12/2003 |
| JP | 2004129871 | A | 4/2004 |
| JP | 2004147701 | A | 5/2004 |
| JP | 2005003496 | A | 1/2005 |
| JP | 2005027026 | A | 1/2005 |
| JP | 2005074088 | A | 3/2005 |
| JP | 2005337119 | A | 12/2005 |
| JP | 2006068396 | A | 3/2006 |
| JP | 2006081664 | A | 3/2006 |
| JP | 2006114072 | A | 4/2006 |
| JP | 2006217716 | A | 8/2006 |
| JP | 2006288431 | A | 10/2006 |
| JP | 2007037568 | A | 2/2007 |
| JP | 200801876 | A | 1/2008 |
| JP | 2008017876 | A | 1/2008 |
| JP | 200833644 | A | 2/2008 |
| JP | 2008188160 | A | 8/2008 |
| JP | D1339835 | S | 8/2008 |
| JP | 2009236177 | A | 10/2009 |
| JP | 2010009686 | A | 1/2010 |
| JP | 2010121865 | A | 6/2010 |
| JP | 2012071186 | A | 4/2012 |
| JP | 2012223582 | A | 11/2012 |
| JP | 2012235658 | A | 11/2012 |
| JP | 2013126430 | A | 6/2013 |
| KR | 100789356 | B1 | 12/2007 |
| KR | 101298237 | B1 | 8/2013 |
| RU | 2154437 | C1 | 8/2000 |
| RU | 22035 | U1 | 3/2002 |
| RU | 2201169 | C2 | 3/2003 |
| RU | 2405603 | C1 | 12/2010 |
| RU | 2013119977 | A | 11/2014 |
| SU | 850068 | A1 | 7/1981 |
| WO | WO-8103272 | A1 | 11/1981 |
| WO | WO-9308757 | A1 | 5/1993 |
| WO | WO-9314708 | A1 | 8/1993 |
| WO | WO-9421183 | A1 | 9/1994 |
| WO | WO-9424949 | A1 | 11/1994 |
| WO | WO-9639086 | A1 | 12/1996 |
| WO | WO-9712557 | A1 | 4/1997 |
| WO | WO-9800069 | A1 | 1/1998 |
| WO | WO-9840015 | A2 | 9/1998 |
| WO | WO-9920213 | A1 | 4/1999 |
| WO | WO-9923960 | A1 | 5/1999 |
| WO | WO-0024330 | A1 | 5/2000 |
| WO | WO-0064358 | A2 | 11/2000 |
| WO | WO-0128444 | A1 | 4/2001 |
| WO | WO-0167970 | A1 | 9/2001 |
| WO | WO-0172251 | A1 | 10/2001 |
| WO | WO-0195810 | A2 | 12/2001 |
| WO | WO-02080793 | A1 | 10/2002 |
| WO | WO-03095028 | A1 | 11/2003 |
| WO | WO-2004037095 | A2 | 5/2004 |
| WO | WO-2004078051 | A2 | 9/2004 |
| WO | WO-2004098426 | A1 | 11/2004 |
| WO | WO-2006091494 | A1 | 8/2006 |
| WO | WO-2007008710 | A2 | 1/2007 |
| WO | WO-2008118709 | A1 | 10/2008 |
| WO | WO-2008130793 | A1 | 10/2008 |
| WO | WO-2010027109 | A1 | 3/2010 |
| WO | WO-2010104755 | A1 | 9/2010 |
| WO | WO-2011008672 | A2 | 1/2011 |
| WO | WO-2011044343 | A2 | 4/2011 |
| WO | WO-2011052939 | A2 | 5/2011 |
| WO | WO-2011060031 | A1 | 5/2011 |
| WO | WO-2011092464 | A1 | 8/2011 |
| WO | WO-2012044606 | A2 | 4/2012 |
| WO | WO-2012061722 | A2 | 5/2012 |
| WO | WO-2012088535 | A1 | 6/2012 |
| WO | WO-2012150567 | A1 | 11/2012 |
| WO | WO-2016130844 | A1 | 8/2016 |
| WO | WO-2019130090 | A1 | 7/2019 |
| WO | WO-2019130113 | A1 | 7/2019 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

(56) References Cited

OTHER PUBLICATIONS

AST Products, Inc., "Principles of Video Contact Angle Analysis," 20 pages, (2006).
Campbell et al., "Thermal Imaging in Surgery," p. 19-3, in Medical Infrared Imaging, N. A. Diakides and J. D. Bronzino, Eds. (2008).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C.," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Covidien 501(k) Summary Sonicision, dated Feb. 24, 2011 (7 pages).
Covidien Brochure, [Value Analysis Brief], LigaSure Advance™ Pistol Grip, dated Rev. Apr. 2010 (7 pages).
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Covidien Brochure, The LigaSure Precise™ Instrument, dated Mar. 2011 (2 pages).
Covidien Brochure, The LigaSure™ 5 mm Blunt Tip Sealer/Divider Family, dated Apr. 2013 (2 pages).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Douglas, S.C. "Introduction to Adaptive Filter". Digital Signal Processing Handbook. Ed. Vijay K. Madisetti and Douglas B. Williams. Boca Raton: CRC Press LLC, 1999.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
F. A. Duck, "Optical Properties of Tissue Including Ultraviolet and Infrared Radiation," pp. 43-71 in Physical Properties of Tissue (1990).
Fowler, K.R., "A Programmable, Arbitrary Waveform Electrosurgical Device," IEEE Engineering in Medicine and Biology Society 10th Annual International Conference, pp. 1324, 1325 (1988).
Gerhard, Glen C., "Surgical Electrotechnology: Quo Vadis?," IEEE Transactions on Biomedical Engineering, vol. BME-31, No. 12, pp. 787-792, Dec. 1984.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Glaser and Subak-Sharpe, Integrated Circuit Engineering, Addison-Wesley Publishing, Reading, MA (1979). (book—not attached).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Graff, K.F., "Elastic Wave Propagation in a Curved Sonic Transmission Line," IEEE Transactions on Sonics and Ultrasonics, SU-17(1), 1-6 (1970).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
http://www.4-traders.com/JOHNSON-JOHNSON-4832/news/Johnson-Johnson-Ethicon-E . . . .
http://www.apicalinstr.com/generators.htm.
http://www.dotmed.com/listing/electrosurical-unit/ethicon/ultracision-g110-/1466724.
http://www.medicalexpo.com/medical-manufacturer/electrosurgical-generator-6951.html.
http://www.megadyne.com/es_generator.php.
http://www.valleylab.com/product/es/generators/index.html.
http:/www.ethicon.com/GB-en/healthcare-professionals/products/energy-devices/capital/ge . . . .
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Humphrey, J.D., "Continuum Thermomechanics and the Clinical Treatment of Disease and Injury," Appl. Mech. Rev., vol. 56, No. 2 pp. 231-260 (Mar. 2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Hörmann et al., "Reversible and irreversible denaturation of collagen fibers." Biochemistry, 10, pp. 932-937 (1971).
IEEE Std 802.3-2012 (Revision of IEEE Std 802.3-2008, published Dec. 28, 2012.
Incropera et al., Fundamentals of Heat and Mass Transfer, Wiley, New York (1990). (Book—not attached).
Jang, J. et al. "Neuro-fuzzy and Soft Computing." Prentice Hall, 1997, pp. 13-89, 199-293, 335-393, 453-496, 535-549.
Kurt Gieck & Reiner Gieck, *Engineering Formulas* § Z.7 (7th ed. 1997).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Lee et al., "A multi-sample denaturation temperature tester for collagenous biomaterials," Med. Eng. Phy., vol. 17, No. 2, pp. 115-121 (Mar. 1995).
Leonard I. Malis, M.D., "The Value of Irrigation During Bipolar Coagulation," 1989.
Lim et al., "A Review of Mechanism Used in Laparoscopic Surgical Instruments," Mechanism and Machine Theory, vol. 38, pp. 1133-1147, (2003).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Missinne, et al. "Stretchable Optical Waveguides," vol. 22, No. 4, Feb. 18, 2014, pp. 4168-4179 (12 pages).
Moraleda et al., A Temperature Sensor Based on a Polymer Optical Fiber Macro-Bend, Sensors 2013, 13, 13076-13089, doi: 10.3390/s131013076, ISSN 1424-8220.
Moran et al., "Thermally Induced Shrinkage of Joint Capsule," Clinical Orthopaedics and Related Research, No. 281, pp. 248-255 (Dec. 2000).
Morley, L. S. D., "Elastic Waves in a Naturally Curved Rod," Quarterly Journal of Mechanics and Applied Mathematics, 14: 155-172 (1961).
National Semiconductors Temperature Sensor Handbook—http://www.national.com/appinfo/tempsensors/files/temphb.pdf; accessed online: Apr. 1, 2011.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

(56) References Cited

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Technology Overview, printed from www.harmonicscalpel.com, Internet site, website accessed on Jun. 13, 2007, (3 pages).
Wall et al., "Thermal modification of collagen," J Shoulder Elbow Surg, No. 8, pp. 339-344 (Jul./Aug. 1999).
Walsh, S. J., White, R. G., "Vibrational Power Transmission in Curved Beams," Journal of Sound and Vibration, 233(3), 455-488 (2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.
International Search Report and Written Opinion received for PCT Application No. PCT/US2013/045820 mailed on Oct. 9, 2013, 14 pages.
U.S. Appl. No. 13/751,680, filed Jan. 28, 2013, 27 pages.

* cited by examiner

CLOSED FEEDBACK CONTROL FOR ELECTROSURGICAL DEVICE

CROSS-REFERENCE TO RELATED APPLICATIONS

The present application is a continuation application claiming priority under 35 U.S.C. § 120 to U.S. patent application Ser. No. 16/732,853, entitled CLOSED FEEDBACK CONTROL FOR ELECTROSURGICAL DEVICE, now U.S. Pat. Application Publication No. 2020/0222135, which is a continuation application claiming priority under 35 U.S.C. § 120 to U.S. patent application Ser. No. 15/613,838, filed Jun. 5, 2017, entitled CLOSED FEEDBACK CONTROL FOR ELECTROSURGICAL DEVICE, now U.S. Pat. No. 10,524,872, which is a continuation application claiming priority under 35 U.S.C. § 120 to U.S. patent application Ser. No. 14/987,161, filed Jan. 4, 2016, entitled CLOSED FEEDBACK CONTROL FOR ELECTROSURGICAL DEVICE, now U.S. Pat. No. 9,713,507, which is a continuation application claiming priority under 35 U.S.C. § 120 to U.S. patent application Ser. No. 13/539,117, filed Jun. 29, 2012, entitled CLOSED FEEDBACK CONTROL FOR ELECTROSURGICAL DEVICE, now U.S. Pat. No. 9,226,767, the entire disclosures of which are hereby incorporated by reference herein.

The present application is related to the following U.S. Patent Applications, filed Jun. 29, 2012, which are incorporated herein by reference in their entirety:

U.S. patent application Ser. No. 13/539,096, entitled HAPTIC FEEDBACK DEVICES FOR SURGICAL ROBOT, now U.S. Pat. No. 9,198,714;

U.S. patent application Ser. No. 13/539,110, entitled LOCKOUT MECHANISM FOR USE WITH ROBOTIC ELECTROSURGICAL DEVICE, now U.S. Pat. No. 9,326,788;

U.S. patent application Ser. No. 13/538,588, entitled SURGICAL INSTRUMENTS WITH ARTICULATING SHAFTS, now U.S. Pat. No. 9,393,037;

U.S. patent application Ser. No. 13/538,601, entitled ULTRASONIC SURGICAL INSTRUMENTS WITH DISTALLY POSITIONED TRANSDUCERS, now U.S. Patent Application Publication No. 2014/0005702;

U.S. patent application Ser. No. 13/538,700, entitled SURGICAL INSTRUMENTS WITH ARTICULATING SHAFTS, now U.S. Pat. No. 9,408,622;

U.S. patent application Ser. No. 13/538,711, entitled ULTRASONIC SURGICAL INSTRUMENTS WITH DISTALLY POSITIONED JAW ASSEMBLIES, now U.S. Pat. No. 9,351,754;

U.S. patent application Ser. No. 13/538,720, entitled SURGICAL INSTRUMENTS WITH ARTICULATING SHAFTS, now U.S. Patent Application Publication No. 2014/0005705;

U.S. patent application Ser. No. 13/538,733, entitled ULTRASONIC SURGICAL INSTRUMENTS WITH CONTROL MECHANISMS, now U.S. Patent Application Publication No. 2014/0005681; and U.S. patent application Ser. No. 13/539,122, entitled SURGICAL INSTRUMENTS WITH FLUID MANAGEMENT SYSTEM, now U.S. Pat. No. 9,283,045.

BACKGROUND

The present disclosure relates generally to the field of robotic surgery. In particular, the present disclosure relates to, although not exclusively, electrosurgical instruments.

More particularly, the present disclosure relates to, although not exclusively, a feedback control for an electrosurgical device.

Ultrasonic surgical devices, such as ultrasonic scalpels, are used in many applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device comprises a proximally-positioned ultrasonic transducer and an instrument coupled to the ultrasonic transducer having a distally-mounted end effector comprising an ultrasonic blade to cut and seal tissue. The end effector is typically coupled either to a handle and/or a robotic surgical implement via a shaft. The blade is acoustically coupled to the transducer via a waveguide extending through the shaft. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a haemostatic seal. A surgeon can control the cutting speed and coagulation by the force applied to the tissue by the end effector, the time over which the force is applied and the selected excursion level of the end effector.

Also used in many surgical applications are electrosurgical devices. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

SUMMARY

Various example embodiments are directed towards systems for closed feedback control of electrosurgical instruments. In one embodiment a robotic surgical system comprises a surgical instrument comprising an end effector comprising (i) a blade, (ii) a first jaw member including a first electrode, and (iii) a second jaw member including a second electrode, wherein the first electrode and the second electrode are configured to receive an electrosurgical energy signal. The robotic surgical system may also comprise a motor to slideably translate the blade within the end effector and a control circuit configured to: (i) produce control signals comprising a first control signal and a second control signal, (ii) deliver the electrosurgical energy signal to the first electrode and the second electrode via the first control signal, (iii) deliver a drive signal to the motor via the second control signal (iv) receive at least one feedback signal indicative of a characteristic of tissue clamped between the first jaw member and the second jaw member, (v) determine a rate of change based on a first feedback signal of the at least one feedback signal, and (vi) maintain the rate of change at a predetermined rate or within a predetermined range.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIGS. 43-46A illustrate an alternate embodiment of the instrument mounting portion showing an alternate example mechanism for differential translation of members along the axis of the shaft (e.g., for articulation).

DESCRIPTION

Figure 1:
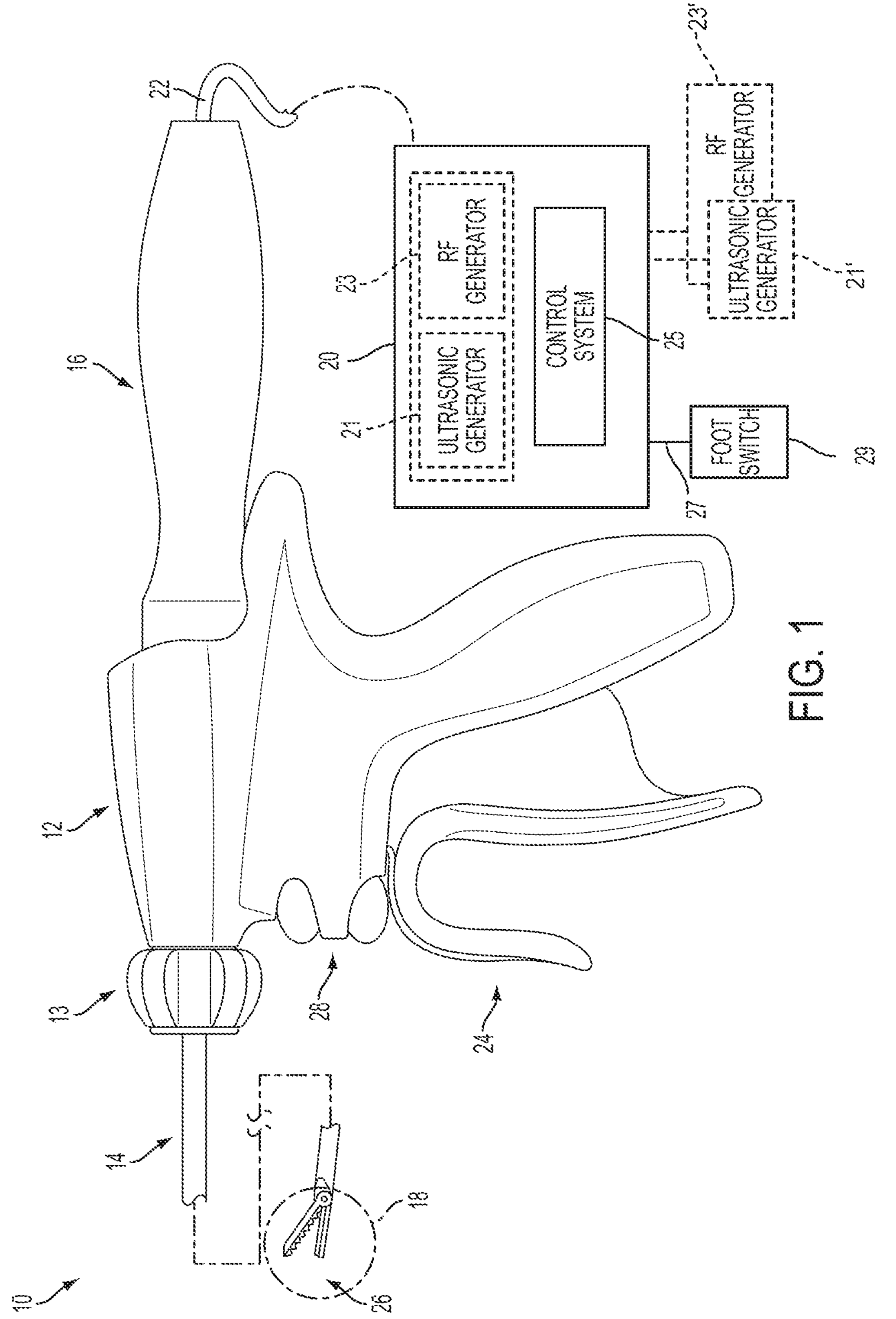
FIG. 1 illustrates one embodiment of a surgical system including a surgical instrument and an ultrasonic generator.

Various example embodiments are directed towards a system and method for closed feedback control of a robotically controlled electrosurgical instrument. In one embodiment, the method comprises applying at least one electrosurgical signal to an electrosurgical end effector a robotically controlled surgical instrument. A feedback signal may be generated by the electrosurgical end effector and provided to a control logic. The control logic may be configured to determine a rate of change of the impedance of a target tissue based on the feedback signal received from the electrosurgical end effector. The control logic may be configured to control or modify the at least one electrosurgical signal such that the rate of change of impedance determined from the feedback signal is maintained at a predetermined rate or within a predetermined range.

Various example embodiments are directed towards modifying an electrosurgical drive signal. The drive signal may be configured to control a movement of an electrosurgical blade along a longitudinal axis of the electrosurgical end effector. The drive signal may be controlled by the control logic to adjust the speed of the electrosurgical blade. By altering the speed of the electrosurgical blade, the controller may maintain a rate of increase of impedance of a target tissue at a predetermined rate or within a predetermined range.

Other example embodiments are directed towards modifying an electrosurgical signal delivered to the electrosurgical end effector for treatment of the target tissue. Electrosurgical signals delivered to the electrosurgical end effector may include ultrasonic or radiofrequency (RF) signals. In one embodiment, an ultrasonic signal is applied to the electrosurgical blade to impart ultrasonic motion to the electrosurgical blade. In an another embodiment, a RF signal is applied to first and second electrodes located on the electrosurgical end effector to transfer the RF signal to the target tissue to cause welding of the target tissue. In yet another embodiment, both ultrasonic and RF energy may be applied to the electrosurgical end effector. The electrosurgical signal may be modified by the control logic to maintain a rate of increase of impedance of the target tissue at a predetermined rate or within a predetermined range.

Reference will now be made in detail to several embodiments, including embodiments showing example implementations of manual and robotic surgical instruments with end effectors comprising ultrasonic and/or electrosurgical elements. Wherever practicable similar or like reference numbers may be used in the figures and may indicate similar or like functionality. The figures depict example embodiments of the disclosed surgical instruments and/or methods of use for purposes of illustration only. One skilled in the art will readily recognize from the following description that alternative example embodiments of the structures and methods illustrated herein may be employed without departing from the principles described herein.

FIG. 1 is a right side view of one embodiment of an ultrasonic surgical instrument 10. In the illustrated embodiment, the ultrasonic surgical instrument 10 may be employed in various surgical procedures including endoscopic or traditional open surgical procedures. In one example embodiment, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures. For the purposes herein, the ultrasonic surgical instrument 10 is described in terms of an endoscopic instrument; however, it is contemplated that open and/or laparoscopic versions of the ultrasonic surgical instrument 10 also may include the same or similar operating components and features as described herein.

Figure 18A:
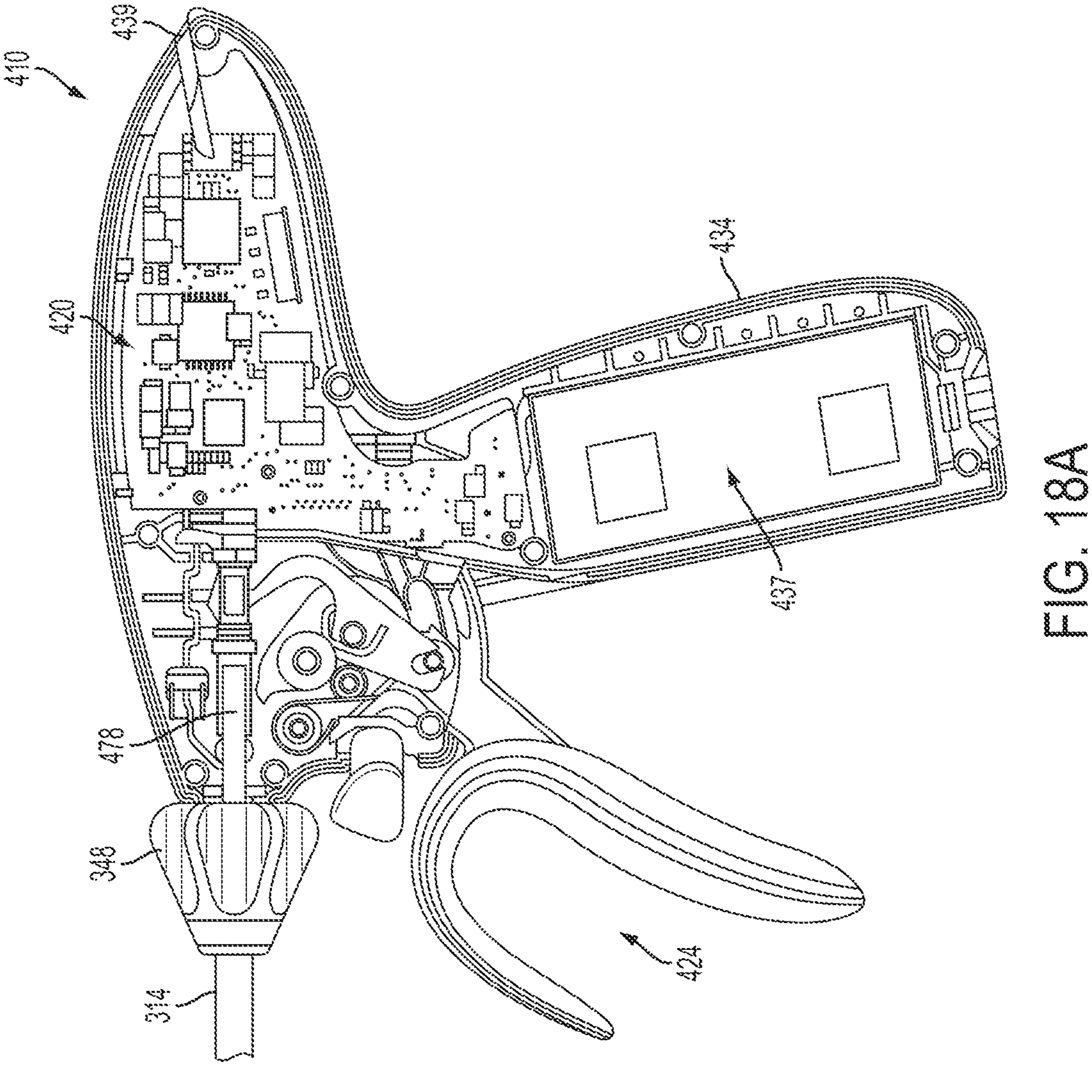
FIG. 18A illustrates a side view of a handle of one embodiment of the surgical instrument of FIG. 17 with a half handle body removed to illustrate various components therein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In various embodiments, the generator 20 may be formed integrally within the handle assembly 12. In such implementations, a battery would be co-located within the handle assembly 12 to act as the energy source. FIG. 18A and accompanying disclosures provide one example of such implementations. As shown in FIG. 1, according to various embodiments, the ultrasonic generator module 21 and/or the electrosurgery/RF generator module 23 may be located external to the generator (shown in phantom as ultrasonic generator module 21' and electrosurgery/RF generator module 23'.

In some embodiments, the electrosurgery/RF generator module 23 may be configured to generate a therapeutic and/or sub-therapeutic energy level. In the example embodiment illustrated in FIG. 1, the generator 20 includes a control system 25 integral with the generator 20 and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level. The generator 20 drives or excites the acoustic assembly at any suitable resonant frequency of the acoustic assembly and/or derives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a sub-therapeutic RF signal to implement a tissue impedance measurement module. In one embodiment, the electrosurgical/RF generator module 23 comprises a bipolar radio frequency generator as described in more detail below. In one embodiment, the electrosurgical/RF generator module 12 may be configured to monitor electrical impedance Z, of tissue T and to control the characteristics of time and power level based on the tissue T by way of a return electrode on provided on a clamp member of the end effector assembly 26. Accordingly, the electrosurgical/RF generator module 23 may be configured for sub-therapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, entitled ELECTROSURGICAL GENERATOR FOR ULTRASONIC SURGICAL INSTRUMENTS, the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,679,899 (Method for Detecting Transverse Vibrations in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

It will be appreciated that in various embodiments, the generator 20 may be configured to operate in several modes. In one mode, the generator 20 may be configured such that the ultrasonic generator module 21 and the electrosurgical/RF generator module 23 may be operated independently. One example of the independent operations of the ultrasonic generator module 21 and the electrosurgical/RF generator module 23 from the generator 20 is shown in FIG. 1, with the modules 21 and 23 optionally placed outside of and coupled to the generator 20.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the subtherapeutic electrosurgical/RF energy may be applied to tissue clamped between claim elements of the end effector assembly 26 to measure tissue impedance to control the activation, or modify the activation, of the ultrasonic generator module 21. Tissue impedance feedback from the application of the subtherapeutic energy also may be employed to activate a therapeutic level of the electrosurgical/RF generator module 23 to seal the tissue (e.g., vessel) clamped between claim elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel).

When the generator 20 is activated via the triggering mechanism, in one embodiment electrical energy is continuously applied by the generator 20 to a transducer stack or assembly of the acoustic assembly. In another embodiment, electrical energy is intermittently applied (e.g., pulsed) by the generator 20. A phase-locked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a preselected constant level in order to achieve substantially constant excursion at the end effector 18 of the acoustic assembly. In yet another embodiment, a third feedback loop in the control system 25 monitors impedance between electrodes located in the end effector assembly 26. Although FIGS. 1-9 show a manually operated ultrasonic surgical instrument, it will be appreciated that ultrasonic surgical instruments may also be used in robotic applications, for example, as described herein as well as combinations of manual and robotic applications.

In ultrasonic operation mode, the electrical signal supplied to the acoustic assembly may cause the distal end of the end effector 18, to vibrate longitudinally in the range of, for example, approximately 20 kHz to 250 kHz. According to various embodiments, the blade 22 may vibrate in the range of about 54 kHz to 56 kHz, for example, at about 55.5 kHz. In other embodiments, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

Figure 2:
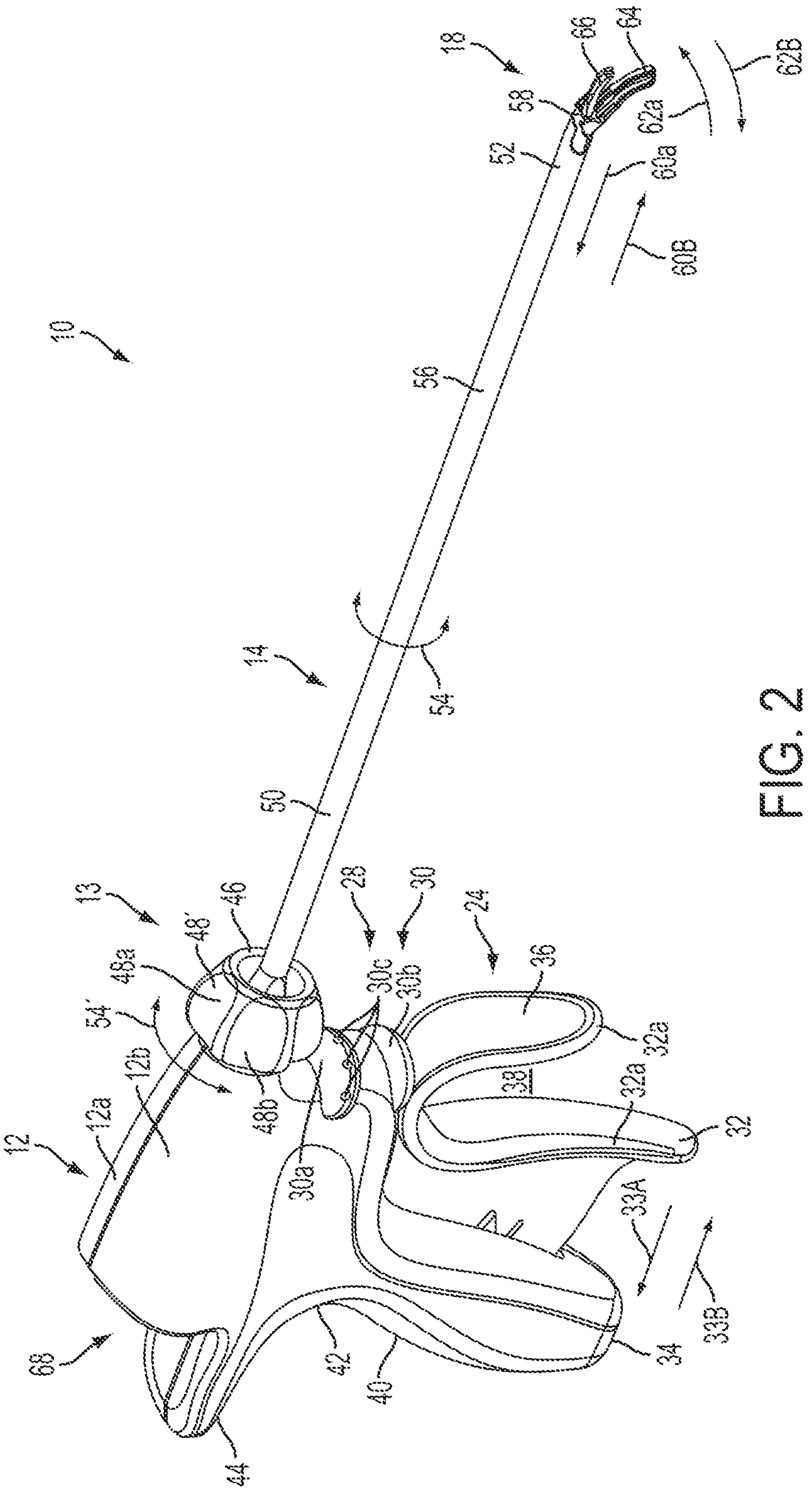
FIG. 2 illustrates one embodiment of the surgical instrument shown in FIG. 1.

FIG. 2 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated endoscopic shaft assembly 14 is received within the handle assembly 12 and the distal rotation assembly 13. More details relating to the connections between the elongated shaft assembly 14, the handle assembly 12, and the distal rotation assembly 13 are provided in the description of FIGS. 5 and 7.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element 98 (FIG. 5) causes the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32*a* molded over the trigger 32 substrate. The overmolded resilient portion 32*a* is formed to provide a more comfortable contact surface for control of the trigger 32 in outward direction 33B. In one example embodiment, the overmolded resilient portion 32*a* may be provided over a portion of the elongated trigger hook 36. The proximal surface of the elongated trigger hook 32 remains uncoated or coated with a non-resilient substrate to enable the user to easily slide their fingers in and out of the aperture 38. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob 30*a* and a second projecting knob 30*b* to set the power setting of the ultrasonic transducer 16 between a minimum power level (e.g., MIN) and a maximum power level (e.g., MAX). In another embodiment, the rocker switch may pivot between a standard setting and a special setting. The special setting may allow one or more special programs to be implemented by the device. The toggle switch 30 rotates about the central pivot as the first projecting knob 30*a* and the second projecting knob 30*b* are actuated. The one or more projecting knobs 30*a*, 30*b* are coupled to one or more arms that move through a small arc and cause electrical contacts to close or open an electric circuit to electrically energize or de-energize the ultrasonic transducer 16 in accordance with the activation of the first or second projecting knobs 30*a*, 30*b*. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example embodiment, the first and second projecting knobs 30*a*, 30*b* are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30*a*, 30*b* may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30*a* comprises a plurality of tactile elements 30*c*, e.g., textured projections or "bumps" in the illustrated embodiment, to allow the user to differentiate the first projecting knob 30*a* from the second projecting knob 30*b*. It will be appreciated by those skilled in the art that several ergonomic features may be incorporated into the handle assembly 12. Such ergonomic features are described in U.S. Pat. No. 8,623,027 entitled "Ergonomic Surgical Instruments" which is incorporated by reference herein in its entirety.

In one example embodiment, the toggle switch 30 may be operated by the hand of the user. The user may easily access the first and second projecting knobs 30*a,* 30*b* at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30*a* to turn on the ultrasonic assembly 16 to a maximum (MAX) power level. The index finger may be employed to activate the second contact portion 30*b* to turn on the ultrasonic assembly 16 to a minimum (MIN) power level. In another embodiment, the rocker switch may pivot the instrument 10 between a standard setting and a special setting. The special setting may allow one or more special programs to be implemented by the instrument 10. The toggle switch 30 may be operated without the user having to look at the first or second projecting knob 30*a,* 30*b.* For example, the first projecting knob 30*a* or the second projecting knob 30*b* may comprise a texture or projections to tactilely differentiate between the first and second projecting knobs 30*a,* 30*b* without looking.

In other embodiments, the trigger 32 and/or the toggle switch 30 may be employed to actuate the electrosurgical/RF generator module 23 individually or in combination with activation of the ultrasonic generator module 21.

In one example embodiment, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46*a* that is exposed at the distal end. The end cap portion 46*a* of the hub 46 may contact the surface of a trocar during laparoscopic procedures. The hub 46 may be formed of a hard durable plastic such as polycarbonate to alleviate any friction that may occur between the end cap portion 46*a* and the trocar. The rotation knob 48 may comprise "scallops" or flutes formed of raised ribs 48*a* and concave portions 48*b* located between the ribs 48*a* to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12*a* and a second portion 12*b.* From the perspective of a user viewing the handle assembly 12 from the distal end towards the proximal end, the first portion 12*a* is considered the right portion and the second portion 12*b* is considered the left portion. Each of the first and second portions 12*a,* 12*b* includes a plurality of interfaces 69 (FIG. 7) dimensioned to mechanically align and engage each another to form the handle assembly 12 and enclosing the internal working components thereof. The fixed handle 34, which is integrally associated with the handle assembly 12, takes shape upon the assembly of the first and second portions 12*a* and 12*b* of the handle assembly 12. A plurality of additional interfaces (not shown) may be disposed at various points around the periphery of the first and second portions 12*a* and 12*b* of the handle assembly 12 for ultrasonic welding purposes, e.g., energy direction/deflection points. The first and second portions 12*a* and 12*b* (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example embodiment, the elongated endoscopic shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp arm assembly 64, which is pivotable about a pivot point 70, to open and close the clamp arm assembly 64 in response to the actuation and/or release of the trigger 32. For example, in the illustrated embodiment, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp arm assembly 64 and a blade 66. The jaws of the clamping mechanism of the end effector assembly 26 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad (not shown) to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example embodiment, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 36 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 5) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

Figure 3:
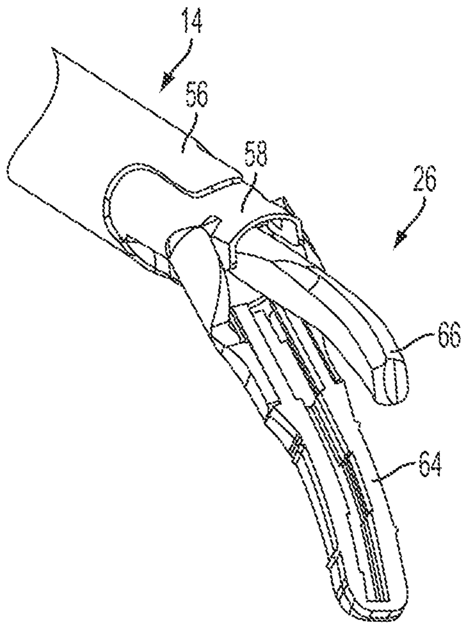
FIG. 3 illustrates one embodiment of an ultrasonic end effector.
Figure 4:
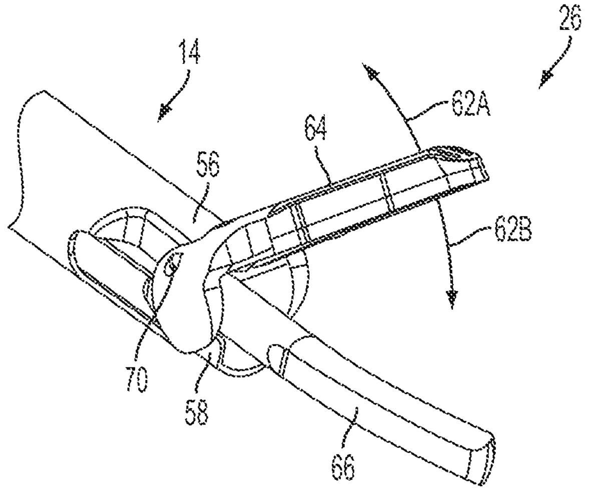
FIG. 4 illustrates another embodiment of an ultrasonic end effector.

FIGS. 3-4 illustrate the connection of the elongated endoscopic shaft assembly 14 relative to the end effector assembly 26. As previously described, in the illustrated embodiment, the end effector assembly 26 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad (not shown) to engage tissue between the blade 66 and the clamp arm 64. The distal end of the tubular reciprocating tubular actuating member 58 is mechanically engaged to the end effector assembly 26. In the illustrated embodiment, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated embodiment, the clamp arm assembly 64 is movable from an open position to a closed position in direction 62B about a pivot point 70 when the trigger 32 is squeezed in direction 33A. The clamp arm assembly 64 is movable from a closed position to an open position in direction 62B about the pivot point 70 when the trigger 32 is released or outwardly contacted in direction 33B.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non-simultaneously with the ultrasonic energy being applied to the blade 66. Such energy activations may be applied in any suitable combination to achieve a desired tissue effect in cooperation with an algorithm or other control logic.

Figure 5:
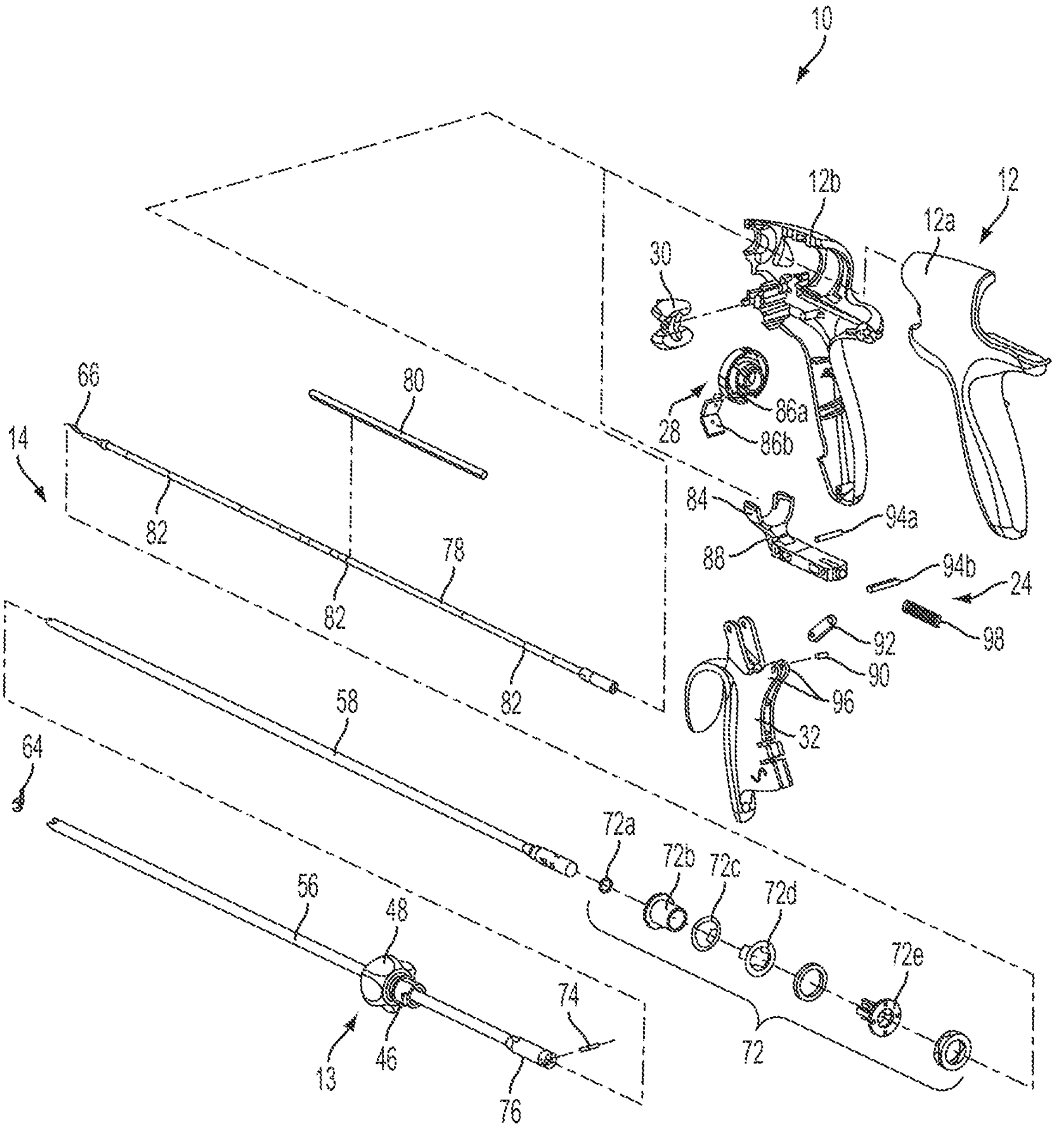
FIG. 5 illustrates an exploded view of one embodiment of the surgical instrument shown in FIG. 1.
Figure 7:
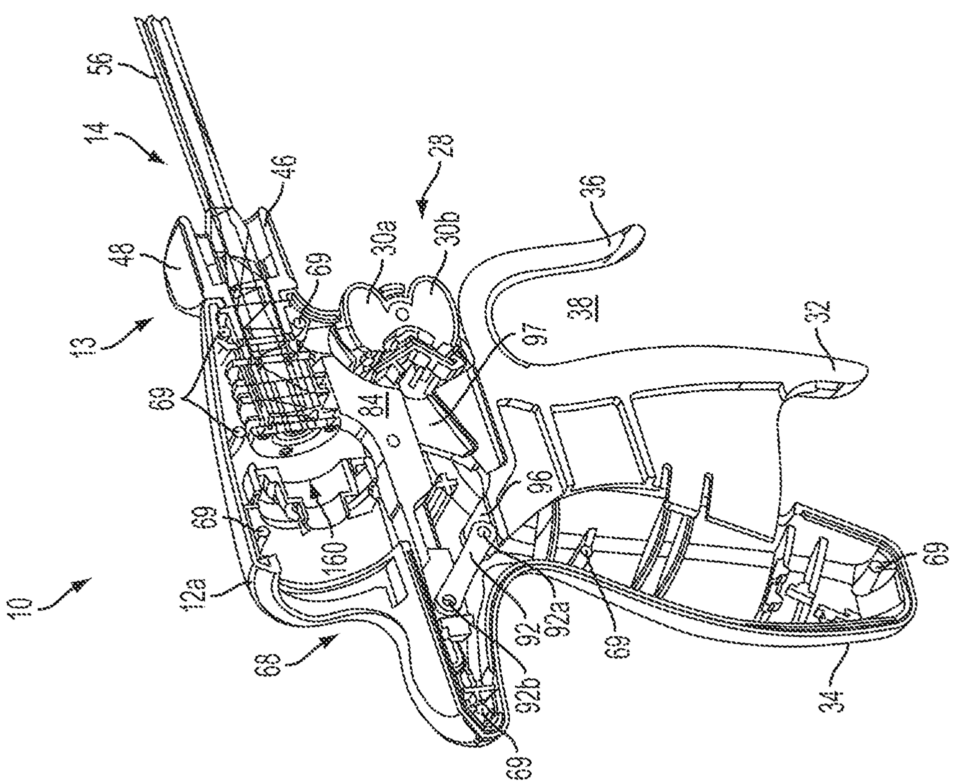
FIG. 7 illustrates various internal components of one example embodiment of the surgical instrument shown in FIG. 1
Figure 6:
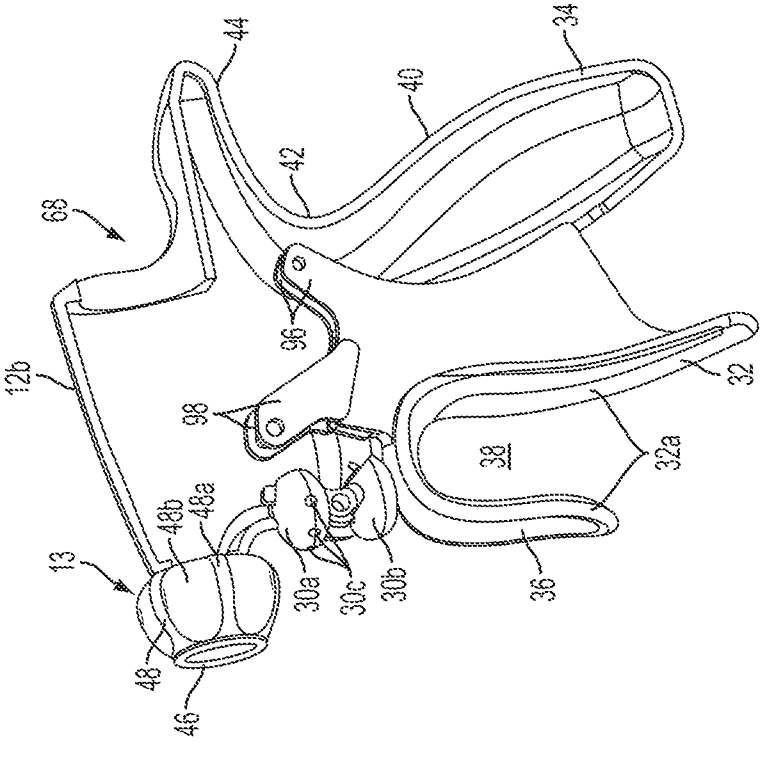
FIG. 6 illustrates a cut-away view of one embodiment of the surgical instrument shown in FIG. 1.

FIG. 5 is an exploded view of the ultrasonic surgical instrument 10 shown in FIG. 2. In the illustrated embodiment, the exploded view shows the internal elements of the handle assembly 12, the handle assembly 12, the distal rotation assembly 13, the switch assembly 28, and the elongated shaft assembly 14. In the illustrated embodiment, the first and second portions 12*a*, 12*b* mate to form the handle assembly 12. The first and second portions 12*a*, 12*b* each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72*a*, a tube collar cap 72*b*, a distal washer 72*c*, a proximal washer 72*d*, and a thread tube collar 72*e*. The reciprocating tubular actuating member 58 is located within a reciprocating yoke 84, which is retained between the first and second portions 12*a*, 12*b* of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example embodiment, a four-link design provides mechanical advantage in a relatively short rotation span, for example.

In one example embodiment, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16 as discussed in more detail below. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86*a,b* to electrically energize the ultrasonic transducer 16 in accordance with the activation of the first or second projecting knobs 30*a,* 30*b*.

In one example embodiment, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 78 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 may allow the assembly to be torqued to a required level. In one example embodiment, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example embodiment, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example embodiment, the trigger 32 is coupled to a linkage mechanism to translate the rotational motion of the trigger 32 in directions 33A and 33B to the linear motion of the reciprocating tubular actuating member 58 in corresponding directions 60A and 60B. The trigger 32 comprises a first set of flanges 97 with openings formed therein to receive a first yoke pin 94*a*. The first yoke pin 94*a* is also located through a set of openings formed at the distal end of the yoke 84. The trigger 32 also comprises a second set of flanges 96 to receive a first end 92*a* of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12*a,* 12*b* of the handle assembly 12 to form a trigger pivot point for the trigger 32. A second end 92*b* of the link 92 is received in a slot 93 formed in a proximal end of the yoke 84 and is retained therein by a second yoke pin 94*b*. As the trigger 32 is pivotally rotated about the pivot point 190 formed by the trigger pin 90, the yoke translates horizontally along longitudinal axis "T" in a direction indicated by arrows 60A,B.

Figure 8:
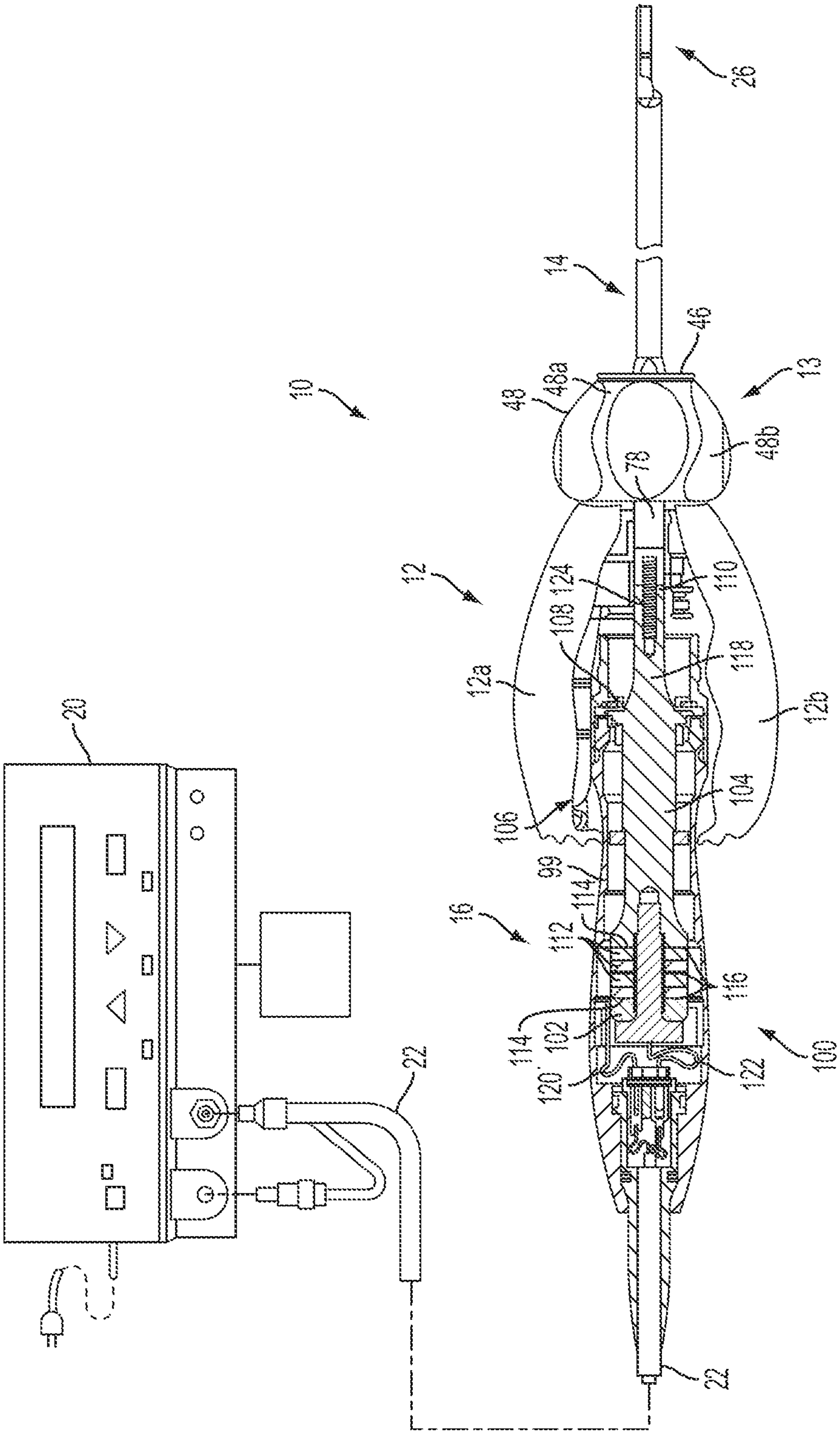
FIG. 8 illustrates a top view of one embodiment of a surgical system including a surgical instrument and an ultrasonic generator.

FIG. 8 illustrates one example embodiment of an ultrasonic surgical instrument 10. In the illustrated embodiment, a cross-sectional view of the ultrasonic transducer 16 is shown within a partial cutaway view of the handle assembly 12. One example embodiment of the ultrasonic surgical instrument 10 comprises the ultrasonic signal generator 20 coupled to the ultrasonic transducer 16, comprising a hand piece housing 99, and an ultrasonically actuatable single or multiple element end effector assembly 26. As previously discussed, the end effector assembly 26 comprises the ultrasonically actuatable blade 66 and the clamp arm 64. The ultrasonic transducer 16, which is known as a "Langevin stack", generally includes a transduction portion 100, a first resonator portion or end-bell 102, and a second resonator portion or fore-bell 104, and ancillary components. The total construction of these components is a resonator. The ultrasonic transducer 16 is preferably an integral number of one-half system wavelengths ($n\lambda/2$; where "n" is any positive integer; e.g., n=1, 2, 3 . . . ) in length as will be described in more detail later. An acoustic assembly 106 includes the ultrasonic transducer 16, a nose cone 108, a velocity transformer 118, and a surface 110.

In one example embodiment, the distal end of the end-bell 102 is connected to the proximal end of the transduction portion 100, and the proximal end of the fore-bell 104 is connected to the distal end of the transduction portion 100. The fore-bell 104 and the end-bell 102 have a length determined by a number of variables, including the thickness of the transduction portion 100, the density and modulus of elasticity of the material used to manufacture the end-bell 102 and the fore-bell 22, and the resonant frequency of the ultrasonic transducer 16. The fore-bell 104 may be tapered inwardly from its proximal end to its distal end to amplify the ultrasonic vibration amplitude as the velocity transformer 118, or alternately may have no amplification. A suitable vibrational frequency range may be about 20 Hz to 32 kHz and a well-suited vibrational frequency range may be about 30-10 kHz. A suitable operational vibrational frequency may be approximately 55.5 kHz, for example.

In one example embodiment, the piezoelectric elements 112 may be fabricated from any suitable material, such as, for example, lead zirconate-titanate, lead meta-niobate, lead titanate, barium titanate, or other piezoelectric ceramic material. Each of positive electrodes 114, negative electrodes 116, and the piezoelectric elements 112 has a bore extending through the center. The positive and negative electrodes 114 and 116 are electrically coupled to wires 120 and 122, respectively. The wires 120 and 122 are encased within the cable 22 and electrically connectable to the ultrasonic signal generator 20.

The ultrasonic transducer 16 of the acoustic assembly 106 converts the electrical signal from the ultrasonic signal generator 20 into mechanical energy that results in primarily a standing acoustic wave of longitudinal vibratory motion of the ultrasonic transducer 16 and the blade 66 portion of the end effector assembly 26 at ultrasonic frequencies. In another embodiment, the vibratory motion of the ultrasonic transducer may act in a different direction. For example, the vibratory motion may comprise a local longitudinal component of a more complicated motion of the tip of the elongated shaft assembly 14. A suitable generator is available as model number GEN11, from Ethicon Endo-Surgery, Inc., Cincinnati, Ohio. When the acoustic assembly 106 is energized, a vibratory motion standing wave is generated through the acoustic assembly 106. The ultrasonic surgical instrument 10 is designed to operate at a resonance such that an acoustic standing wave pattern of predetermined amplitude is produced. The amplitude of the vibratory motion at any point along the acoustic assembly 106 depends upon the location along the acoustic assembly 106 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength (λ/4).

The wires 120 and 122 transmit an electrical signal from the ultrasonic signal generator 20 to the positive electrodes 114 and the negative electrodes 116. The piezoelectric elements 112 are energized by the electrical signal supplied from the ultrasonic signal generator 20 in response to an actuator 224, such as a foot switch, for example, to produce an acoustic standing wave in the acoustic assembly 106. The electrical signal causes disturbances in the piezoelectric elements 112 in the form of repeated small displacements resulting in large alternating compression and tension forces within the material. The repeated small displacements cause the piezoelectric elements 112 to expand and contract in a continuous manner along the axis of the voltage gradient, producing longitudinal waves of ultrasonic energy. The ultrasonic energy is transmitted through the acoustic assembly 106 to the blade 66 portion of the end effector assembly 26 via a transmission component or an ultrasonic transmission waveguide portion 78 of the elongated shaft assembly 14.

In one example embodiment, in order for the acoustic assembly 106 to deliver energy to the blade 66 portion of the end effector assembly 26, all components of the acoustic assembly 106 must be acoustically coupled to the blade 66. The distal end of the ultrasonic transducer 16 may be acoustically coupled at the surface 110 to the proximal end of the ultrasonic transmission waveguide 78 by a threaded connection such as a stud 124.

In one example embodiment, the components of the acoustic assembly 106 are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 106. It is also contemplated that the acoustic assembly 106 may incorporate any suitable arrangement of acoustic elements.

In one example embodiment, the blade 66 may have a length substantially equal to an integral multiple of one-half system wavelengths (nλ/2). A distal end of the blade 66 may be disposed near an antinode in order to provide the maximum longitudinal excursion of the distal end. When the transducer assembly is energized, the distal end of the blade 66 may be configured to move in the range of, for example, approximately 10 to 500 microns peak-to-peak, and preferably in the range of about 30 to 64 microns at a predetermined vibrational frequency of 55 kHz, for example.

In one example embodiment, the blade 66 may be coupled to the ultrasonic transmission waveguide 78. The blade 66 and the ultrasonic transmission waveguide 78 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 66 may be separable (and of differing composition) from the ultrasonic transmission waveguide 78, and coupled by, for example, a stud, weld, glue, quick connect, or other suitable known methods. The length of the ultrasonic transmission waveguide 78 may be substantially equal to an integral number of one-half wavelengths (nλ/2), for example. The ultrasonic transmission waveguide 78 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In one example embodiment, the ultrasonic transmission waveguide 78 comprises a longitudinally projecting attachment post at a proximal end to couple to the surface 110 of the ultrasonic transmission waveguide 78 by a threaded connection such as the stud 124. The ultrasonic transmission waveguide 78 may include a plurality of stabilizing silicone rings or compliant supports 82 (FIG. 5) positioned at a plurality of nodes. The silicone rings 82 dampen undesirable vibration and isolate the ultrasonic energy from an outer protective sheath 80 (FIG. 5) assuring the flow of ultrasonic energy in a longitudinal direction to the distal end of the blade 66 with maximum efficiency.

Figure 9:
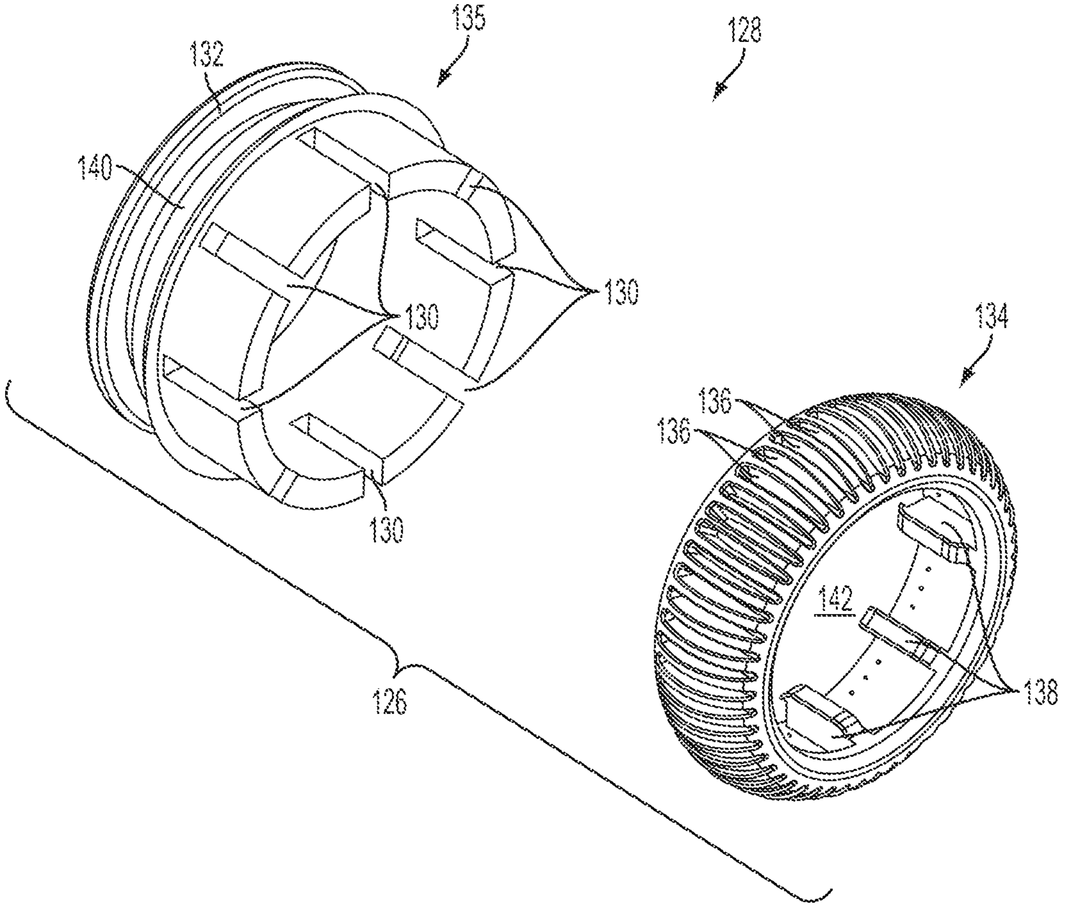
FIG. 9 illustrates one embodiment of a rotation assembly included in one example embodiment of the surgical instrument of FIG. 1.

FIG. 9 illustrates one example embodiment of the proximal rotation assembly 128. In the illustrated embodiment, the proximal rotation assembly 128 comprises the proximal rotation knob 134 inserted over the cylindrical hub 135. The proximal rotation knob 134 comprises a plurality of radial projections 138 that are received in corresponding slots 130 formed on a proximal end of the cylindrical hub 135. The proximal rotation knob 134 defines an opening 142 to receive the distal end of the ultrasonic transducer 16. The radial projections 138 are formed of a soft polymeric material and define a diameter that is undersized relative to the outside diameter of the ultrasonic transducer 16 to create a friction interference fit when the distal end of the ultrasonic transducer 16. The polymeric radial projections 138 protrude radially into the opening 142 to form "gripper" ribs that firmly grip the exterior housing of the ultrasonic transducer 16. Therefore, the proximal rotation knob 134 securely grips the ultrasonic transducer 16.

The distal end of the cylindrical hub 135 comprises a circumferential lip 132 and a circumferential bearing surface 140. The circumferential lip engages a groove formed in the housing 12 and the circumferential bearing surface 140 engages the housing 12. Thus, the cylindrical hub 135 is mechanically retained within the two housing portions (not shown) of the housing 12. The circumferential lip 132 of the cylindrical hub 135 is located or "trapped" between the first and second housing portions 12*a*, 12*b* and is free to rotate in place within the groove. The circumferential bearing surface 140 bears against interior portions of the housing to assist proper rotation. Thus, the cylindrical hub 135 is free to rotate in place within the housing. The user engages the flutes 136 formed on the proximal rotation knob 134 with either the finger or the thumb to rotate the cylindrical hub 135 within the housing 12.

In one example embodiment, the cylindrical hub 135 may be formed of a durable plastic such as polycarbonate. In one example embodiment, the cylindrical hub 135 may be formed of a siliconized polycarbonate material. In one example embodiment, the proximal rotation knob 134 may be formed of pliable, resilient, flexible polymeric materials including Versaflex® TPE alloys made by GLS Corporation, for example. The proximal rotation knob 134 may be formed of elastomeric materials, thermoplastic rubber known as Santoprene®, other thermoplastic vulcanizates (TPVs), or elastomers, for example. The embodiments, however, are not limited in this context.

Figure 10:
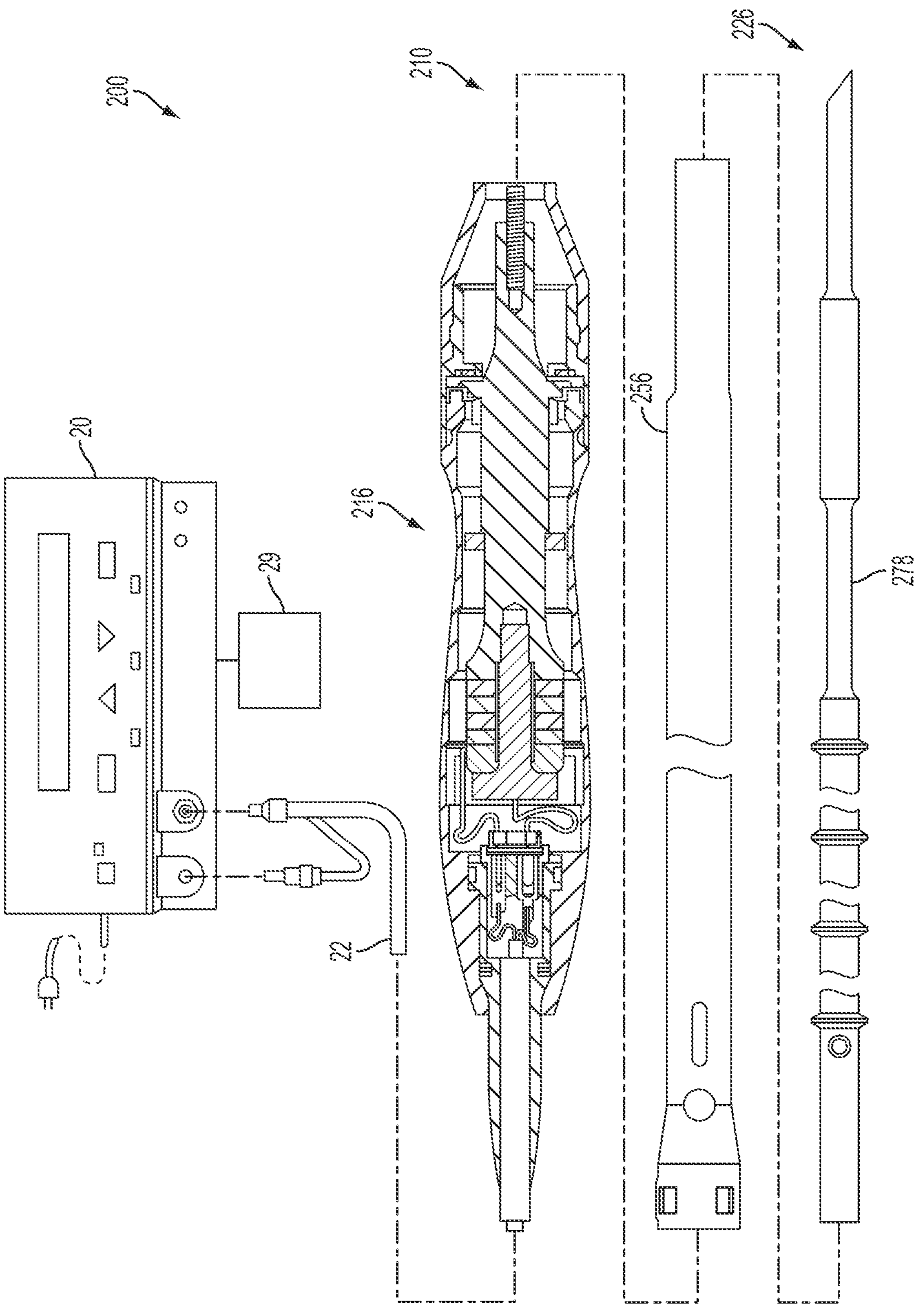
FIG. 10 illustrates one embodiment of a surgical system including a surgical instrument having a single element end effector.

FIG. 10 illustrates one example embodiment of a surgical system 200 including a surgical instrument 210 having single element end effector 278. The system 200 may include a transducer assembly 216 coupled to the end effector 278 and a sheath 256 positioned around the proximal portions of the end effector 278 as shown. The transducer assembly 216 and end effector 278 may operate in a manner similar to that of the transducer assembly 16 and end effector 18 described above to produce ultrasonic energy that may be transmitted to tissue via blade 226.

Figure 11:
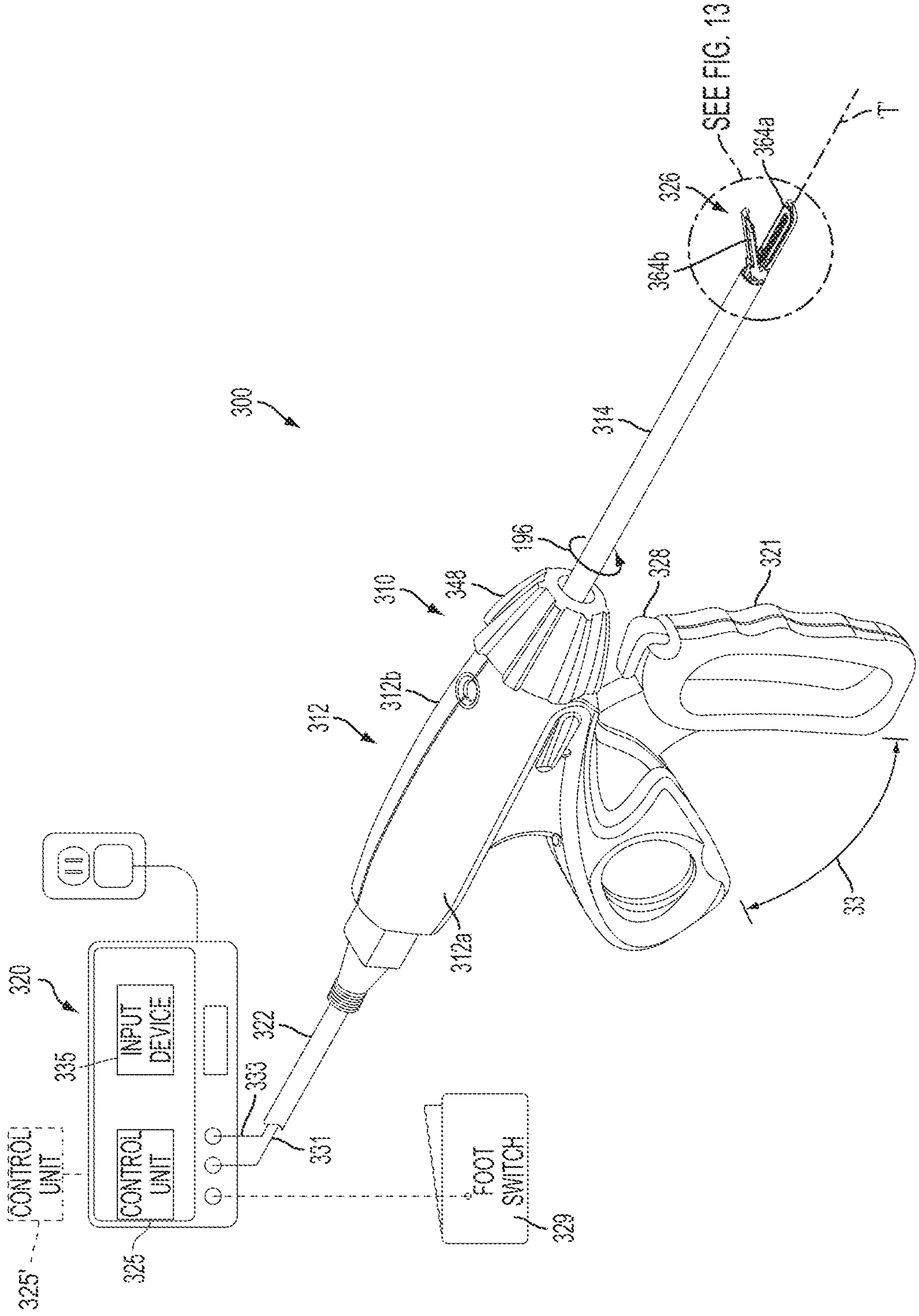
FIG. 11 is a perspective view of one embodiment of an electrical energy surgical instrument.

FIGS. 11-18C illustrate various embodiments of surgical instruments that utilize therapeutic and/or sub-therapeutic electrical energy to treat and/or destroy tissue or provide feedback to the generators (e.g., electrosurgical instruments). The embodiments of FIGS. 11-18C are adapted for use in a manual or hand-operated manner although electrosurgical instruments may be utilized in robotic applications as well. FIG. 11 is a perspective view of one example embodiment of a surgical instrument system 300 comprising an electrical energy surgical instrument 310. The electrosurgical instrument 310 may comprise a proximal handle 312, a distal working end or end effector 326 and an introducer or elongated shaft 314 disposed in-between.

The electrosurgical system 300 can be configured to supply energy, such as electrical energy, ultrasonic energy, heat energy, or any combination thereof, to the tissue of a patient either independently or simultaneously as described, for example, in connection with FIG. 1, for example. In one example embodiment, the electrosurgical system 300 includes a generator 320 in electrical communication with the electrosurgical instrument 310. The generator 320 is connected to electrosurgical instrument 310 via a suitable transmission medium such as a cable 322. In one example embodiment, the generator 320 is coupled to a controller, such as a control unit 325, for example. In various embodiments, the control unit 325 may be formed integrally with the generator 320 or may be provided as a separate circuit module or device electrically coupled to the generator 320 (shown in phantom as 325' to illustrate this option). Although in the presently disclosed embodiment, the generator 320 is shown separate from the electrosurgical instrument 310, in one example embodiment, the generator 320 (and/or the control unit 325) may be formed integrally with the electrosurgical instrument 310 to form a unitary electrosurgical system 300 where a battery located within the electrosurgical instrument 310 is the energy source and a circuit coupled to the battery produces the suitable electrical energy, ultrasonic energy, or heat energy. One such example is described herein below in connection with FIGS. 17-18C.

The generator 320 may comprise an input device 335 located on a front panel of the generator 320 console. The input device 335 may comprise any suitable device that generates signals suitable for programming the operation of the generator 320, such as a keyboard, or input port, for example. In one example embodiment, various electrodes in the first jaw 364A and the second jaw 364B may be coupled to the generator 320. The cable 322 may comprise multiple electrical conductors for the application of electrical energy to positive (+) and negative (−) electrodes of the electrosurgical instrument 310. The control unit 325 may be used to activate the generator 320, which may serve as an electrical source. In various embodiments, the generator 320 may comprise an RF source, an ultrasonic source, a direct current source, and/or any other suitable type of electrical energy source, for example, which may be activated independently or simultaneously.

In various embodiments, the electrosurgical system 300 may comprise at least one supply conductor 331 and at least one return conductor 333, wherein current can be supplied to electrosurgical instrument 300 via the supply conductor 331 and wherein the current can flow back to the generator 320 via the return conductor 333. In various embodiments, the supply conductor 331 and the return conductor 333 may comprise insulated wires and/or any other suitable type of conductor. In certain embodiments, as described below, the supply conductor 331 and the return conductor 333 may be contained within and/or may comprise the cable 322 extending between, or at least partially between, the generator 320 and the end effector 326 of the electrosurgical instrument 310. In any event, the generator 320 can be configured to apply a sufficient voltage differential between the supply conductor 331 and the return conductor 333 such that sufficient current can be supplied to the end effector 110.

Figure 12:
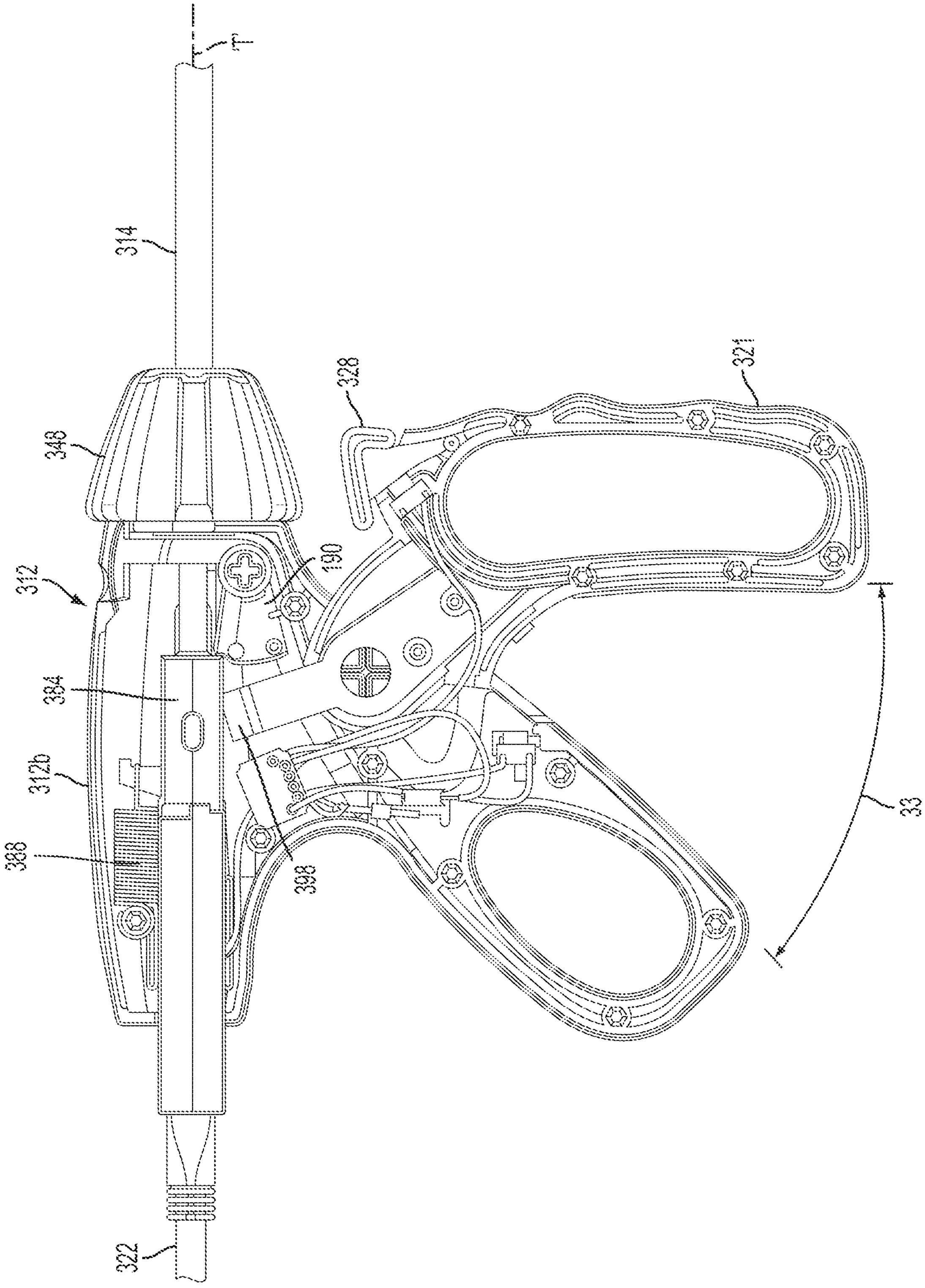
FIG. 12 is a side view of a handle of one embodiment of the surgical instrument of FIG. 11 with a half of a handle body removed to illustrate some of the components therein.

FIG. 12 is a side view of one example embodiment of the handle 312 of the surgical instrument 310. In FIG. 12, the handle 312 is shown with half of a first handle body 312A (see FIG. 11) removed to illustrate various components within second handle body 312B. The handle 312 may comprise a lever arm 321 (e.g., a trigger) which may be pulled along a path 33. The lever arm 321 may be coupled to an axially moveable member 378 (FIGS. 13-16) disposed within elongated shaft 314 by a shuttle 384 operably engaged to an extension 398 of lever arm 321. The shuttle 384 may further be connected to a biasing device, such as a spring 388, which may also be connected to the second handle body 312B, to bias the shuttle 384 and thus the axially moveable member 378 in a proximal direction, thereby urging the jaws 364A and 364B to an open position as seen in FIG. 11. Also, referring to FIGS. 11-12, a locking member 190 (see FIG. 12) may be moved by a locking switch 328 (see FIG. 11) between a locked position, where the shuttle 384 is substantially prevented from moving distally as illustrated, and an unlocked position, where the shuttle 384 may be allowed to freely move in the distal direction, toward the elongated shaft 314. In some embodiments, the locking switch 328 may be implemented as a button. The handle 312 can be any type of pistol-grip or other type of handle known in the art that is configured to carry actuator levers, triggers or sliders for actuating the first jaw 364A and the second jaw 364B. The elongated shaft 314 may have a cylindrical or rectangular cross-section, for example, and can comprise a thin-wall tubular sleeve that extends from handle 312. The elongated shaft 314 may include a bore extending therethrough for carrying actuator mechanisms, for example, the axially moveable member 378, for actuating the jaws and for carrying electrical leads for delivery of electrical energy to electrosurgical components of the end effector 326.

The end effector 326 may be adapted for capturing and transecting tissue and for the contemporaneously welding the captured tissue with controlled application of energy (e.g., RF energy). The first jaw 364A and the second jaw 364B may close to thereby capture or engage tissue about a longitudinal axis "T" defined by the axially moveable member 378. The first jaw 364A and second jaw 364B may also apply compression to the tissue. In some embodiments, the elongated shaft 314, along with first jaw 364A and second jaw 364B, can be rotated a full 360° degrees, as shown by arrow 196 (see FIG. 11), relative to handle 312. For example, a rotation knob 348 may be rotatable about the longitudinal axis of the shaft 314 and may be coupled to the shaft 314 such that rotation of the knob 348 causes corresponding rotation of the shaft 314. The first jaw 364A and the second jaw 364B can remain openable and/or closeable while rotated.

Figure 13:
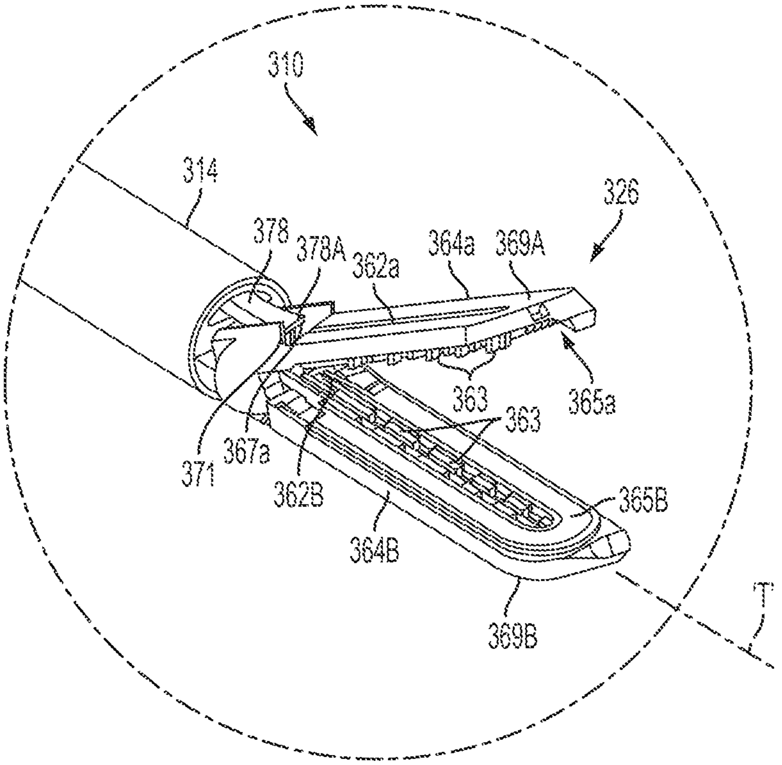
FIG. 13 illustrates a perspective view of one embodiment of the end effector of the surgical instrument of FIG. 11 with the jaws open and the distal end of an axially movable member in a retracted position.
Figure 14:
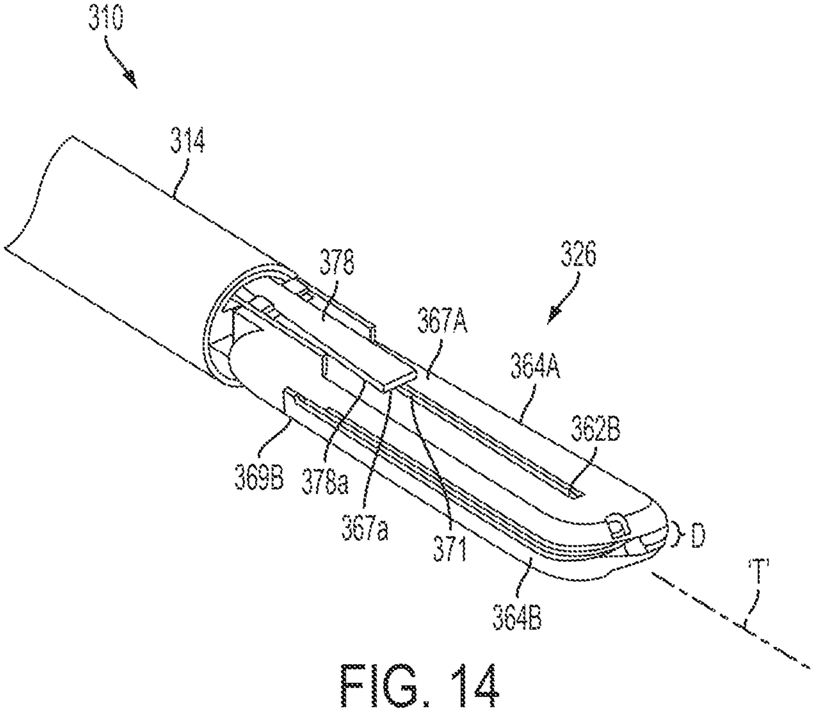
FIG. 14 illustrates a perspective view of one embodiment of the end effector of the surgical instrument of FIG. 11 with the jaws closed and the distal end of an axially movable member in a partially advanced position.

FIG. 13 shows a perspective view of one example embodiment of the end effector 326 with the jaws 364A, 364B open, while FIG. 14 shows a perspective view of one example embodiment of the end effector 326 with the jaws 364A, 364B closed. As noted above, the end effector 326 may comprise the upper first jaw 364A and the lower second jaw 364B, which may be straight or curved. The first jaw 364A and the second jaw 364B may each comprise an elongated slot or channel 362A and 362B, respectively, disposed outwardly along their respective middle portions. Further, the first jaw 364A and second jaw 364B may each have tissue-gripping elements, such as teeth 363, disposed on the inner portions of first jaw 364A and second jaw 364B. The first jaw 364A may comprise an upper first outward-facing surface 369A and an upper first energy delivery surface 365A. The second jaw 364B may comprise a lower second outward-facing surface 369B and a lower second energy delivery surface 365B. The first energy delivery surface 365A and the second energy delivery surface 365B may both extend in a "U" shape about the distal end of the end effector 326.

The lever arm 321 of the handle 312 (FIG. 12) may be adapted to actuate the axially moveable member 378, which may also function as a jaw-closing mechanism. For example, the axially moveable member 378 may be urged distally as the lever arm 321 is pulled proximally along the path 33 via the shuttle 384, as shown in FIG. 12 and discussed above.

Figure 15:
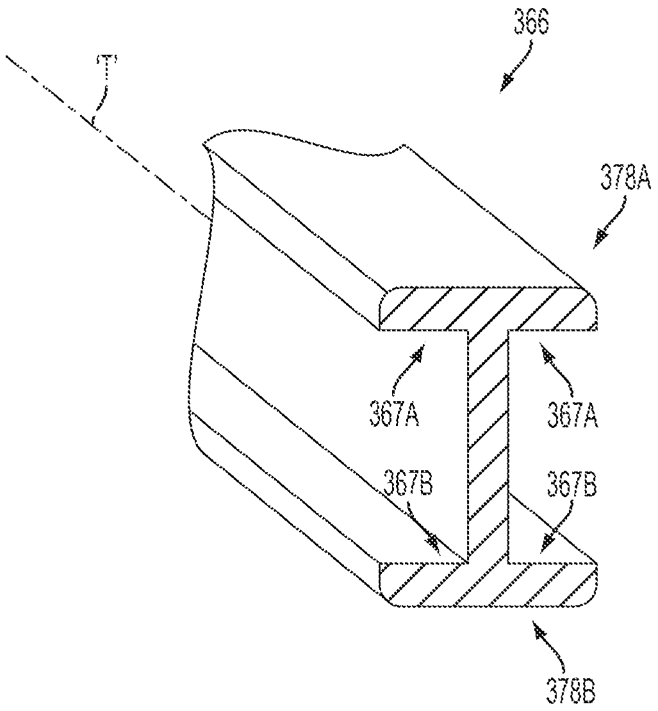
FIG. 15 illustrates a perspective view of one embodiment of the axially moveable member of the surgical instrument of FIG. 1.

FIG. 15 is a perspective view of one example embodiment of the axially moveable member 378 of the surgical instrument 310. The axially moveable member 378 may comprise one or several pieces, but in any event, may be movable or translatable with respect to the elongated shaft 314 and/or the jaws 364A, 364B. Also, in at least one example embodiment, the axially moveable member 378 may be made of 17-4 precipitation hardened stainless steel. The distal end of axially moveable member 378 may comprise a flanged "I"-beam configured to slide within the channels 362A and 362B in jaws 364A and 364B. The axially moveable member 378 may slide within the channels 362A, 362B to open and close first jaw 364A and second jaw 364B. The distal end of the axially moveable member 378 may also comprise an upper flange or "c"-shaped portion 378A and a lower flange or "c"-shaped portion 378B. The flanges 378A and 378B respectively define inner cam surfaces 367A and 367B for engaging outward facing surfaces of the first jaw 364A and the second jaw 364B. The opening-closing of jaws 364A and 364B can apply very high compressive forces on tissue using cam mechanisms which may include movable "I-beam" axially moveable member 378 and the outward facing surfaces 369A, 369B of jaws 364A, 364B.

More specifically, referring now to FIGS. 13-15, collectively, the inner cam surfaces 367A and 367B of the distal end of axially moveable member 378 may be adapted to slidably engage the first outward-facing surface 369A and the second outward-facing surface 369B of the first jaw 364A and the second jaw 364B, respectively. The channel 362A within first jaw 364A and the channel 362B within the second jaw 364B may be sized and configured to accommodate the movement of the axially moveable member 378, which may comprise a tissue-cutting element 371, for example, comprising a sharp distal edge. FIG. 14, for example, shows the distal end of the axially moveable member 378 advanced at least partially through channels 362A and 362B (FIG. 13). The advancement of the axially moveable member 378 may close the end effector 326 from the open configuration shown in FIG. 13. In the closed position shown by FIG. 14, the upper first jaw 364A and lower second jaw 364B define a gap or dimension D between the first energy delivery surface 365A and second energy delivery surface 365B of first jaw 364A and second jaw 364B, respectively. In various embodiments, dimension D can equal from about 0.0005" to about 0.040", for example, and in some embodiments, between about 0.001" to about 0.010", for example. Also, the edges of the first energy delivery surface 365A and the second energy delivery surface 365B may be rounded to prevent the dissection of tissue.

Figure 16:
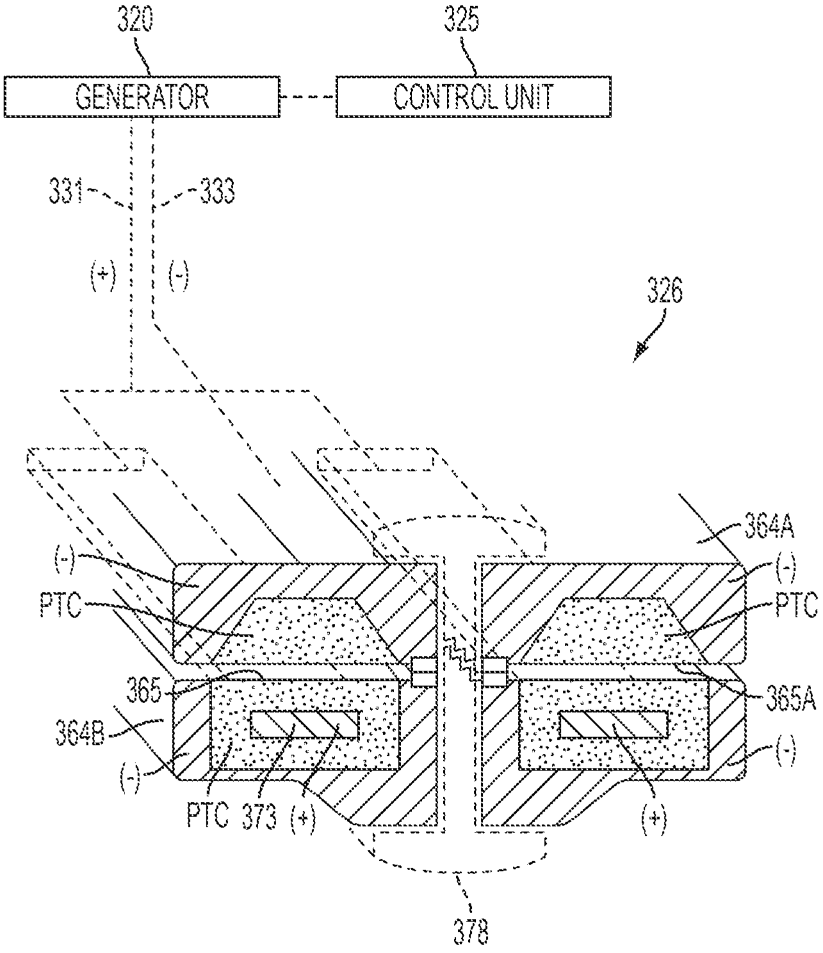
FIG. 16 illustrates a section view of one embodiment of the end effector of the surgical instrument of FIG. 1.

FIG. 16 is a section view of one example embodiment of the end effector 326 of the surgical instrument 310. The engagement, or tissue-contacting, surface 365B of the lower jaw 364B is adapted to deliver energy to tissue, at least in part, through a conductive-resistive matrix, such as a variable resistive positive temperature coefficient (PTC) body, as discussed in more detail below. At least one of the upper and lower jaws 364A, 364B may carry at least one electrode 373 configured to deliver the energy from the generator 320 to the captured tissue. The engagement, or tissue-contacting, surface 365A of upper jaw 364A may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 365A and the second energy delivery surface 365B may each be in electrical communication with the generator 320. The first energy delivery surface 365A and the second energy delivery surface 365B may be configured to contact tissue and deliver electrosurgical energy to captured tissue which are adapted to seal or weld the tissue. The control unit 325 regulates the electrical energy delivered by electrical generator 320 which in turn delivers electrosurgical energy to the first energy delivery surface 365A and the second energy delivery surface 365B. The energy delivery may be initiated by an activation button 328 (FIG. 12) operably engaged with the lever arm 321 and in electrical communication with the generator 320 via cable 322. In one example embodiment, the electrosurgical instrument 310 may be energized by the generator 320 by way of a foot switch 216 (FIG. 11). When actuated, the foot switch 329 triggers the generator 320 to deliver electrical energy to the end effector 326, for example. The control unit 325 may regulate the power generated by the generator 320 during activation. Although the foot switch 329 may be suitable in many circumstances, other suitable types of switches can be used.

As mentioned above, the electrosurgical energy delivered by electrical generator 320 and regulated, or otherwise controlled, by the control unit 325 may comprise radio frequency (RF) energy, or other suitable forms of electrical energy. Further, the opposing first and second energy delivery surfaces 365A and 365B may carry variable resistive positive temperature coefficient (PTC) bodies that are in electrical communication with the generator 320 and the control unit 325. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,312; and U.S. Pat. App. Pub. Nos. 2010/0036370 and 2009/0076506, all of which are incorporated herein in their entirety by reference and made a part of this specification.

In one example embodiment, the generator 320 may be implemented as an electrosurgery unit (ESU) capable of supplying power sufficient to perform bipolar electrosurgery using radio frequency (RF) energy. In one example embodiment, the ESU can be a bipolar ERBE ICC 350 sold by ERBE USA, Inc. of Marietta, Ga. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the positive temperature coefficient (PTC) bodies and to the return electrode through the tissue. Thus, in various embodiments, the electrosurgical system 300 may comprise a supply path and a return path, wherein the captured tissue being treated completes, or closes, the circuit. In one example embodiment, the generator 320 may be a monopolar RF ESU and the electrosurgical instrument 310 may comprise a monopolar end effector 326 in which one or more active electrodes are integrated. For such a system, the generator 320 may require a return pad in intimate contact with the patient at a location remote from the operative site and/or other suitable return path. The return pad may be connected via a cable to the generator 320. In other embodiments, the operator 20 may provide sub-therapeutic RF energy levels for purposes of evaluating tissue conditions and providing feedback in the electrosurgical system 300. Such feed back may be employed to control the therapeutic RF energy output of the electrosurgical instrument 310.

During operation of electrosurgical instrument 300, the user generally grasps tissue, supplies energy to the captured tissue to form a weld or a seal (e.g., by actuating button 328 and/or pedal 216), and then drives a tissue-cutting element 371 at the distal end of the axially moveable member 378 through the captured tissue. According to various embodiments, the translation of the axial movement of the axially moveable member 378 may be paced, or otherwise controlled, to aid in driving the axially moveable member 378 at a suitable rate of travel. By controlling the rate of the travel, the likelihood that the captured tissue has been properly and functionally sealed prior to transection with the cutting element 371 is increased.

Figure 17:
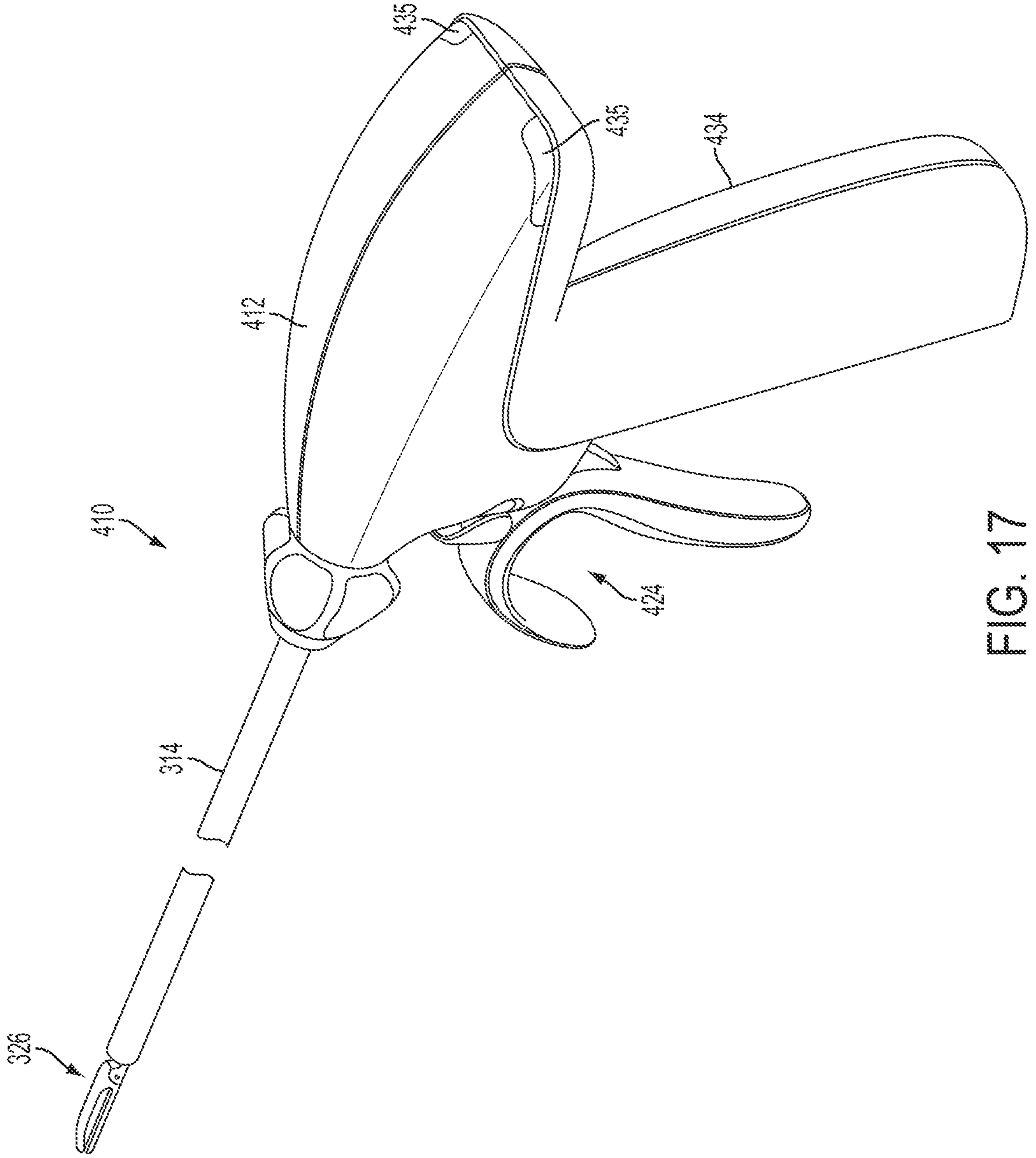
FIG. 17 illustrates a section a perspective view of one embodiment of a cordless electrical energy surgical instrument.

FIG. 17 is a perspective view of one example embodiment of a surgical instrument system comprising a cordless electrical energy surgical instrument 410. The electrosurgical system is similar to the electrosurgical system 300. The electrosurgical system 300 can be configured to supply energy, such as electrical energy, ultrasonic energy, heat energy, or any combination thereof, to the tissue of a patient either independently or simultaneously as described in connection with FIGS. 1 and 11, for example. The electrosurgical instrument may utilize the end effector 326 and elongated shaft 314 described herein in conjunction with a cordless proximal handle 412. In one example embodiment, the handle 412 includes a generator circuit 420 (see FIG. 18A). The generator circuit 420 performs a function substantially similar to that of generator 320. In one example embodiment, the generator circuit 420 is coupled to a controller, such as a control circuit. In the illustrated embodiment, the control circuit is integrated into the generator circuit 420. In other embodiments, the control circuit may be separate from the generator circuit 420.

In one example embodiment, various electrodes in the end effector 326 (including jaws 364A, 364B thereof) may be coupled to the generator circuit 420. The control circuit may be used to activate the generator 420, which may serve as an electrical source. In various embodiments, the generator 420 may comprise an RF source, an ultrasonic source, a direct current source, and/or any other suitable type of electrical energy source, for example. In one example embodiment, a button 328 may be provided to activate the generator circuit 420 to provide energy to the end effectors 326, 326.

FIG. 18A is a side view of one example embodiment of the handle 412 of the cordless surgical instrument 410. In FIG. 18A, the handle 412 is shown with half of a first handle body removed to illustrate various components within second handle body 434. The handle 412 may comprise a lever arm 424 (e.g., a trigger) which may be pulled along a path 33 around a pivot point. The lever arm 424 may be coupled to an axially moveable member 478 disposed within elongated shaft 314 by a shuttle operably engaged to an extension of lever arm 424. In one example embodiment, the lever arm 424 defines a shepherd's hook shape comprising a distal member 424*a* and a proximal member 424*b*.

In one example embodiment, the cordless electrosurgical instrument comprises a battery 437. The battery 437 provides electrical energy to the generator circuit 420. The battery 437 may be any battery suitable for driving the generator circuit 420 at the desired energy levels. In one example embodiment, the battery 437 is a 100 mAh, triple-cell Lithium Ion Polymer battery. The battery may be fully charged prior to use in a surgical procedure, and may hold a voltage of about 12.6V. The battery 437 may have two fuses fitted to the cordless electrosurgical instrument 410, arranged in line with each battery terminal. In one example embodiment, a charging port 439 is provided to connect the battery 437 to a DC current source (not shown).

Figure 18B:
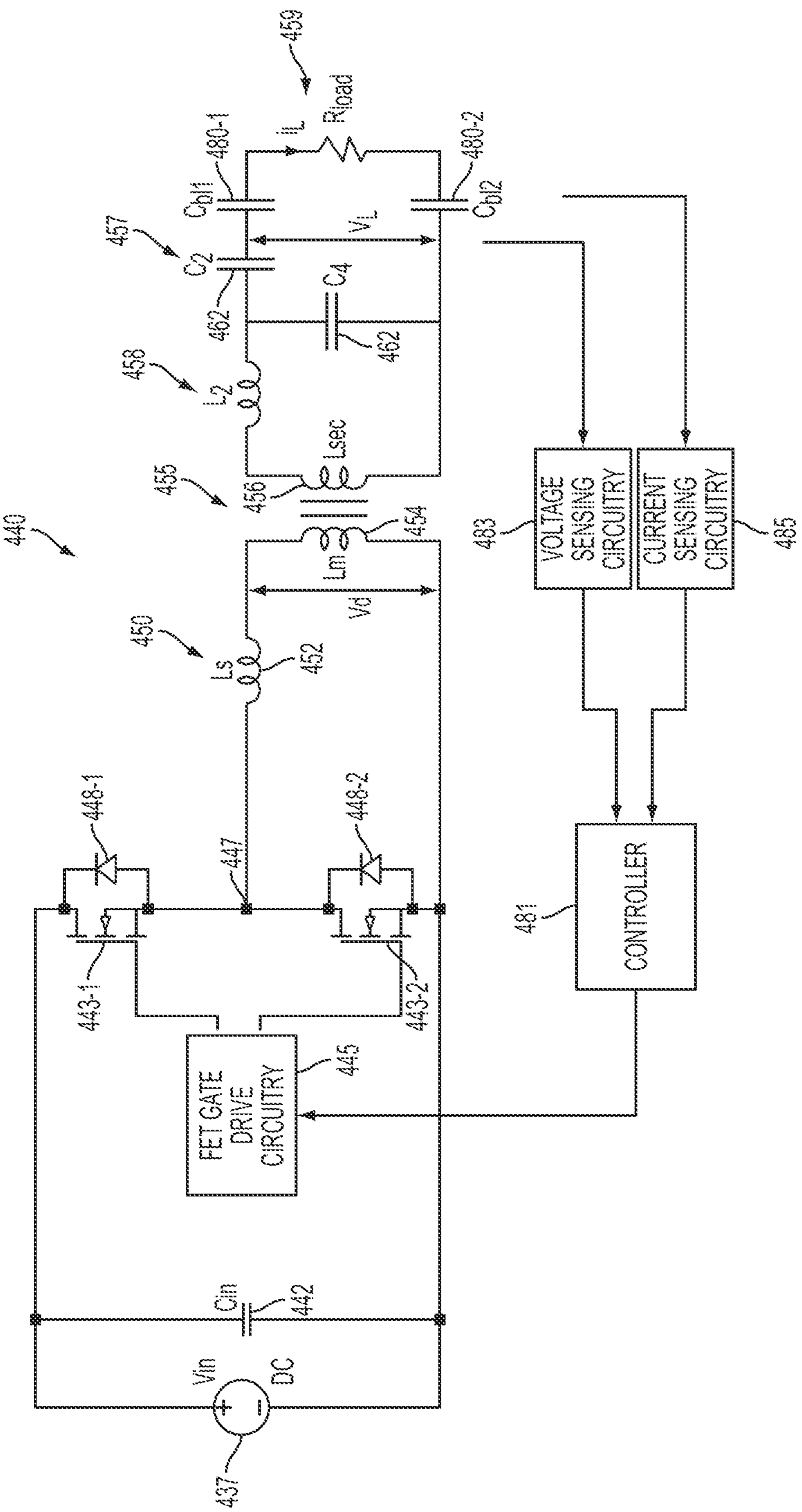
FIG. 18B illustrates an RF drive and control circuit, according to one embodiment.

The generator circuit 420 may be configured in any suitable manner. In some embodiments, the generator circuit comprises an RF drive and control circuit 440. FIG. 18B illustrates an RF drive and control circuit 440, according to one embodiment. FIG. 18B is a part schematic part block diagram illustrating the RF drive and control circuitry 440 used in this embodiment to generate and control the RF electrical energy supplied to the end effector 326. As will be explained in more detail below, in this embodiment, the drive circuitry 440 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 326. The way that this is achieved will become apparent from the following description.

As shown in FIG. 18B, the RF drive and control circuit 440 comprises the above described battery 437 are arranged to supply, in this example, about 0V and about 12V rails. An input capacitor ($C_{in}$) 442 is connected between the 0V and the 12V for providing a low source impedance. A pair of FET switches 443-1 and 443-2 (both of which are N-channel in this embodiment to reduce power losses) is connected in series between the 0V rail and the 12V rail. FET gate drive circuitry 805 is provided that generates two drive signals—one for driving each of the two FETs 443. The FET gate drive circuitry 445 generates drive signals that causes the upper FET (443-1) to be on when the lower FET (443-2) is off and vice versa. This causes the node 447 to be alternately connected to the 12V rail (when the FET 443-1 is switched on) and the 0V rail (when the FET 443-2 is switched on). FIG. 18B also shows the internal parasitic diodes 448-1 and 448-2 of the corresponding FETs 443, which conduct during any periods that the FETs 443 are open.

As shown in FIG. 18B, the node 447 is connected to an inductor-inductor resonant circuit 450 formed by inductor $L_s$ 452 and inductor $L_m$ 454. The FET gate driving circuitry 445 is arranged to generate drive signals at a drive frequency ($f_d$) that opens and crosses the FET switches 443 at the resonant frequency of the parallel resonant circuit 450. As a result of the resonant characteristic of the resonant circuit 450, the square wave voltage at node 447 will cause a substantially sinusoidal current at the drive frequency ($f_d$) to flow within the resonant circuit 450. As illustrated in FIG. 18B, the inductor $L_m$ 454 is the primary of a transformer 455, the secondary of which is formed by inductor $L_{sec}$ 456. The inductor $L_{sec}$ 456 of the transformer 455 secondary is connected to an inductor-capacitor-capacitor parallel resonant circuit 457 formed by inductor $L_2$ 458, capacitor $C_4$ 460, and capacitor $C_2$ 462. The transformer 455 up-converts the drive voltage ($V_d$) across the inductor $L_m$ 454 to the voltage that is applied to the output parallel resonant circuit 457. The load voltage ($V_L$) is output by the parallel resonant circuit 457 and is applied to the load (represented by the load resistance $R_{load}$ 459 in FIG. 18B) corresponding to the impedance of the forceps' jaws and any tissue or vessel gripped by the end effector 326. As shown in FIG. 18B, a pair of DC blocking capacitors $C_{bl}$ 480-1 and 480-2 is provided to prevent any DC signal being applied to the load 459.

In one embodiment, the transformer 455 may be implemented with a Core Diameter (mm), Wire Diameter (mm), and Gap between secondary windings in accordance with the following specifications:

Core Diameter, D (mm)

D=19.9×10−3

Wire diameter, W (mm) for 22 AWG wire

W=7.366×10−4

Gap between secondary windings, in gap=0.125

G=gap/25.4

In this embodiment, the amount of electrical power supplied to the end effector 326 is controlled by varying the frequency of the switching signals used to switch the FETs 443. This works because the resonant circuit 450 acts as a frequency dependent (loss less) attenuator. The closer the drive signal is to the resonant frequency of the resonant circuit 450, the less the drive signal is attenuated. Similarly, as the frequency of the drive signal is moved away from the resonant frequency of the circuit 450, the more the drive signal is attenuated and so the power supplied to the load reduces. In this embodiment, the frequency of the switching signals generated by the FET gate drive circuitry 445 is controlled by a controller 481 based on a desired power to be delivered to the load 459 and measurements of the load voltage ($V_L$) and of the load current ($I_L$) obtained by conventional voltage sensing circuitry 483 and current sensing circuitry 485. The way that the controller 481 operates will be described in more detail below.

In one embodiment, the voltage sensing circuitry 483 and the current sensing circuitry 485 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 483 and the current sensing circuitry 485. In one-embodiment, a step-down regulator (e.g., LT3502 by Linear Technologies) may be employed by the power save circuit to reduce the supply voltage of the rail-to-rail amplifiers and thus extend the life of the battery 437.

Figure 18C:
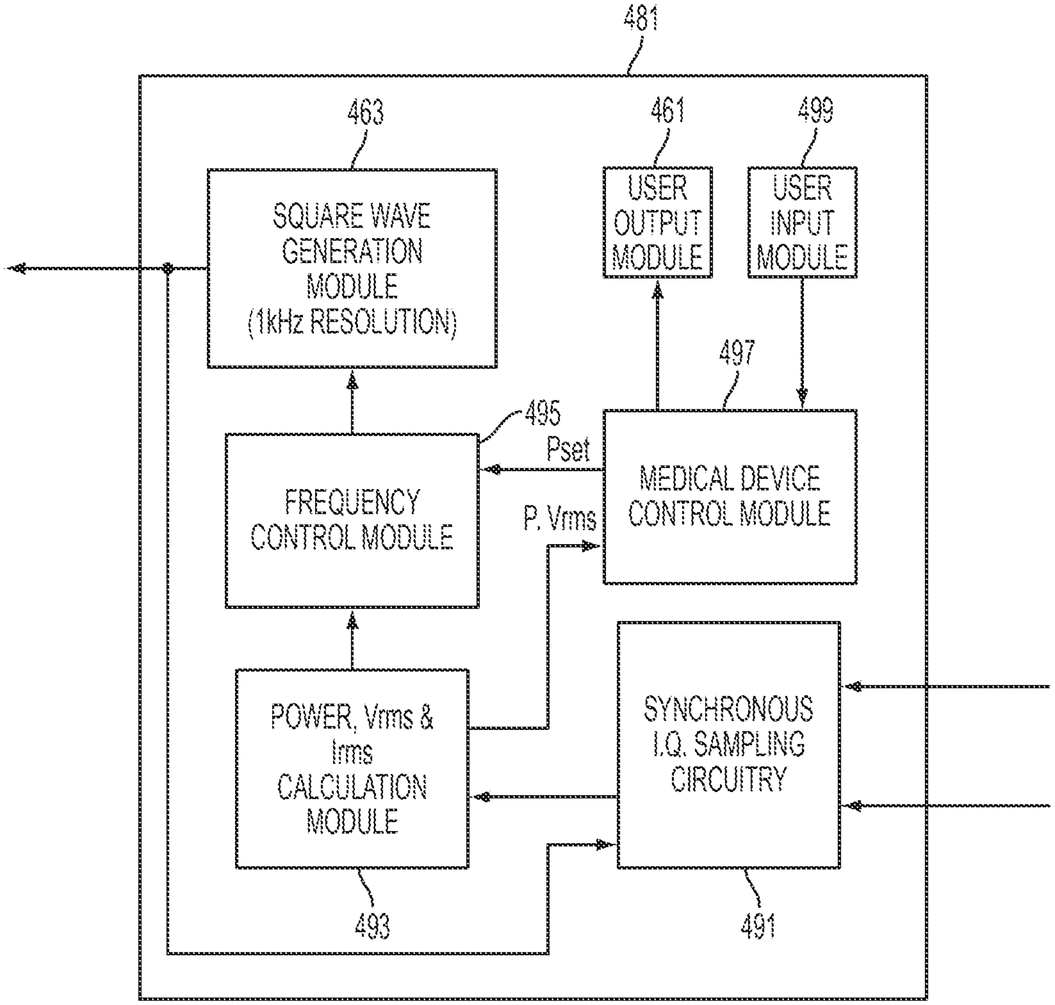
FIG. 18C illustrates the main components of the controller, according to one embodiment.

FIG. 18C illustrates the main components of the controller 481, according to one embodiment. In the embodiment illustrated in FIG. 18C, the controller 481 is a microprocessor based controller and so most of the components illustrated in FIG. 16 are software based components. Nevertheless, a hardware based controller 481 may be used instead. As shown, the controller 481 includes synchronous I,Q sampling circuitry 491 that receives the sensed voltage and current signals from the sensing circuitry 483 and 485 and obtains corresponding samples which are passed to a power, $V_{rms}$ and $I_{rms}$ calculation module 493. The calculation module 493 uses the received samples to calculate the RMS voltage and RMS current applied to the load 459 (FIG. 18B; end effector 326 and tissue/vessel gripped thereby) and from them the power that is presently being supplied to the load 459. The determined values are then passed to a frequency control module 495 and a medical device control module 497. The medical device control module 497 uses the values to determine the present impedance of the load 459 and based on this determined impedance and a pre-defined algorithm, determines what set point power ($P_{set}$) should be applied to the frequency control module 495. The medical device control module 497 is in turn controlled by signals received from a user input module 499 that receives inputs from the user (for example pressing buttons or activating the control levers 114, 110 on the handle 104) and also controls output devices (lights, a display, speaker or the like) on the handle 104 via a user output module 461.

The frequency control module 495 uses the values obtained from the calculation module 493 and the power set point ($P_{set}$) obtained from the medical device control module 497 and predefined system limits (to be explained below), to determine whether or not to increase or decrease the applied frequency. The result of this decision is then passed to a square wave generation module 463 which, in this embodiment, increments or decrements the frequency of a square wave signal that it generates by 1 kHz, depending on the received decision. As those skilled in the art will appreciate, in an alternative embodiment, the frequency control module 495 may determine not only whether to increase or decrease the frequency, but also the amount of frequency change required. In this case, the square wave generation module 463 would generate the corresponding square wave signal with the desired frequency shift. In this embodiment, the square wave signal generated by the square wave generation module 463 is output to the FET gate drive circuitry 445, which amplifies the signal and then applies it to the FET 443-1. The FET gate drive circuitry 445 also inverts the signal applied to the FET 443-1 and applies the inverted signal to the FET 443-2.

The electrosurgical instrument 410 may comprise additional features as discussed with respect to electrosurgical system 300. Those skilled in the art will recognize that electrosurgical instrument 410 may include a rotation knob 348, an elongate shaft 314, and an end effector 326. These elements function in a substantially similar manner to that discussed above with respect to the electrosurgical system 300. In one example embodiment, the cordless electrosurgical instrument 410 may include visual indicators 435. The visual indicators 435 may provide a visual indication signal to an operator. In one example embodiment, the visual indication signal may alert an operator that the device is on, or that the device is applying energy to the end effector. Those skilled in the art will recognize that the visual indicators 435 may be configured to provide information on multiple states of the device.

Over the years a variety of minimally invasive robotic (or "telesurgical") systems have been developed to increase surgical dexterity as well as to permit a surgeon to operate on a patient in an intuitive manner. Robotic surgical systems can be used with many different types of surgical instruments including, for example, ultrasonic or electrosurgical instruments, as described herein. Example robotic systems include those manufactured by Intuitive Surgical, Inc., of Sunnyvale, Calif., U.S.A. Such systems, as well as robotic systems from other manufacturers, are disclosed in the following U.S. Patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors". Many of such systems, however, have in the past been unable to generate the magnitude of forces required to effectively cut and fasten tissue.

FIGS. 19-46 illustrate example embodiments of robotic surgical systems compatible with the disclosed robotic surgical control systems. In some embodiments, the disclosed robotic surgical systems may utilize the ultrasonic or electrosurgical instruments described herein. Those skilled in the art will appreciate that the illustrated robotic surgical systems are not limited to only those instruments described herein, and may utilize any compatible surgical instruments. Those skilled in the art will further appreciate that while various embodiments described herein may be used with the described robotic surgical systems, the disclosure is not so limited, and may be used with any compatible robotic surgical system.

Figure 19:
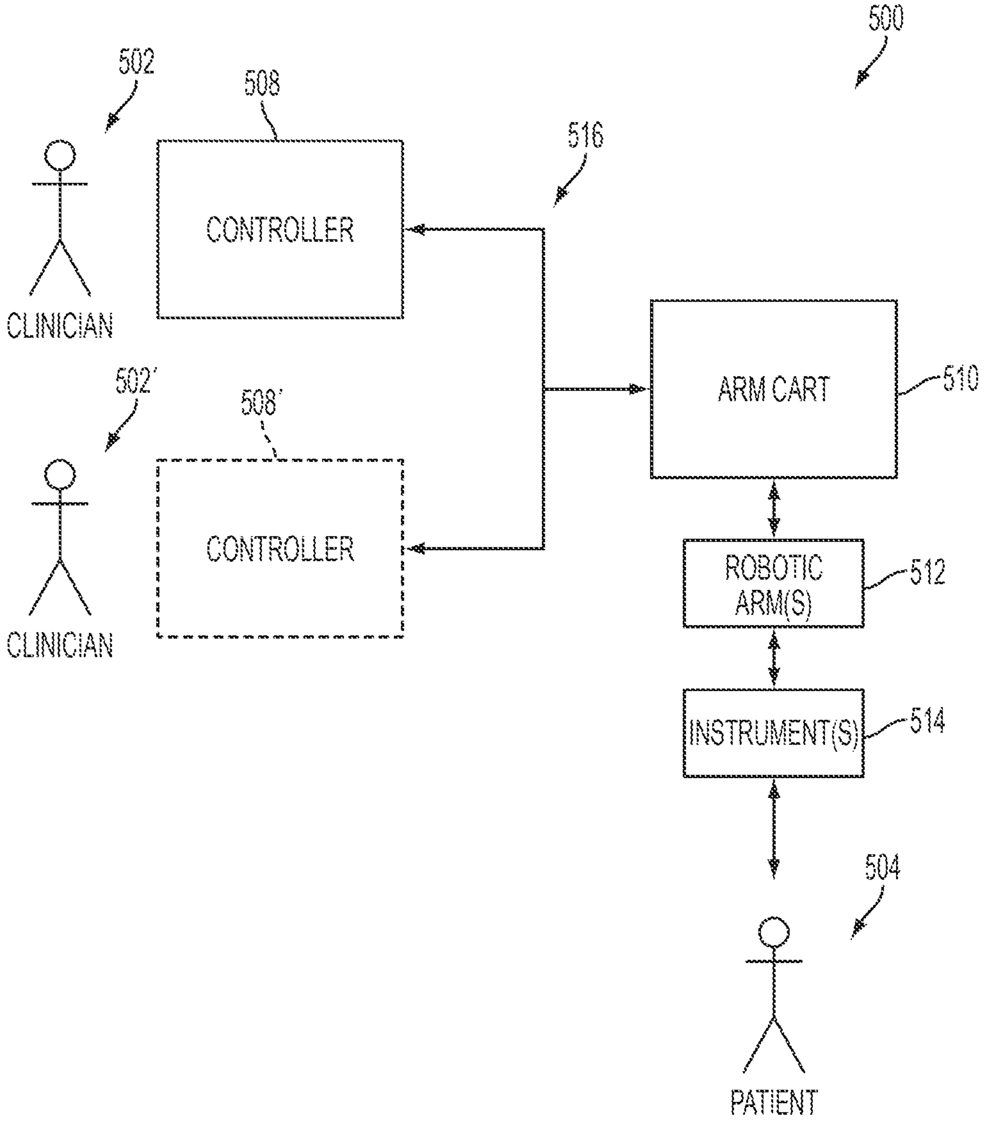
FIG. 19 illustrates a block diagram of one example embodiment of a robotic surgical system.

FIGS. 19-25 illustrate the structure and operation of several example robotic surgical systems and components thereof. FIG. 19 shows a block diagram of an example robotic surgical system 500. The system 500 comprises at least one controller 508 and at least one arm cart 510. The arm cart 510 may be mechanically coupled to one or more robotic manipulators or arms, indicated by box 512. Each of the robotic arms 512 may comprise one or more surgical instruments 514 for performing various surgical tasks on a patient 504. Operation of the arm cart 510, including the arms 512 and instruments 514 may be directed by a clinician 502 from a controller 508. In some embodiments, a second controller 508', operated by a second clinician 502' may also direct operation of the arm cart 510 in conjunction with the first clinician 502'. For example, each of the clinicians 502, 502' may control different arms 512 of the cart or, in some cases, complete control of the arm cart 510 may be passed between the clinicians 502, 502'. In some embodiments, additional arm carts (not shown) may be utilized on the patient 504. These additional arm carts may be controlled by one or more of the controllers 508, 508'. The arm cart(s) 510 and controllers 508, 508' may be in communication with one another via a communications link 516, which may be any suitable type of wired or wireless communications link carrying any suitable type of signal (e.g., electrical, optical, infrared, etc.) according to any suitable communications protocol. Example implementations of robotic surgical systems, such as the system 500, are disclosed in U.S. Pat. No. 7,524,320 which has been herein incorporated by reference. Thus, various details of such devices will not be described in detail herein beyond that which may be necessary to understand various embodiments of the claimed device.

Figure 20:
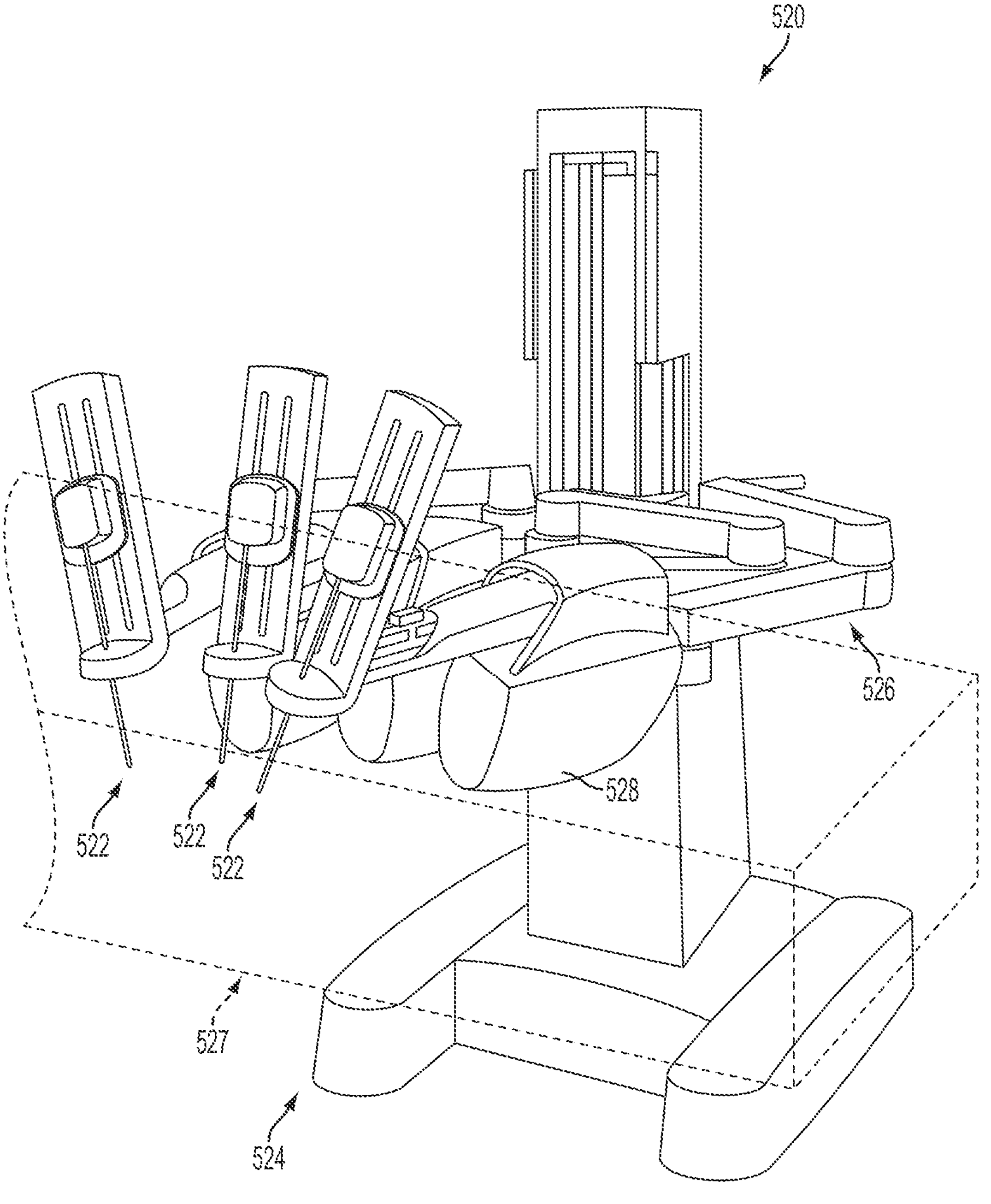
FIG. 20 illustrates one embodiment of a robotic arm cart.

FIG. 20 shows one example embodiment of a robotic arm cart 520. The robotic arm cart 520 is configured to actuate a plurality of surgical instruments or instruments, generally designated as 522 within a work envelope 527. Various robotic surgery systems and methods employing master controller and robotic arm cart arrangements are disclosed in U.S. Pat. No. 6,132,368, entitled MULTI-COMPONENT TELEPRESENCE SYSTEM AND METHOD, the full disclosure of which is incorporated herein by reference. In various forms, the robotic arm cart 520 includes a base 524 from which, in the illustrated embodiment, three surgical instruments 522 are supported. In various forms, the surgical instruments 522 are each supported by a series of manually articulatable linkages, generally referred to as set-up joints 526, and a robotic manipulator 528. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 520. Cart 520 will generally have dimensions suitable for transporting the cart 520 between operating rooms. The cart 520 may be configured to typically fit through standard operating room doors and onto standard hospital elevators. In various forms, the cart 520 would preferably have a weight and include a wheel (or other transportation) system that allows the cart 520 to be positioned adjacent an operating table by a single attendant.

Figure 21:
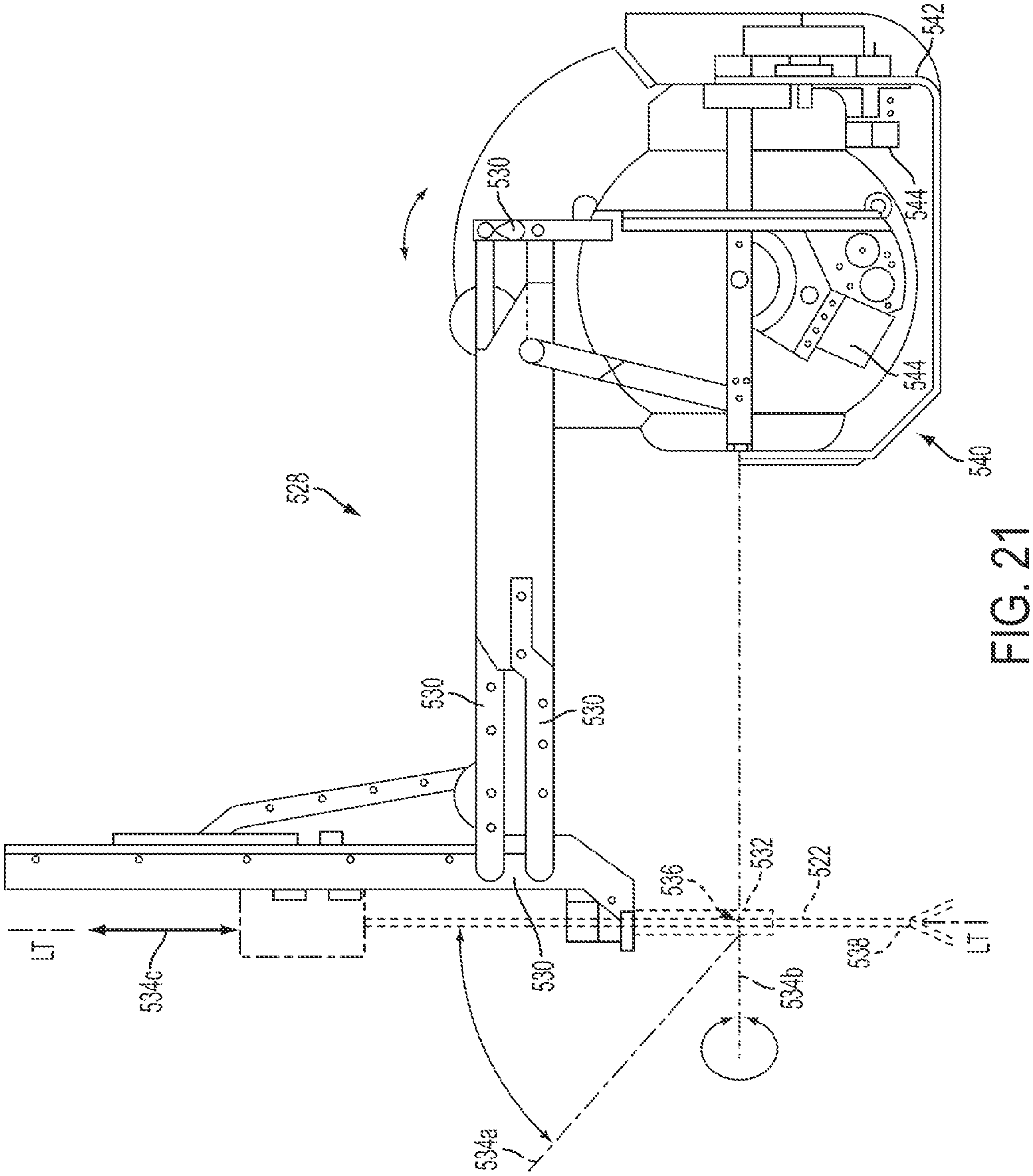
FIG. 21 illustrates one embodiment of the robotic manipulator of the robotic arm cart of FIG. 20.

FIG. 21 shows one example embodiment of the robotic manipulator 528 of the robotic arm cart 520. In the example shown in FIG. 21, the robotic manipulators 528 may include a linkage 530 that constrains movement of the surgical instrument 522. In various embodiments, linkage 530 includes rigid links coupled together by rotational joints in a parallelogram arrangement so that the surgical instrument 522 rotates around a point in space 532, as more fully described in issued U.S. Pat. No. 5,817,084, the full disclosure of which is herein incorporated by reference. The parallelogram arrangement constrains rotation to pivoting about an axis 534*a*, sometimes called the pitch axis. The links supporting the parallelogram linkage are pivotally mounted to set-up joints 526 (FIG. 20) so that the surgical instrument 522 further rotates about an axis 534*b*, sometimes called the yaw axis. The pitch and yaw axes 534*a*, 534*b* intersect at the remote center 536, which is aligned along a shaft 538 of the surgical instrument 522. The surgical instrument 522 may have further degrees of driven freedom as supported by manipulator 540, including sliding motion of the surgical instrument 522 along the longitudinal instrument axis "LT-LT". As the surgical instrument 522 slides along the instrument axis LT-LT relative to manipulator 540 (arrow 534*c*), remote center 536 remains fixed relative to base 542 of manipulator 540. Hence, the entire manipulator 540 is generally moved to re-position remote center 536. Linkage 530 of manipulator 540 is driven by a series of motors 544. These motors 544 actively move linkage 530 in response to commands from a processor of a control system. As will be discussed in further detail below, motors 544 are also employed to manipulate the surgical instrument 522.

Figure 22:
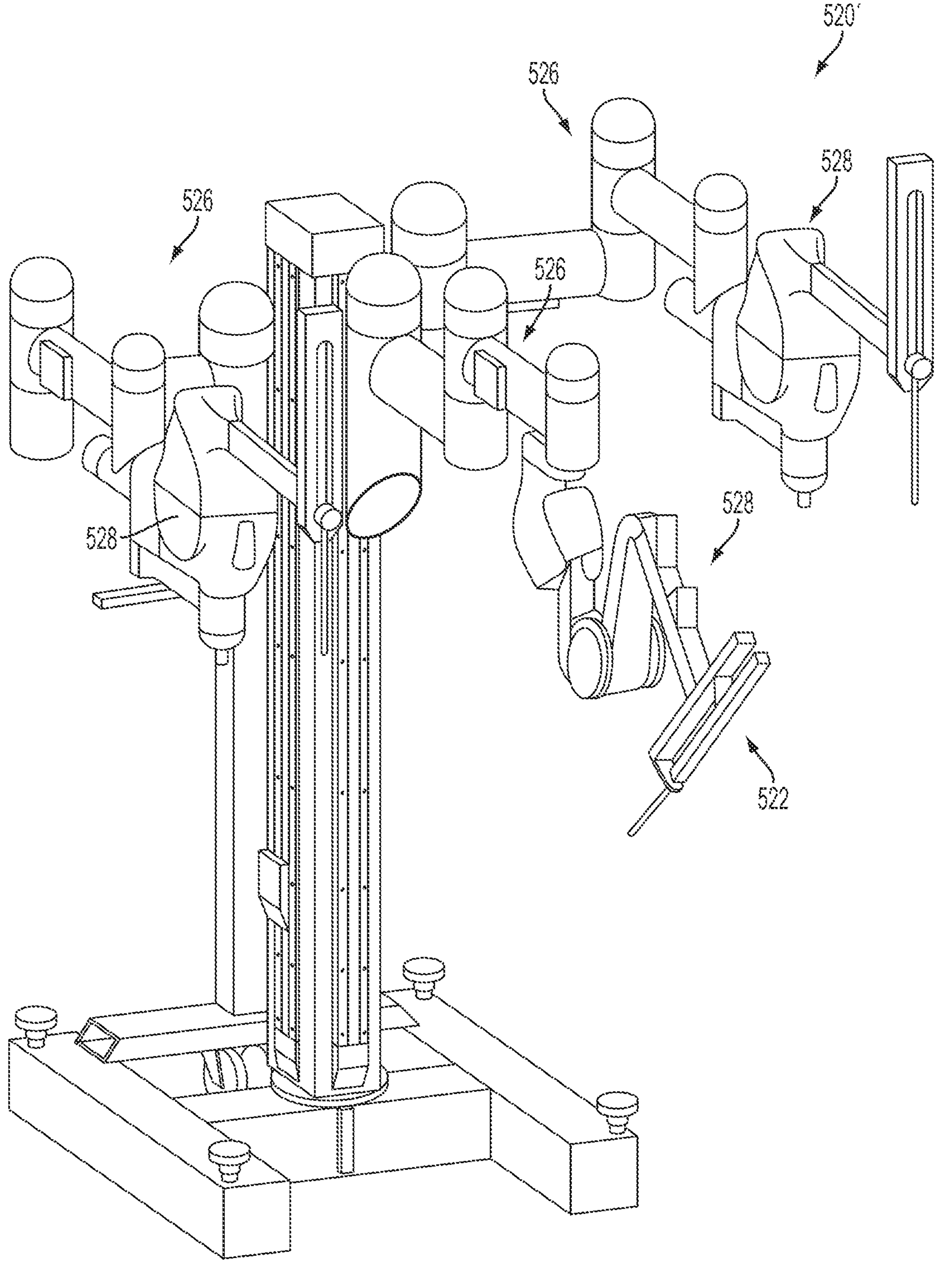
FIG. 22 illustrates one embodiment of a robotic arm cart having an alternative set-up joint structure.

FIG. 22 shows one example embodiment of a robotic arm cart 520' having an alternative set-up joint structure. In this example embodiment, a surgical instrument 522 is supported by an alternative manipulator structure 528' between two tissue manipulation instruments. Those of ordinary skill in the art will appreciate that various embodiments of the claimed device may incorporate a wide variety of alternative robotic structures, including those described in U.S. Pat. No. 5,878,193, the full disclosure of which is incorporated herein by reference. Additionally, while the data communication between a robotic component and the processor of the robotic surgical system is primarily described herein with reference to communication between the surgical instrument 522 and the controller, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 23:
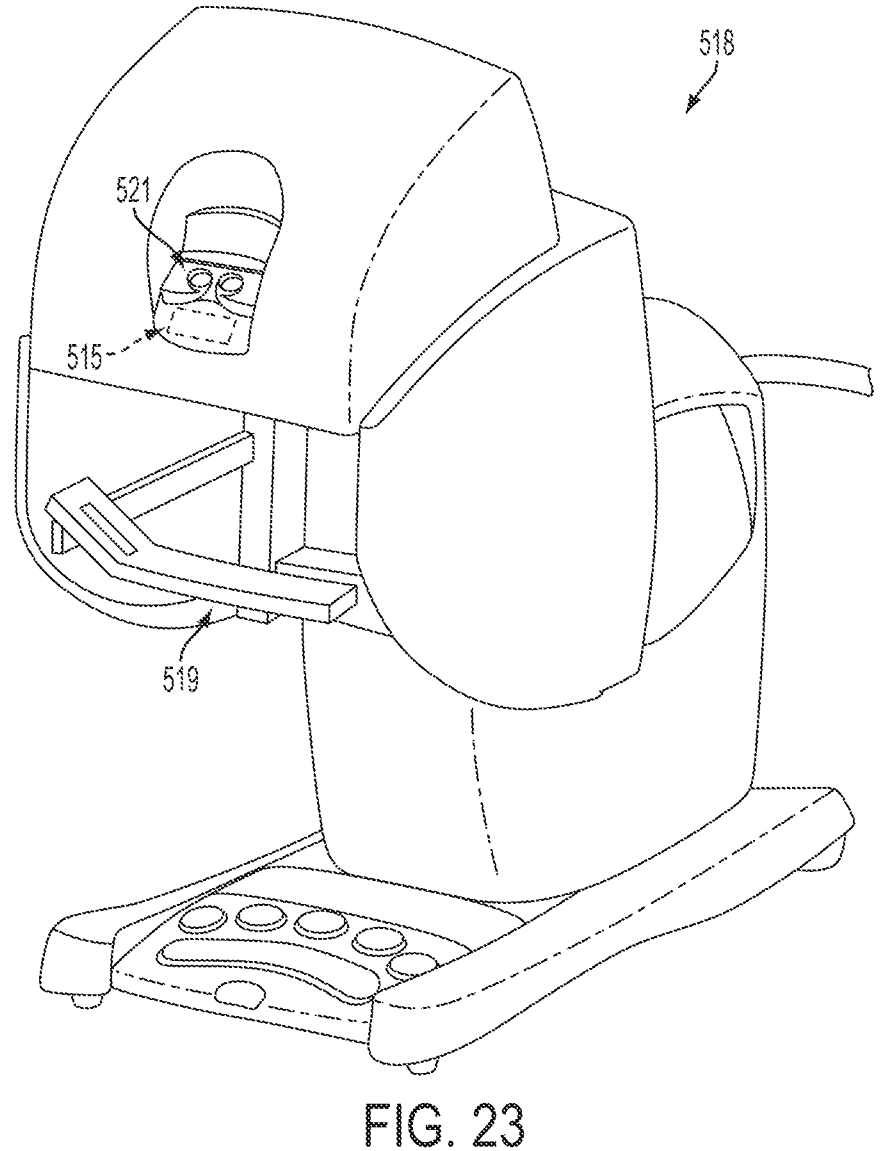
FIG. 23 illustrates one embodiment of a controller that may be used in conjunction with a robotic arm cart, such as the robotic arm carts of FIGS. 19-22.

FIG. 23 shows one example embodiment of a controller 518 that may be used in conjunction with a robotic arm cart, such as the robotic arm carts 520, 520' depicted in FIGS. 20-22. The controller 518 generally includes master controllers (generally represented as 519 in FIG. 23) which are grasped by the clinician and manipulated in space while the clinician views the procedure via a stereo display 521. A surgeon feed back meter 515 may be viewed via the display 521 and provide the surgeon with a visual indication of the amount of force being applied to the cutting instrument or dynamic clamping member. The master controllers 519 generally comprise manual input devices which preferably move with multiple degrees of freedom, and which often further have a handle or trigger for actuating instruments (for example, for closing grasping saws, applying an electrical potential to an electrode, or the like).

Figure 24:
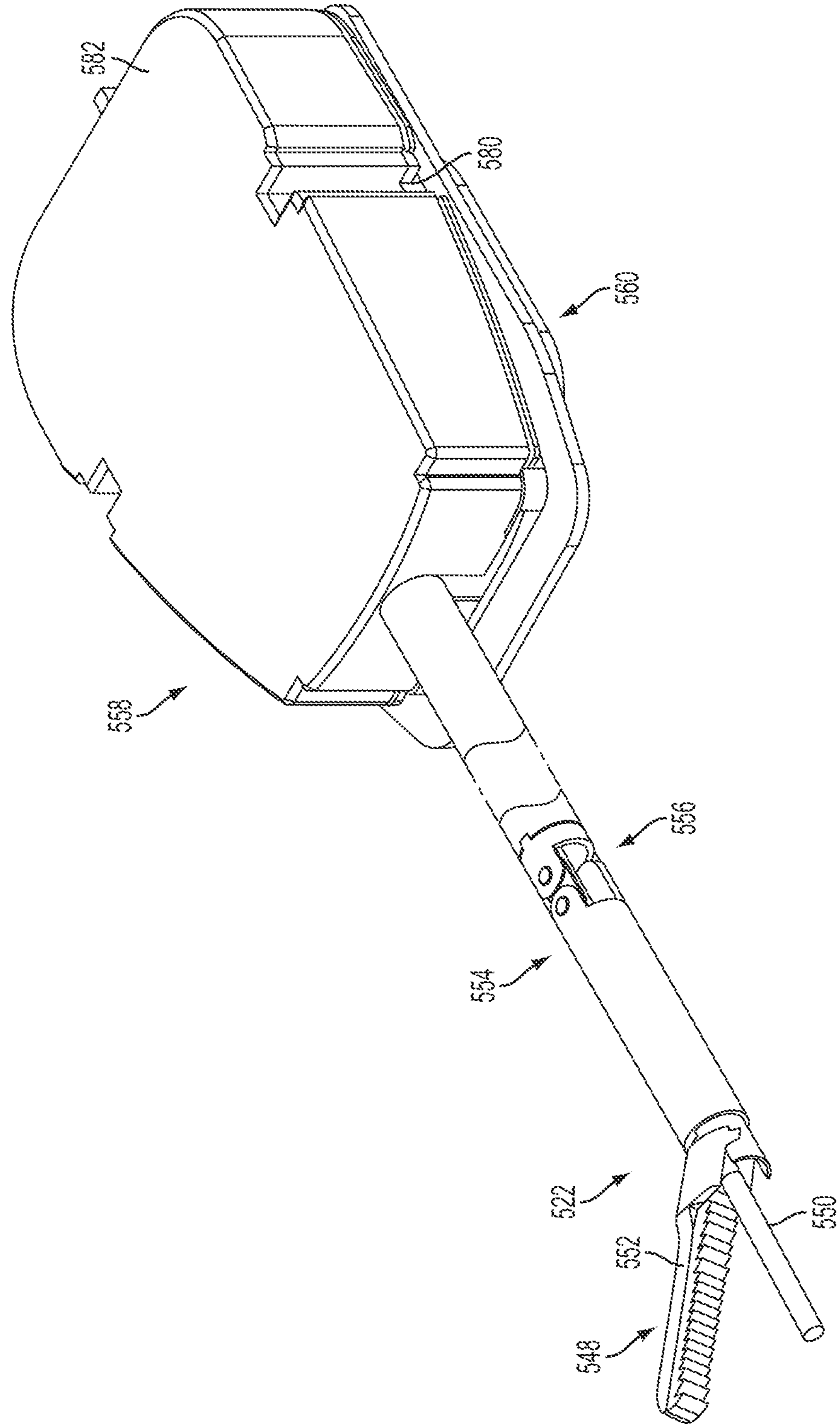
FIG. 24 illustrates one embodiment of an ultrasonic surgical instrument adapted for use with a robotic system.
Figure 25:
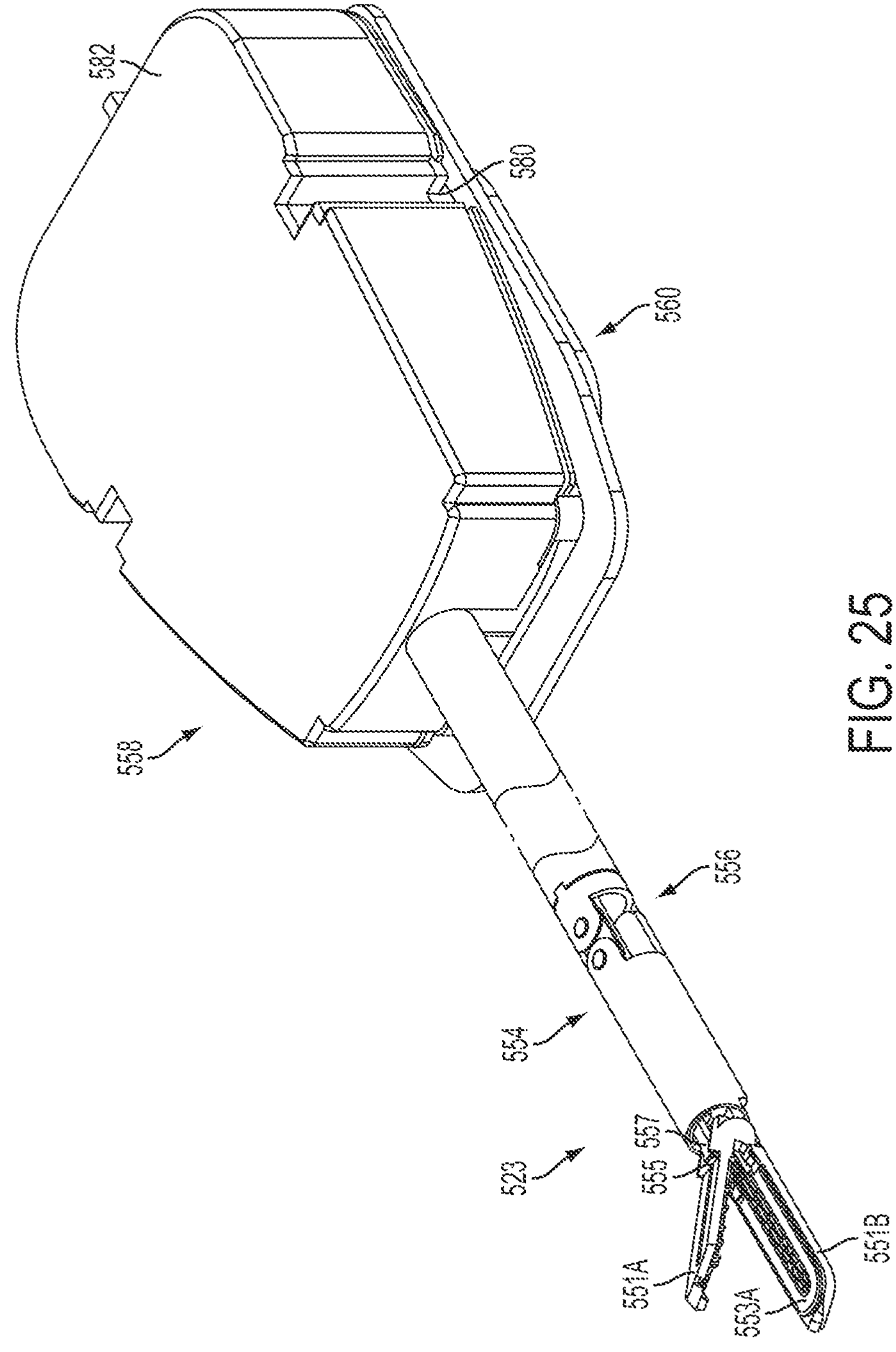
FIG. 25 illustrates one embodiment of an electrosurgical instrument adapted for use with a robotic system.
Figure 26:
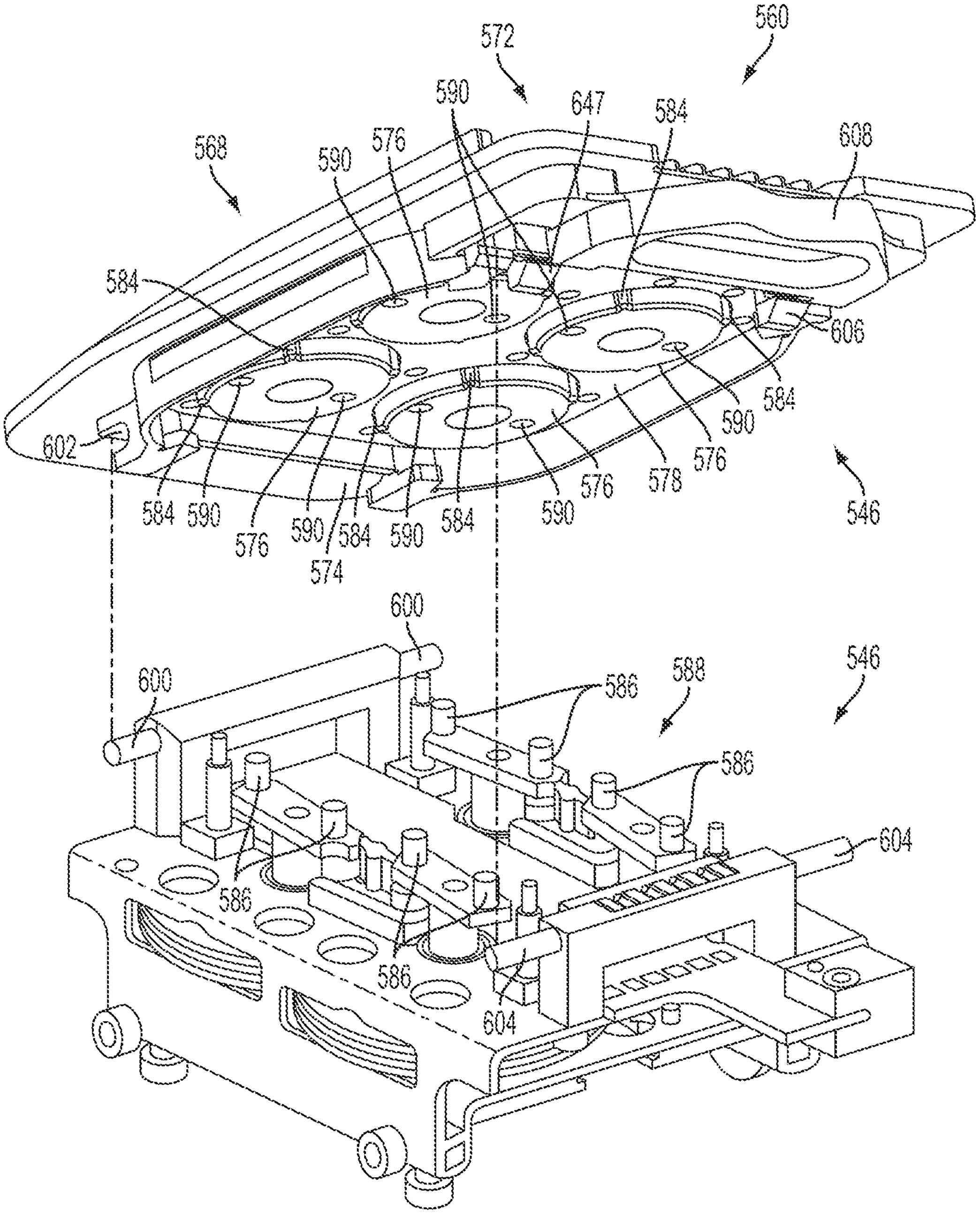
FIG. 26 illustrates one embodiment of an instrument drive assembly that may be coupled to surgical manipulators to receive and control the surgical instrument shown in FIG. 24.

FIG. 24 shows one example embodiment of an ultrasonic surgical instrument 522 adapted for use with a robotic surgical system. For example, the surgical instrument 522 may be coupled to one of the surgical manipulators 528, 528' described hereinabove. As can be seen in FIG. 24, the surgical instrument 522 comprises a surgical end effector 548 that comprises an ultrasonic blade 550 and clamp arm 552, which may be coupled to an elongated shaft assembly 554 that, in some embodiments, may comprise an articulation joint 556. FIG. 25 shows another example embodiment having an electrosurgical instrument 523 in place of the ultrasonic surgical instrument 522. The surgical instrument 523 comprises a surgical end effector 548 that comprises closable jaws 551A, 551B having energy deliver surfaces 553A, 553B for engaging and providing electrical energy to tissue between the jaws 551A, 551B. A tissue cutting element or knife 555 may be positioned at the distal end of an axially movable member 557 that may extend through the elongated shaft assembly 554 to the instrument mounting portion 558. FIG. 26 shows one example embodiment of an instrument drive assembly 546 that may be coupled to one of the surgical manipulators 528, 528' to receive and control the surgical instruments 522, 523. The instrument drive assembly 546 may also be operatively coupled to the controller 518 to receive inputs from the clinician for controlling the instruments 522, 523. For example, actuation (i.e., opening and closing) of the clamp arm 552, actuation (i.e., opening and closing) of the jaws 551A, 551B, actuation of the ultrasonic blade 550, extension of the knife 555 and actuation of the energy delivery surfaces 553A, 553B, etc. may be controlled through the instrument drive assembly 546 based on inputs from the clinician provided through the controller 518. The surgical instrument 522 is operably coupled to the manipulator by an instrument mounting portion, generally designated as 558. The surgical instrument 522 further includes an interface 560 which mechanically and electrically couples the instrument mounting portion 558 to the manipulator.

Figure 27:
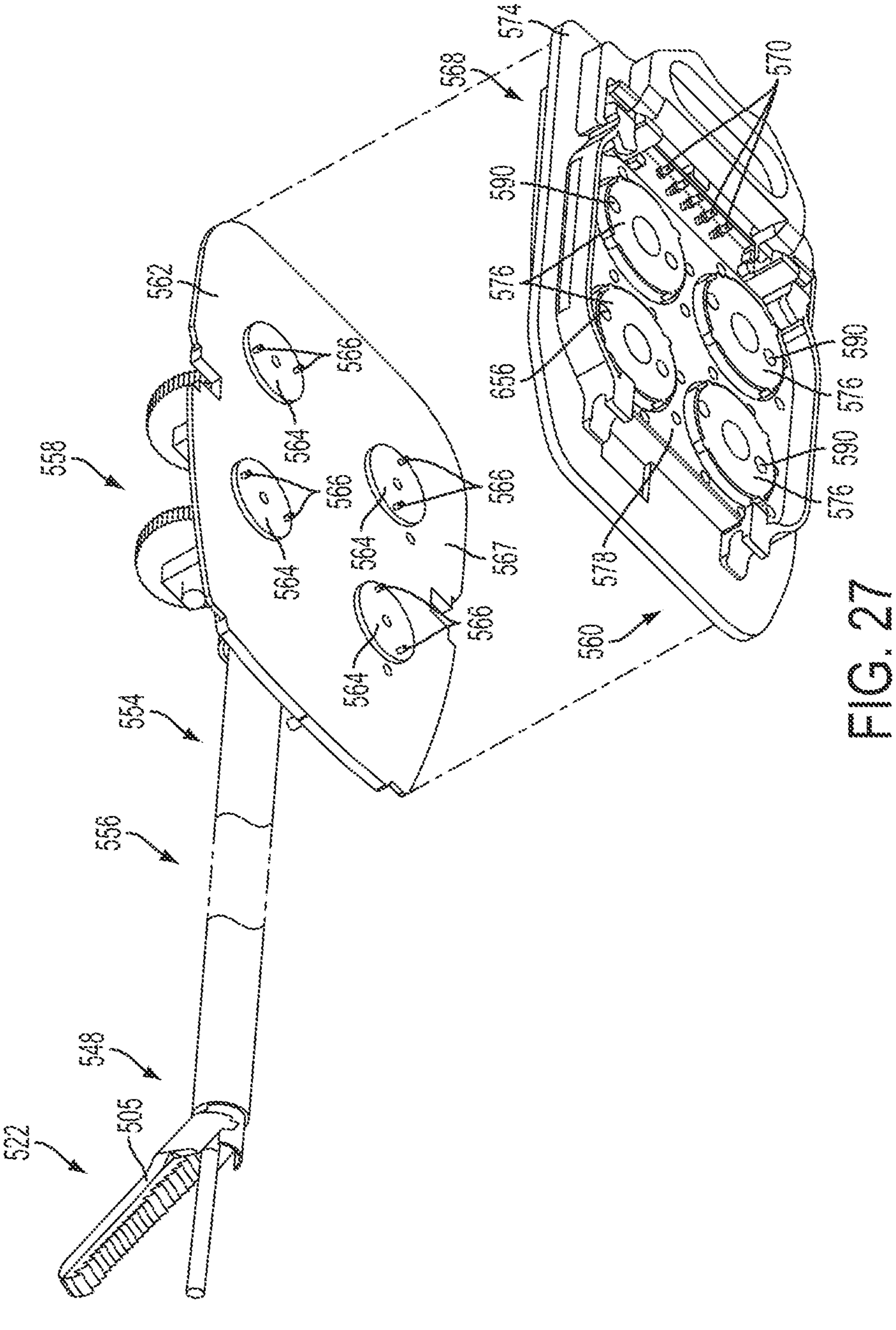
FIG. 27 illustrates another view of an instrument drive assembly embodiment of FIG. 26 including the surgical tool of FIG. 24.
Figure 28:
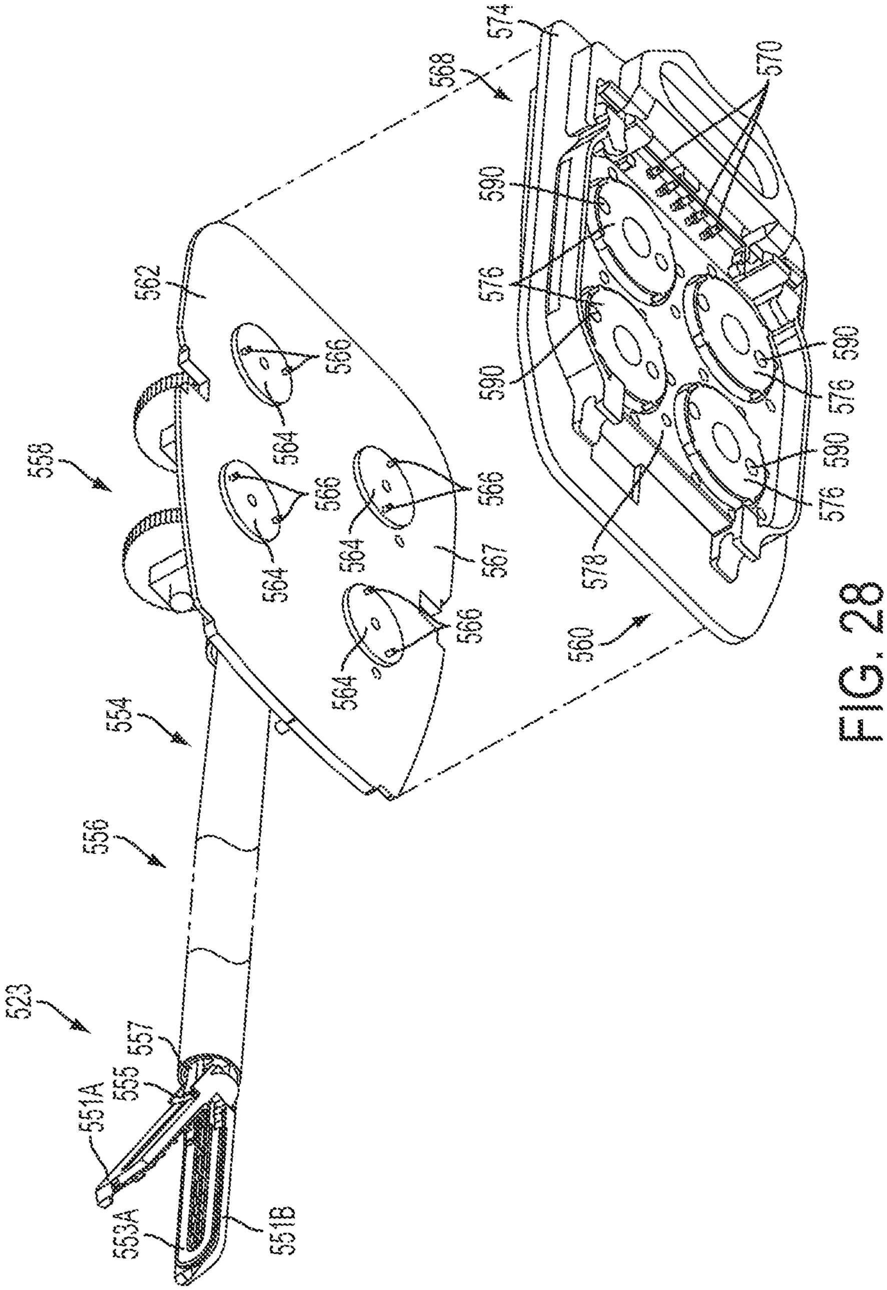
FIG. 28 illustrates another view of an instrument drive assembly of FIG. 26 including the electrosurgical tool of FIG. 25.

FIG. 27 shows another view of the instrument drive assembly of FIG. 26 including the ultrasonic surgical instrument 522. FIG. 28 shows another view of the instrument drive assembly of FIG. 26 including the electrosurgical instrument 523. The instrument mounting portion 558 includes a instrument mounting plate 562 that operably supports a plurality of (four are shown in FIG. 26) rotatable body portions, driven discs or elements 564, that each include a pair of pins 566 that extend from a surface of the driven element 564. One pin 566 is closer to an axis of rotation of each driven elements 564 than the other pin 566 on the same driven element 564, which helps to ensure positive angular alignment of the driven element 564. The driven elements 564 and pints 566 may be positioned on an adapter side 567 of the instrument mounting plate 562.

Interface 560 also includes an adaptor portion 568 that is configured to mountingly engage the mounting plate 562 as will be further discussed below. The adaptor portion 568 may include an array of electrical connecting pins 570, which may be coupled to a memory structure by a circuit board within the instrument mounting portion 558. While interface 560 is described herein with reference to mechanical, electrical, and magnetic coupling elements, it should be understood that a wide variety of telemetry modalities might be used, including infrared, inductive coupling, or the like.

Figure 29:
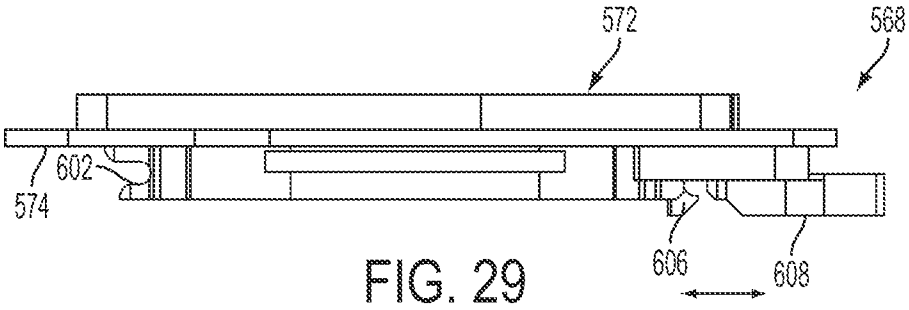
FIGS. 29-31 illustrates additional views of the adapter portion of the instrument drive assembly of FIG. 26.
Figure 30:
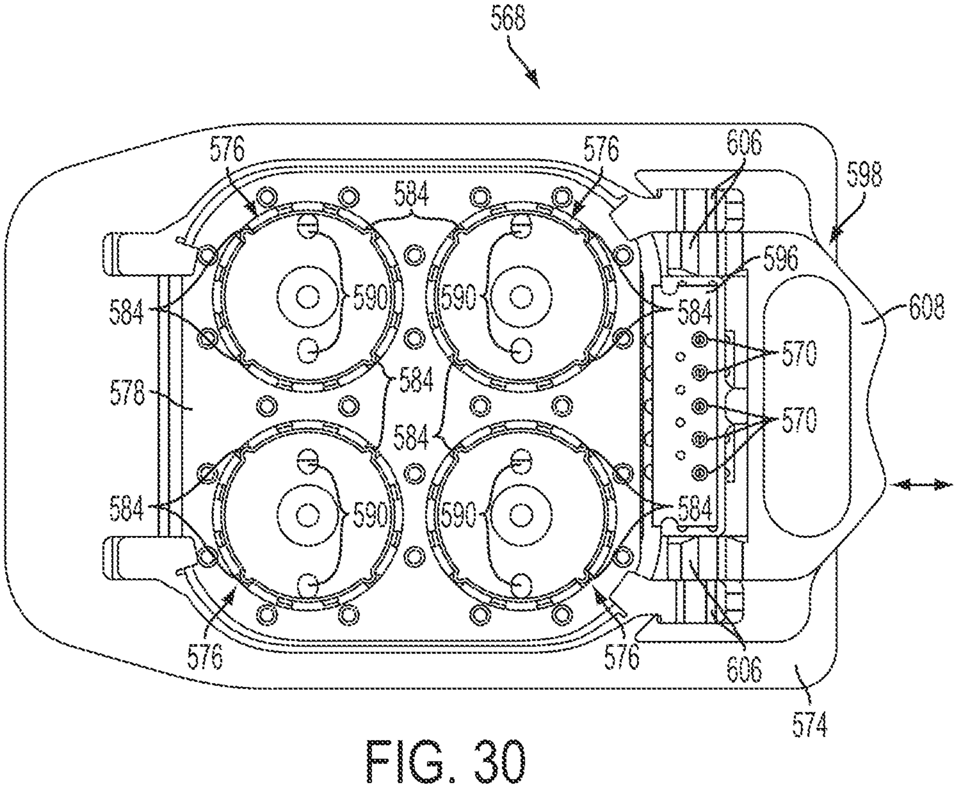
Figure 31:
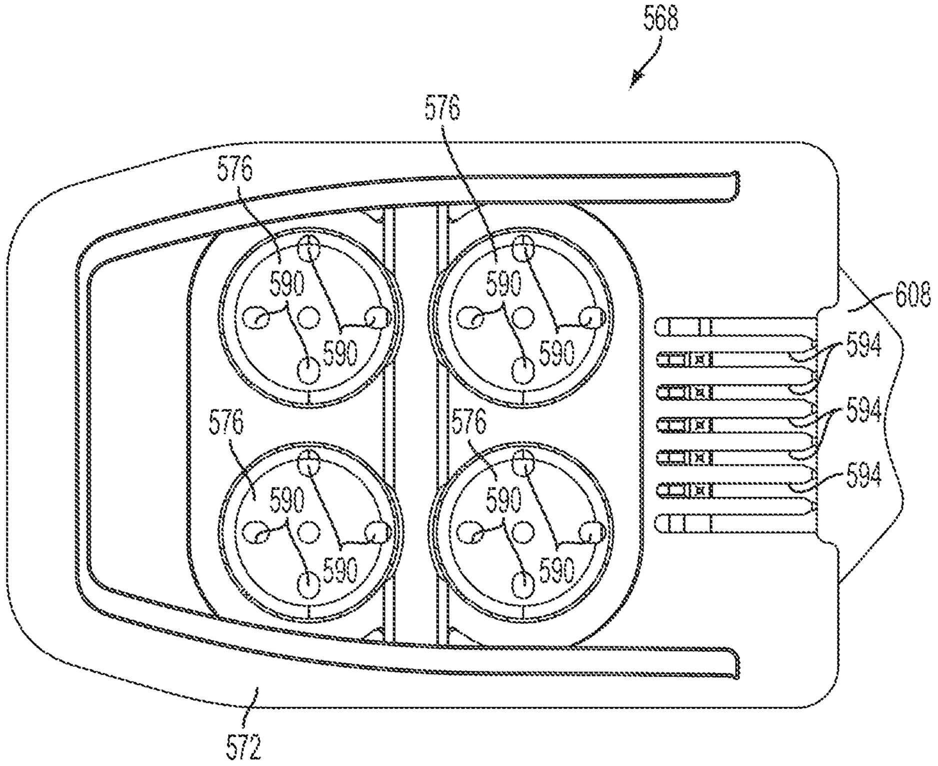

FIGS. 29-31 show additional views of the adapter portion 568 of the instrument drive assembly 546 of FIG. 26. The adapter portion 568 generally includes an instrument side 572 and a holder side 574 (FIG. 29). In various embodiments, a plurality of rotatable bodies 576 are mounted to a floating plate 578 which has a limited range of movement relative to the surrounding adaptor structure normal to the major surfaces of the adaptor 568. Axial movement of the floating plate 578 helps decouple the rotatable bodies 576 from the instrument mounting portion 558 when the levers 580 along the sides of the instrument mounting portion housing 582 are actuated (See FIGS. 24, 25) Other mechanisms/arrangements may be employed for releasably coupling the instrument mounting portion 558 to the adaptor 568. In at least one form, rotatable bodies 576 are resiliently mounted to floating plate 578 by resilient radial members which extend into a circumferential indentation about the rotatable bodies 576. The rotatable bodies 576 can move axially relative to plate 578 by deflection of these resilient structures. When disposed in a first axial position (toward instrument side 572) the rotatable bodies 576 are free to rotate without angular limitation. However, as the rotatable bodies 576 move axially toward instrument side 572, tabs

584 (extending radially from the rotatable bodies 576) laterally engage detents on the floating plates so as to limit angular rotation of the rotatable bodies 576 about their axes. This limited rotation can be used to help drivingly engage the rotatable bodies 576 with drive pins 586 of a corresponding instrument holder portion 588 of the robotic system, as the drive pins 586 will push the rotatable bodies 576 into the limited rotation position until the pins 586 are aligned with (and slide into) openings 590.

Openings 590 on the instrument side 572 and openings 590 on the holder side 574 of rotatable bodies 576 are configured to accurately align the driven elements 564 (FIGS. 27, 28) of the instrument mounting portion 558 with the drive elements 592 of the instrument holder 588. As described above regarding inner and outer pins 566 of driven elements 564, the openings 590 are at differing distances from the axis of rotation on their respective rotatable bodies 576 so as to ensure that the alignment is not 33 degrees from its intended position. Additionally, each of the openings 590 may be slightly radially elongated so as to fittingly receive the pins 566 in the circumferential orientation. This allows the pins 566 to slide radially within the openings 590 and accommodate some axial misalignment between the instrument 522, 523 and instrument holder 588, while minimizing any angular misalignment and backlash between the drive and driven elements. Openings 590 on the instrument side 572 may be offset by about 90 degrees from the openings 590 (shown in broken lines) on the holder side 574, as can be seen most clearly in FIG. 31.

Various embodiments may further include an array of electrical connector pins 570 located on holder side 574 of adaptor 568, and the instrument side 572 of the adaptor 568 may include slots 594 (FIG. 31) for receiving a pin array (not shown) from the instrument mounting portion 558. In addition to transmitting electrical signals between the surgical instrument 522, 523 and the instrument holder 588, at least some of these electrical connections may be coupled to an adaptor memory device 596 (FIG. 30) by a circuit board of the adaptor 568.

A detachable latch arrangement 598 may be employed to releasably affix the adaptor 568 to the instrument holder 588. As used herein, the term "instrument drive assembly" when used in the context of the robotic system, at least encompasses various embodiments of the adapter 568 and instrument holder 588 and which has been generally designated as 546 in FIG. 26. For example, as can be seen in FIG. 26, the instrument holder 588 may include a first latch pin arrangement 600 that is sized to be received in corresponding clevis slots 602 provided in the adaptor 568. In addition, the instrument holder 588 may further have second latch pins 604 that are sized to be retained in corresponding latch clevises 606 in the adaptor 568. See FIG. 30. In at least one form, a latch assembly 608 is movably supported on the adapter 568 and is biasable between a first latched position wherein the latch pins 600 are retained within their respective latch clevis 602 and an unlatched position wherein the second latch pins 604 may be into or removed from the latch clevises 606. A spring or springs (not shown) are employed to bias the latch assembly into the latched position. A lip on the instrument side 572 of adaptor 568 may slidably receive laterally extending tabs of instrument mounting housing 582.

As described the driven elements 564 may be aligned with the drive elements 592 of the instrument holder 588 such that rotational motion of the drive elements 592 causes corresponding rotational motion of the driven elements 564. The rotation of the drive elements 592 and driven elements 564 may be electronically controlled, for example, via the robotic arm 512, in response to instructions received from the clinician 502 via a controller 508. The instrument mounting portion 558 may translate rotation of the driven elements 564 into motion of the surgical instrument 522, 523.

Figure 32:
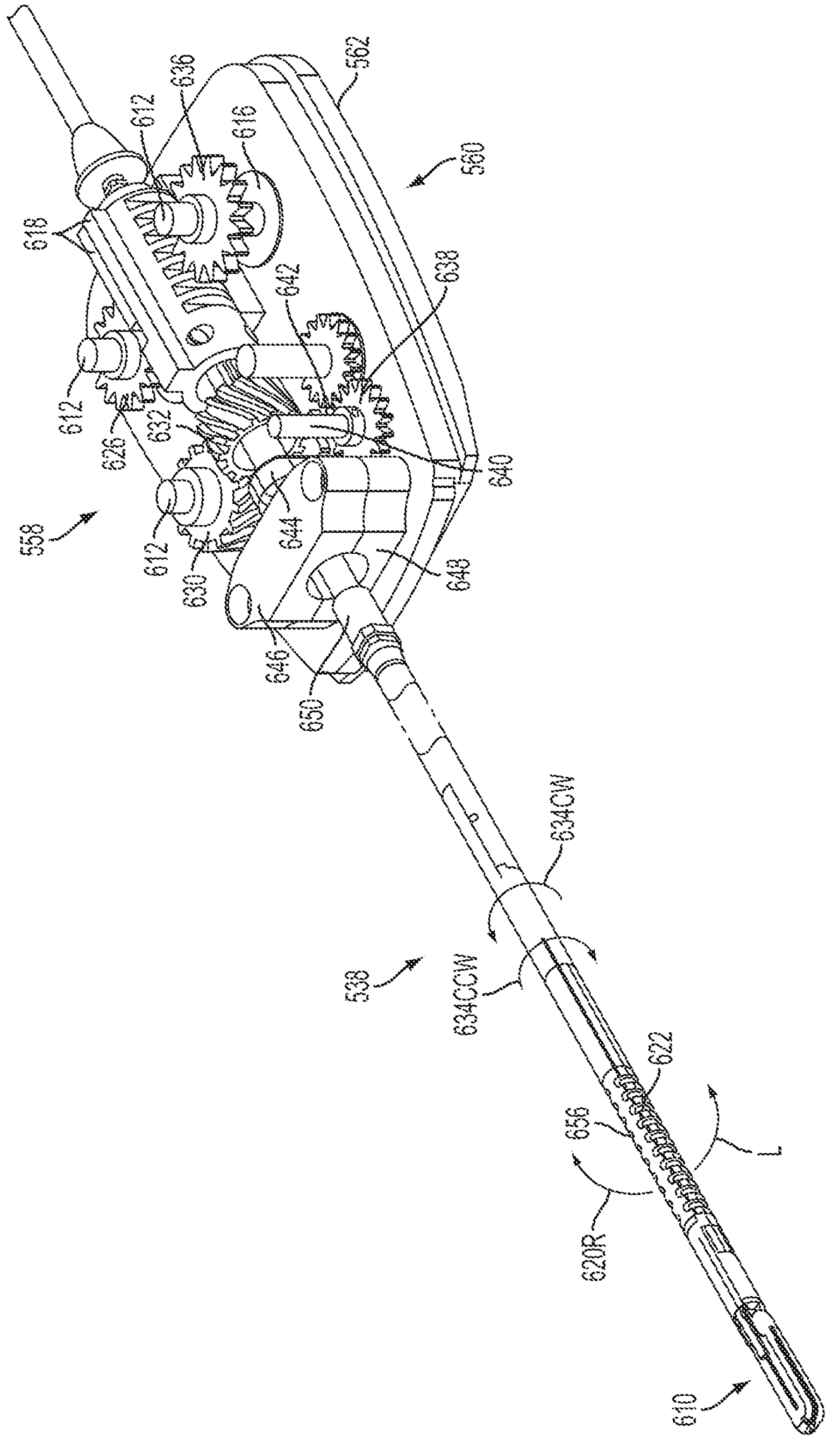
FIGS. 32-34 illustrate one embodiment of the instrument mounting portion of FIGS. 24-25 showing components for translating motion of the driven elements into motion of the surgical instrument.
Figure 33:
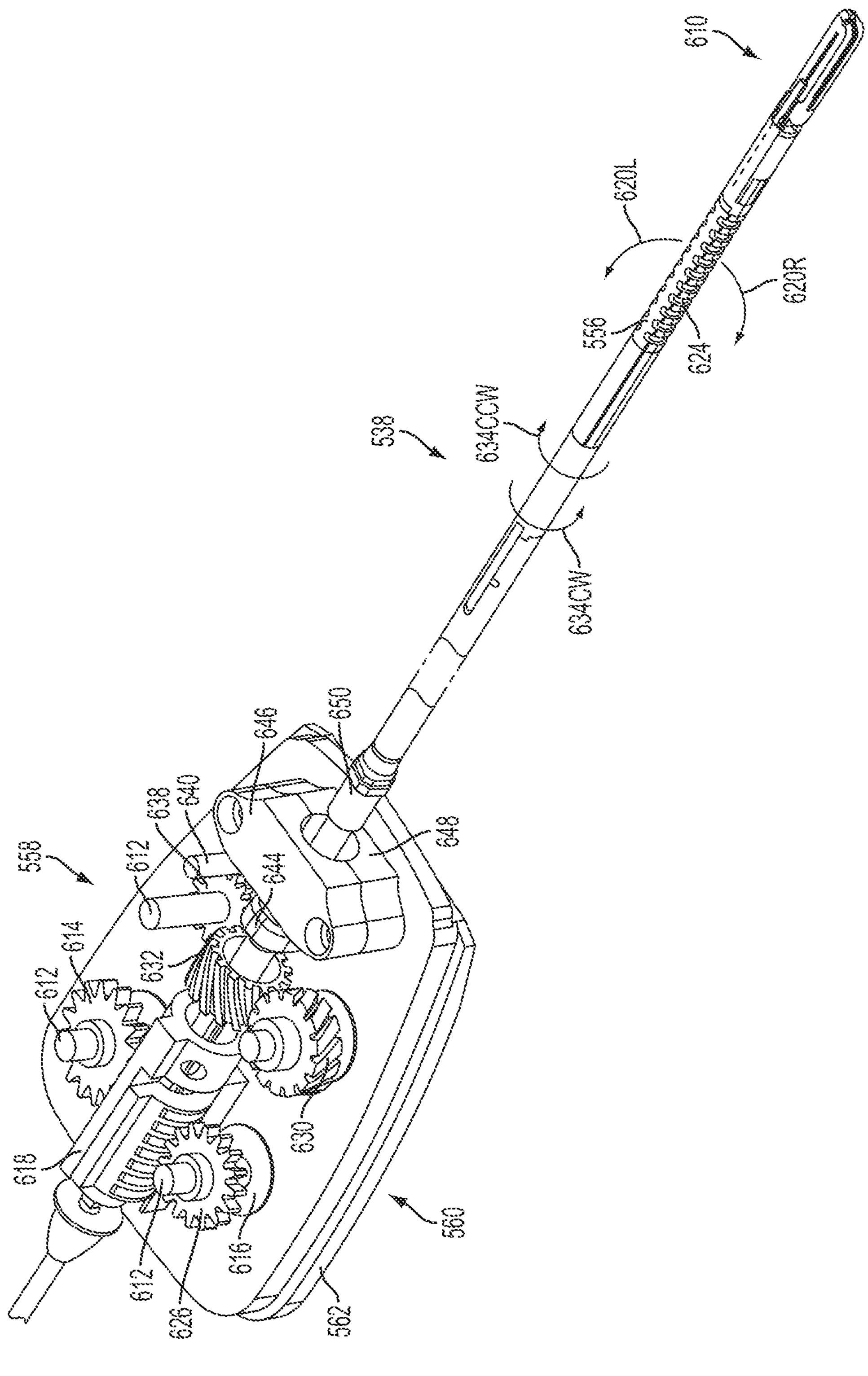
Figure 34:
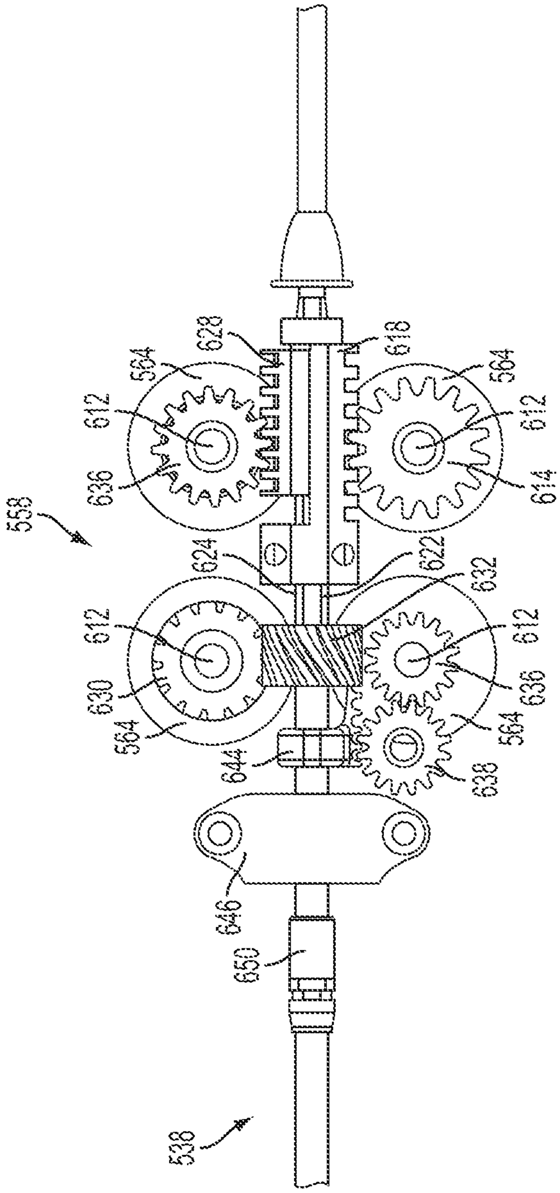

FIGS. 32-34 show one example embodiment of the instrument mounting portion 558 showing components for translating motion of the driven elements 564 into motion of the surgical instrument 522, 523. FIGS. 32-34 show the instrument mounting portion with a shaft 538 having a surgical end effector 610 at a distal end thereof. The end effector 610 may be any suitable type of end effector for performing a surgical task on a patient. For example, the end effector may be configured to provide RF and/or ultrasonic energy to tissue at a surgical site. The shaft 538 may be rotatably coupled to the instrument mounting portion 558 and secured by a top shaft holder 646 and a bottom shaft holder 648 at a coupler 650 of the shaft 538.

In one example embodiment, the instrument mounting portion 558 comprises a mechanism for translating rotation of the various driven elements 564 into rotation of the shaft 538, differential translation of members along the axis of the shaft (e.g., for articulation), and reciprocating translation of one or more members along the axis of the shaft 538 (e.g., for extending and retracting tissue cutting elements such as 555, overtubes and/or other components). In one example embodiment, the rotatable bodies 612 (e.g., rotatable spools) are coupled to the driven elements 564. The rotatable bodies 612 may be formed integrally with the driven elements 564. In some embodiments, the rotatable bodies 612 may be formed separately from the driven elements 564 provided that the rotatable bodies 612 and the driven elements 564 are fixedly coupled such that driving the driven elements 564 causes rotation of the rotatable bodies 612. Each of the rotatable bodies 612 is coupled to a gear train or gear mechanism to provide shaft articulation and rotation and clamp jaw open/close and knife actuation.

In one example embodiment, the instrument mounting portion 558 comprises a mechanism for causing differential translation of two or more members along the axis of the shaft 538. In the example provided in FIGS. 32-34, this motion is used to manipulate articulation joint 556. In the illustrated embodiment, for example, the instrument mounting portion 558 comprises a rack and pinion gearing mechanism to provide the differential translation and thus the shaft articulation functionality. In one example embodiment, the rack and pinion gearing mechanism comprises a first pinion gear 614 coupled to a rotatable body 612 such that rotation of the corresponding driven element 564 causes the first pinion gear 614 to rotate. A bearing 616 is coupled to the rotatable body 612 and is provided between the driven element 564 and the first pinion gear 614. The first pinion gear 614 is meshed to a first rack gear 618 to convert the rotational motion of the first pinion gear 614 into linear motion of the first rack gear 618 to control the articulation of the articulation section 556 of the shaft assembly 538 in a left direction 620L. The first rack gear 618 is attached to a first articulation band 622 (FIG. 32) such that linear motion of the first rack gear 618 in a distal direction causes the articulation section 556 of the shaft assembly 538 to articulate in the left direction 620L. A second pinion gear 626 is coupled to another rotatable body 612 such that rotation of the corresponding driven element 564 causes the second pinion gear 626 to rotate. A bearing 616 is coupled to the rotatable body 612 and is provided between the driven element 564 and the second pinion gear 626. The second pinion gear 626 is meshed to a second rack gear 628 to convert the rotational motion of the second pinion gear 626 into linear motion of the second rack gear 628 to control the articulation of the articulation section 556 in a right direction 620R. The second rack gear 628 is attached to a second articulation band 624 (FIG. 33) such that linear motion of the second rack gear 628 in a distal direction causes the articulation section 556 of the shaft assembly 538 to articulate in the right direction 620R. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 further comprises a mechanism for translating rotation of the driven elements 564 into rotational motion about the axis of the shaft 538. For example, the rotational motion may be rotation of the shaft 538 itself. In the illustrated embodiment, a first spiral worm gear 630 coupled to a rotatable body 612 and a second spiral worm gear 632 coupled to the shaft assembly 538. A bearing 616 (FIG. 17) is coupled to a rotatable body 612 and is provided between a driven element 564 and the first spiral worm gear 630. The first spiral worm gear 630 is meshed to the second spiral worm gear 632, which may be coupled to the shaft assembly 538 and/or to another component of the instrument 522, 523 for which longitudinal rotation is desired. Rotation may be caused in a clockwise (CW) and counter-clockwise (CCW) direction based on the rotational direction of the first and second spiral worm gears 630, 632. Accordingly, rotation of the first spiral worm gear 630 about a first axis is converted to rotation of the second spiral worm gear 632 about a second axis, which is orthogonal to the first axis. As shown in FIGS. 32-33, for example, a CW rotation of the second spiral worm gear 632 results in a CW rotation of the shaft assembly 538 in the direction indicated by 634CW. A CCW rotation of the second spiral worm gear 632 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

In one example embodiment, the instrument mounting portion 558 comprises a mechanism for generating reciprocating translation of one or more members along the axis of the shaft 538. Such translation may be used, for example to drive a tissue cutting element, such as 555, drive an overtube for closure and/or articulation of the end effector 610, etc. In the illustrated embodiment, for example, a rack and pinion gearing mechanism may provide the reciprocating translation. A first gear 636 is coupled to a rotatable body 612 such that rotation of the corresponding driven element 564 causes the first gear 636 to rotate in a first direction. A second gear 638 is free to rotate about a post 640 formed in the instrument mounting plate 562. The first gear 636 is meshed to the second gear 638 such that the second gear 638 rotates in a direction that is opposite of the first gear 636. In one example embodiment, the second gear 638 is a pinion gear meshed to a rack gear 642, which moves in a liner direction. The rack gear 642 is coupled to a translating block 644, which may translate distally and proximally with the rack gear 642. The translation block 644 may be coupled to any suitable component of the shaft assembly 538 and/or the end effector 610 so as to provide reciprocating longitudinal motion. For example, the translation block 644 may be mechanically coupled to the tissue cutting element 555 of the RF surgical device 523. In some embodiments, the translation block 644 may be coupled to an overtube, or other component of the end effector 610 or shaft 538.

Figure 35:
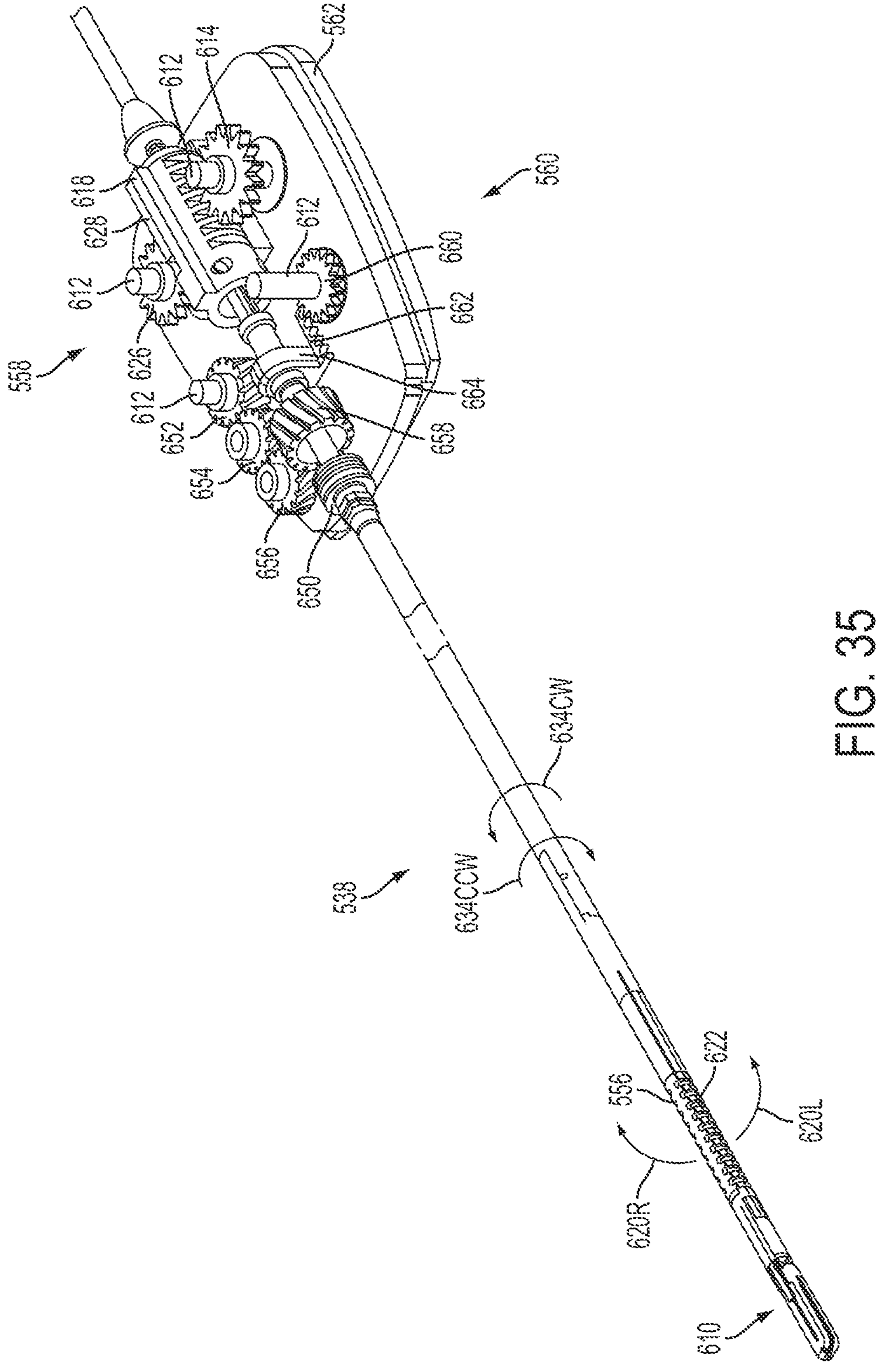
FIGS. 35-37 illustrate an alternate embodiment of the instrument mounting portion of FIGS. 24-25 showing an alternate example mechanism for translating rotation of the driven elements into rotational motion about the axis of the shaft and an alternate example mechanism for generating reciprocating translation of one or more members along the axis of the shaft 538.
Figure 36:
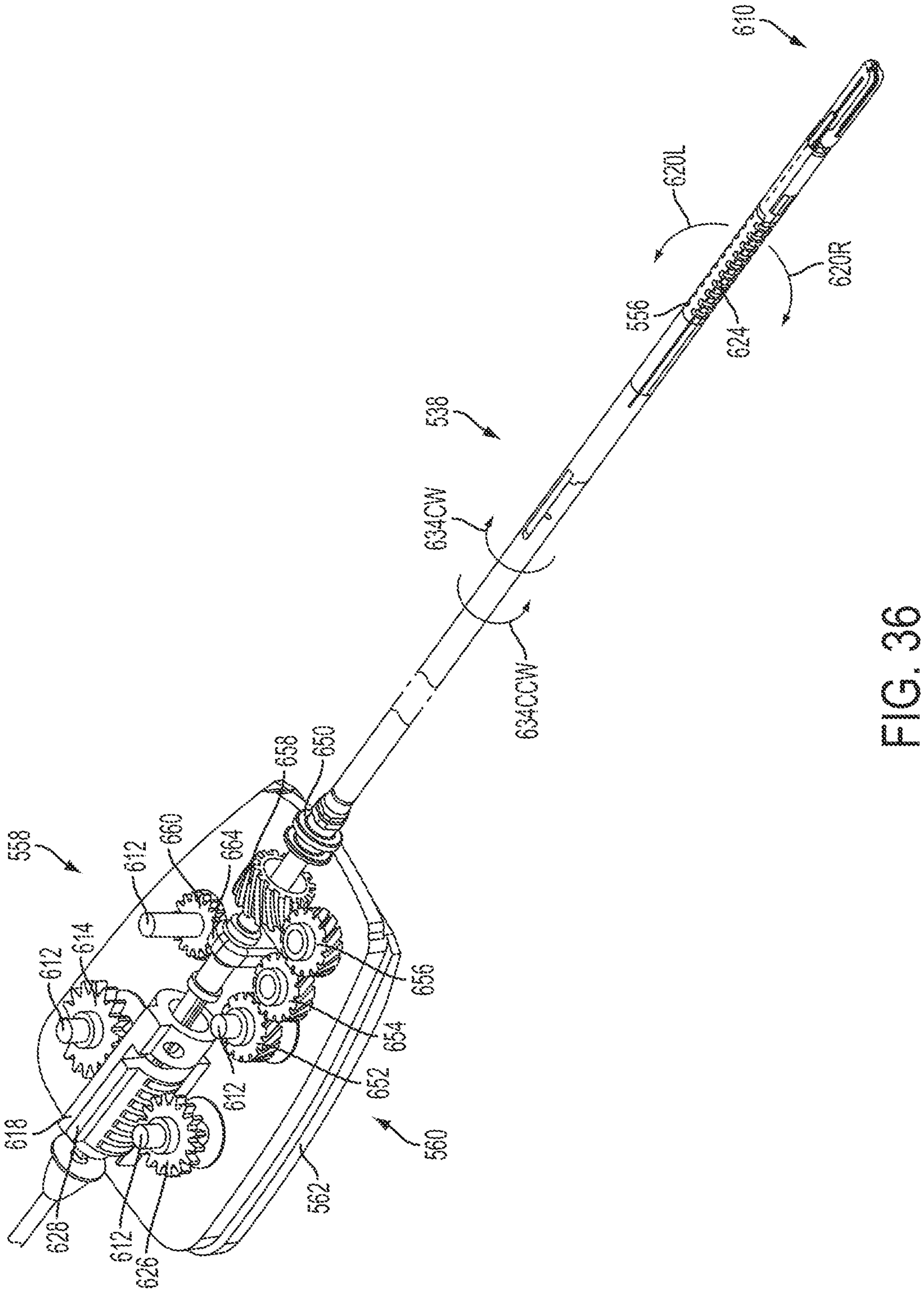
Figure 37:
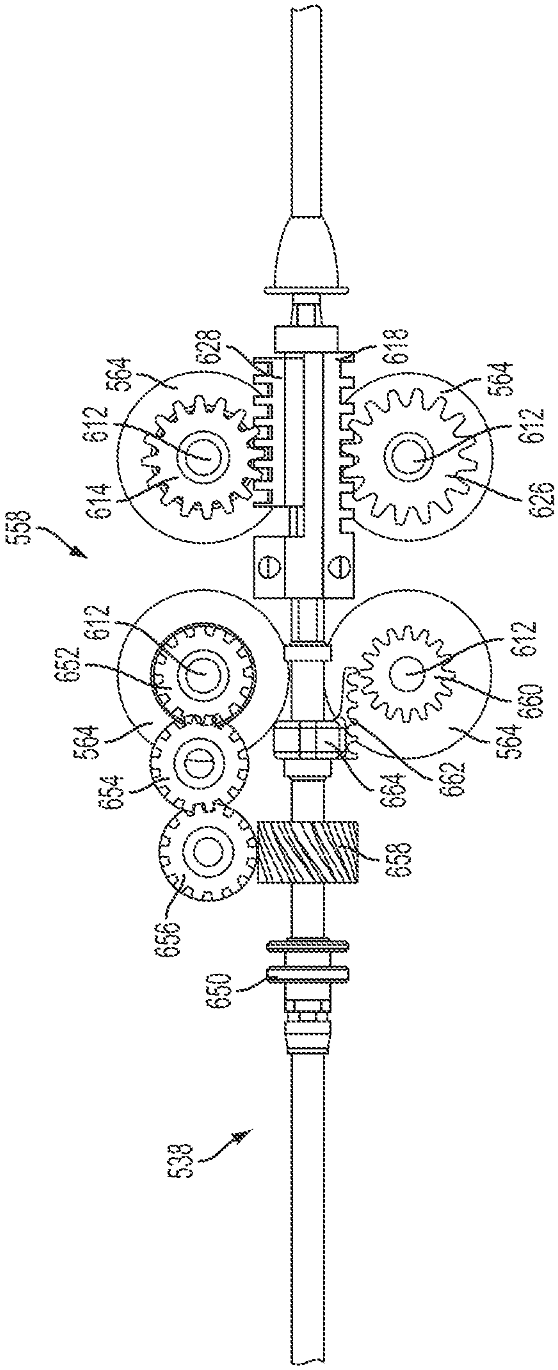

FIGS. 35-37 illustrate an alternate embodiment of the instrument mounting portion 558 showing an alternate example mechanism for translating rotation of the driven elements 564 into rotational motion about the axis of the shaft 538 and an alternate example mechanism for generating reciprocating translation of one or more members along the axis of the shaft 538. Referring now to the alternate rotational mechanism, a first spiral worm gear 652 is coupled to a second spiral worm gear 654, which is coupled to a third spiral worm gear 656. Such an arrangement may be provided for various reasons including maintaining compatibility with existing robotic systems 500 and/or where space may be limited. The first spiral worm gear 652 is coupled to a rotatable body 612. The third spiral worm gear 656 is meshed with a fourth spiral worm gear 658 coupled to the shaft assembly 538. A bearing 760 is coupled to a rotatable body 612 and is provided between a driven element 564 and the first spiral worm gear 738. Another bearing 760 is coupled to a rotatable body 612 and is provided between a driven element 564 and the third spiral worm gear 652. The third spiral worm gear 652 is meshed to the fourth spiral worm gear 658, which may be coupled to the shaft assembly 538 and/or to another component of the instrument 522, 523 for which longitudinal rotation is desired. Rotation may be caused in a CW and a CCW direction based on the rotational direction of the spiral worm gears 656, 658. Accordingly, rotation of the third spiral worm gear 656 about a first axis is converted to rotation of the fourth spiral worm gear 658 about a second axis, which is orthogonal to the first axis. As shown in FIGS. 36 and 37, for example, the fourth spiral worm gear 658 is coupled to the shaft 538, and a CW rotation of the fourth spiral worm gear 658 results in a CW rotation of the shaft assembly 538 in the direction indicated by 634CW. A CCW rotation of the fourth spiral worm gear 658 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Referring now to the alternate example mechanism for generating reciprocating translation of one or more members along the axis of the shaft 538, the instrument mounting portion 558 comprises a rack and pinion gearing mechanism to provide reciprocating translation along the axis of the shaft 538 (e.g., translation of a tissue cutting element 555 of the RF surgical device 523). In one example embodiment, a third pinion gear 660 is coupled to a rotatable body 612 such that rotation of the corresponding driven element 564 causes the third pinion gear 660 to rotate in a first direction. The third pinion gear 660 is meshed to a rack gear 662, which moves in a linear direction. The rack gear 662 is coupled to a translating block 664. The translating block 664 may be coupled to a component of the device 522, 523, such as, for example, the tissue cutting element 555 of the RF surgical device and/or an overtube or other component which is desired to be translated longitudinally.

Figure 38:
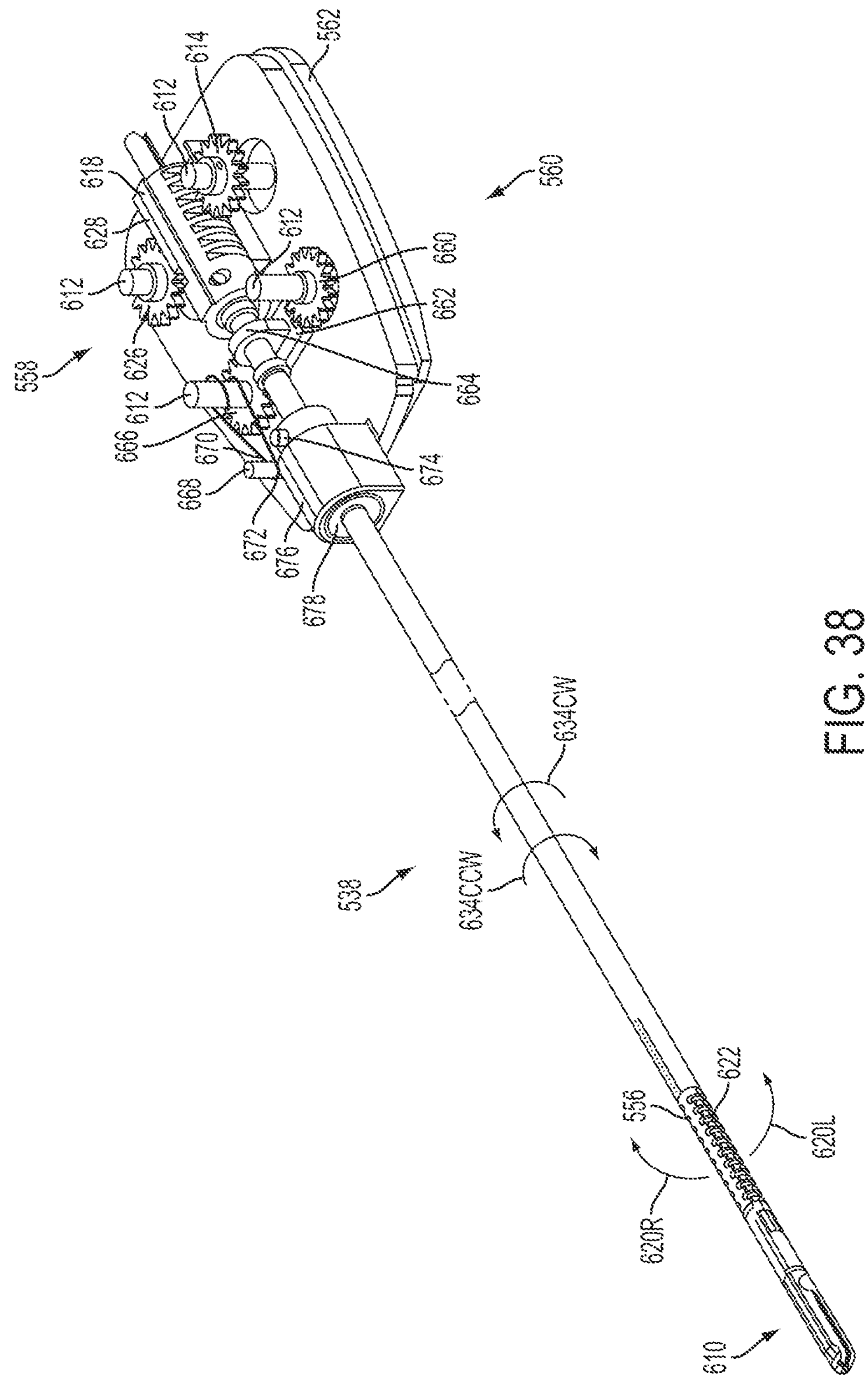
FIGS. 38-42 illustrate an alternate embodiment of the instrument mounting portion FIGS. 24-25 showing another alternate example mechanism for translating rotation of the driven elements into rotational motion about the axis of the shaft.
Figure 39:
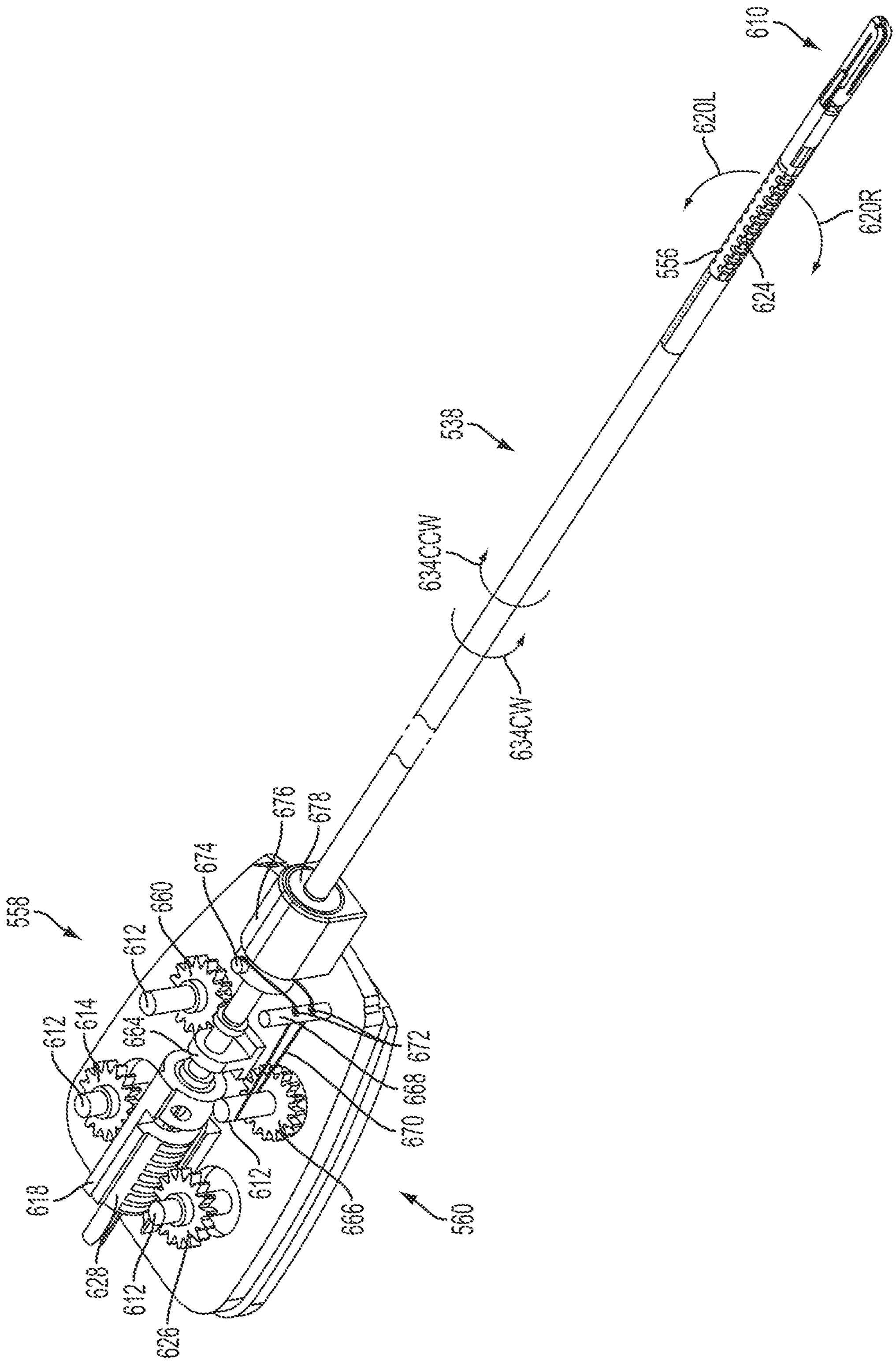
Figure 40:
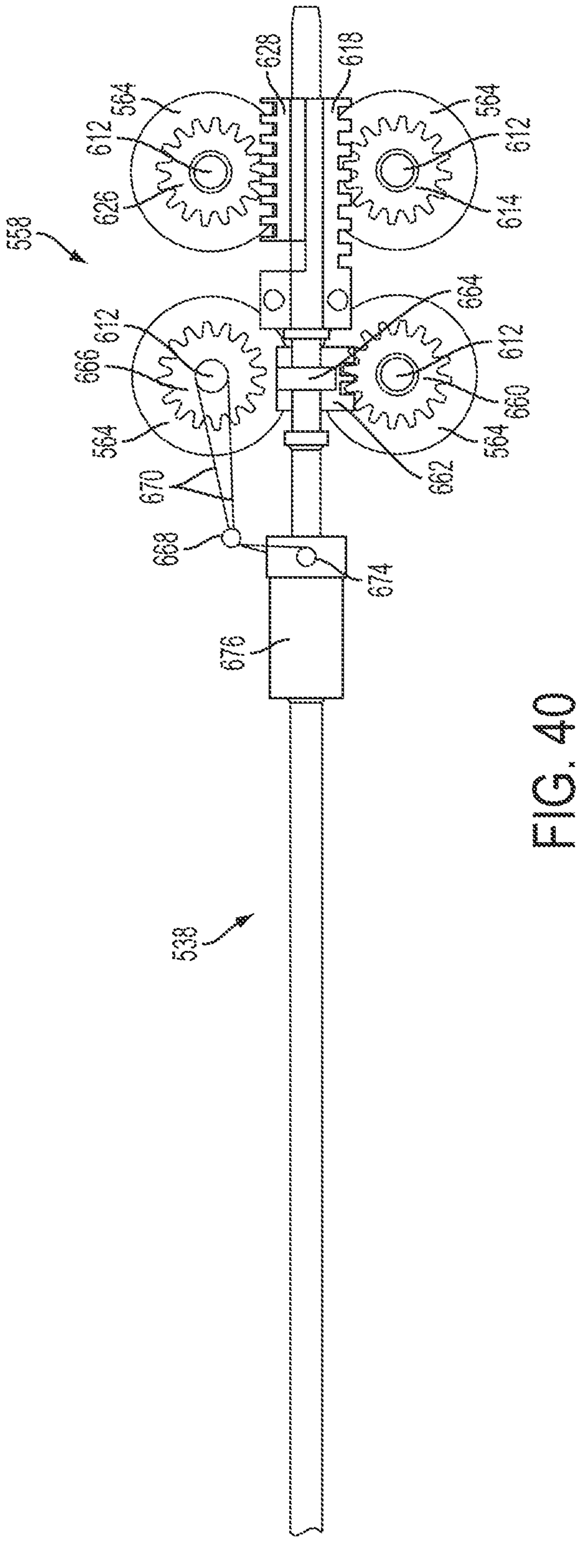
Figure 41:
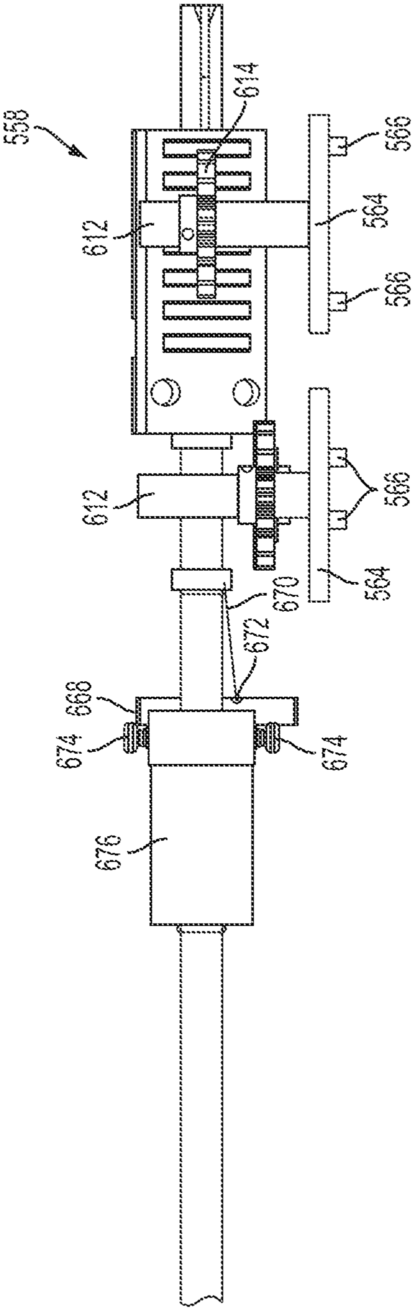
Figure 42:
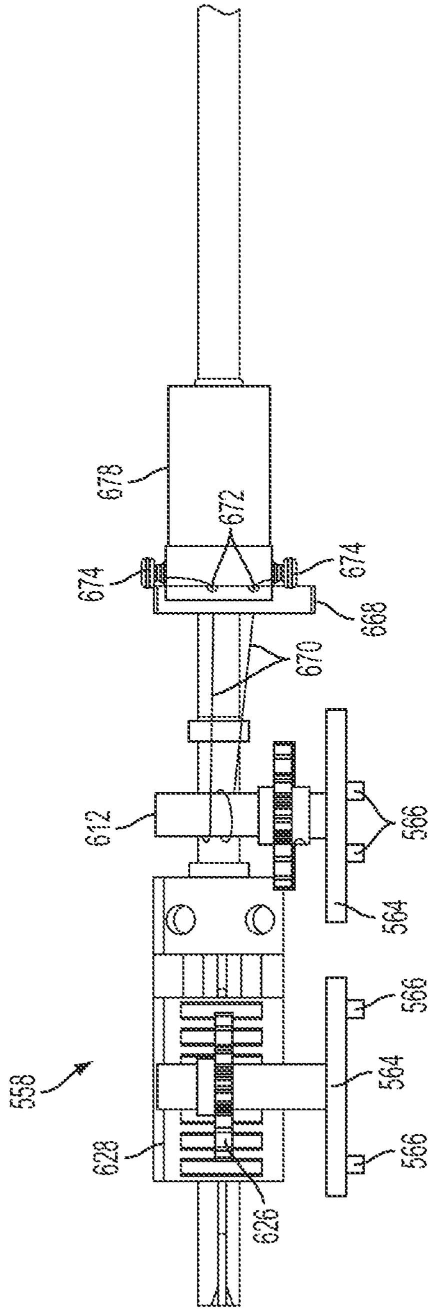
Figure 43:
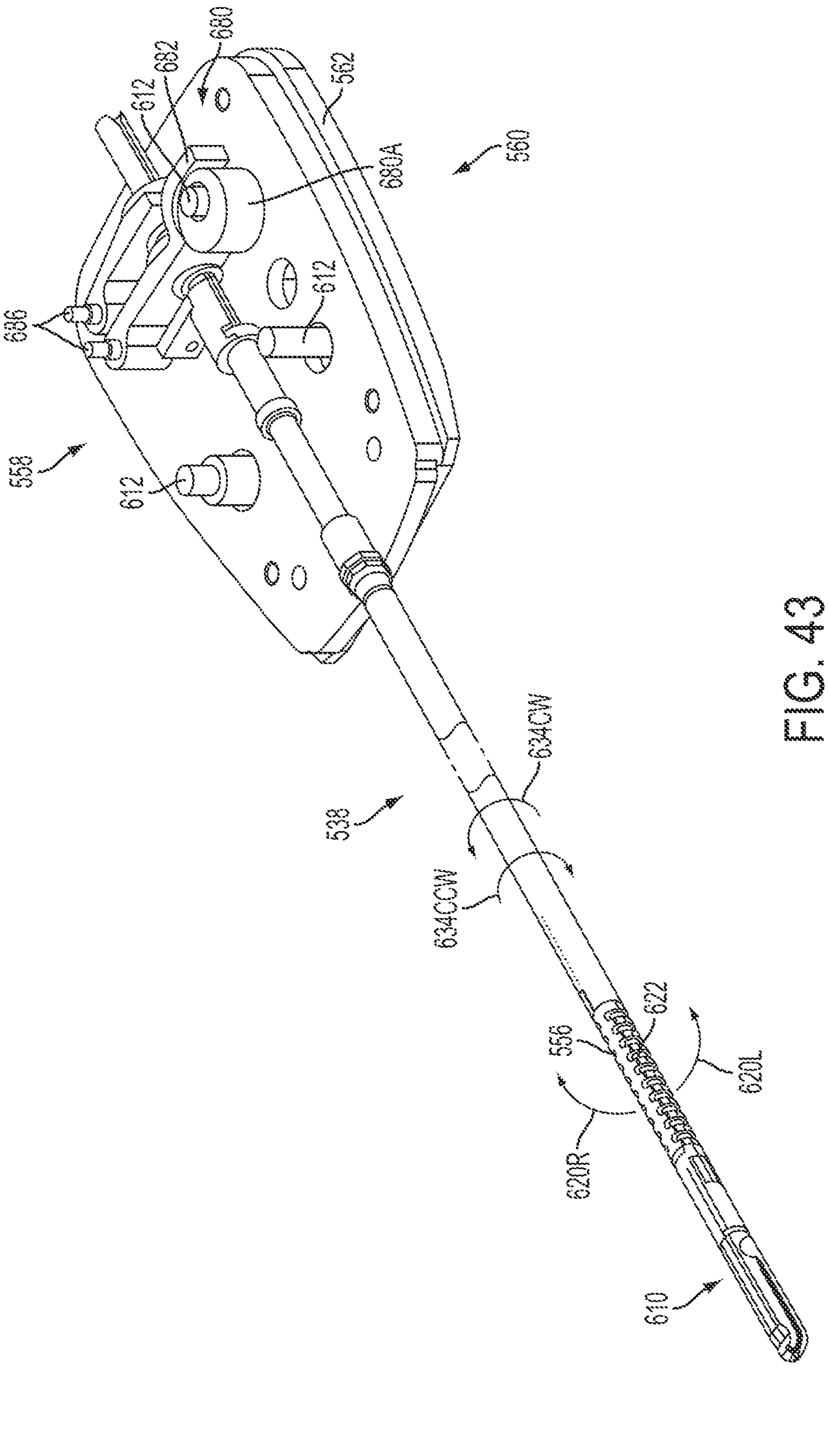
Figure 44:
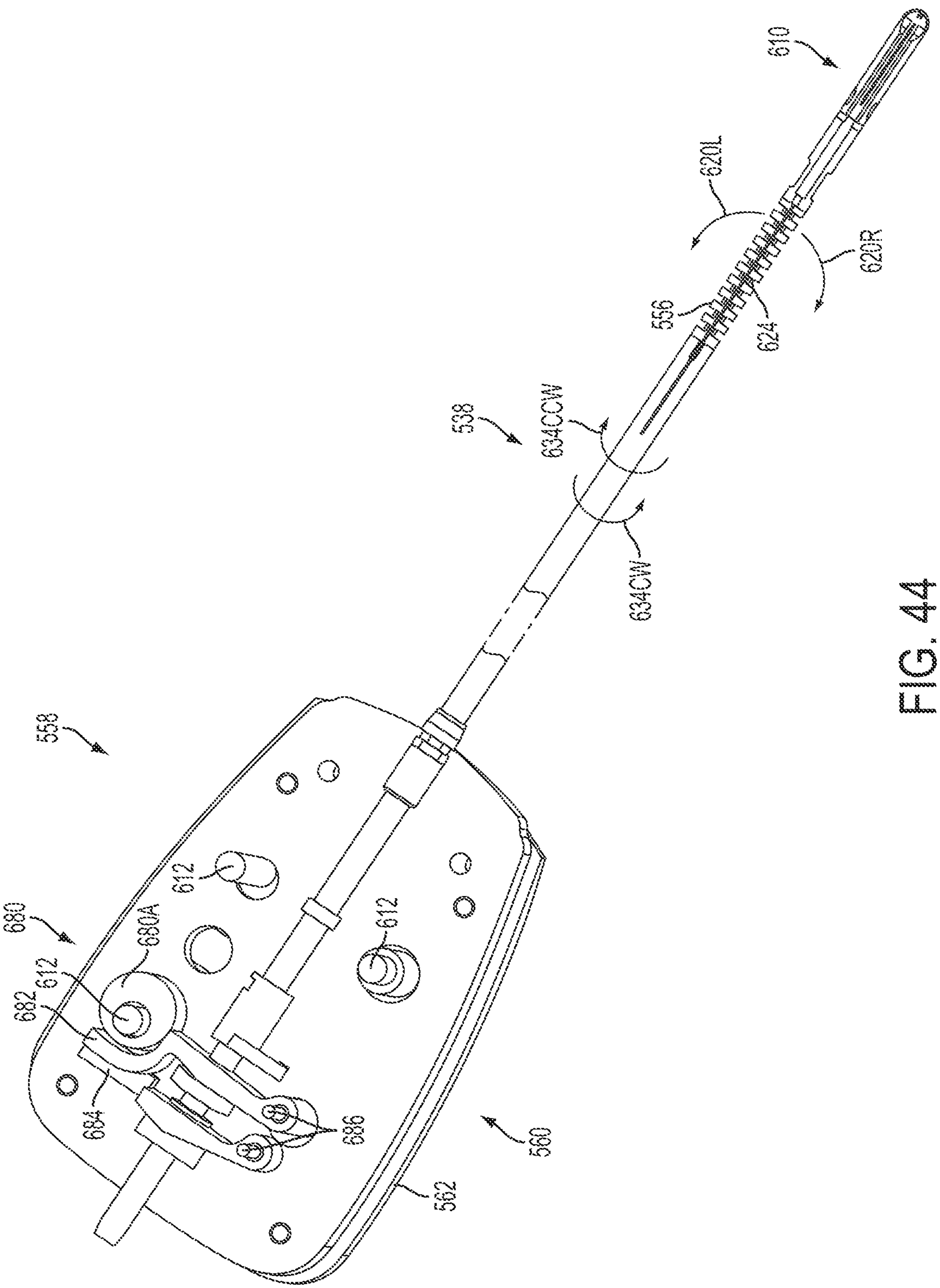
Figure 45:
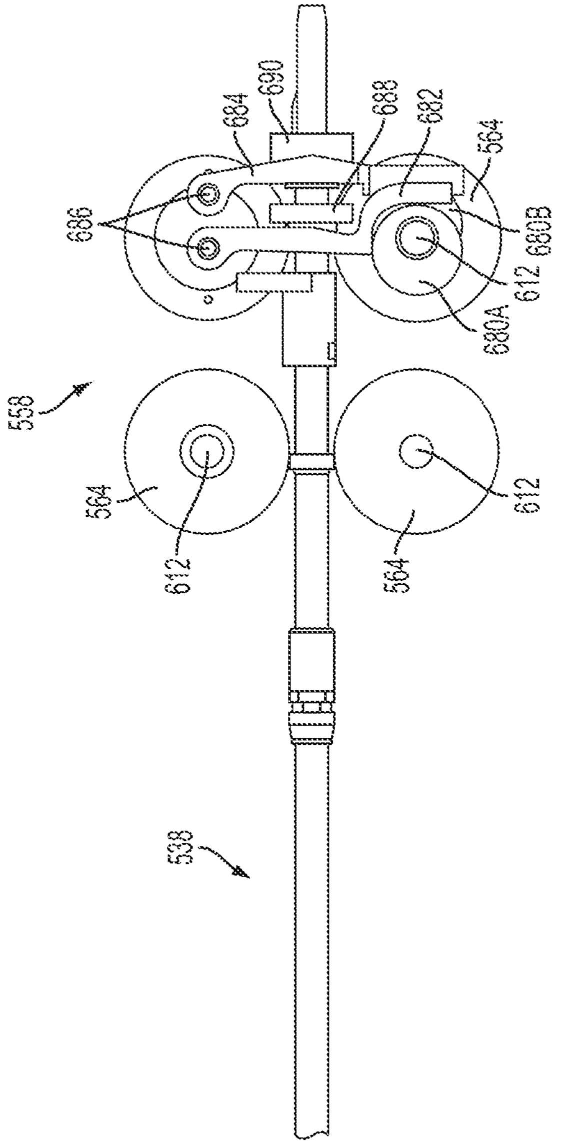

FIGS. 38-42 illustrate an alternate embodiment of the instrument mounting portion 558 showing another alternate example mechanism for translating rotation of the driven elements 564 into rotational motion about the axis of the shaft 538. In FIGS. 38-42, the shaft 538 is coupled to the remainder of the mounting portion 558 via a coupler 676 and a bushing 678. A first gear 666 coupled to a rotatable body 612, a fixed post 668 comprising first and second openings 672, first and second rotatable pins 674 coupled to the shaft assembly, and a cable 670 (or rope). The cable is wrapped around the rotatable body 612. One end of the cable 670 is located through a top opening 672 of the fixed post 668 and fixedly coupled to a top rotatable pin 674. Another end of the cable 670 is located through a bottom opening 672 of the fixed post 668 and fixedly coupled to a bottom rotating pin 674. Such an arrangement is provided for various reasons including maintaining compatibility with existing robotic systems 500 and/or where space may be limited. Accordingly, rotation of the rotatable body 612 causes the rotation about the shaft assembly 538 in a CW and a CCW direction based on the rotational direction of the rotatable body 612 (e.g., rotation of the shaft 538 itself). Accordingly, rotation of the rotatable body 612 about a first axis is converted to rotation of the shaft assembly 538 about a second axis, which is orthogonal to the first axis. As shown in FIGS. 38-39, for example, a CW rotation of the rotatable body 612 results in a CW rotation of the shaft assembly 538 in the direction indicated by 634CW. A CCW rotation of the rotatable body 612 results in a CCW rotation of the shaft assembly 538 in the direction indicated by 634CCW. Additional bearings may be provided between the rotatable bodies and the corresponding gears. Any suitable bearings may be provided to support and stabilize the mounting and reduce rotary friction of shaft and gears, for example.

Figure 46A:
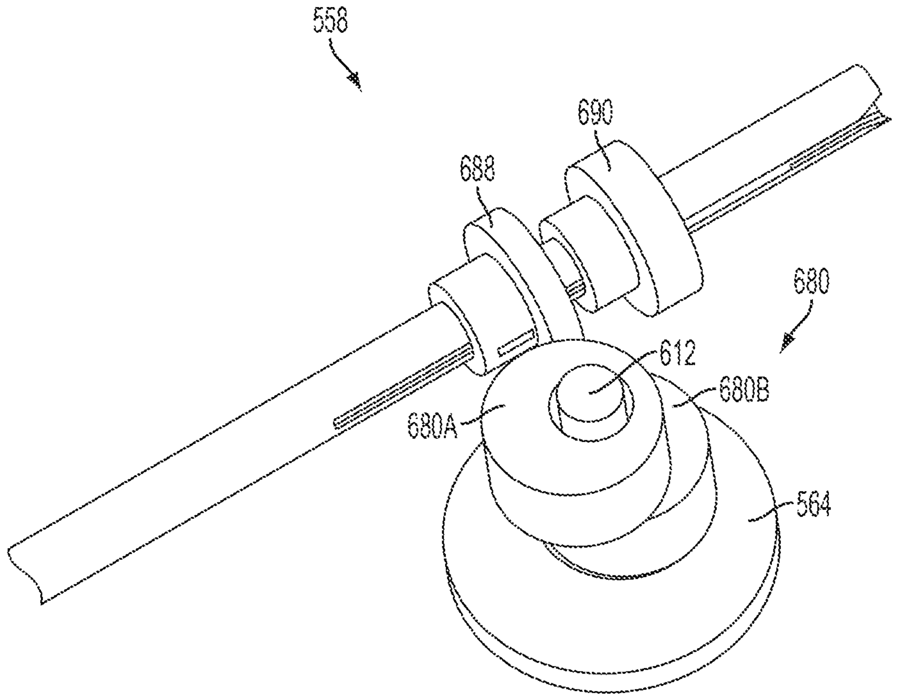

FIGS. 43-46A illustrate an alternate embodiment of the instrument mounting portion 558 showing an alternate example mechanism for differential translation of members along the axis of the shaft 538 (e.g., for articulation). For example, as illustrated in FIGS. 43-46A, the instrument mounting portion 558 comprises a double cam mechanism 680 to provide the shaft articulation functionality. In one example embodiment, the double cam mechanism 680 comprises first and second cam portions 680A, 680B. First and second follower arms 682, 684 are pivotally coupled to corresponding pivot spools 686. As the rotatable body 612 coupled to the double cam mechanism 680 rotates, the first cam portion 680A acts on the first follower arm 682 and the second cam portion 680B acts on the second follower arm 684. As the cam mechanism 680 rotates the follower arms 682, 684 pivot about the pivot spools 686. The first follower arm 682 may be attached to a first member that is to be differentially translated (e.g., the first articulation band 622). The second follower arm 684 is attached to a second member that is to be differentially translated (e.g., the second articulation band 624). As the top cam portion 680A acts on the first follower arm 682, the first and second members are differentially translated. In the example embodiment where the first and second members are the respective articulation bands 622 and 624, the shaft assembly 538 articulates in a left direction 620L. As the bottom cam portion 680B acts of the second follower arm 684, the shaft assembly 538 articulates in a right direction 620R. In some example embodiments, two separate bushings 688, 690 are mounted beneath the respective first and second follower arms 682, 684 to allow the rotation of the shaft without affecting the articulating positions of the first and second follower arms 682, 684. For articulation motion, these bushings reciprocate with the first and second follower arms 682, 684 without affecting the rotary position of the jaw 902. FIG. 46A shows the bushings 688, 690 and the dual cam assembly 680, including the first and second cam portions 680B, 680B, with the first and second follower arms 682, 684 removed to provide a more detailed and clearer view.

Figure 46B:
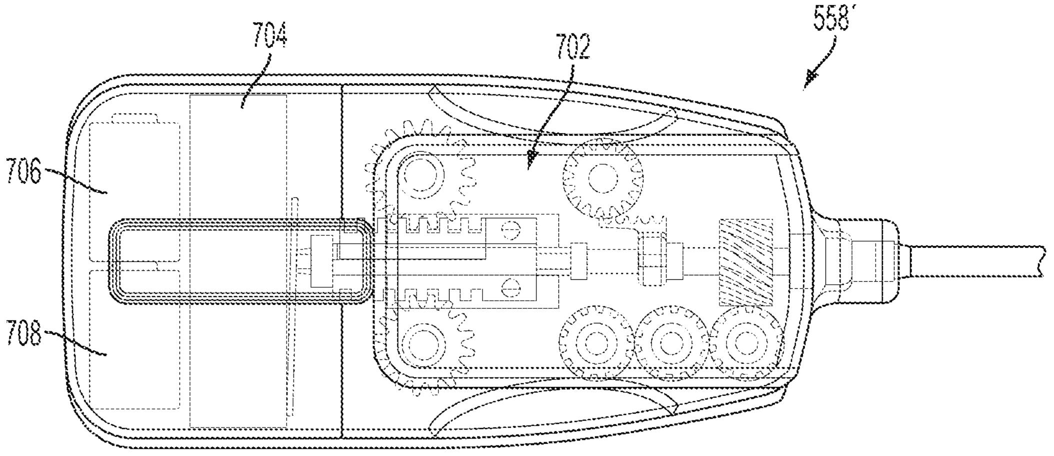
FIGS. 46B-46C illustrate one embodiment of an instrument mounting portion comprising internal power and energy sources.
Figure 46C:
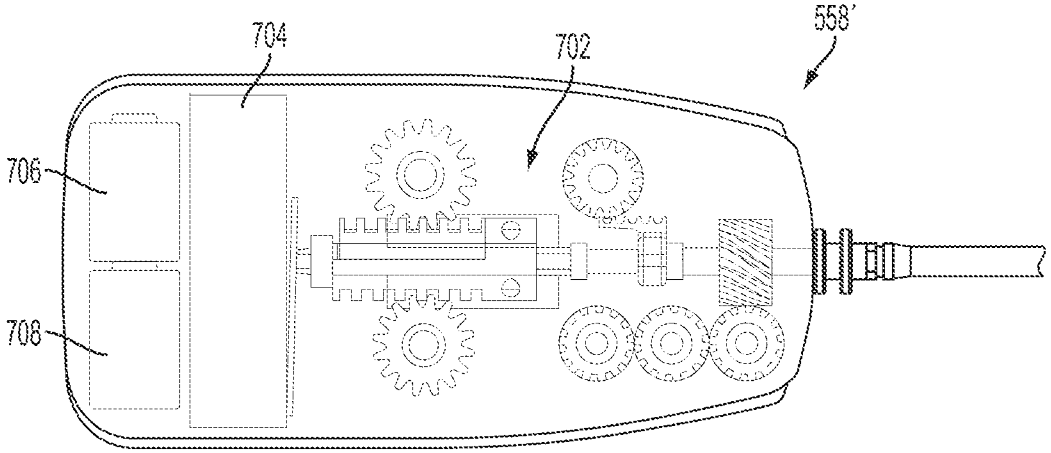

In various embodiments, the instrument mounting portion 558 may additionally comprise internal energy sources for driving electronics and provided desired ultrasonic and/or RF frequency signals to surgical tools. FIGS. 46B-46C illustrate one embodiment of a instrument mounting portion 558' comprising internal power and energy sources. For example, surgical instruments (e.g., instruments 522, 523) mounted utilizing the instrument mounting portion 558' need not be wired to an external generator or other power source. Instead, the functionality of the various generators 20, 320 described herein may be implemented on board the mounting portion 558.

As illustrated in FIGS. 46B-46C, the instrument mounting portion 558' may comprise a distal portion 702. The distal portion 702 may comprise various mechanisms for coupling rotation of drive elements 592 to end effectors of the various surgical instruments 522, 523, for example, as described herein above. Proximal of the distal portion 702, the instrument mounting portion 558' comprises an internal direct current (DC) energy source and an internal drive and control circuit 704. In the illustrated embodiment, the energy source comprises a first and second battery 706, 708. In other respects, the instrument mounting portion 558' is similar to the various embodiments of the instrument mounting portion 558 described herein above.

Figure 47:
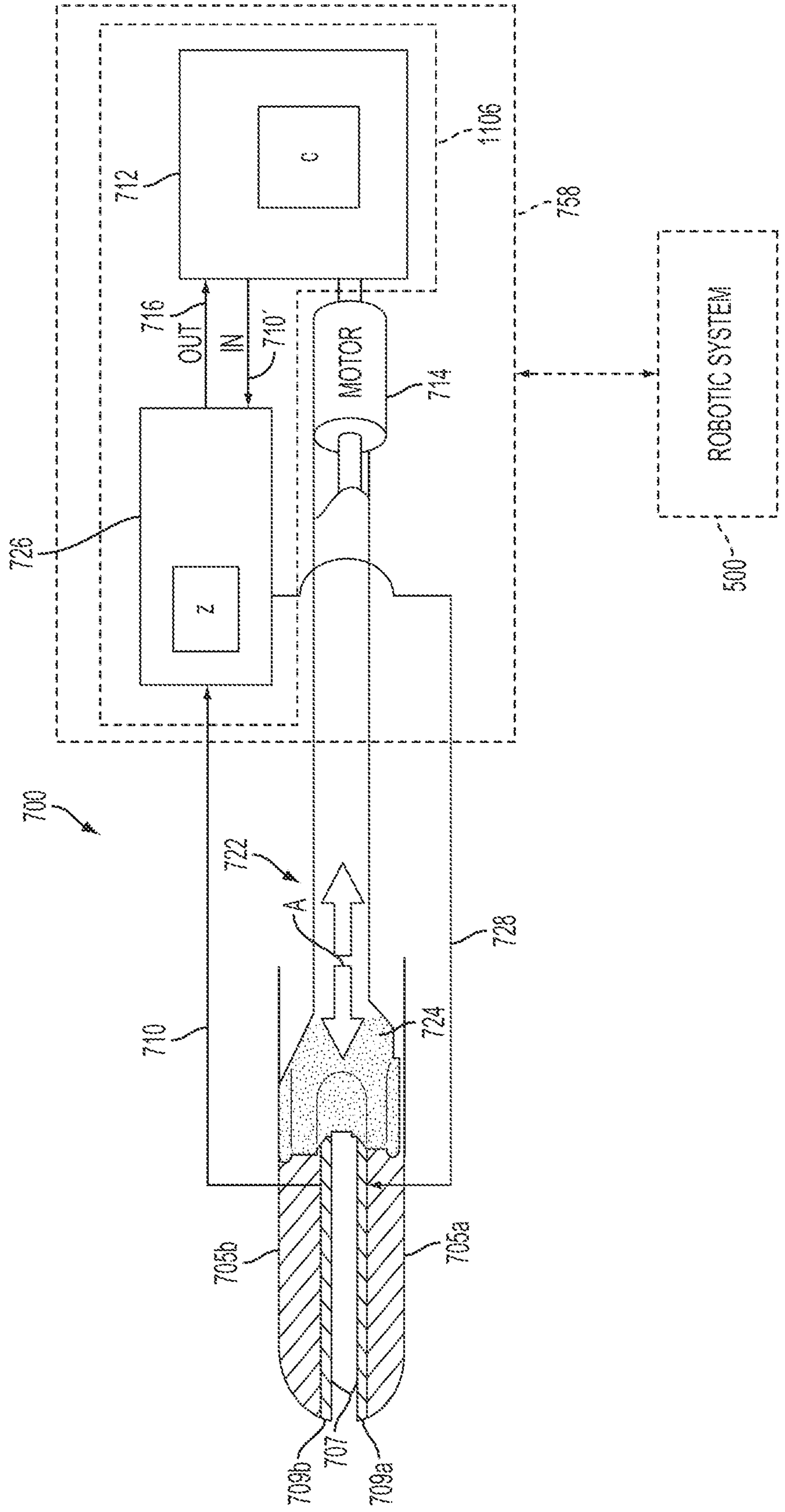
FIG. 47 illustrates one embodiment of an electrosurgical instrument capable of implementing a method to control an electrosurgical end effector.

In one embodiment, an electrosurgical end effector may be controlled to ensure proper sealing of a target tissue during operation. FIG. 47 illustrates one example embodiment of an electrosurgical instrument 700 capable of implementing a method to control an electrosurgical end effector 722. In one embodiment, the electrosurgical end effector 722 comprises a motor driven slideable blade 724, a first jaw member 705*a* and a second jaw member 705*b* for grasping the target tissue 707 therebetween. The first and second jaw members 705*a*, 705*b* comprise first and second electrodes 709*a*, 709*b*, respectively, to conduct therapeutic and/or sub-therapeutic energy to the target tissue 707. In one embodiment, the therapeutic levels of RF energy may be sufficient to seal the target tissue 707. It will be appreciated that the term target tissue applies to that portion of the tissue or vessel clamped between the first and second jaw members 705*a*, 705*b*. The blade 724 may be driven by a motor 714. The motor 714 is connected to a motor control logic 712, which may vary the speed of the motor 714 and thereby vary the reciprocating movement of the blade 724. In one embodiment, the motor 714 may be a servo motor. In one embodiment, once the target tissue 707 is sealed, the blade 724 is advanced by the motor 714 to cut the sealed target tissue 707.

The electrosurgical instrument 700 may be integrated with the robotic surgical system shown in FIGS. 19-46. The electrosurgical instrument 700 may be configured to operate with any one of the configurations shown in FIGS. 19-46. In one embodiment, the motor control logic 712 and the control logic 726 may be integral with the electrosurgical instrument 700 and located within an instrument mounting portion, such as, for example, the instrument mounting portion 758 (shown in phantom in FIG. 47). In another embodiment, the control logic 726 and the motor control logic 712 may be integral with the robotic surgical system, such as, for example, the robotic surgical system 500 (shown in phantom in FIG. 47). In yet another embodiment, the control logic 726 and the motor control logic 712 may be incorporated into one or more controllers for independent communication with the robotic surgical control system 500.

In one embodiment, a control logic 726 is coupled to the motor control logic 712 and the electrosurgical end effector

722. In one embodiment, the control logic 726 may be configured to modify the one or more signals applied to the electrosurgical end effector 722. For example, the control logic 726 may provide a control signal to the motor control logic 712 to adjust the speed of the motor 714. As another example, the control logic 726 may be coupled to a generator to control an ultrasonic or radiofrequency signal generated by the generator and applied to the electrosurgical end effector 722. The control logic 726 may be implemented in any suitable digital logic circuit, such as, for example, a processor, a digital signal processor, a state-machine implemented by a field programmable gate array (FPGA), or any other suitable logic circuit. The control logic 726 may be implemented in hardware, software, or any combination thereof.

In one embodiment, the first and second electrodes 709*a*, 709*b* receive an electrosurgical signal 728, such as, for example, an RF signal. The RF signal may be a therapeutic or sub-therapeutic RF signal. The electrosurgical signal 728 may be generated by a generator, such as, for example, the generator 320 shown in, and described in connection with, FIG. 11. In the illustrated embodiment, the electrosurgical signal 728 may be controlled by the control logic 726. In one embodiment, the control logic 726 enables delivery of the electrosurgical signal 728 by controlling the function of the electrosurgical generator. In another embodiment, the control logic 726 may enable delivery of the electrosurgical signal 728 through a control signal and one or more control blocks.

In one embodiment, a first feedback signal 710 is generated by the conducting energy trough the target tissue 707 and is transmitted to the control logic 726. In one embodiment, the energy conducted by the target tissue 707 for purposes of operating the first feedback signal 710 may be therapeutic, sub-therapeutic, or a combination thereof. The feedback signal 710 may, in one embodiment, be a measurement of the impedance of the target tissue 707. As the target tissue 707 is cut and sealed, the impedance of the target tissue 707 increases proportionally. By measuring the increase in impedance, the control logic 726 may determine whether the electrosurgical end effector 722 is properly sealing and cutting the target tissue 707 and apply any suitable control signal in response thereto. The control logic 726 may adjust the reciprocating movement speed of the blade 724, the energy level of the electrosurgical signal 728, or any combination thereof, in order to ensure that the target tissue 707 is suitably sealed.

In one embodiment, the motor 714 may comprise a servo motor. A servo motor is a motor which forms part of a servomechanism. In one embodiment, an encoder is located on the shaft of the servo motor to provide a feedback signal to the motor control logic 712. The encoder may be any suitable encoder for use with a servo motor, such as, for example, a rotary encoder which may provide a signal indicative of a rotational position. In one embodiment, the rotation of a shaft of the servo motor may correspond to a movement of the blade 724. For example, a rotary encoder may be disposed on the shaft of the servo motor. Each rotational degree of the servo motor may correspond to a specific distal movement distance of the blade 724. The motor control logic 712 may receive a signal from the encoder and may convert the signal into a position of the blade 724 based on the known ratio between the rotation of the shaft and the distal movement of the blade 724.

In another embodiment, the motor 714 may comprise a stepper motor. A stepper motor is a brushless DC motor that divides a full rotation of the motor into a number of equal steps. The motor's position can be controlled by a pulsed DC signal causing the motor to advance a certain number of steps with each pulse. In one embodiment, a single step of a stepper motor may correspond to a known distal movement distance of the blade 724. The position of the blade 724 can be precisely controlled by applying a pulsed control signal to the stepper motor. In one embodiment, the motor control logic 712 may generate the pulsed DC control signal for the stepper motor based on input from the control logic 726, one or more feedback signals 710, 710' received from the end effector, or any combination thereof.

In one embodiment, the control logic 726 may maintain a rate of increase of the impedance by varying the speed of the motor 714. The control logic 726 may provide a control signal to the motor control logic 712. The motor control logic 712 may vary the output signal to the motor 714 to increase or decrease the longitudinal speed of the blade 724 to ensure proper cutting and sealing of the target tissue 707. The motor control logic 712 may be any suitable motor controller, such as, for example, an adjustable-speed driver or an intelligent motor controller. An adjustable-speed driver is a control circuit that may vary the output voltage or current to the motor resulting in the motor running at faster or slower speeds, proportional to the voltage. An intelligent motor controller is a logic circuit which may control the voltage, current, or other output to the motor to increase or decrease the longitudinal speed. The motor control logic 712 may be implemented in any suitable digital logic circuit, such as, for example, a processor, a digital signal processor, a state machine implemented by a field programmable gate array (FPGA), or any other suitable logic circuit. The motor control logic 712 may be implemented in hardware, software, or any combination thereof.

The control logic 726 and the motor control logic 712 may comprise one or more circuit components for converting or generating control signals. In one embodiment, the motor control logic 712 may comprise a Digital-to-Analog Converter (DAC) to convert a digital control signal from the control logic 726 to an analog input signal for the motor 714. In other embodiments, the control logic 726 or the motor control logic 712 may comprise one or more components for generating a pulse-width modulation signal for controlling the motor 714, including, but not limited to, a crystal oscillator, one or more latches, or any other digital or analog components for generating appropriate control signals.

In one embodiment, the control logic 726 may apply at least one electrosurgical signal 728 to the electrosurgical instrument 700. The electrosurgical signal 728 may comprise, in various embodiments, a drive signal 716 for the motor control logic 712, an RF signal applied to the first and second electrodes 709*a*, 709*b* in respective first and second jaw members 705*a*, 705*b* for electrosurgical treatment of the target tissue 707, or an ultrasonic drive signal to impart ultrasonic motion to the blade 724. The control logic 726 may be configured to vary one or more of the at least one electrosurgical signals 708 to maintain a predetermined rate of change of impedance of the target tissue 707.

In one embodiment, the impedance of the target tissue 707 may increase during the tissue treatment process, which may include the operations of sealing and cutting the target tissue 707, either independently or simultaneously, for example. As the blade 724 is translated along the longitudinal axis, the tissue impedance may generally increase in response to coagulation, tissue welding, and/or cutting of the target tissue 707. In some embodiments, tissue impedance may display a sudden impedance increase indicating successful coagulation (sealing). The increase in impedance may be due to physiological changes in the tissue, a positive temperature coefficient (PTC) material reaching a trigger threshold, etc., and may occur at any point during the tissue treatment process. The change in impedance, either gradual or sudden, may be monitored by the control logic 726 which may modulate one or more electrosurgical signals to maintain the rate of change of impedance at a predetermined level or within a predetermined range. The term modulation is intended to cover any suitable form of signal modulation, such as, for example, amplitude modulation, frequency modulation, phase modulation, or any combination thereof without limitation. The amount of energy, the travel time of the blade 724, or the combination of the two that may be required to maintain the predetermined rate of change of impedance may be related to the thermal mass of the target tissue 707. The thermal mass of any given target tissue 707, in turn, may be related to the type and amount of tissue located at the target tissue 707.

The feedback signal 710 may be used to calculate the rate of change of impedance of the target tissue 707 during the treatment process. In one embodiment, the feedback signal 710 may be indicative of one or more characteristics of the electrosurgical end effector 722 or the target tissue 707, such as, for example, the voltage drop across the target tissue 707, the current flow through the target tissue 707, the first and second electrodes 709*a,* 709*b* of the respective first and second jaw members 705*a,* 705*b,* or any combination thereof. The feedback signal 710 provides a measurement of the one or more characteristics to the control logic 726, which may then calculate the impedance at the site of the target tissue 707. The feedback signal 710 may be compared over one or more clock cycles of the control logic 726 to generate a rate of change of the impedance. The rate of change of the impedance may be monitored by the control logic 726 during treatment of the target tissue 707, and one or more electrosurgical signals 708 may be modulated by the control logic 726 to maintain the rate of change of impedance at a predetermined rate or within a predetermined range. The predetermined rate or predetermined range may be determined based on the treatment being applied to the target tissue 707. For example, a first predetermined rate may be used for coagulation and cutting of a tissue target 707 at the target site, a second predetermined rate may be used for welding and cutting of a tissue target 707 at the target site, and a third predetermined rate may be used for a combination of treatment including both coagulation and welding.

In another embodiment, a second feedback signal 710' may be provided by the motor control logic 712 to the control logic 726. The motor 714 may be configured to provide a signal indicating load on the motor 714 during movement of the blade 724. If the blade 724 is transecting a tissue target 707, at the target site, which comprises a thicker tissue type, the load on the motor 714 may be greater than the tissue target 707 at the target site which comprises a thinner tissue type. The motor control circuit 712 may monitor the load on the motor 714 and generate the second feedback signal 710' indicative of the load. The second feedback signal 710' may be applied to the control logic 726 which may alter one or more electrosurgical signals 708 in response to the second feedback signal 710' generated by the motor control logic 712.

In one embodiment, the electrosurgical instrument 700 may be configured to control the movement speed of the blade 724 in response to the first and second feedback signals 710, 710', alone or in combination. For example, the control logic 726 may modulate a drive control signal 716 applied to the motor control logic 712 to adjust the speed of the motor 714. The drive control signal 716 may be modulated in any suitable manner. For example, the voltage and/or current of the drive control signal 716 may be modulated. In various embodiments, modulation may be based on amplitude, frequency, phase, or any combination thereof, based on voltage and current measurements. In various embodiments, the drive control signal 716 may be a pulsed signal. In such embodiments, the control logic 726 may modulate the drive control signal 716 by changing the pulse width, duty cycle, etc., of the drive signal. By modulating the drive control signal 716, the control logic 726 may ensure proper treatment of the target tissue 707 by increasing or decreasing the speed of the blade 724 to allow a longer or shorter application of energy to the target tissue 707.

In one embodiment, the electrosurgical instrument 700 may be configured to control ultrasonic or RF energy delivered to the electrosurgical end effector 722 in response to the first feedback signal 710, the second feedback signal 710', or a combination thereof. In one embodiment, the ultrasonic or RF energy may be delivered to the electrosurgical end effector 722. In another embodiment, the RF energy may be delivered to the first and second electrodes 709*a,* 709*b* located on respective first and second jaw members 705*a,* 705*b*. In another embodiment, the blade 724 may be implemented as an ultrasonic blade, in which case ultrasonic energy may be applied to the ultrasonic blade for cutting the target tissue 707. The control logic 726 may be electrically coupled to a generator (not shown) to generate the ultrasonic or RF energy. The control logic 726 may modulate a generator control signal applied to the generator to adjust an output signal of the generator. By adjusting the output signal of the generator, the control logic 726 can increase or decrease the energy delivered to the target tissue 707. As discussed above, as the coagulation, sealing, or welding of the target tissue 707 increases, the impedance of the target tissue 707 also increases. By modulating the energy delivered to the target tissue 707, the control logic 726 may decrease the amount of time required to adequately coagulate, seal, or weld the target tissue and thereby increase the rate of change of tissue impedance.

Figure 48:
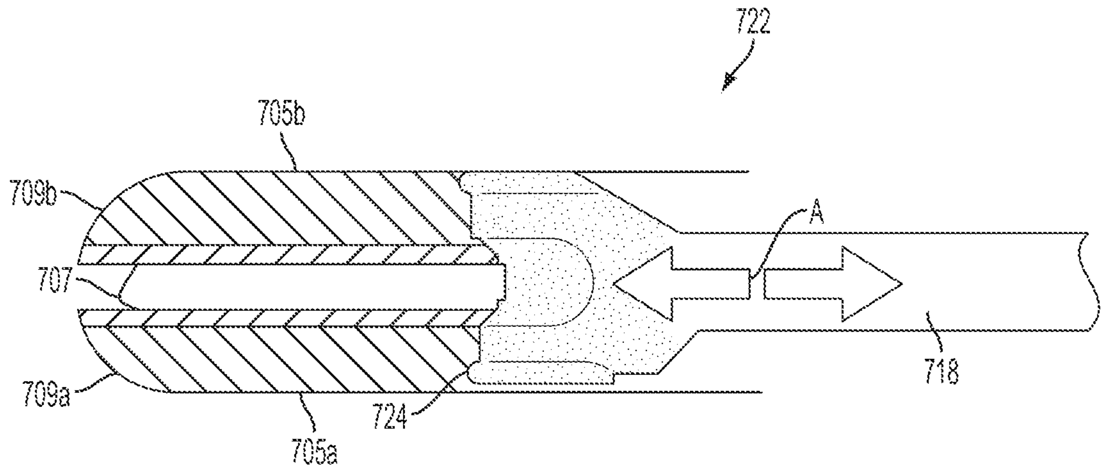
FIG. 48 illustrates one embodiment of an electrosurgical end effector for use with a closed feedback control method.

FIG. 48 illustrates one embodiment of the end effector 722. The end effector 722 may comprise first and second jaw members 705*a,* 705*b,* first and second electrodes 709*a,* 709*b,* a motor driven slideable blade 724, and an actuator 718. In one embodiment, the actuator 718 may be coupled to the blade 724 to control movement of the blade 724 along the longitudinal axis (shown as arrow "A"). In another embodiment, the actuator 718 may be configured to control an opening and closing movement of the first and second jaw members 705*a,* 705*b*. As shown in FIG. 47, an electrosurgical signal 728 may be applied to the end effector 722 to electrosurgically treat the target tissue 707. In the embodiment shown in FIG. 48, an RF signal is applied to the first and second electrodes 709*a,* 709*b* to create an electrosurgical weld of the target tissue 707. The blade 724 may be slideably translated in a distal direction along the longitudinal axis to cut the target tissue 707 in conjunction with, or immediately following, the application of the RF energy to the first and second electrodes 709*a,* 709*b* to seal the target tissue 707. As described above, a control logic 726 may control the energy level of the RF energy, the movement speed of the blade 724, or both to ensure proper treatment, or cooking, of the target tissue during the treatment and cutting process.

Figure 49:
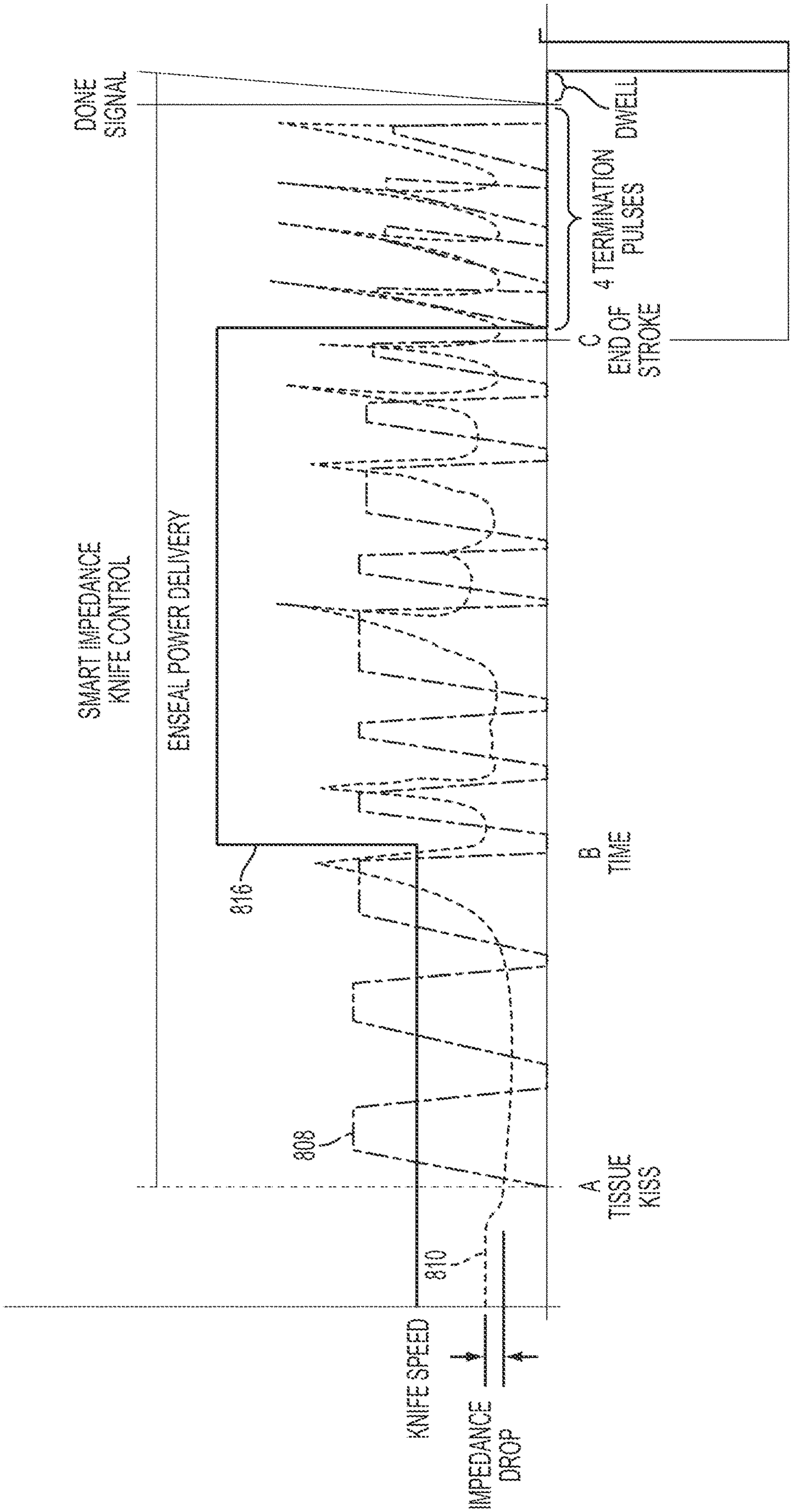
FIG. 49 illustrates one embodiment of a method for closed feedback control.

FIG. 49 is a graphical representation of the electrosurgical energy signals applied to the end effector 722 by the control logic 726. With reference now to FIGS. 47-49, one embodiment of a method for controlling an end effector based on a feedback signal is described. In accordance with the embodiment illustrated in FIGS. 47-48 and aided by the schematic of electrosurgical instrument 700 in FIG. 47, a tissue 707 treatment site is located between first and second jaw member 705*a,* 705*b* of the end effector 722. More particularly, the tissue 707 is located between the first and second electrodes 709*a,* 709*b* of the corresponding first and second jaw members 705*a,* 705*b*. A drive control signal 716 and an electrosurgical energy signal 808 are delivered to the end effector 722 by the control logic 726. An impedance feedback signal 810 is and applied to the control logic 726. The drive control signal 816 is applied to advance the blade 724 in a distal direction along a longitudinal axis of the end effector. The blade 724 has a blade speed which may be adjusted by modulating the drive control signal 816. The tissue 707 impedance feedback signal 810 is generated at the end effector 722 and is monitored by the control logic 726. At a time 'A,' an electrosurgical energy signal 808, such as, for example, a RF waveform sufficient to cause tissue welding, is applied to the target tissue 707 through the first and second electrodes 709*a,* 709*b* of the end effector 722. From time 'A' to time 'B' the speed of the blade 724 and the electrosurgical energy signal 808 are held constant while the impedance feedback signal 810 is measured. During the period from time 'A' to time 'B,' the rate of change of the impedance of the target tissue 707 is kept within the predetermined range.

At time 'B,' the blade speed 816 is increased in response to a decrease in the impedance of the target tissue 707 indicated by the change in the tissue impedance feedback signal 810. From time 'B' to time 'C,' the blade speed 816 is kept at a constant rate by the control logic 726. During the time period from 'B' to 'C,' the control logic 726 modulates the electrosurgical energy signal 808 in response to the rate of change of the tissue 707 impedance as indicated by the tissue 707 impedance feedback signal 810. As shown in the illustrated embodiment, the electrosurgical energy signal 808 is modulated over the time period from 'B' to 'C' to increase or decrease the pulse width or pulse time of the applied electrosurgical energy signal 808 to maintain the rate of change of the tissue 707 impedance at a predetermined rate.

In the illustrated embodiment, the blade 724 reaches a distal-most displacement at time 'C,' causing an end-of-stroke algorithm to activate and reverse the direction of the blade 724. Accordingly, the blade 724 is returned to a proximal-most, or starting, position within the end effector 722. During the proximal movement of the blade 724, one or more termination pulses, such as, for example, four termination pulses, may be applied to the end effector 722 by the control logic 726. The termination pulses may be a predetermined pulse pattern independent of the tissue 707 impedance feedback signal 810. Although a method for modulating one or more signals 716, 808 in response to a feedback signal 810 has been described with reference to FIG. 49, those skilled in the art will recognize that any suitable waveforms, modulation, or signals may be used and are within the scope of the appended claims.

Figure 50:
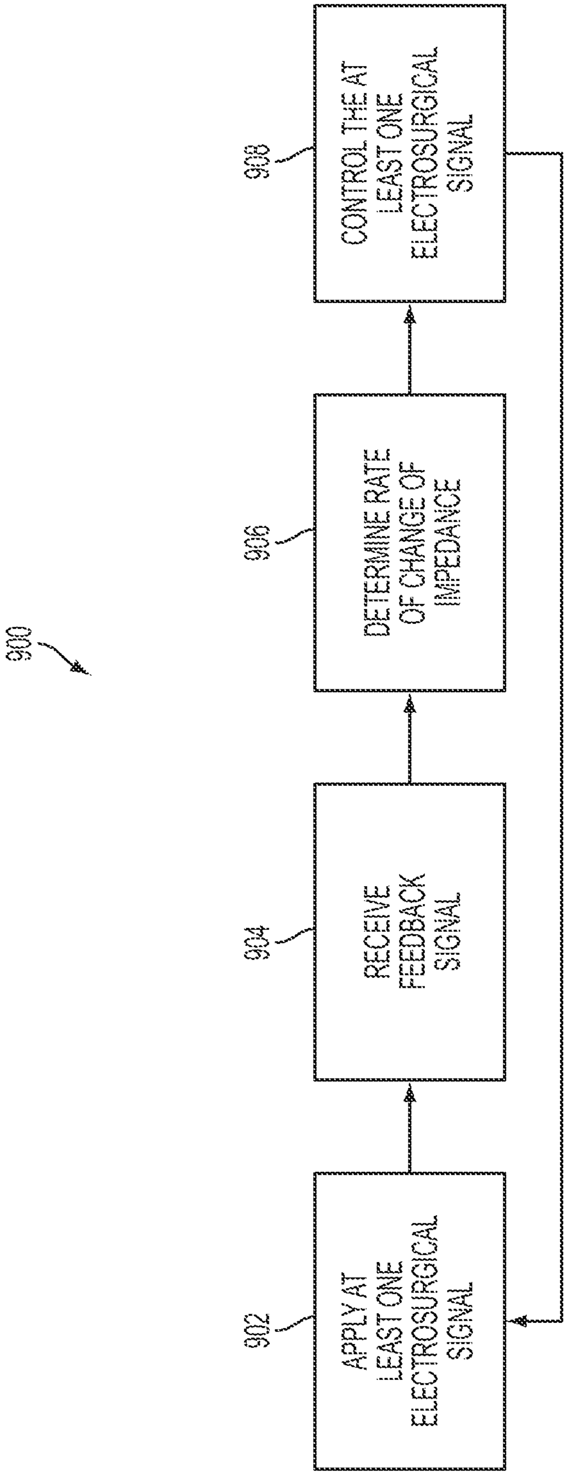
FIG. 50 illustrates an alternative embodiment of the method for closed feedback control.

FIG. 50 illustrates a logic flow 900 depicting one embodiment of the method for controlling the electrosurgical end effector 722. In one embodiment, at least one electrosurgical signal is applied 902 to an electrosurgical end effector, such as, for example, the electrosurgical end effector 722. The electrosurgical end effector 722 generates a feedback signal based on one or more conditions of the electrosurgical end effector 722. The feedback signal is received 904 by a control logic. In one embodiment, the control logic may be formed integrally with the electrosurgical end effector 722. In another embodiment, the control logic may be located within a surgical robot or a controller for the surgical robot.

In one embodiment, the control logic uses the feedback signal to determine 906 a rate of change of the impedance of the treatment site. The control logic may control 908 the one or more electrosurgical signals to maintain the rate of change of the impedance at a predetermined rate or within a predetermined range. In one embodiment, the predetermined range is a rate of change of the impedance that is equal to or greater than a threshold value. The control logic may monitor the feedback signal during the entire treatment period and modify the at least one electrosurgical signal to maintain the predetermined rate of change of impedance during the treatment period.

Figure 51:
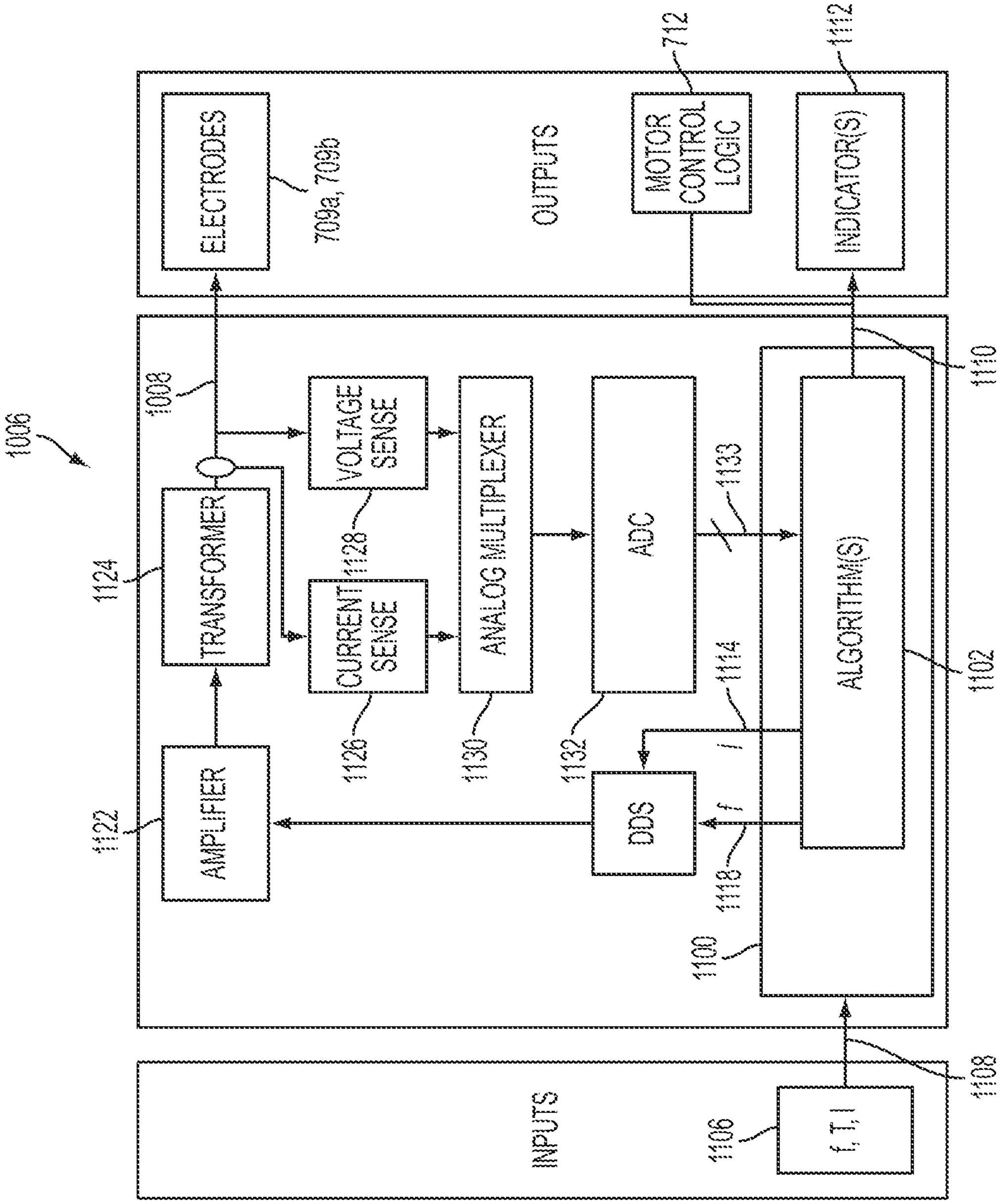
FIG. 51 illustrates one embodiment of a control logic of the end effector of FIGS. 47-48.

FIG. 51 illustrates one embodiment of a control logic 1006 of the end effector 722 shown in FIGS. 47-48. With reference now to FIGS. 47-48 and 51, the control logic 1006 creates an RF signal 1008 for delivery to the first and second electrodes 709, 709*b* of the end effector 722. The control logic 1006 is flexible and can create an RF signal 1008 at a desired frequency and power level setting to produce therapeutic RF signals, sub-therapeutic RF signals, or a combination thereof. In various embodiments, the control logic 1006 may control one or more generators, such as, for example, generators 20, 320 shown in FIGS. 1 and 11, to produce the RF signal 1008. The generator may comprise, in various embodiments, several separate functional elements, such as modules and/or blocks. Although certain modules and/or blocks may be described by way of example, it can be appreciated that a greater or lesser number of modules and/or bocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers, and/or software components, e.g., programs, sub-routines, logic, and/or combinations of hardware and software components.

In one embodiment, the control logic 1006 may comprise one or more embedded applications implemented as firmware, software, hardware, or any combination thereof. The control logic 1006 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EEPROM), or battery backed random-access memory (RAM) such as dynamic RAM (DRAM), Double-Data-Ram (DDRAM), and/or synchronous DRAM (SDRAM).

In one embodiment, the control logic 1006 comprises a hardware component implemented as a processor 1100 for executing program instructions for monitoring various measurable characteristics of the electrosurgical instrument 700 and generating an output signal for delivering a therapeutic RF signal, sub-therapeutic RF signal, or combination RF signal to the first and second electrodes 709*a,* 709*b*. It will be appreciated by those skilled in the art that the control logic 1006 may comprise additional or fewer components and only a simplified version of the control logic 1006 are described herein for conciseness and clarity. In various embodiments, as previously discussed, the hardware component may be implemented as a DSP, PLD, ASIC, circuits, and/or registers. In one embodiment, the processor 1100 may be configured to store and execute computer software program instructions to generate the output signals for driving various components of the ultrasonic surgical instrument 700, such as the first and second electrodes 709*a*, 709*b*, the motor control logic 712, the motor 714, or the blade 724.

In one embodiment, under control of one or more software program routines, the processor 1100 executes the methods in accordance with the described embodiments to generate a step function formed by a stepwise waveform of input RF signals 1108 comprising any and/or all inputs 1106 current (I), voltage (V), and/or frequency (f) for various time intervals or periods (T). The stepwise waveforms of the input RF signals 1108 may be generated by forming a piecewise linear combination of constant functions over a plurality of time intervals created by stepping the RF generator module drive signals, e.g., output drive current (I), voltage (V), and/or frequency (f). The time intervals or periods (T) may be predetermined (e.g., fixed and/or programmed by the user) or may be variable. Variable time intervals may be defined by setting the RF signal to a first value and maintaining the RF signal at that value until a change is detected in a monitored characteristic. Examples of monitored characteristics may comprise, for example, tissue impedance, tissue heating, tissue transection, tissue coagulation, and the like. The RF signals generated by the control logic 1006 include, without limitation, therapeutic, sub-therapeutic, and combination RF signals.

In one embodiment, the executable modules comprise one or more step function algorithm(s) 1102 stored in memory that when executed causes the processor 1100 to generate a step function formed by a stepwise waveform of RF signals comprising current (I), voltage (V), and/or frequency (f) for various time intervals or periods (T). The stepwise waveforms of the RF signals may be generated by forming a piecewise linear combination of constant functions over two or more time intervals created by stepping the generator's output drive current (I), voltage (V), and/or frequency (f). The RF signals may be generated either for predetermined fixed time intervals or periods (T) of time or variable time intervals or periods of time in accordance with the one or more stepped output algorithm(s) 1102. Under control of the processor 1100, the control logic 1006 steps (e.g., increment or decrement) the current (I), voltage (V), and/or frequency (f) up or down at a particular resolution for a predetermined period (T) or until a predetermined condition is detected, such as a change in a monitored characteristic (e.g., tissue impedance). The steps can change in programmed increments or decrements. If other steps are desired, the control logic 1006 can increase or decrease the step adaptively based on measured system characteristics.

In various embodiments, the output indicator 1112 may provide visual, audible, and/or tactile feedback to the surgeon, based on output RF signals 1110 supplied by the processor 1100, to indicate the status of a surgical procedure, such as, for example, when tissue sealing and cutting is complete based on a measured characteristic of the electrosurgical instrument 700, e.g., tissue impedance or other measurements as subsequently described. By way of example, and not limitation, visual feedback comprises any type of visual indication device including incandescent lamps or light emitting diodes (LEDs), graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through the robotic controller.

In one embodiment, the processor 1100 may be configured or programmed to generate a digital current signal 1114 and a digital frequency signal 1118. These signals 1114, 1118 are applied to a direct digital synthesizer (DDS) circuit 1120 to adjust the amplitude and the frequency (f) of the current output signal 1116 to the first and second electrode 709*a*, 709*b*. The output of the DDS circuit 1120 is applied to an amplifier 1122 whose output is applied to a transformer 1124. The output of the transformer 1124 is the signal 1116 applied to the first and second electrodes 709*a*, 709*b*.

In one embodiment, the control logic 1006 comprises one or more measurement modules or components that may be configured to monitor measurable characteristics of the electrosurgical instrument 700. In embodiment illustrated in FIG. 51, the processor 1100 may be employed to monitor and calculate system characteristics. As shown, the processor 1100 measures the impedance Z of the tissue site 707 by monitoring the current supplied to the tissue site 707 and the voltage applied to the tissue site 707. In one embodiment, a current sense circuit 1126 is employed to sense the current flowing through the tissue site 707 and a voltage sense circuit 1128 is employed to sense the output voltage applied to the tissue site. These signals may be applied to the analog-to-digital converter 1132 (ADC) via an analog multiplexer 1130 circuit or switching circuit arrangement. The analog multiplexer 1130 routes the appropriate analog signal to the ADC 1132 for conversion. In other embodiments, multiple ADCs 1132 may be employed for each measured characteristic instead of the multiplexer 1130 circuit. The processor 1100 receives the digital output 1133 of the ADC 1132 and calculates the tissue impedance Z based on the measured values of current and voltage. The processor 1100 adjusts the output drive signal 1116 such that it can generate a desired power versus load curve. In accordance with programmed step function algorithms 1102, the processor 1100 can step the RF signal 1116, e.g., the current or frequency, in any suitable increment or decrement in response to the tissue impedance Z.

The operation of the control logic 1006 may be programmed to provide a variety of output drive signals to measure electrical properties of current, voltage, power, impedance, and frequency associated with the tissue site 707 and the first and second electrodes 709*a*, 709*b* in a therapeutic, sub-therapeutic, or combination state, for example, based on the tissue located between the first and second jaw members 705*a*, 705*b*. When the tissue site is a thinner tissue type, the output may be stepped in a first sequence, for example. When the tissue site is a thicker tissue type, the output may be stepped in a second sequence which delivers a higher voltage, current, or time interval to the tissue site 707.

It will be appreciated by those skilled in the art that the current step function set points (e.g., $I_1$, $I_2$, $I_3$) and the time intervals or periods (e.g., $T_1$, $T_2$) of duration for each of the step function set points described above are not limited to the values described herein and may be adjusted to any suitable value as may be desired for a given set of surgical procedures. Additional or fewer current set points and periods of duration may be selected as may be desired for a given set of design characteristics or performance constraints. As previously discussed, the periods may be predetermined by programming or may be variable based on measurable system characteristics. The embodiments are not limited in this context.

Having described operational details of various embodiments of the surgical system 700, operations for the above surgical system 700 may be further described in terms of a process for sealing and cutting a blood vessel employing a surgical instrument comprising the control logic 1006 and the tissue impedance measurement capabilities described with reference to FIG. 51. Although a particular process is described in connection with the operational details, it can be appreciated that the process merely provides an example of how the general functionality described herein can be implemented by the surgical system 700. Further, the given process does not necessarily have to be executed in the order presented herein unless otherwise indicated. As previously discussed, the control logic 1006 may be employed to program the stepped output (e.g., current, voltage, frequency) to the first and second electrodes 709*a*, 709*b*.

Accordingly, one technique for sealing and cutting a vessel includes clamping the target tissue between the first and second jaw members 705*a*, 705*b*. It will be appreciated that first and second jaw members 705*a*, 705*b* may comprise one or more styles of jaws for grasping and sealing tissue, such as, for example, paddle jaw members, serrated jaw members and may include one or more pivoting jaw members for applying pressure to the tissue site 707 located between the first and second jaw members 705*a*, 705*b*. In one embodiment, the first and second jaw members 705*a*, 705*b* may comprise a blunt dissection portion.

In one embodiment, a first RF signal may be applied to the first and second electrodes 709*a*, 709*b* to seal the tissue site 707 located between the first and second jaw members 705*a*, 705*b*. By way of example, and not limitation, and in accordance with one implementation of the control logic 726, the control logic 1006 is programmed to output a first RF energy signal $f_1$ for a first period $T_1$ of time is applied to cause therapeutic treatment of the tissue site 707. In one embodiment, the first time period $T_1$ may be determined by measuring one or more characteristics of the tissue site 707, such as, for example, the tissue impedance. As discussed above with respect to FIG. 51, the control logic 1006 may monitor the current supplied to the tissue site 707 and the voltage applied to the tissue site 707 to calculate the impedance of the tissue site 707.

In one embodiment, a second RF signal may be applied to the first and second electrodes 709*a*, 709*b*. The second RF signal may be a sub-therapeutic RF signal. The second RF signal may be applied to the tissue site 707 for a second period $T_2$. The current and the voltage applied to the tissue site 707 by the second RF signal may be monitored and used to calculate the impedance of the tissue site 707.

In one embodiment, the tissue/vessel sealing and cutting process may be automated by sensing the impedance Z characteristics of the tissue site 707 to detect when the sealing of the tissue/vessel occurs. The impedance Z can be correlated to the sealing of the tissue site 707 and to the transection/sealing of the vessel to provide a trigger for the processor 1100 to provide a drive signal for the motor control logic 712 to cause the blade 724 to transect the tissue. As previously discussed with reference to FIG. 51, the impedance Z of the tissue 707 may be calculated by the processor 1100 based on the current flowing through tissue 707 and the voltage applied to the tissue 707 while the tissue 707 and the first and second electrodes 709*a*, 709*b* are under certain loads. Because the impedance Z of the tissue 707 is proportional to the sealing state of the tissue 707, as the sealing state of the tissue 707 increases the impedance Z of the tissue 707 increases. Accordingly, the impedance Z of the tissue 707 can be monitored to detect the sealing of the tissue 707 and determine when it is safe to transect the tissue using the blade 724.

In one embodiment, the control logic 1006 may provide a control signal to the motor control logic 712. The control signal may be generated based upon the impedance Z of the tissue 707. For example, in one embodiment, a certain tissue impedance Z may indicate that the tissue has been successfully sealed by the application of therapeutic RF energy to the tissue site 707. The control logic 1006 may send a control signal to the motor control logic 712 indicating that the tissue impedance Z has reached a predetermined level. The motor control logic 712 may then advance the blade 724 to transect the tissue 707 located between the first and second jaw members 705*a*, 705*b*.

In one embodiment, the electrosurgical instrument 700 may be operated in accordance with a programmed step function algorithm responsive to the tissue impedance Z. In one embodiment, a frequency step function output may be initiated based on a comparison of the tissue impedance Z and one or more predetermined thresholds that have been correlated with tissue 707 sealing states. When the tissue impedance Z transitions above or below (e.g., crosses) a threshold, the processor 1100 applies a digital frequency signal 1118 to the DDS circuit 1120 to change the frequency of the drive signal 1116 by a predetermined step in accordance with the step function algorithm(s) 1102 responsive to the tissue impedance Z.

Figure 52:
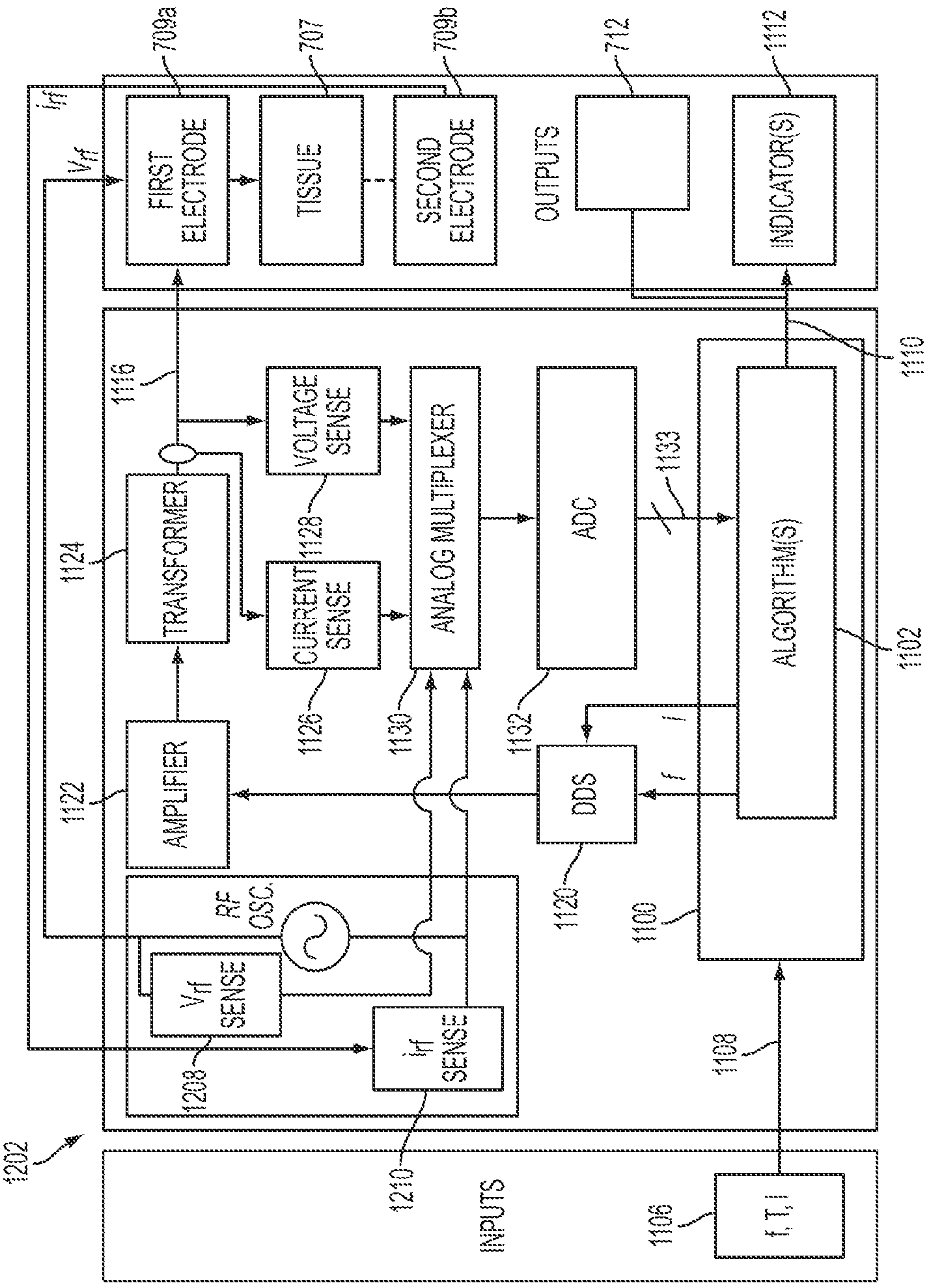
FIG. 52 illustrates one embodiment of a control logic comprising a signal generator module formed integrally with the electrosurgical instrument of FIG. 47.

With reference now to FIGS. 47 and 52, in one embodiment, the control logic 1006 comprises a signal generator module. In one embodiment, the signal generator module may be implemented as a tissue impedance module 1202. Although in the presently disclosed embodiment, the control logic 1006 is shown separate from the electrosurgical instrument, in one embodiment, the control logic 1006 may be formed integrally with the electrosurgical instrument, as shown in phantom in FIG. 47 (e.g., the control logic 726 may be implemented by the control logic 1006). In one embodiment, the signal generator module may be configured to monitor the electrical impedance $Z_t$ of the tissue 707 to control the characteristics of time and power level based on the impedance $Z_t$ of the tissue T. In one embodiment, the tissue impedance $Z_t$ may be determined by applying a subtherapeutic radio frequency (RF) signal to the tissue T and measuring the current through the tissue T by way of a the first and second electrodes 709*a*, 709*b*, as previously discussed. In the schematic diagram shown in FIG. 52, the end effector 722 comprises first and second electrodes 709*a*, 709*b* disposed on respective first and second jaw members 705*a*, 705*b*. The tissue impedance module 1202 is coupled to first and second electrodes 709*a*, 709*b* through a suitable transmission medium such as a cable. The cable comprises multiple electrical conductors for applying a voltage to the tissue 707 and providing a return path for current flowing through the tissue 707 back to the impedance module 1202. In various embodiments, the tissue impedance module 1202 may be formed integrally with the instrument mounting portion, the robotic surgical system, a control system for the robotic surgical system or may be provided as a separate circuit coupled to the robotic surgical system.

Still with reference to FIG. 52, as shown, the signal generator module is configured as a tissue impedance module 1202. In one embodiment, an integrated generator module may generate an ultrasonic electrical drive signal to drive an ultrasonic transducer coupled to the blade 724. In one embodiment, the tissue impedance module 1202 may be configured to measure the impedance $Z_t$ of the tissue 707 grasped between the first and second jaw members 705*a*, 705*b*. The tissue impedance module 1202 comprises an RF oscillator 506, a voltage sensing circuit 1208, and a current sensing circuit 1210. The voltage and current sensing circuits 1208, 1210 respond to the RF voltage $v_{rf}$ applied to the first and second electrodes 709*a*, 709*b* and the RF current $i_{rf}$ flowing through the first electrode 709*a*, the tissue, and the second electrode 709*b*. The sensed voltage $v_{rf}$ and current $i_{rf}$ are converted to digital form by the ADC 1132 via the analog multiplexer 1130. The processor 1100 receives the digitized output 1133 of the ADC 1132 and determines the tissue impedance $Z_t$ by calculating the ratio of the RF voltage $v_{rf}$ to current $i_{rf}$ measured by the voltage sense circuit 1208 and the current sense circuit 1210. In one embodiment, the sealing of the tissue 707 may be determined by sensing the tissue impedance $Z_t$. Accordingly, detection of the tissue impedance $Z_t$ may be integrated with an automated process for sealing the tissue prior to transection of the tissue by the blade 724.

Figure 53:
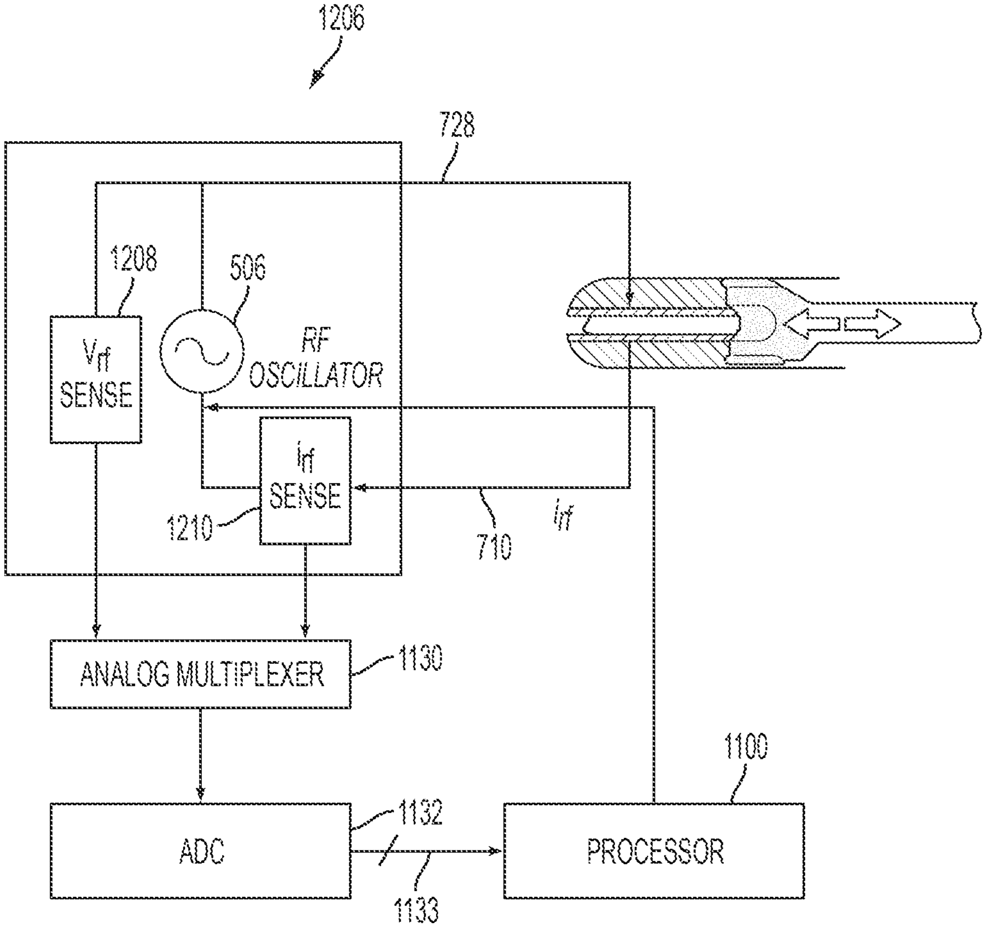
FIG. 53 illustrates a schematic diagram of the control logic coupled to the electrodes of FIG. 47.

FIG. 53 is a schematic diagram of the control logic 1006 configured as the tissue impedance module 1202 coupled to the first and second electrode 709*a*, 709*b* with the tissue 707 site located therebetween. With reference now to FIGS. 47 and 51-53, the control logic 1006 comprises a signal generator module configured as the tissue impedance module 1202 configured for monitoring the impedance $Z_t$ of the tissue T located between the first and second electrodes 709*a*, 709*b* during the tissue sealing and cutting process. The tissue impedance module 1202 may be coupled to the electrosurgical instrument 700 by way of the cables. The cable includes a first "energizing" conductor connected to the first electrode 709*a* and a second "return" conductor connected to the second electrode 709*b* (e.g., negative [−] electrode). In one embodiment, RF voltage $v_{rf}$ is applied to the first electrode 709*a* to cause RF current $i_{rf}$ to flow through the tissue 707. The second electrode 709*b* provides the return path for the current $i_{rf}$ back to the tissue impedance module 1202. The distal end of the second electrode 709*b* is connected to the conductive jacket such that the current $i_{rf}$ can flow from the blade first electrode 709*a*, through the tissue 707 positioned intermediate between the first and second jaw members 705*a*, 705*b*, and the second electrode 709*b*. The impedance module 1202 connects in circuit, by way of the first and second electrodes 709*a*, 709*b*. In one embodiment, the RF energy applied to the tissue 707 for purposes of measuring the tissue impedance $Z_t$ may be a low level subtherapeutic signal that does not contribute in a significant manner, or at all, to the treatment of the tissue 707. In another embodiment, the RF energy applied to the tissue 707 is a therapeutic signal for treatment of the tissue 707.

NON-LIMITING EXAMPLES

In one embodiment a robotic surgical system is provided. The robotic surgical system comprises a surgical tool comprising an end effector comprising a first jaw member, a second jaw member, the first and second jaw members comprising corresponding first and second electrodes, and a blade, the end effector configured to receive at least one signal; an actuator for reciprocating the blade along a longitudinal axis; and a control circuit for controlling the actuator, wherein the control circuit: provides the at least one signal to the end effector receives a feedback signal indicative of a tissue impedance of tissue in contact with the end effector; determines a rate of change of the tissue impedance based on the feedback signal; controls the at least one signal to maintain a predetermined rate of change of the tissue impedance.

In one embodiment a surgical tool is provided. The surgical tool comprises an end effector comprising a first jaw member, a second jaw member, the first and second jaw members comprising corresponding first and second electrodes, and a blade, the end effector configured to receive at least one signal; an actuator for reciprocating the blade along a longitudinal axis; and a control circuit for controlling the actuator, wherein the control circuit: provides the at least one signal to the end effector; receives a feedback signal indicative of a tissue impedance of tissue in contact with the end effector; determines a rate of change of the tissue impedance based on the feedback signal; controls the at least one signal to maintain a predetermined rate of change of the tissue impedance.

Applicant also owns the following patent applications that are each incorporated by reference in their respective entireties:

U.S. patent application Ser. No. 13/536,271, filed on Jun. 28, 2012 and entitled FLEXIBLE DRIVE MEMBER, now U.S. Pat. No. 9,204,879;

U.S. patent application Ser. No. 13/536,288, filed on Jun. 28, 2012 and entitled MULTI-FUNCTIONAL POWERED SURGICAL DEVICE WITH EXTERNAL DISSECTION FEATURES, now U.S. Patent Application Publication No. 2014/0005718;

U.S. patent application Ser. No. 13/536,295, filed on Jun. 28, 2012 and entitled ROTARY ACTUATABLE CLOSURE ARRANGEMENT FOR SURGICAL END EFFECTOR, now U.S. Pat. No. 9,119,657;

U.S. patent application Ser. No. 13/536,326, filed on Jun. 28, 2012 and entitled SURGICAL END EFFECTORS HAVING ANGLED TISSUE-CONTACTING SURFACES, now U.S. Pat. No. 9,289,256;

U.S. patent application Ser. No. 13/536,303, filed on Jun. 28, 2012 and entitled INTERCHANGEABLE END EFFECTOR COUPLING ARRANGEMENT, now U.S. Pat. No. 9,028,494;

U.S. patent application Ser. No. 13/536,393, filed on Jun. 28, 2012 and entitled SURGICAL END EFFECTOR JAW AND ELECTRODE CONFIGURATIONS, now U.S. Patent Application Publication No. 2014/0005640;

U.S. patent application Ser. No. 13/536,362, filed on Jun. 28, 2012 and entitled MULTI-AXIS ARTICULATING AND ROTATING SURGICAL TOOLS, now U.S. Pat. No. 9,125,662; and U.S. patent application Ser. No. 13/536,417, filed on Jun. 28, 2012 and entitled ELECTRODE CONNECTIONS FOR ROTARY DRIVEN SURGICAL TOOLS, now U.S. Pat. No. 9,101,385.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system, comprising:
- a robotic surgical system;
- a surgical instrument, comprising:
  - a tool mounting portion configured to removably couple to the robotic surgical system;
  - an elongate shaft extending from the tool mounting portion; and
  - an end effector extending from the elongate shaft, wherein the end effector comprises:
    - a first jaw comprising a first electrode;
    - a second jaw comprising a second electrode, wherein the first electrode and the second electrode are configured to couple to an energy generator; and
    - a blade;
- a motion driving system configured to drive the blade, the motion driving system comprising a motion driver; and
- a control circuit, configured to:
  - transmit a first control signal to the motion driving system, wherein the first control signal is configured to control a speed of the blade;
  - transmit a second control signal to the energy generator, wherein the second control signal is configured to control an amount of energy to apply to the first electrode and the second electrode;
  - receive a first feedback signal indicative of an impedance of tissue in electrical contact with the first electrode and the second electrode;
  - receive a second feedback signal indicative of a load on the motion driver;
  - determine a rate of change of the impedance based on the first feedback signal;
  - determine a tissue type of the tissue based on the second feedback signal; and
  - modulate at least one of the first control signal and the second control signal to maintain the rate of change of the impedance within a predetermined range, wherein the predetermined range is based at least in part on the tissue type.

2. The system of claim 1, wherein the motion driving system comprises a motorized system.

3. The system of claim 1, wherein the motion driving system comprises an ultrasonic transducer.

4. The system of claim 1, wherein the motion driving system comprises:
- control logic in operable communication with the motion driver and the control circuit.

5. The system of claim 1, wherein the surgical instrument comprises the control circuit.

6. The system of claim 1, wherein the robotic surgical system comprises the control circuit.

7. A system, comprising:
- a robotic surgical system;
- a surgical instrument, comprising:
  - a tool mounting portion configured to removably couple to the robotic surgical system;

an elongate shaft extending from the tool mounting portion; and an end effector extending from the elongate shaft, wherein the end effector comprises:

a first jaw comprising a first electrode;

a second jaw comprising a second electrode, wherein the first electrode and the second electrode are configured to operably couple to an energy generator; and a blade;

a motion driving system configured to drive the blade, the motion driving system comprising a motion driver; and a controller comprising a processor and a memory in communication with the processor, wherein the memory stores instructions that, when executed by the processor, cause the processor to:

transmit a first control signal to the motion driving system, wherein the first control signal is configured to control a speed of the blade;

transmit a second control signal to the energy generator, wherein the second control signal is configured to control an amount of energy to apply to the first electrode and the second electrode;

receive a first feedback signal indicative of an impedance of tissue in electrical contact with first electrode and the second electrode;

receive a second feedback signal indicative of a load on the motion driver;

determine a rate of change of the impedance based on the first feedback signal;

determine a tissue type of the tissue based on the second feedback signal; and modulate at least one of the first control signal and the second control signal to maintain the rate of change of the impedance at predetermined rate, wherein the predetermined rate is based at least in part on the tissue type.

8. The system of claim 7, wherein the motion driving system comprises a motorized system.

9. The system of claim 7, wherein the motion driving system comprises an ultrasonic transducer.

10. The system of claim 7, wherein the motion driving system comprises:

control logic in operable communication with the motion driver and the controller.

11. The system of claim 7, wherein the surgical instrument comprises the controller.

12. The system of claim 7, wherein the robotic surgical system comprises the controller.

13. A surgical system usable with a robotic system, wherein the surgical system comprises:

a surgical instrument, comprising:

a tool mounting portion configured to removably couple to the robotic system; and an end effector, comprising:

a first jaw comprising a first electrode;

a second jaw comprising a second electrode, wherein the first electrode and the second electrode are configured to operable couple to an energy generator; and a blade;

a motion driving system configured to drive the blade, the motion driving system comprising a motion driver; and a control circuit, configured to:

transmit a first control signal to the motion driving system, wherein the first control signal is configured to control the blade;

transmit a second control signal to the energy generator, wherein the second control signal is configured to control an amount of energy to apply to the first electrode and the second electrode;

receive a first feedback signal indicative of an impedance of tissue in electrical contact with the first electrode and the second electrode;

receive a second feedback signal indicative of a load on the motion driver;

determine a rate of change of the impedance based on the first feedback signal;

determine a tissue type of the tissue based on the second feedback signal; and modulate at least one of the first control signal and the second control signal to maintain the rate of change of the impedance at a predetermined rate or within a predetermined range, wherein the predetermined range is based at least in part on the tissue type.

14. The surgical system of claim 13, wherein the motion driving system comprises a motorized system.

15. The surgical system of claim 13, wherein the motion driving system comprises an ultrasonic transducer.

* * * * *